(12) United States Patent
Yamada et al.

(10) Patent No.: US 7,160,894 B2
(45) Date of Patent: Jan. 9, 2007

(54) TRICYCLIC COMPOUND

(75) Inventors: Rintaro Yamada, Shizuoka (JP); Minoru Seto, Shizuoka (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 0 days.

(21) Appl. No.: 10/859,098

(22) Filed: Jun. 3, 2004

(65) Prior Publication Data
US 2005/0096310 A1    May 5, 2005

(30) Foreign Application Priority Data

Jun. 6, 2003 (JP) .............................. 2003-161835
Feb. 6, 2004 (JP) .............................. 2004-031068

(51) Int. Cl.
- A01N 43/42 (2006.01)
- A61K 31/44 (2006.01)
- C07D 455/04 (2006.01)
- C07D 471/00 (2006.01)
- C07D 491/00 (2006.01)

(52) U.S. Cl. ..................... 514/292; 546/80; 546/81
(58) Field of Classification Search .................. 546/80, 546/81; 514/292
See application file for complete search history.

(56) References Cited

U.S. PATENT DOCUMENTS

| 6,153,608 A | 11/2000 | Hidaka et al. |
| 2004/0102437 A1 | 5/2004 | Takami et al. |

FOREIGN PATENT DOCUMENTS

| EP | 0956865 A1 | 11/1999 |
| EP | 1403255 A1 | 3/2004 |
| EP | 1 541 599 A1 | 6/2005 |
| JP | 52-27800 | 3/1977 |
| JP | 54-54140 A | 4/1979 |
| JP | 2001-261556 A | 9/2001 |
| WO | WO-95/05824 A1 | 3/1995 |
| WO | WO99/20620 A1 | 4/1999 |
| WO | WO 00/09162 A1 | 2/2000 |
| WO | WO 01/68607 A1 | 9/2001 |

OTHER PUBLICATIONS

Piantanida et al., "4,9-Diazapyrenium cation. Synthesis, physicochemical properties and binding of nucleotides in water", Perkin 2, vol. 2, pp. 375-383.*
Barany et al., Biochemistry of Smooth Muscle Contraction, pp. 321-339, (1996).
Kamm et al., Annu. Rev. Physoil., vol. 51, pp. 299-313, (1989).
Schmidt et al., J. Neurobiol., vol. 52, No. 3, pp. 175-188, (2002).
Niggli, V., FEBS Letters, vol. 445, pp. 69-72, (1999).
Kitani et al., Biochem. Biophys. Res. Commun., vol. 183, No. 1, pp. 48-54, (1992).
Itoh et al., Biochem. Biophys. Acta., vol. 1136, pp. 52-56, (1992).
Mills et al., J. Cell Biol., Vol. 140, No. 3, pp. 627-636, (1998).
Suzuki et al., Br. J. Pharmacol., vol. 109, pp. 703-712, (1993).
Howe et al., Biochem. J., vol. 255, pp. 423-429, (1988).
Mobley et al., Exp. Cell Res., vol. 214, pp. 55-66, (1994).
Woodgate et al., Heterocycles, vol. 26, No. 4, pp. 1029-1036, (1987).
Herbert et al., J. Med. Chem., vol. 30, pp. 2081-2086, (1987).

* cited by examiner

*Primary Examiner*—Thomas C. McKenzie
*Assistant Examiner*—Niloofar Rahmani
(74) *Attorney, Agent, or Firm*—Birch, Stewart, Kolasch & Birch, LLP

(57) ABSTRACT

A novel compound represented by the formula (1):

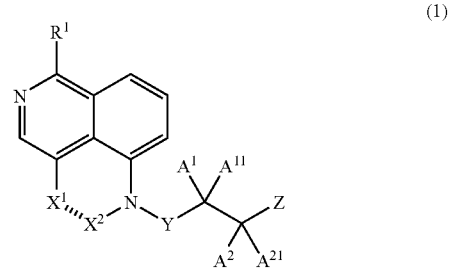

(1)

[$R^1$ represents hydrogen atom, chlorine atom, or hydroxyl group; $X^1 \ldots X^2$ represents —CH($R^2$)—CH($R^3$)—, —CH($R^2$)—CH($R^3$)—CH($R^4$)—, etc.; $R^2$ to $R^4$ represent hydrogen atom, or an alkyl group; $A^1$, $A^{11}$, $A^2$, and $A^{21}$ represent hydrogen atom, or an alkyl group; Y represents —CH($A^3$)—, —CH($A^3$)—C($A^4$)($A^{41}$)—, —CH($A^3$)—C($A^4$)($A^{41}$)—C($A^5$)($A^{51}$)—, or a single bond; $A^3$, $A^4$, $A^{41}$, $A^5$, and $A^{51}$ represent hydrogen atom, or an alkyl group; Z represents hydroxyl group, or —N($A^6$)($A^{61}$); $A^6$ represents hydrogen atom, or an alkyl group, $A^{61}$ represents hydrogen atom, an alkyl group, an aralkyl group, etc.; and groups in each of one or more combinations selected from the group consisting of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ may bind to each other to form a 5- or 6-membered ring], or a salt thereof, which potently inhibits the phosphorylation of myosin regulatory light chain.

16 Claims, No Drawings

TRICYCLIC COMPOUND

TECHNICAL FIELD

The present invention relates to a novel tricyclic compound or a salt thereof, and a medicament comprising said tricyclic compound or a salt thereof as an active ingredient.

BACKGROUND ART

Movements of cells include contraction, migration, release, aggregation and the like, and phosphorylation of the myosin regulatory light chain is important for these cell movements. The myosin regulatory light chain is a subunit having a molecular weight of 20 kDa and constituting myosin, which exists in smooth muscle cells and various non-muscle cells such as neutrophils, leukocytes, platelets and nerve cells of warm-blooded animals (Barany, K., et al., Biochemistry of Smooth Muscle Contraction, pp. 21–35, 1996). Myosin existing in smooth muscle cells and various non-muscle cells such as neutrophils, leukocytes, platelets and nerve cells of warm-blooded animals is constituted by a myosin heavy chain subunit having a molecular weight of about 200 kDa, the myosin regulatory light chain subunit having a molecular weight of about 20 kDa, and a myosin constitutive light chain subunit having a molecular weight of about 17 kDa. The myosin regulatory light chain is mainly phosphorylated by the myosin light chain kinase to increase the activity of myosin ATPase existing in the myosin heavy chain subunit (Barany, M., et al., Biochemistry of Smooth Muscle Contraction, pp. 321–339, 1996). It is known that the activated myosin having the increased ATPase activity becomes possible to interact with actin and activates movement apparatuses of cytoskeleton to activate cell movements. That is, it is known that activation of myosin relates to cell contraction (Kamm, K., et al., Annu. Rev. Physiol., 51, pp. 299–313, 1989). It is also known that activation of myosin relates to change of cell morphology (Schmidt, J. T. et al., J, Neurobiol., 52 (3), pp. 175–188, 2002). It is known that activation of myosin relates to cell migration (Niggli, V., FEBS Lett., 445, pp. 69–72, 1999). Further, it is known that activation of myosin relates to cell release (Kitani, S., et al., Biochem. Biophys. Res. Commun., 183, pp. 48–54, 1992). It is further known that activation of myosin relates to cell aggregation (Itoh, K., et al., Biochim. Biophys. Acta., 1136, pp. 52–56, 1992). It is also known that activation of myosin relates to cell apoptosis (Mills, J. C. et al., J. Cell Biol., Vol. 140, No. 3, pp. 627–636, 1998). Based on these findings, it is considered that an agent which inhibits the phosphorylation of the myosin regulatory light chain suppresses cell contraction, regulates change of cell morphology, suppresses cell migration, suppresses cell release, suppresses cell aggregation and suppresses cell apoptosis.

Cell contraction is deeply involved in diseases relating to contraction of various smooth muscle layers. Examples of such diseases include, for example, hypertension (Samlyo, A. P., et al., Rev. Physiol. Biochem. Pharmacol., Vol. 134, pp. 209–34, 1999), angina pectoris (Shimokawa et al., Cardiovasc. Res., Vol. 43, No. 4, pp. 1029–39, 1999; Satoh, H., et al., Jpn. J. Pharmacol., 79 (suppl.), p. 211, 1999), cerebral vascular spasm (M. Satoh et al., the 57th General Meeting of Japan Neurosurgical Society, Collection of Abstracts, 153, 1998; N. Ono et al., Pharmacol. Ther., Vol. 82, No. 2–3, pp. 123–31, 1991; Shimokawa et al., Cardiovasc. Res., Vol. 43, No. 4, pp. 1029–39, 1999), erectile dysfunction (Andersson, K E. et al., World J. Vrol., 15, pp. 14–20, 1997), bronchial asthma (K. Iidzuka, Allergy, 47, 943, 1998; K. Iidzuka et al., Jpn. J. Respirology Society, 37, 196, 1999) and the like.

Change of cell morphology is deeply involved in diseases relating to morphological change of various cells. Examples of the diseases relating to change of cell morphology include, for example, various nerve dysfunctions as those relating to nerve cells. As the nerve dysfunctions, for example, neural damages caused by trauma, neurodegenerative diseases such as Alzheimer's disease, Parkinson's disease, diabetic retinopathy, glaucoma and the like can be exemplified (Arakawa, Y., et al., BIO Clinica, 17 (13), pp. 26–28, 2002). Further, cell migration is deeply involved in diseases relating to migration of various cells. Examples of such diseases include, for example, cancer invasion and metastasis (Itoh, K. et al., Nat. Med., Vol. 5, No. 2, pp. 221–5, 1999; Keely, P. et al., Trends Cell Biol., Vol. 8, No. 3, pp. 101–6, 1998), nephritis (Fujimoto, O. et al., Journal of Japanese Society of Internal Medicine, 88 (1), pp. 148–58, 1998) and the like.

Furthermore, it is considered that cell release is deeply involved in various allergies and the like (Keane-Myers A. et al., Curr. Allergy Asthma Rep., 1(6):550–557, 2001), and further, cell aggregation is considered to be deeply involved in thrombosis and the like (Nakai, K. et al., Blood, Vol. 90, No. 10, pp. 3736–42., 1997). Further, it is known that cell apoptosis is involved in neurodegenerative diseases such as Alzheimer's disease, Parkinson's disease and glaucoma, viral diseases, hepatic diseases and the like (Thompson, C. B., Science, Vol. 267, pp. 1456–1462, 1995).

Based on these findings, it is considered that the inhibitor of the phosphorylation of myosin regulatory light chain of the present invention, which is an agent inhibiting the phosphorylation of the myosin regulatory light chain, is useful as an active ingredient of a medicament for prophylactic and/or therapeutic treatment of a disease relating to cell contraction, disease relating to change of cell morphology, disease relating to cell migration, disease relating to cell release, disease relating to cell aggregation, and/or disease relating to cell apoptosis.

It has been reported that 1-(5-isoquinolinesulfonyl)-2-methylpiperazine (H-7), which is an isoquinoline derivative, inhibits phosphorylation of the myosin regulatory light chain of mesenteric artery (Suzuki, A. et al., Br. J. Pharmacol., 109, pp. 703–712, 1993), iris smooth muscle (Howe, P. H. et al., Biochem J., 255, pp. 423–429, 1988), and astrocyte (Mobley P. L., et al., Exp. Cell Res., 214, pp. 55–66, 1994).

DISCLOSURE OF THE INVENTION

Conventionally, it has been desired to provide a novel compound having an action of strongly inhibiting the phosphorylation of myosin regulatory light chain. The inventors of the present invention synthesized various novel compounds and studied pharmacological actions thereof. As a result, it was found that the compounds represented by the following formula (1) and salts thereof had the desired pharmacological action, and were useful as an active ingredient of a medicament for prophylactic and/or therapeutic treatment of diseases relating to cell contraction, those relating to change of cell morphology, those relating to cell migration, those relating to cell release, those relating to cell aggregation, and those relating to cell apoptosis. The present invention was achieved on the basis of these findings.

The present invention thus provides a compound represented by the following formula (1) or a salt thereof:

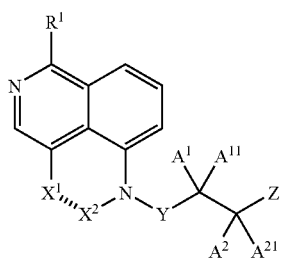

(1)

wherein $R^1$ represents hydrogen atom, chlorine atom, or hydroxyl group;

$X^1 \ldots X^2$ represents —CH($R^2$)—CH($R^3$)—, —CH($R^2$)—CH($R^3$)—CH($R^4$)—, —C($R^2$)=C($R^3$)—, or —C($R^2$)=C($R^3$)—CH($R^4$)—;

$R^2$, $R^3$, and $R^4$ independently represent hydrogen atom, or an alkyl group;

$A^1$, $A^{11}$, $A^2$, and $A^{21}$ independently represent hydrogen atom, or an alkyl group;

Y represents —CH($A^3$)—, —CH($A^3$)—C($A^4$)($A^{41}$)—, —CH($A^3$)—C($A^4$)($A^{41}$)—C($A^5$)($A^{51}$)—, or a single bond;

$A^3$, $A^4$, $A^{41}$, $A^5$, and $A^{51}$ independently represent hydrogen atom, or an alkyl group;

Z represents hydroxyl group, or —N($A^6$)($A^{61}$);

$A^6$ represents hydrogen atom, or an alkyl group, $A^{61}$ represents hydrogen atom, an alkyl group, an aralkyl group, an alkyl group substituted with carboxyl group, an alkyl group substituted with cyano group, an alkyl group substituted with hydroxyl group, an alkyl group substituted with an alkoxyl group, an alkyl group substituted with an amino group, an alkyl group substituted with aminocarbonyl group, or an alkyl group of which end is substituted with N($A^7$) (—$X^3$—$A^{71}$), where —$X^3$— represents carbonyl group, $A^7$ represents hydrogen atom, or an alkyl group, and $A^{71}$ represents an alkyl group, an aralkyl group, or an aryl group, or $A^7$ and $A^{71}$ may combine together to form an alkylene group, or an alkylene group substituted with an alkyl group to form a ring; and groups in each of one or more combinations selected from the group consisting of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ may bind to each other to form a 5- or 6-membered ring.

From another aspect, the present invention provides a medicament containing a compound represented by the aforementioned formula (1) or a physiologically acceptable salt thereof as an active ingredient. The aforementioned medicament has an inhibitory action on phosphorylation of myosin regulatory light chain, and is useful as a medicament for prophylactic and/or therapeutic treatment of, for example, a disease relating to cell contraction, disease relating to change of cell morphology, disease relating to cell migration, disease relating to cell release, disease relating to cell aggregation, and/or disease relating to cell apoptosis, and the like.

More specifically, there are provided a medicament for decreasing phosphorylation amount of myosin regulatory light chain in a cell, which comprises a compound represented by the aforementioned formula (1) or a physiologically acceptable salt thereof as an active ingredient, a medicament having a cell contraction inhibitory action, which comprises a compound represented by the aforementioned formula (1) or a physiologically acceptable salt thereof as an active ingredient, a medicament having an action to regulate change of cell morphology, which comprises a compound represented by the aforementioned formula (1) or a physiologically acceptable salt thereof as an active ingredient, a medicament having a cell migration inhibitory action, which comprises a compound represented by the aforementioned formula (1) or a physiologically acceptable salt thereof as an active ingredient, a medicament having a cell release inhibitory action, which comprises a compound represented by the aforementioned formula (1) or a physiologically acceptable salt thereof as an active ingredient, a medicament having a cell aggregation inhibitory action, which comprises a compound represented by the aforementioned formula (1) or a physiologically acceptable salt thereof as an active ingredient, a medicament having a cell apoptosis inhibitory action, which comprises a compound represented by the aforementioned formula (1) or a physiologically acceptable salt thereof as an active ingredient, and a medicament for inhibiting the Rho/Rho kinase pathway, which comprises a compound represented by the aforementioned formula (1) or a physiologically acceptable salt thereof as an active ingredient.

The present invention also provides an inhibitor of the phosphorylation of myosin regulatory light chain containing a compound represented by the aforementioned formula (1) or a physiologically acceptable salt thereof, and an inhibitor of the Rho/Rho kinase pathway comprising a compound represented by the aforementioned formula (1) or a physiologically acceptable salt thereof.

From another aspect, the present invention provides use of a compound represented by the aforementioned formula (1) or a physiologically acceptable salt thereof for manufacture of the aforementioned medicaments. The present invention also provides a method for prophylactic and/or therapeutic treatment of a disease relating to cell contraction, disease relating to change of cell morphology, disease relating to cell migration, disease relating to cell release, disease relating to cell aggregation, and/or disease relating to cell apoptosis and the like, which comprises the step of administrating a prophylactically and/or therapeutically effective amount of a compound represented by the aforementioned formula (1) or a physiologically acceptable salt thereof to a mammal including human, a method for decreasing phosphorylation amount of myosin regulatory light chain in a cell, which comprises the step of administrating an effective amount of a compound represented by the aforementioned formula (1) or a physiologically acceptable salt thereof to a mammal including human, a method for inhibiting cell contraction, which comprises the step of administrating an effective amount of a compound represented by the aforementioned formula (1) or a physiologically acceptable salt thereof to a mammal including human, a method for regulating change of cell morphology, which comprises the step of administrating an effective amount of a compound represented by the aforementioned formula (1) or a physiologically acceptable salt thereof to a mammal including human, a method for inhibiting cell migration, which comprises the step of administrating an effective amount of a compound represented by the aforementioned formula (1) or a physiologically acceptable salt thereof to a mammal including human, a method for inhibiting cell release, which comprises the step of administrating an effective amount of a compound represented by the aforementioned formula (1) or a physiologically acceptable salt thereof to a mammal including human, a method for inhibiting cell aggregation, which comprises the step of administrating an effective amount of a compound represented by the aforementioned formula (1) or a physiologically acceptable salt thereof to a mammal including human, a method for inhibiting cell apoptosis, which comprises the step of administrating an effective amount of a compound represented by the aforementioned formula (1) or a physiologically acceptable salt thereof to a mammal including human, and a method for inhibiting the Rho/Rho kinase pathway, which comprises the step of administrating an effective amount of a compound represented by the aforementioned formula (1) or a physiologically acceptable salt thereof to a mammal including human.

BEST MODE FOR CARRYING OUT THE INVENTION

The alkyl group mentioned in this specification may be a linear or branched alkyl group, and for example, a lower alkyl group is preferred. The lower alkyl group include linear or branched alkyl groups having 1 to 6 carbon atoms, and specific examples are, for example, methyl group, ethyl group, propyl group, isopropyl group, butyl group, secondary butyl group, tertiary butyl group, pentyl group, 2-methylbutyl group, hexyl group, and the like. As the lower alkyl group in $R^2$, $R^3$, $R^4$, $A^1$, $A^{11}$, $A^2$, $A^{21}$, $A^3$, $A^4$, $A^{41}$, $A^5$, $A^{51}$, $A^6$, and $A^{61}$, methyl group, or ethyl group is independently preferred.

Examples of $R^1$ include hydrogen atom, chlorine atom, and hydroxyl group. Preferred examples of $R^1$ are hydrogen atom, and hydroxyl group. It is preferable to choose these two as $R^1$, and it is also preferable to choose each of hydrogen atom and hydroxyl group.

Examples of $—X^1 \ldots X^2—$ include $—CH(R^2)—CH(R^3)—$, $—CH(R^2)—CH(R^3)—CH(R^4)—$, $—C(R^2)=C(R^3)—$, and $—C(R^2)=C(R^3)—CH(R^4)—$. As $—X^1 \ldots X^2—$, $—CH(R^2)—CH(R^3)—$, $—CH(R^2)—CH(R^3)—CH(R^4)—$, or $—C(R^2)=C(R^3)—$ is preferred, $—CH(R^2)—CH(R^3)—$, or $—C(R^2)=C(R^3)—$ is particularly preferred. $R^2$, $R^3$, and $R^4$ may be the same or different, and they are preferably represent hydrogen atom, or a lower alkyl group, more preferably hydrogen atom, or methyl group. It is particularly preferred that all of these substituents are hydrogen atoms, and it is also preferred that an arbitrary one of these substituents is methyl group, and all of the remaining substituents are hydrogen atoms. Preferred example of $—CH(R^2)—CH(R^3)—$ include $—CH_2—CH_2—$, $—CH(CH_3)—CH_2—$, and $—CH_2—CH(CH_3)—$, and preferred examples of $—C(R^2)=C(R^3)—$ include $—CH=CH—$, $—C(CH_3)=CH—$, and $—CH=C(CH_3)—$.

$A^1$, $A^{11}$, $A^2$, and $A^{21}$ may be the same or different, and they preferably represent hydrogen atom, or a lower alkyl group, more preferably hydrogen atom, or methyl group. It is particularly preferred that all of these substituents are hydrogen atoms, and it is also preferred that an arbitrary one of these substituents is methyl group, and all of the remaining substituents are hydrogen atoms.

Y represents $—CH(A^3)—$, $—CH(A^3)—C(A^4)(A^{41})—$, $—CH(A^3)—C(A^4)(A^{41})—C(A^5)(A^{51})—$, or a single bond, and as for $—CH(A^3)—C(A^4)(A^{41})—$, and $—CH(A^3)—C(A^4)(A^{41})—C(A^5)(A^{51})—$, $—CH(A^3)—$ binds to N (nitrogen atom) bonding to $X^2$. As Y, $—CH(A^3)—$, $—CH(A^3)—C(A^4)(A^{41})—$, or a single bond is preferred.

$A^3$ preferably represents hydrogen atom, or a lower alkyl group, and a more preferred example is hydrogen atom. $A^3$ is also preferably a lower alkyl group, and particularly preferred examples are methyl group, and ethyl group.

It is preferred that $A^4$ and $A^{41}$ independently represent hydrogen atom, or a lower alkyl group, and it is preferred that, for example, both of them represent hydrogen atom. It is also preferred that either one of $A^4$ and $A^{41}$ is hydrogen atom, and the other is a lower alkyl group. Further, it is also preferred that $A^4$ and $A^{41}$ are lower alkyl groups, which may be the same or different. Preferred examples of the lower alkyl group as $A^4$ or $A^{41}$ are methyl group, and ethyl group.

It is preferred that $A^5$ and $A^{51}$ independently represent hydrogen atom, or a lower alkyl group, and it is preferred that, for example, both of them are hydrogen atoms. It is also preferred that either one of $A^5$ and $A^{51}$ is hydrogen atom, and the other is a lower alkyl group. Further, it is also preferred that $A^5$ and $A^{51}$ are lower alkyl groups, which may be the same or different. Preferred examples of the lower alkyl group as $A^5$ or $A^{51}$ are methyl group, and ethyl group.

Z represents hydroxyl group, or $N(A^6)(A^{61})$. Z is preferably hydroxyl group. It is also preferred that Z is $N(A^6)(A^{61})$. In such a compound, $A^6$ is hydrogen atom or an alkyl group, preferably hydrogen atom, or a lower alkyl group, most preferably hydrogen atom, or methyl group. It is also preferred that, for example, $A^6$ represents either one of them, or a combination of two of them.

As $A^{61}$, hydrogen atom, an alkyl group, an aralkyl group, an alkyl group substituted with carboxyl group, an alkyl group substituted with cyano group, an alkyl group substituted with hydroxyl group, an alkyl group substituted with an alkoxyl group, an alkyl group substituted with an amino group, and an alkyl group substituted with aminocarbonyl group are preferred. Alternatively, $A^{61}$ is preferably an alkyl group of which end is substituted with $N(A^7)(—X^3—A^{71})$. $—X^3—$ represents carbonyl group. $A^7$ preferably represents hydrogen atom, or an alkyl group. $A^7$ is preferably hydrogen atom. Further, it is also preferred that $A^7$ is an alkyl group. Examples of this alkyl group include lower alkyl groups, and methyl group is especially preferred. $A^{71}$ preferably represents an alkyl group, an aralkyl group, or an aryl group. Among then, an alkyl group is preferred as $A^{71}$, and more preferred examples of this alkyl group include lower alkyl groups. More preferred examples include methyl group, ethyl group, propyl group, isopropyl group, and tert-butyl group, and $A^{71}$ is most preferably methyl group among these. Furthermore, it is also preferred that $A^7$ and $A^{71}$ combine together to form an alkylene group, or an alkylene group substituted with an alkyl group to form a ring together with N to which $A^7$ and $A^{71}$ bind and $—X^3—$. When $A^7$ and $A^{71}$ combine together to become an alkylene group substituted with an alkyl group to form a ring, the alkyl group is preferably a lower alkyl group. Examples of the lower alkyl group include methyl group and ethyl group, and a more preferred example is methyl group. Further, the ring formed by $A^7$ and $A^{71}$ is preferably a 4- to 7-membered ring, and preferred examples include, in particular, 4-, 5-, and 6-membered rings.

Preferred examples of $N(A^7)(—X^3—A^{71})$ mentioned above include acetylamino group, propionylamino group, butyrylamino group, isobutylylamino group, pivaloylamino group, (N-acetyl-N-methyl)amino group, (N-acetyl-N-ethyl)amino group, (N-propionyl-N-methyl)amino group, (N-propionyl-N-ethyl)amino group, (N-butyryl-N-methyl) amino group, (N-butyryl-N-ethyl)amino group, (N-isobutyryl-N-methyl)amino group, (N-isobutyryl-N-ethyl)amino group, (N-pivaloyl-N-methyl)amino group, and (N-pivaloyl-N-ethyl)amino group, and more preferred examples include, in particular, acetylamino group, and (N-acetyl-N-methyl)amino group. More preferred examples further include propionylamino group, and (N-propionyl-N-methyl)

amino group. More preferred examples still further include butyrylamino group, isobutyrylamino group, and pivaloylamino group. Furthermore, $N(A^7)(—X^3—A^{71})$ is also preferably 2-oxo-1-azetidyl group, 2-oxo-1-pyrrolidyl group, 2-oxo-1-piperidyl group, or 2-oxo-1-azepanyl group, and more preferred examples are, in particular, 2-oxo-1-azetidyl group, 2-oxo-1-pyrrolidyl group, and 2-oxo-1-piperidyl group. Further, examples of $A^{61}$ include hydrogen atom, a lower alkyl group, an aralkyl group, a lower alkyl group substituted with carboxyl group, a lower alkyl group substituted with aminocarbonyl group, a lower alkyl group substituted with cyano group, a lower alkyl group substituted with hydroxyl group, a lower alkyl group substituted with a lower alkoxyl group, and a lower alkyl group substituted with an amino group, and preferred examples include an alkyl group of which end is substituted with $N(A^7)(—X^3—A^{71})$.

$A^{61}$ is preferably hydrogen atom.

Further, $A^{61}$ is also preferably a lower alkyl group, and this lower alkyl group is most preferably methyl group, or ethyl group. It is also preferred that, for example, $A^6$ represents either one of them, or a combination of two of them.

$A^{61}$ is also preferably an aralkyl group. Examples of the aralkyl group herein referred to include benzyl group, and 2-phenylethyl group, and a particularly preferred example is benzyl group. These groups may be substituted with a lower alkyl group, or a halogen atom. Preferred examples of this lower alkyl group include methyl group, and ethyl group, and examples of the halogen atom include fluorine atom, chlorine atom, and bromine atom. As for the number of these substituents, the lower alkyl group and the halogen atom, the aryl ring preferably has one or two of these substituents. When the aryl ring is substituted with two or more substituents, these substituents are independently chosen, and either a halogen atom, or a lower alkyl group may be chosen.

As $A^{61}$, a lower alkyl group substituted with carboxyl group is also preferred. In this compound, the lower alkyl group may be substituted with one or more carboxyl groups, and a lower alkyl group substituted with one of carboxyl group is usually preferred. Preferred examples include carboxymethyl group, 2-carboxyethyl group, 3-carboxypropyl group, and 4-carboxybutyl group. In particular, carboxymethyl group and 2-carboxyethyl group are preferred. Preferred examples also include either one of or a combination of any two of the aforementioned groups.

As $A^{61}$, a lower alkyl group substituted with cyano group is also preferred. In this compound, the lower alkyl group may be substituted with one or more cyano groups. A lower alkyl group substituted with one of cyano group is generally preferred, and preferred examples include cyanomethyl group, 2-cyanoethyl group, 3-cyanopropyl group, and 4-cyanobutyl group.

As $A^{61}$, a lower alkyl group substituted with hydroxyl group is also preferred. In this compound, the lower alkyl group may be substituted with one or more hydroxyl groups. A lower alkyl group substituted with one of hydroxyl group is generally preferred, and preferred examples include 2-hydroxyethyl group, 3-hydroxypropyl group, and 4-hydroxybutyl group. In particular, 2-hydroxyethyl group, and 3-hydroxypropyl group are preferred. Preferred examples also include either one of or a combination of any two of these groups.

As $A^{61}$, a lower alkyl group substituted with a lower alkoxyl group is also preferred. The lower alkoxyl group include linear or branched alkoxyl groups having 1 to 4 carbon atoms, and specific examples include, for example, methoxy group, ethoxy group, propoxy group, isopropoxy group, and the like. Methoxy group and ethoxy group are preferred. The lower alkyl group may be substituted with one or more lower alkoxyl groups. A lower alkyl group substituted with one of lower alkoxyl group is generally preferred, and preferred examples include 2-methoxyethyl group, 3-methoxypropyl group, 2-ethoxyethyl group, 3-ethoxypropyl group, and 4-methoxybutyl group. In particular, 2-methoxyethyl group and 3-methoxypropyl group are preferred. Preferred examples also include either one of or a combination of any two of these groups.

As $A^{61}$, a lower alkyl group substituted with an amino group is also preferred. The amino group includes a monoalkyl amino group having one of lower alkyl group as a substituent, and a dialkylamino group having two of lower alkyl group as substituents. As for the dialkylamino group, the alkyl groups may be the same or different. Although the lower alkyl group may be substituted with one or more amino groups, a lower alkyl group substituted with one of amino group is usually preferred, and preferred examples include, for example, 2-aminoethyl group, 2-(methylamino) ethyl group, 2-(dimethylamino)ethyl group, 3-aminopropyl group, 3-(methylamino)propyl group, 3-(dimethylamino) propyl group, 4-aminobutyl group, 4-(methylamino)butyl group, and 4-(dimethylamino)butyl. In particular, 2-aminoethyl group, 2-(methylamino)ethyl group, 2-(dimethylamino)ethyl group, 3-aminopropyl group, 3-(methylamino) propyl group, and 3-(dimethylamino)propyl group are preferred.

As $A^{61}$, a lower alkyl group substituted with aminocarbonyl group is also preferred. The lower alkyl group may be substituted with one or more aminocarbonyl groups. A lower alkyl group substituted with one of aminocarbonyl group is generally preferred, and preferred examples include, for example, aminocarbonylmethyl group and aminocarbonylethyl group. Preferred examples also include either one of or a combination of any two of these groups.

Further, as $A^{61}$, a lower alkyl group of which end is substituted with $N(A^7)(—X^3—A^{71})$ is also preferred. $—X^3—$, $A^{71}$, and $A^7$ have the same meanings as defined above. As for substitution with $N(A^7)(—X^3—A^{71})$, $A^{61}$ may be substituted with one or more $N(A^7)(—X^3—A^{71})$. $A^{61}$ substituted with one of $N(A^7)(—X^3—A^{71})$ is usually preferred. Examples of the "alkyl group of which end is substituted with $N(A^7)(—X^3—A^{71})$" include, for example, 2-(acetylamino)ethyl group, 2-(propionylamino)ethyl group, 2-(butyrylamino)ethyl group, 2-(isobutyrylamino) ethyl group, 2-(pivaloylamino)ethyl group, 2-[(N-acetyl-N-methyl)amino]ethyl group, 2-[(N-acetyl-N-ethyl)amino] ethyl group, 2-[(N-propionyl-N-methyl)amino]ethyl group, 2-[(N-propionyl-N-ethyl)amino]ethyl group, 2-[(N-butyryl-N-methyl)amino]ethyl group, 2-[(N-butyryl-N-ethyl)amino] ethyl group, 2-[(N-isobutyryl-N-methyl)amino]ethyl group, 2-[(N-isobutyryl-N-ethyl)amino]ethyl group, 2-[(N-pivaloyl-N-methyl)amino]ethyl group, 2-[(N-pivaloyl-N-ethyl) amino]ethyl group, 3-(acetylamino)propyl group, 3-(propionylamino)propyl group, 3-(butyrylamino) propyl group, 3-(isobutyrylamino)propyl group, 3-(pivaloylamino)propyl group, 3-[(N-acetyl-N-methyl)amino]propyl group, 3-[(N-acetyl-N-ethyl)amino]propyl group, 3-[(N-propionyl-N-methyl)amino]propyl group, 3-[(N-propionyl-N-ethyl)amino] propyl group, 3-[(N-butyryl-N-methyl)amino]propyl group, 3-[(N-butyryl-N-ethyl)amino]propyl group, 3-[(N-isobutyryl-N-methyl)amino]propyl group, 3-[(N-isobutyryl-N-ethyl)amino]propyl group, 3-[(N-pivaloyl-N-methyl)amino] propyl group, and 3-[(N-pivaloyl-N-ethyl)amino]propyl group, and preferred examples include, in particular, 2-(acetylamino)ethyl group, 3-(acetylamino)propyl group, 2-[(N-acetyl-N-methyl)amino]ethyl group, and 3-[(N-acetyl-N-methyl)amino]propyl group. Further, specific examples of the "alkyl group of which end is substituted with $N(A^7)(-X^3-A^{71})$" where $A^7$ and $A^{71}$ combine together to become an alkylene group, or an alkylene group substituted with an alkyl group to form a ring include 2-(2-oxo-1-azetidyl)ethyl group, 2-(2-oxo-1-pyrrolidyl)ethyl group, 2-(2-oxo-1-piperidyl)ethyl group, 2-(2-oxo-1-azepanyl)ethyl group, 3-(2-oxo-1-azetidyl)propyl group, 3-(2-oxo-1-pyrrolidyl)propyl group, 3-(2-oxo-1-piperidyl)propyl group, and 3-(2-oxo-1-azepanyl)propyl, and preferred examples include, in particular, 2-(2-oxo-1-azetidyl)ethyl group, 2-(2-oxo-1-pyrrolidyl)ethyl group, 2-(2-oxo-1-piperidyl)ethyl group, 3-(2-oxo-1-azetidyl)propyl group, 3-(2-oxo-1-pyrrolidyl)propyl group, and 3-(2-oxo-1-piperidyl)propyl group.

In the present invention, groups in each of one or more combinations selected from the group consisting of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ may bind to each other to form a 5- or 6-membered ring, and a 6-membered ring is particularly preferred. In this compound, it is particularly preferred that one 5- or 6-membered ring is formed with one of the aforementioned combinations. The ring is preferably consists of carbon atoms except for the N atom to which $A^3$ binds. When a ring is formed with $A^6$ and $A^1$, $A^6$ and $A^2$, or $A^6$ and $A^3$, or a ring is formed with $A^2$ and $A^3$, $A^{11}$ and $A^{21}$ are preferably hydrogen atoms, and the ring is most preferably a saturated ring.

Further, when Y is a single bond, and Z is $-N(A^6)(A^{61})$, it is preferred that, for example, the groups of $A^6$ and $A^1$ bind to each other to form a 5- or 6-membered ring.

Moreover, when Y is $-CH(A^3)-$, and Z is $-N(A^6)(A^{61})$, it is preferred that, for example, the groups of $A^6$ and $A^3$ bind to each other to form a 6-membered ring.

Furthermore, when Y is $-CH(A^3)-C(A^4)(A^{41})$, and Z is $-N(A^6)(A^{61})$, it is preferred that, for example, the groups of $A^2$ and $A^3$ bind to each other to form a 6-membered ring.

Specifically, examples of the structure represented by the formula (2):

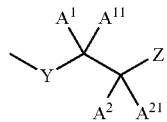

(2)

[the bond on the left of Y binds to N (nitrogen atom) bonding to $X^2$], which is a partial structure in the formula (1), wherein a ring is formed with the aforementioned combinations, include the followings structures containing a 5- or 6-membered ring, i.e., groups represented by the formula, (2-1), formula (2-2), formula (2-3), formula (2-4-t), formula (2-4-c), formula (2-5-t), formula (2-5-c), formula (2-6-t), and formula (2-6-c):

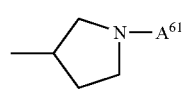

(2-1)

(2-2)

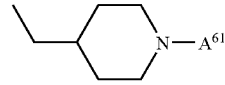

(2-3)

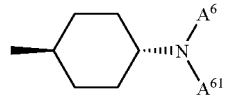

(2-4-t)

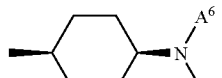

(2-4-c)

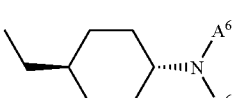

(2-5-t)

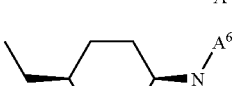

(2-5-c)

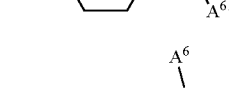

(2-6-t)

(2-6-c)

wherein $A^6$ represents hydrogen atom, or an alkyl group, $A^{61}$ represents hydrogen atom, an alkyl group, an aralkyl group, an alkyl group substituted with carboxyl group, an alkyl group substituted with aminocarbonyl group, an alkyl group substituted with cyano group, an alkyl group substituted with hydroxyl group, an alkyl group substituted with an alkoxyl group, an alkyl group substituted with an amino group, or an alkyl group of which end is substituted with $N(A^7)(-X^3-A^{71})$, and the leftmost single bond in each group binds to N (nitrogen atom) bonding to $X^2$ in the formula (1). In the groups of these formulas, the bonds in the cyclohexane ring are in the trans-conformation in the groups represented by the formula (2-4-t), formula (2-5-t), and formula (2-6-t), or cis-conformation in the groups represented by the formula (2-4-c), formula (2-5-c), and formula (2-6-c).

Among them, the groups represented by the formula (2-1), formula (2-2), formula (2-4-t), and formula (2-4-c) are preferred, and the groups represented by the formula (2-1), formula (2-2), and formula (2-4-t) are particularly preferred. Preferred examples also include either one of or a combination of any two of these groups. Preferred examples of $A^6$ and $A^{61}$ are as mentioned above.

Preferred examples of the compounds represented by the formula (1) are mentioned below.

Compounds wherein $R^1$ is hydrogen atom, chlorine atom, or hydroxyl group, and $X^1 \ldots X^2$ is ethylene group, or 1,3-propylene group;

compounds wherein $R^1$ is hydrogen atom, or hydroxyl group, and $X^1 \ldots X^2$ is ethylene group, or 1,3-propylene group;

compounds wherein $R^1$ is hydrogen atom, and $X^1 \ldots X^2$ is ethylene group, or 1,3-propylene group;

compounds wherein $R^1$ is hydroxyl group, and $X^1 \ldots X^2$ is ethylene group, or 1,3-propylene group;

compounds wherein $R^1$ is hydrogen atom, chlorine atom, or hydroxyl group, and $X^1 \ldots X^2$ is ethylene group;

compounds wherein $R^1$ is hydrogen atom, or hydroxyl group, and $X^1 \ldots X^2$ is ethylene group;

compounds wherein $R^1$ is hydrogen atom, and $X^1 \ldots X^2$ is ethylene group;

compounds wherein $R^1$ is hydroxyl group, and $X^1 \ldots X^2$ is ethylene group;

compounds wherein $R^1$ is hydrogen atom, chlorine atom, or hydroxyl group, $X^1 \ldots X^2$ is ethylene group, or 1,3-propylene group, and $A^6$ is hydrogen atom, or a lower alkyl group;

compounds wherein $R^1$ is hydrogen atom, or hydroxyl group, $X^1 \ldots X^2$ is ethylene group, or 1,3-propylene group, $A^6$ is hydrogen atom, or a lower alkyl group;

compounds wherein $R^1$ is hydrogen atom, $X^1 \ldots X^2$ is ethylene group, or 1,3-propylene group, and $A^6$ is hydrogen atom, or a lower alkyl group;

compounds wherein $R^1$ is hydroxyl group, $X^1 \ldots X^2$ is ethylene group, or 1,3-propylene group, and $A^6$ is hydrogen atom, or a lower alkyl group;

compounds wherein $R^1$ is hydrogen atom, chlorine atom, or hydroxyl group, $X^1 \ldots X^2$ is ethylene group, and $A^6$ is hydrogen atom, or a lower alkyl group;

compounds wherein $R^1$ is hydrogen atom, or hydroxyl group, $X^1 \ldots X^2$ is ethylene group, and $A^6$ is hydrogen atom, or a lower alkyl group;

compounds wherein $R^1$ is hydrogen atom, $X^1 \ldots X^2$ is ethylene group, and $A^6$ is hydrogen atom, or a lower alkyl group;

compounds wherein $R^1$ is hydroxyl group, $X^1 \ldots X^2$ is ethylene group, and $A^6$ is hydrogen atom, or a lower alkyl group;

compounds wherein $R^1$ is hydrogen atom, chlorine atom, or hydroxyl group, $X^1 \ldots X^2$ is ethylene group, or 1,3-propylene group, and $A^6$ is hydrogen atom;

compounds wherein $R^1$ is hydrogen atom, or hydroxyl group, $X^1 \ldots X^2$ is ethylene group, or 1,3-propylene group, and $A^6$ is hydrogen atom;

compounds wherein $R^1$ is hydrogen atom, $X^1 \ldots X^2$ is ethylene group, or 1,3-propylene group, and $A^6$ is hydrogen atom;

compounds wherein $R^1$ is hydroxyl group, $X^1 \ldots X^2$ is ethylene group, or 1,3-propylene group, and $A^6$ is hydrogen atom;

compounds wherein $R^1$ is hydrogen atom, chlorine atom, or hydroxyl group, $X^1 \ldots X^2$ is ethylene group, and $A^6$ is hydrogen atom;

compounds wherein $R^1$ is hydrogen atom, or hydroxyl group, $X^1 \ldots X^2$ is ethylene group, and $A^6$ is hydrogen atom;

compounds wherein $R^1$ is hydrogen atom, $X^1 \ldots X^2$ is ethylene group, and $A^6$ is hydrogen atom;

compounds wherein $R^1$ is hydroxyl group, $X^1 \ldots X^2$ is ethylene group, and $A^6$ is hydrogen atom;

compounds wherein $R^1$ is hydrogen atom, chlorine atom, or hydroxyl group, $X^1 \ldots X^2$ is ethylene group, or 1,3-propylene group, $A^6$ is hydrogen atom, and $A^{61}$ is hydrogen atom;

compounds wherein $R^1$ is hydrogen atom, or hydroxyl group, $X^1 \ldots X^2$ is ethylene group, or 1,3-propylene group, $A^6$ is hydrogen atom, and $A^{61}$ is hydrogen atom;

compounds wherein $R^1$ is hydrogen atom, $X^1 \ldots X^2$ is ethylene group, or 1,3-propylene group, $A^6$ is hydrogen atom, and $A^{61}$ is hydrogen atom;

compounds wherein $R^1$ is hydroxyl group, $X^1 \ldots X^2$ is ethylene group, or 1,3-propylene group, $A^6$ is hydrogen atom, and $A^{61}$ is hydrogen atom;

compounds wherein $R^1$ is hydrogen atom, chlorine atom, or hydroxyl group, $X^1 \ldots X^2$ is ethylene group, $A^6$ is hydrogen atom, and $A^{61}$ is hydrogen atom;

compounds wherein $R^1$ is hydrogen atom, or hydroxyl group, $X^1 \ldots X^2$ is ethylene group, $A^6$ is hydrogen atom, and $A^{61}$ is hydrogen atom;

compounds wherein $R^1$ is hydrogen atom, $X^1 \ldots X^2$ is ethylene group, $A^6$ is hydrogen atom, and $A^{61}$ is hydrogen atom;

compounds wherein $R^1$ is hydroxyl group, $X^1 \ldots X^2$ is ethylene group, $A^6$ is hydrogen atom, and $A^{61}$ is hydrogen atom;

compounds wherein $R^1$ is hydrogen atom, chlorine atom, or hydroxyl group, $X^1 \ldots X^2$ is ethylene group, or 1,3-propylene group, $A^6$ is hydrogen atom, and $A^{61}$ is a lower alkyl group;

compounds wherein $R^1$ is hydrogen atom, or hydroxyl group, $X^1 \ldots X^2$ is ethylene group, or 1,3-propylene group, $A^6$ is hydrogen atom, and $A^{61}$ is a lower alkyl group;

compounds wherein $R^1$ is hydrogen atom, $X^1 \ldots X^2$ is ethylene group, or 1,3-propylene group, $A^6$ is hydrogen atom, and $A^{61}$ is a lower alkyl group;

compounds wherein $R^1$ is hydroxyl group, $X^1 \ldots X^2$ is ethylene group, or 1,3-propylene group, $A^6$ is hydrogen atom, and $A^{61}$ is a lower alkyl group;

compounds wherein $R^1$ is hydrogen atom, chlorine atom, or hydroxyl group, $X^1 \ldots X^2$ is ethylene group, $A^6$ is hydrogen atom, and $A^{61}$ is a lower alkyl group;

compounds wherein $R^1$ is hydrogen atom, or hydroxyl group, $X^1 \ldots X^2$ is ethylene group, $A^6$ is hydrogen atom, and $A^{61}$ is a lower alkyl group;

compounds wherein $R^1$ is hydrogen atom, $X^1 \ldots X^2$ is ethylene group, $A^6$ is hydrogen atom, and $A^{61}$ is a lower alkyl group;

compounds wherein $R^1$ is hydroxyl group, $X^1 \ldots X^2$ is ethylene group, $A^6$ is hydrogen atom, and $A^{61}$ is a lower alkyl group;

compounds wherein $R^1$ is hydrogen atom, chlorine atom, or hydroxyl group, $X^1 \ldots X^2$ is ethylene group, or 1,3-propylene group, $A^6$ is hydrogen atom, and $A^{61}$ is an aralkyl group;

compounds wherein $R^1$ is hydrogen atom, or hydroxyl group, $X^1 \ldots X^2$ is ethylene group, or 1,3-propylene group, $A^6$ is hydrogen atom, and $A^{61}$ is an aralkyl group;

compounds wherein $R^1$ is hydrogen atom, $X^1 \ldots X^2$ is ethylene group, or 1,3-propylene group, $A^6$ is hydrogen atom, and $A^{61}$ is an aralkyl group;

compounds wherein $R^1$ is hydroxyl group, $X^1 \ldots X^2$ is ethylene group, or 1,3-propylene group, $A^6$ is hydrogen atom, and $A^{61}$ is an aralkyl group;

compounds wherein $R^1$ is hydrogen atom, chlorine atom, or hydroxyl group, $X^1 \ldots X^2$ is ethylene group, $A^6$ is hydrogen atom, and $A^{61}$ is an aralkyl group;

compounds wherein $R^1$ is hydrogen atom, or hydroxyl group, $X^1 \ldots X^2$ is ethylene group, $A^6$ is hydrogen atom, and $A^{61}$ is an aralkyl group;

compounds wherein $R^1$ is hydrogen atom, $X^1 \ldots X^2$ is ethylene group, $A^6$ is hydrogen atom, and $A^{61}$ is an aralkyl group;

compounds wherein $R^1$ is hydroxyl group, $X^1 \ldots X^2$ is ethylene group, $A^6$ is hydrogen atom, and $A^{61}$ is an aralkyl group;

compounds wherein $R^1$ is hydrogen atom, chlorine atom, or hydroxyl group, $X^1 \ldots X^2$ is ethylene group, or 1,3-propylene group, $A^6$ is hydrogen atom, and $A^{61}$ is a lower alkyl group substituted with carboxyl group;

compounds wherein $R^1$ is hydrogen atom, or hydroxyl group, $X^1 \ldots X^2$ is ethylene group, or 1,3-propylene group, $A^6$ is hydrogen atom, and $A^{61}$ is a lower alkyl group substituted with carboxyl group;

compounds wherein $R^1$ is hydrogen atom, $X^1 \ldots X^2$ is ethylene group, or 1,3-propylene group, $A^6$ is hydrogen atom, and $A^{61}$ is a lower alkyl group substituted with carboxyl group;

compounds wherein $R^1$ is hydroxyl group, $X^1 \ldots X^2$ is ethylene group, or 1,3-propylene group, $A^6$ is hydrogen atom, and $A^{61}$ is a lower alkyl group substituted with carboxyl group;

compounds wherein $R^1$ is hydrogen atom, chlorine atom, or hydroxyl group, $X^1 \ldots X^2$ is ethylene group, $A^6$ is hydrogen atom, and $A^{61}$ is a lower alkyl group substituted with carboxyl group;

compounds wherein $R^1$ is hydrogen atom, or hydroxyl group, $X^1 \ldots X^2$ is ethylene group, $A^6$ is hydrogen atom, and $A^{61}$ is a lower alkyl group substituted with carboxyl group;

compounds wherein $R^1$ is hydrogen atom, $X^1 \ldots X^2$ is ethylene group, $A^6$ is hydrogen atom, and $A^{61}$ is a lower alkyl group substituted with carboxyl group;

compounds wherein $R^1$ is hydroxyl group, $X^1 \ldots X^2$ is ethylene group, $A^6$ is hydrogen atom, and $A^{61}$ is a lower alkyl group substituted with carboxyl group;

compounds wherein $R^1$ is hydrogen atom, chlorine atom, or hydroxyl group, $X^1 \ldots X^2$ is ethylene group, or 1,3-propylene group, $A^6$ is hydrogen atom, and $A^{61}$ is a lower alkyl group substituted with cyano group;

compounds wherein $R^1$ is hydrogen atom, or hydroxyl group, $X^1 \ldots X^2$ is ethylene group, or 1,3-propylene group, $A^6$ is hydrogen atom, and $A^{61}$ is a lower alkyl group substituted with cyano group;

compounds wherein $R^1$ is hydrogen atom, $X^1 \ldots X^2$ is ethylene group, or 1,3-propylene group, $A^6$ is hydrogen atom, and $A^{61}$ is a lower alkyl group substituted with cyano group;

compounds wherein $R^1$ is hydroxyl group, $X^1 \ldots X^2$ is ethylene group, or 1,3-propylene group, $A^6$ is hydrogen atom, and $A^{61}$ is a lower alkyl group substituted with cyano group;

compounds wherein $R^1$ is hydrogen atom, chlorine atom, or hydroxyl group, $X^1 \ldots X^2$ is ethylene group, $A^6$ is hydrogen atom, and $A^{61}$ is a lower alkyl group substituted with cyano group;

compounds wherein $R^1$ is hydrogen atom, or hydroxyl group, $X^1 \ldots X^2$ is ethylene group, $A^6$ is hydrogen atom, and $A^{61}$ is a lower alkyl group substituted with cyano group;

compounds wherein $R^1$ is hydrogen atom, $X^1 \ldots X^2$ is ethylene group, $A^6$ is hydrogen atom, and $A^{61}$ is a lower alkyl group substituted with cyano group;

compounds wherein $R^1$ is hydroxyl group, $X^1 \ldots X^2$ is ethylene group, $A^6$ is hydrogen atom, and $A^{61}$ is a lower alkyl group substituted with cyano group;

compounds wherein $R^1$ is hydrogen atom, chlorine atom, or hydroxyl group, $X^1 \ldots X^2$ is ethylene group, or 1,3-propylene group, $A^6$ is hydrogen atom, and $A^{61}$ is a lower alkyl group substituted with hydroxyl group;

compounds wherein $R^1$ is hydrogen atom, or hydroxyl group, $X^1 \ldots X^2$ is ethylene group, or 1,3-propylene group, $A^6$ is hydrogen atom, and $A^{61}$ is a lower alkyl group substituted with hydroxyl group;

compounds wherein $R^1$ is hydrogen atom, $X^1 \ldots X^2$ is ethylene group, or 1,3-propylene group, $A^6$ is hydrogen atom, and $A^{61}$ is a lower alkyl group substituted with hydroxyl group;

compounds wherein $R^1$ is hydroxyl group, $X^1 \ldots X^2$ is ethylene group, or 1,3-propylene group, $A^6$ is hydrogen atom, and $A^{61}$ is a lower alkyl group substituted with hydroxyl group;

compounds wherein $R^1$ is hydrogen atom, chlorine atom, or hydroxyl group, $X^1 \ldots X^2$ is ethylene group, $A^6$ is hydrogen atom, and $A^{61}$ is a lower alkyl group substituted with hydroxyl group;

compounds wherein $R^1$ is hydrogen atom, or hydroxyl group, $X^1 \ldots X^2$ is ethylene group, $A^6$ is hydrogen atom, and $A^{61}$ is a lower alkyl group substituted with hydroxyl group;

compounds wherein $R^1$ is hydrogen atom, $X^1 \ldots X^2$ is ethylene group, $A^6$ is hydrogen atom, and $A^{61}$ is a lower alkyl group substituted with hydroxyl group;

compounds wherein $R^1$ is hydroxyl group, $X^1 \ldots X^2$ is ethylene group, $A^6$ is hydrogen atom, and $A^{61}$ is a lower alkyl group substituted with hydroxyl group;

compounds wherein $R^1$ is hydrogen atom, chlorine atom, or hydroxyl group, $X^1 \ldots X^2$ is ethylene group, or 1,3-propylene group, $A^6$ is hydrogen atom, and $A^{61}$ is a lower alkyl group substituted with a lower alkoxyl group;

compounds wherein $R^1$ is hydrogen atom, or hydroxyl group, $X^1 \ldots X^2$ is ethylene group, or 1,3-propylene group, $A^6$ is hydrogen atom, and $A^{61}$ is a lower alkyl group substituted with a lower alkoxyl group;

compounds wherein $R^1$ is hydrogen atom, $X^1 \ldots X^2$ is ethylene group, or 1,3-propylene group, $A^6$ is hydrogen atom, and $A^{61}$ is a lower alkyl group substituted with a lower alkoxyl group;

compounds wherein $R^1$ is hydroxyl group, $X^1 \ldots X^2$ is ethylene group, or 1,3-propylene group, $A^6$ is hydrogen atom, and $A^{61}$ is a lower alkyl group substituted with a lower alkoxyl group;

compounds wherein $R^1$ is hydrogen atom, chlorine atom, or hydroxyl group, $X^1 \ldots X^2$ is ethylene group, $A^6$ is hydrogen atom, and $A^{61}$ is a lower alkyl group substituted with a lower alkoxyl group;

compounds wherein $R^1$ is hydrogen atom, or hydroxyl group, $X^1 \ldots X^2$ is ethylene group, $A^6$ is hydrogen atom, and $A^{61}$ is a lower alkyl group substituted with a lower alkoxyl group;

compounds wherein $R^1$ is hydrogen atom, $X^1 \ldots X^2$ is ethylene group, $A^6$ is hydrogen atom, and $A^{61}$ is a lower alkyl group substituted with a lower alkoxyl group;

compounds wherein $R^1$ is hydroxyl group, $X^1 \ldots X^2$ is ethylene group, $A^6$ is hydrogen atom, and $A^{61}$ is a lower alkyl group substituted with a lower alkoxyl group;

compounds wherein $R^1$ is hydrogen atom, chlorine atom, or hydroxyl group, $X^1 \ldots X^2$ is ethylene group, or 1,3-propylene group, $A^6$ is hydrogen atom, and $A^{61}$ is a lower alkyl group substituted with an amino group;

compounds wherein $R^1$ is hydrogen atom, or hydroxyl group, $X^1 \ldots X^2$ is ethylene group, or 1,3-propylene group, $A^6$ is hydrogen atom, and $A^{61}$ is a lower alkyl group substituted with an amino group;

compounds wherein $R^1$ is hydrogen atom, $X^1 \ldots X^2$ is ethylene group, or 1,3-propylene group, $A^6$ is hydrogen atom, and $A^{61}$ is a lower alkyl group substituted with an amino group;

compounds wherein $R^1$ is hydroxyl group, $X^1 \ldots X^2$ is ethylene group, or 1,3-propylene group, $A^6$ is hydrogen atom, and $A^{61}$ is a lower alkyl group substituted with an amino group;

compounds wherein $R^1$ is hydrogen atom, chlorine atom, or hydroxyl group, $X^1 \ldots X^2$ is ethylene group, $A^6$ is hydrogen atom, and $A^{61}$ is a lower alkyl group substituted with an amino group;

compounds wherein $R^1$ is hydrogen atom, or hydroxyl group, $X^1 \ldots X^2$ is ethylene group, $A^6$ is hydrogen atom, and $A^{61}$ is a lower alkyl group substituted with an amino group;

compounds wherein $R^1$ is hydrogen atom, $X^1 \ldots X^2$ is ethylene group, $A^6$ is hydrogen atom, and $A^{61}$ is a lower alkyl group substituted with an amino group;

compounds wherein $R^1$ is hydroxyl group, $X^1 \ldots X^2$ is ethylene group, $A^6$ is hydrogen atom, and $A^{61}$ is a lower alkyl group substituted with an amino group;

compounds wherein $R^1$ is hydrogen atom, chlorine atom, or hydroxyl group, $X^1 \ldots X^2$ is ethylene group, or 1,3-propylene group, $A^6$ is hydrogen atom, and $A^{61}$ is a lower alkyl group of which end is substituted with $N(A^7)(-X^3-A^{71})$;

compounds wherein $R^1$ is hydrogen atom, or hydroxyl group, $X^1 \ldots X^2$ is ethylene group, or 1,3-propylene group, $A^6$ is hydrogen atom, and $A^{61}$ is a lower alkyl group of which end is substituted with $N(A^7)(-X^3-A^{71})$;

compounds wherein $R^1$ is hydrogen atom, $X^1 \ldots X^2$ is ethylene group, or 1,3-propylene group, $A^6$ is hydrogen atom, and $A^{61}$ is a lower alkyl group of which end is substituted with $N(A^7)(-X^3-A^{71})$;

compounds wherein $R^1$ is hydroxyl group, $X^1 \ldots X^2$ is ethylene group, or 1,3-propylene group, $A^6$ is hydrogen atom, and $A^{61}$ is a lower alkyl group of which end is substituted with $N(A^7)(-X^3-A^{71})$;

compounds wherein $R^1$ is hydrogen atom, chlorine atom, or hydroxyl group, $X^1 \ldots X^2$ is ethylene group, $A^6$ is hydrogen atom, and $A^{61}$ is a lower alkyl group of which end is substituted with $N(A^7)(-X^3-A^{71})$;

compounds wherein $R^1$ is hydrogen atom, or hydroxyl group, $X^1 \ldots X^2$ is ethylene group, $A^6$ is hydrogen atom, and $A^{61}$ is a lower alkyl group of which end is substituted with $N(A^7)(-X^3-A^{71})$;

compounds wherein $R^1$ is hydrogen atom, $X^1 \ldots X^2$ is ethylene group, $A^6$ is hydrogen atom, and $A^{61}$ is a lower alkyl group of which end is substituted with $N(A^7)(-X^3-A^{71})$;

compounds wherein $R^1$ is hydroxyl group, $X^1 \ldots X^2$ is ethylene group, $A^6$ is hydrogen atom, and $A^{61}$ is a lower alkyl group of which end is substituted with $N(A^7)(-X^3-A^{71})$;

compounds wherein $R^1$ is hydrogen atom, chlorine atom, or hydroxyl group, $X^1 \ldots X^2$ is ethylene group, or 1,3-propylene group, $A^6$ is hydrogen atom, and $A^{61}$ is a lower alkyl group substituted with a lower alkylcarbonylamino group;

compounds wherein $R^1$ is hydrogen atom, or hydroxyl group, $X^1 \ldots X^2$ is ethylene group, or 1,3-propylene group, $A^6$ is hydrogen atom, and $A^{61}$ is a lower alkyl group substituted with a lower alkylcarbonylamino group;

compounds wherein $R^1$ is hydrogen atom, $X^1 \ldots X^2$ is ethylene group, or 1,3-propylene group, $A^6$ is hydrogen atom, and $A^{61}$ is a lower alkyl group substituted with a lower alkylcarbonylamino group;

compounds wherein $R^1$ is hydroxyl group, $X^1 \ldots X^2$ is ethylene group, or 1,3-propylene group, $A^6$ is hydrogen atom, and $A^{61}$ is a lower alkyl group substituted with a lower alkylcarbonylamino group;

compounds wherein $R^1$ is hydrogen atom, chlorine atom, or hydroxyl group, $X^1 \ldots X^2$ is ethylene group, $A^6$ is hydrogen atom, and $A^{61}$ is a lower alkyl group substituted with a lower alkylcarbonylamino group;

compounds wherein $R^1$ is hydrogen atom, or hydroxyl group, $X^1 \ldots X^2$ is ethylene group, $A^6$ is hydrogen atom, and $A^{61}$ is a lower alkyl group substituted with a lower alkylcarbonylamino group;

compounds wherein $R^1$ is hydrogen atom, $X^1 \ldots X^2$ is ethylene group, $A^6$ is hydrogen atom, and $A^{61}$ is a lower alkyl group substituted with a lower alkylcarbonylamino group;

compounds wherein $R^1$ is hydroxyl group, $X^1 \ldots X^2$ is ethylene group, $A^6$ is hydrogen atom, and $A^{61}$ is a lower alkyl group substituted with a lower alkylcarbonylamino group;

compounds wherein $R^1$ is hydrogen atom, chlorine atom, or hydroxyl group, $X^1 \ldots X^2$ is ethylene group, or 1,3-propylene group, $A^6$ is hydrogen atom, and $A^{61}$ is a lower alkyl group substituted with aminocarbonyl group;

compounds wherein $R^1$ is hydrogen atom, or hydroxyl group, $X^1 \ldots X^2$ is ethylene group, or 1,3-propylene group, $A^6$ is hydrogen atom, and $A^{61}$ is a lower alkyl group substituted with aminocarbonyl group;

compounds wherein $R^1$ is hydrogen atom, $X^1 \ldots X^2$ is ethylene group, or 1,3-propylene group, $A^6$ is hydrogen atom, and $A^{61}$ is a lower alkyl group substituted with aminocarbonyl group;

compounds wherein $R^1$ is hydroxyl group, $X^1 \ldots X^2$ is ethylene group, or 1,3-propylene group, $A^6$ is hydrogen atom, and $A^{61}$ is a lower alkyl group substituted with aminocarbonyl group;

compounds wherein $R^1$ is hydrogen atom, chlorine atom, or hydroxyl group, $X^1 \ldots X^2$ is ethylene group, $A^6$ is hydrogen atom, and $A^{61}$ is a lower alkyl group substituted with aminocarbonyl group;

compounds wherein $R^1$ is hydrogen atom, or hydroxyl group, $X^1 \ldots X^2$ is ethylene group, $A^6$ is hydrogen atom, and $A^{61}$ is a lower alkyl group substituted with aminocarbonyl group;

compounds wherein $R^1$ is hydrogen atom, $X^1 \ldots X^2$ is ethylene group, $A^6$ is hydrogen atom, and $A^{61}$ is a lower alkyl group substituted with aminocarbonyl group;

compounds wherein $R^1$ is hydroxyl group, $X^1 \ldots X^2$ is ethylene group, $A^6$ is hydrogen atom, and $A^{61}$ is a lower alkyl group substituted with aminocarbonyl group;

compounds wherein $R^1$ is hydrogen atom, chlorine atom, or hydroxyl group, $X^1 \ldots X^2$ is 1,3-propylene group, and Y is $-CH(A^3)-$;

compounds wherein $R^1$ is hydrogen atom, or hydroxyl group, $X^1 \ldots X^2$ is 1,3-propylene group, and Y is $-CH(A^3)-$;

compounds wherein $R^1$ is hydrogen atom, $X^1 \ldots X^2$ is 1,3-propylene group, and Y is $-CH(A^3)-$;

compounds wherein $R^1$ is hydroxyl group, $X^1 \ldots X^2$ is 1,3-propylene group, and Y is $-CH(A^3)-$;

compounds wherein $R^1$ is hydrogen atom, chlorine atom, or hydroxyl group, $X^1 \ldots X^2$ is ethylene group, or 1,3-propylene group, and Y is $-CH(A^3)-$;

compounds wherein $R^1$ is hydrogen atom, or hydroxyl group, $X^1 \ldots X^2$ is ethylene group, or 1,3-propylene group, and Y is $-CH(A^3)-$;

compounds wherein $R^1$ is hydrogen atom, $X^1 \ldots X^2$ is ethylene group, or 1,3-propylene group, and Y is —CH($A^3$)—;

compounds wherein $R^1$ is hydroxyl group, $X^1 \ldots X^2$ is ethylene group, or 1,3-propylene group, and Y is —CH($A^3$)—;

compounds wherein $R^1$ is hydrogen atom, chlorine atom, or hydroxyl group, $X^1 \ldots X^2$ is ethylene group, and Y is —CH($A^3$)—;

compounds wherein $R^1$ is hydrogen atom, or hydroxyl group, $X^1 \ldots X^2$ is ethylene group, and Y is —CH($A^3$)—;

compounds wherein $R^1$ is hydrogen atom, $X^1 \ldots X^2$ is ethylene group, and Y is —CH($A^3$)—;

compounds wherein $R^1$ is hydroxyl group, $X^1 \ldots X^2$ is ethylene group, and Y is —CH($A^3$)—;

compounds wherein $R^1$ is hydrogen atom, chlorine atom, or hydroxyl group, $X^1 \ldots X^2$ is 1,3-propylene group, and Y is —CH($A^3$)—;

compounds wherein $R^1$ is hydrogen atom, or hydroxyl group, $X^1 \ldots X^2$ is 1,3-propylene group, and Y is —CH($A^3$)—;

compounds wherein $R^1$ is hydrogen atom, $X^1 \ldots X^2$ is 1,3-propylene group, and Y is —CH($A^3$)—;

compounds wherein $R^1$ is hydroxyl group, $X^1 \ldots X^2$ is 1,3-propylene group, and Y is —CH($A^3$)—;

compounds wherein $R^1$ is hydrogen atom, chlorine atom, or hydroxyl group, $X^1 \ldots X^2$ is ethylene group, or 1,3-propylene group, and Y is methylene group;

compounds wherein $R^1$ is hydrogen atom, or hydroxyl group, $X^1 \ldots X^2$ is ethylene group, or 1,3-propylene group, and Y is methylene group;

compounds wherein $R^1$ is hydrogen atom, $X^1 \ldots X^2$ is ethylene group, or 1,3-propylene group, and Y is methylene group;

compounds wherein $R^1$ is hydroxyl group, $X^1 \ldots X^2$ is ethylene group, or 1,3-propylene group, and Y is methylene group;

compounds wherein $R^1$ is hydrogen atom, chlorine atom, or hydroxyl group, $X^1 \ldots X^2$ is ethylene group, and Y is methylene group;

compounds wherein $R^1$ is hydrogen atom, or hydroxyl group, $X^1 \ldots X^2$ is ethylene group, and Y is methylene group;

compounds wherein $R^1$ is hydrogen atom, $X^1 \ldots X^2$ is ethylene group, and Y is methylene group;

compounds wherein $R^1$ is hydroxyl group, $X^1 \ldots X^2$ is ethylene group, and Y is methylene group;

compounds wherein $R^1$ is hydrogen atom, chlorine atom, or hydroxyl group, $X^1 \ldots X^2$ is 1,3-propylene group, and Y is methylene group;

compounds wherein $R^1$ is hydrogen atom, or hydroxyl group, $X^1 \ldots X^2$ is 1,3-propylene group, and Y is methylene group;

compounds wherein $R^1$ is hydrogen atom, $X^1 \ldots X^2$ is 1,3-propylene group, and Y is methylene group;

compounds wherein $R^1$ is hydroxyl group, $X^1 \ldots X^2$ is 1,3-propylene group, and Y is methylene group;

compounds wherein $R^1$ is hydrogen atom, chlorine atom, or hydroxyl group, $X^1 \ldots X^2$ is ethylene group, and groups in each of one or more combinations selected from the group consisting of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ bind to each other to form a 5- or 6-membered ring;

compounds wherein $R^1$ is hydrogen atom, or hydroxyl group, $X^1 \ldots X^2$ is ethylene group, and groups in each of one or more combinations selected from the group consisting of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ bind to each other to form a 5- or 6-membered ring;

compounds wherein $R^1$ is hydrogen atom, $X^1 \ldots X^2$ is ethylene group, and groups in each of one or more combinations selected from the group consisting of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ bind to each other to form a 5- or 6-membered ring;

compounds wherein $R^1$ is hydroxyl group, $X^1 \ldots X^2$ is ethylene group, and groups in each of one or more combinations selected from the group consisting of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ bind to each other to form a 5- or 6-membered ring;

compounds wherein $R^1$ is hydrogen atom, chlorine atom, or hydroxyl group, $X^1 \ldots X^2$ is ethylene group, and groups in each of one or more combinations selected from the group consisting of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ bind to each other to form a 5-membered ring;

compounds wherein $R^1$ is hydrogen atom, or hydroxyl group, $X^1 \ldots X^2$ is ethylene group, and groups in each of one or more combinations selected from the group consisting of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ bind to each other to form a 5-membered ring;

compounds wherein $R^1$ is hydrogen atom, $X^1 \ldots X^2$ is ethylene group, and groups in each of one or more combinations selected from the group consisting of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ bind to each other to form a 5-membered ring;

compounds wherein $R^1$ is hydroxyl group, $X^1 \ldots X^2$ is ethylene group, and groups in each of one or more combinations selected from the group consisting of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ bind to each other to form a 5-membered ring;

compounds wherein $R^1$ is hydrogen atom, chlorine atom, or hydroxyl group, $X^1 \ldots X^2$ is ethylene group, and groups in each of one or more combinations selected from the group consisting of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ bind to each other to form a 6-membered ring;

compounds wherein $R^1$ is hydrogen atom, or hydroxyl group, $X^1 \ldots X^2$ is ethylene group, and groups in each of one or more combinations selected from the group consisting of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ bind to each other to form a 6-membered ring;

compounds wherein $R^1$ is hydrogen atom, $X^1 \ldots X^2$ is ethylene group, and groups in each of one or more combinations selected from the group consisting of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ bind to each other to form a 6-membered ring;

compounds wherein $R^1$ is hydroxyl group, $X^1 \ldots X^2$ is ethylene group, and groups in each of one or more combinations selected from the group consisting of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ bind to each other to form a 6-membered ring;

compounds wherein $R^1$ is hydrogen atom, chlorine atom, or hydroxyl group, $X^1 \ldots X^2$ is ethylene group, and the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c);

compounds wherein $R^1$ is hydrogen atom, or hydroxyl group, $X^1 \ldots X^2$ is ethylene group, and the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c);

compounds wherein $R^1$ is hydrogen atom, $X^1 \ldots X^2$ is ethylene group, and the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c);

compounds wherein $R^1$ is hydroxyl group, $X^1 \ldots X^2$ is ethylene group, and the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c);

compounds wherein $R^1$ is hydrogen atom, chlorine atom, or hydroxyl group, $X^1 \ldots X^2$ is ethylene group, and the moiety of the formula (2) is represented by the formula (2-1), formula (2-2), formula (2-4-t), or formula (2-4-c);

compounds wherein $R^1$ is hydrogen atom, or hydroxyl group, $X^1 \ldots X^2$ is ethylene group, and the moiety of the formula (2) is represented by the formula (2-1), formula (2-2), formula (2-4-t), or formula (2-4-c);

compounds wherein $R^1$ is hydrogen atom, $X^1 \ldots X^2$ is ethylene group, and the moiety of the formula (2) is represented by the formula (2-1), formula (2-2), formula (2-4-t), or formula (2-4-c);

compounds wherein $R^1$ is hydroxyl group, $X^1 \ldots X^2$ is ethylene group, and the moiety of the formula (2) is represented by the formula (2-1), formula (2-2), formula (2-4-t), or formula (2-4-c);

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c), $A^{61}$ is hydrogen atom, a lower alkyl group, an aralkyl group, a lower alkyl group substituted with carboxyl group, a lower alkyl group substituted with aminocarbonyl group, a lower alkyl group substituted with cyano group, a lower alkyl group substituted with hydroxyl group, a lower alkyl group substituted with a lower alkoxyl group, or a lower alkyl group substituted with an amino group, and when the moiety of the formula (2) is represented by the formula (2-4-t), formula (2-4-c), formula (2-5-t), formula (2-5-c), formula (2-6-t), or formula (2-6-c), $A^6$ is hydrogen atom, or a lower alkyl group (preferred examples also include compounds wherein $A^{61}$ is a lower alkyl group of which end is substituted with $N(A^7)(—X^3—A^{71})$, and the other groups consist of the same combination as mentioned above);

compounds wherein $R^1$ is hydrogen atom, or hydroxyl group, $X^1 \ldots X^2$ is ethylene group, the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), formula (2-4-c), formula (2-5-t), formula (2-5-c), formula (2-6-t), or formula (2-6-c), $A^6$ is hydrogen atom, or a lower alkyl group (preferred examples also include compounds wherein $A^{61}$ is a lower alkyl group of which end is substituted with $N(A^7)(—X^3—A^{71})$, and the other groups consist of the same combination as mentioned above);

compounds wherein $R^1$ is hydrogen atom, $X^1 \ldots X^2$ is ethylene group, the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), formula (2-4-c), formula (2-5-t), formula (2-5-c), formula (2-6-t), or formula (2-6-c), $A^6$ is hydrogen atom, or a lower alkyl group (preferred examples also include compounds wherein $A^{61}$ is a lower alkyl group of which end is substituted with $N(A^7)(—X^3—A^{71})$, and the other groups consist of the same combination as mentioned above);

compounds wherein $R^1$ is hydroxyl group, $X^1 \ldots X^2$ is ethylene group, the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), formula (2-4-c), formula (2-5-t), formula (2-5-c), formula (2-6-t), or formula (2-6-c), $A^6$ is hydrogen atom, or a lower alkyl group (preferred examples also include compounds wherein $A^{61}$ is a lower alkyl group of which end is substituted with $N(A^7)(—X^3—A^{71})$, and the other groups consist of the same combination as mentioned above);

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), formula (2-4-c), formula (2-5-t), formula (2-5-c), formula (2-6-t), or formula (2-6-c), $A^6$ is hydrogen atom, or methyl group (preferred examples also include compounds wherein $A^{61}$ is a lower alkyl group of which end is substituted with $N(A^7)(—X^3—A^{71})$, and the other groups consist of the same combination as mentioned above);

compounds wherein $R^1$ is hydrogen atom, or hydroxyl group, $X^1 \ldots X^2$ is ethylene group, the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), formula (2-4-c), formula (2-5-t), formula (2-5-c), formula (2-6-t), or formula (2-6-c), $A^6$ is hydrogen atom, or methyl group (preferred examples also include compounds wherein $A^{61}$ is a lower alkyl group of which end is substituted with $N(A^7)(-X^3-A^{71})$, and the other groups consist of the same combination as mentioned above);

compounds wherein $R^1$ is hydrogen atom, $X^1 \ldots X^2$ is ethylene group, the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), formula (2-4-c), formula (2-5-t), formula (2-5-c), formula (2-6-t), or formula (2-6-c), $A^6$ is hydrogen atom, or methyl group (preferred examples also include compounds wherein $A^{61}$ is a lower alkyl group of which end is substituted with $N(A^7)(-X^3-A^{71})$, and the other groups consist of the same combination as mentioned above);

compounds wherein $R^1$ is hydroxyl group, $X^1 \ldots X^2$ is ethylene group, the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), formula (2-4-c), formula (2-5-t), formula (2-5-c), formula (2-6-t), or formula (2-6-c), $A^6$ is hydrogen atom, or methyl group (preferred examples also include compounds wherein $A^{61}$ is a lower alkyl group of which end is substituted with $N(A^7)(-X^3-A^{71})$, and the other groups consist of the same combination as mentioned above);

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), formula (2-4-c), formula (2-5-t), formula (2-5-c), formula (2-6-t), or formula (2-6-c), $A^6$ is hydrogen atom (preferred examples also include compounds wherein $A^{61}$ is a lower alkyl group of which end is substituted with $N(A^7)(-X^3-A^{71})$, and the other groups consist of the same combination as mentioned above);

compounds wherein $R^1$ is hydrogen atom, or hydroxyl group, $X^1 \ldots X^2$ is ethylene group, the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), formula (2-4-c), formula (2-5-t), formula (2-5-c), formula (2-6-t), or formula (2-6-c), $A^6$ is hydrogen atom (preferred examples also include compounds wherein $A^{61}$ is a lower alkyl group of which end is substituted with $N(A^7)(-X^3-A^{71})$, and the other groups consist of the same combination as mentioned above);

compounds wherein $R^1$ is hydrogen atom, $X^1 \ldots X^2$ is ethylene group, the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), formula (2-4-c), formula (2-5-t), formula (2-5-c), formula (2-6-t), or formula (2-6-c), $A^6$ is hydrogen atom (preferred examples also include compounds wherein $A^{61}$ is a lower alkyl group of which end is substituted with $N(A^7)(-X^3-A^{71})$, and the other groups consist of the same combination as mentioned above);

compounds wherein $R^1$ is hydroxyl group, $X^1 \ldots X^2$ is ethylene group, the moiety of the formula (2) is represented by the formula (2-1), formula (2-2), formula (2-3), formula (2-4-t), formula (2-4-c), formula (2-5-t), formula (2-5-c), formula (2-6-t), or formula (2-6-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), formula (2-4-c), formula (2-5-t), formula (2-5-c), formula (2-6-t), or formula (2-6-c), $A^6$ is hydrogen atom (preferred examples also include compounds wherein $A^{61}$ is a lower alkyl group of which end is substituted with $N(A^7)(-X^3-A^{71})$, and the other groups consist of the same combination as mentioned above);

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), or formula (2-4-c), $A^6$ is hydrogen atom, or a lower alkyl group (preferred examples also include compounds wherein $A^{61}$ is a lower alkyl group of which end is substituted with $N(A^7)$ (—$X^3$—$A^{71}$), and the other groups consist of the same combination as mentioned above);

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), or formula (2-4-c), $A^6$ is hydrogen atom, or a lower alkyl group (preferred examples also include compounds wherein $A^{61}$ is a lower alkyl group of which end is substituted with $N(A^7)$(—$X^3$—$A^{71}$), and the other groups consist of the same combination as mentioned above);

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), or formula (2-4-c), $A^6$ is hydrogen atom, or a lower alkyl group (preferred examples also include compounds wherein $A^{61}$ is a lower alkyl group of which end is substituted with $N(A^7)$(—$X^3$—$A^{71}$), and the other groups consist of the same combination as mentioned above);

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), or formula (2-4-c), $A^6$ is hydrogen atom, or a lower alkyl group (preferred examples also include compounds wherein $A^{61}$ is a lower alkyl group of which end is substituted with $N(A^7)$(—$X^3$—$A^{71}$), and the other groups consist of the same combination as mentioned above);

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), or formula (2-4-c), $A^6$ is hydrogen atom, or methyl group (preferred examples also include compounds wherein $A^{61}$ is a lower alkyl group of which end is substituted with $N(A^7)$(—$X^3$—$A^{71}$), and the other groups consist of the same combination as mentioned above);

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), or formula (2-4-c), $A^6$ is hydrogen atom, or methyl group (preferred examples also include compounds wherein $A^{61}$ is a lower alkyl group of which end is substituted with $N(A^7)$(—$X^3$—$A^{71}$), and the other groups consist of the same combination as mentioned above);

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), or formula (2-4-c), $A^6$ is hydrogen atom, or methyl group (preferred examples also include compounds wherein $A^{61}$ is a lower alkyl group of which end is substituted with $N(A^7)$(—$X^3$—$A^{71}$), and the other groups consist of the same combination as mentioned above);

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), or formula (2-4-c), $A^6$ is hydrogen atom, or methyl group (preferred examples also include compounds wherein $A^{61}$ is a lower alkyl group of which end is substituted with $N(A^7)$(—$X^3$—$A^{71}$), and the other groups consist of the same combination as mentioned above);

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), or formula (2-4-c), $A^6$ is hydrogen atom (preferred examples also include compounds wherein $A^{61}$ is a lower alkyl group of which end is substituted with $N(A^7)(-X^3-A^{71})$, and the other groups consist of the same combination as mentioned above);

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), or formula (2-4-c), $A^6$ is hydrogen atom (preferred examples also include compounds wherein $A^{61}$ is a lower alkyl group of which end is substituted with $N(A^7)(-X^3-A^{71})$, and the other groups consist of the same combination as mentioned above);

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), or formula (2-4-c), $A^6$ is hydrogen atom (preferred examples also include compounds wherein $A^{61}$ is a lower alkyl group of which end is substituted with $N(A^7)(-X^3-A^{71})$, and the other groups consist of the same combination as mentioned above);

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, a lower alkyl group, an aralkyl group, a lower alkyl group substituted with carboxyl group, a lower alkyl group substituted with cyano group, a lower alkyl group substituted with hydroxyl group, a lower alkyl group substituted with a lower alkoxyl group, a lower alkyl group substituted with an amino group, or a lower alkyl group substituted with aminocarbonyl group, and when the moiety of the formula (2) is represented by the formula (2-4-t), or formula (2-4-c), $A^6$ is hydrogen atom (preferred examples also include compounds wherein $A^{61}$ is a lower alkyl group of which end is substituted with $N(A^7)(-X^3-A^{71})$, and the other groups consist of the same combination as mentioned above);

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, and when the moiety of the formula (2) is represented by the formula (2-4-t), or formula (2-4-c), $A^6$ is hydrogen atom, a lower alkyl group, or an aralkyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, and when the moiety of the formula (2) is represented by the formula (2-4-t), or formula (2-4-c), $A^6$ is hydrogen atom, or a lower alkyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is hydrogen atom, and when the moiety of the formula (2) is represented by the formula (2-4-t), or formula (2-4-c), $A^6$ is hydrogen atom, or a lower alkyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, and when the moiety of the formula (2) is represented by the formula (2-4-t), or formula (2-4-c), $A^6$ is hydrogen atom, or a lower alkyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group, and when the moiety of the formula (2) is represented by the formula (2-4-t), or formula (2-4-c), $A^6$ is hydrogen atom, or a lower alkyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group, and when the moiety of the formula (2) is represented by the formula (2-4-t), or formula (2-4-c), $A^6$ is hydrogen atom, or a lower alkyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group, and when the moiety of the formula (2) is represented by the formula (2-4-t), or formula (2-4-c), $A^6$ is hydrogen atom, or a lower alkyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group, and when the moiety of the formula (2) is represented by the formula (2-4-t), or formula (2-4-c), $A^6$ is hydrogen atom, or a lower alkyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is an aralkyl group, and when the moiety of the formula (2) is represented by the formula (2-4-t), or formula (2-4-c), $A^6$ is hydrogen atom, or a lower alkyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is an aralkyl group, and when the moiety of the formula (2) is represented by the formula (2-4-t), or formula (2-4-c), $A^6$ is hydrogen atom, or a lower alkyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is an aralkyl group, and when the moiety of the formula (2) is represented by the formula (2-4-t), or formula (2-4-c), $A^6$ is hydrogen atom, or a lower alkyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is an aralkyl group, and when the moiety of the formula (2) is represented by the formula (2-4-t), or formula (2-4-c), $A^6$ is hydrogen atom, or a lower alkyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with carboxyl group, and when the moiety of the formula (2) is represented by the formula (2-4-t), or formula (2-4-c), $A^6$ is hydrogen atom, or a lower alkyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with carboxyl group, and when the moiety of the formula (2) is represented by the formula (2-4-t), or formula (2-4-c), $A^6$ is hydrogen atom, or a lower alkyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with carboxyl group, and when the moiety of the formula (2) is represented by the formula (2-4-t), or formula (2-4-c), $A^6$ is hydrogen atom, or a lower alkyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with carboxyl group, and when the moiety of the formula (2) is represented by the formula (2-4-t), or formula (2-4-c), $A^6$ is hydrogen atom, or a lower alkyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with cyano group, and when the moiety of the formula (2) is represented by the formula (2-4-t), or formula (2-4-c), $A^6$ is hydrogen atom, or a lower alkyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with cyano group, and when the moiety of the formula (2) is represented by the formula (2-4-t), or formula (2-4-c), $A^6$ is hydrogen atom, or a lower alkyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with cyano group, and when the moiety of the formula (2) is represented by the formula (2-4-t), or formula (2-4-c), $A^6$ is hydrogen atom, or a lower alkyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with cyano group, and when the moiety of the formula (2) is represented by the formula (2-4-t), or formula (2-4-c), $A^6$ is hydrogen atom, or a lower alkyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with hydroxyl group, and when the moiety of the formula (2) is represented by the formula (2-4-t), or formula (2-4-c), $A^6$ is hydrogen atom, or a lower alkyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with hydroxyl group, and when the moiety of the formula (2) is represented by the formula (2-4-t), or formula (2-4-c), $A^6$ is hydrogen atom, or a lower alkyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with hydroxyl group, and when the moiety of the formula (2) is represented by the formula (2-4-t), or formula (2-4-c), $A^6$ is hydrogen atom, or a lower alkyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with hydroxyl group, and when the moiety of the formula (2) is represented by the formula (2-4-t), or formula (2-4-c), $A^6$ is hydrogen atom, or a lower alkyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkoxyl group, and when the moiety of the formula (2) is represented by the formula (2-4-t), or formula (2-4-c), $A^6$ is hydrogen atom, or a lower alkyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkoxyl group, and when the moiety of the formula (2) is represented by the formula (2-4-t), or formula (2-4-c), $A^6$ is hydrogen atom, or a lower alkyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkoxyl group, and when the moiety of the formula (2) is represented by the formula (2-4-t), or formula (2-4-c), $A^6$ is hydrogen atom, or a lower alkyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkoxyl group, and when the moiety of the formula (2) is represented by the formula (2-4-t), or formula (2-4-c), $A^6$ is hydrogen atom, or a lower alkyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with an amino group, and when the moiety of the formula (2) is represented by the formula (2-4-t), or formula (2-4-c), $A^6$ is hydrogen atom, or a lower alkyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with an amino group, and when the moiety of the formula (2) is represented by the formula (2-4-t), or formula (2-4-c), $A^6$ is hydrogen atom, or a lower alkyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with an amino group, and when the moiety of the formula (2) is represented by the formula (2-4-t), or formula (2-4-c), $A^6$ is hydrogen atom, or a lower alkyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with an amino group, and when the moiety of the formula (2) is represented by the formula (2-4-t), or formula (2-4-c), $A^6$ is hydrogen atom, or a lower alkyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group of which end is substituted with $N(A^7)(-X^3-A^{71})$, and when the moiety of the formula (2) is represented by the formula (2-4-t), or formula (2-4-c), $A^6$ is hydrogen atom, or a lower alkyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group of which end is substituted with $N(A^7)(-X^3-A^{71})$, and when the moiety of the formula (2) is represented by the formula (2-4-t), or formula (2-4-c), $A^6$ is hydrogen atom, or a lower alkyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group of which end is substituted with $N(A^7)(-X^3-A^{71})$, and when the moiety of the formula (2) is represented by the formula (2-4-t), or formula (2-4-c), $A^6$ is hydrogen atom, or a lower alkyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group of which end is substituted with $N(A^7)(-X^3-A^{71})$, and when the moiety of the formula (2) is represented by the formula (2-4-t), or formula (2-4-c), $A^6$ is hydrogen atom, or a lower alkyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkylcarbonylamino group, and when the moiety of the formula (2) is represented by the formula (2-4-t), or formula (2-4-c), $A^6$ is hydrogen atom, or a lower alkyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkylcarbonylamino group, and when the moiety of the formula (2) is represented by the formula (2-4-t), or formula (2-4-c), $A^6$ is hydrogen atom, or a lower alkyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkylcarbonylamino group, and when the moiety of the formula (2) is represented by the formula (2-4-t), or formula (2-4-c), $A^6$ is hydrogen atom, or a lower alkyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkylcarbonylamino group, and when the moiety of the formula (2) is represented by the formula (2-4-t), or formula (2-4-c), $A^6$ is hydrogen atom, or a lower alkyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with aminocarbonyl group, and when the moiety of the formula (2) is represented by the formula (2-4-t), or formula (2-4-c), $A^6$ is hydrogen atom, or a lower alkyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with aminocarbonyl group, and when the moiety of the formula (2) is represented by the formula (2-4-t), or formula (2-4-c), $A^6$ is hydrogen atom, or a lower alkyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with aminocarbonyl group, and when the moiety of the formula (2) is represented by the formula (2-4-t), or formula (2-4-c), $A^6$ is hydrogen atom, or a lower alkyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with aminocarbonyl group, and when the moiety of the formula (2) is represented by the formula (2-4-t), or formula (2-4-c), $A^6$ is hydrogen atom, or a lower alkyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, and when the moiety of the formula (2) is represented by the formula (2-4-t), or formula (2-4-c), $A^6$ is hydrogen atom, or methyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, and when the moiety of the formula (2) is represented by the formula (2-4-t), or formula (2-4-c), $A^6$ is hydrogen atom, or methyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is hydrogen atom, and when the moiety of the formula (2) is represented by the formula (2-4-t), or formula (2-4-c), $A^6$ is hydrogen atom, or methyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, and when the moiety of the formula (2) is represented by the formula (2-4-t), or formula (2-4-c), $A^6$ is hydrogen atom, or methyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group, and when the moiety of the formula (2) is represented by the formula (2-4-t), or formula (2-4-c), $A^6$ is hydrogen atom, or methyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group, and when the moiety of the formula (2) is represented by the formula (2-4-t), or formula (2-4-c), $A^6$ is hydrogen atom, or methyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group, and when the moiety of the formula (2) is represented by the formula (2-4-t), or formula (2-4-c), $A^6$ is hydrogen atom, or methyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group, and when the moiety of the formula (2) is represented by the formula (2-4-t), or formula (2-4-c), $A^6$ is hydrogen atom, or methyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is an aralkyl group, and when the moiety of the formula (2) is represented by the formula (2-4-t), or formula (2-4-c), $A^6$ is hydrogen atom, or methyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is an aralkyl group, and when the moiety of the formula (2) is represented by the formula (2-4-t), or formula (2-4-c), $A^6$ is hydrogen atom, or methyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is an aralkyl group, and when the moiety of the formula (2) is represented by the formula (2-4-t), or formula (2-4-c), $A^6$ is hydrogen atom, or methyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is an aralkyl group, and when the moiety of the formula (2) is represented by the formula (2-4-t), or formula (2-4-c), $A^6$ is hydrogen atom, or methyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with carboxyl group, and when the moiety of the formula (2) is represented by the formula (2-4-t), or formula (2-4-c), $A^6$ is hydrogen atom, or methyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with carboxyl group, and when the moiety of the formula (2) is represented by the formula (2-4-t), or formula (2-4-c), $A^6$ is hydrogen atom, or methyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with carboxyl group, and when the moiety of the formula (2) is represented by the formula (2-4-t), or formula (2-4-c), $A^6$ is hydrogen atom, or methyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with carboxyl group, and when the moiety of the formula (2) is represented by the formula (2-4-t), or formula (2-4-c), $A^6$ is hydrogen atom, or methyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with cyano group, and when the moiety of the formula (2) is represented by the formula (2-4-t), or formula (2-4-c), $A^6$ is hydrogen atom, or methyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with cyano group, and when the moiety of the formula (2) is represented by the formula (2-4-t), or formula (2-4-c), $A^6$ is hydrogen atom, or methyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with cyano group, and when the moiety of the formula (2) is represented by the formula (2-4-t), or formula (2-4-c), $A^6$ is hydrogen atom, or methyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with cyano group, and when the moiety of the formula (2) is represented by the formula (2-4-t), or formula (2-4-c), $A^6$ is hydrogen atom, or methyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with hydroxyl group, and when the moiety of the formula (2) is represented by the formula (2-4-t), or formula (2-4-c), $A^6$ is hydrogen atom, or methyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with hydroxyl group, and when the moiety of the formula (2) is represented by the formula (2-4-t), or formula (2-4-c), $A^6$ is hydrogen atom, or methyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with hydroxyl group, and when the moiety of the formula (2) is represented by the formula (2-4-t), or formula (2-4-c), $A^6$ is hydrogen atom, or methyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with hydroxyl group, and when the moiety of the formula (2) is represented by the formula (2-4-t), or formula (2-4-c), $A^6$ is hydrogen atom, or methyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkoxyl group, and when the moiety of the formula (2) is represented by the formula (2-4-t), or formula (2-4-c), $A^6$ is hydrogen atom, or methyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkoxyl group, and when the moiety of the formula (2) is represented by the formula (2-4-t), or formula (2-4-c), $A^6$ is hydrogen atom, or methyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkoxyl group, and when the moiety of the formula (2) is represented by the formula (2-4-t), or formula (2-4-c), $A^6$ is hydrogen atom, or methyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkoxyl group, and when the moiety of the formula (2) is represented by the formula (2-4-t), or formula (2-4-c), $A^6$ is hydrogen atom, or methyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with an amino group, and when the moiety of the formula (2) is represented by the formula (2-4-t), or formula (2-4-c), $A^6$ is hydrogen atom, or methyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with an amino group, and when the moiety of the formula (2) is represented by the formula (2-4-t), or formula (2-4-c), $A^6$ is hydrogen atom, or methyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with an amino group, and when the moiety of the formula (2) is represented by the formula (2-4-t), or formula (2-4-c), $A^6$ is hydrogen atom, or methyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with an amino group, and when the moiety of the formula (2) is represented by the formula (2-4-t), or formula (2-4-c), $A^6$ is hydrogen atom, or methyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group of which end is substituted with $N(A^7)(—X^3—A^{71})$, and when the moiety of the formula (2) is represented by the formula (2-4-t), or formula (2-4-c), $A^6$ is hydrogen atom, or methyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group of which end is substituted with $N(A^7)(—X^3—A^{71})$, and when the moiety of the formula (2) is represented by the formula (2-4-t), or formula (2-4-c), $A^6$ is hydrogen atom, or methyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group of which end is substituted with $N(A^7)(—X^3—A^{71})$, and when the moiety of the formula (2) is represented by the formula (2-4-t), or formula (2-4-c), $A^6$ is hydrogen atom, or methyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group of which end is substituted with $N(A^7)(—X^3—A^{71})$, and when the moiety of the formula (2) is represented by the formula (2-4-t), or formula (2-4-c), $A^6$ is hydrogen atom, or methyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^6$ is a lower alkyl group substituted with a lower alkylcarbonylamino group, and when the moiety of the formula (2) is represented by the formula (2-4-t), or formula (2-4-c), $A^6$ is hydrogen atom, or methyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^6$ is a lower alkyl group substituted with a lower alkylcarbonylamino group, and when the moiety of the formula (2) is represented by the formula (2-4-t), or formula (2-4-c), $A^6$ is hydrogen atom, or methyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^6$ is a lower alkyl group substituted with a lower alkylcarbonylamino group, and when the moiety of the formula (2) is represented by the formula (2-4-t), or formula (2-4-c), $A^6$ is hydrogen atom, or methyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^6$ is a lower alkyl group substituted with a lower alkylcarbonylamino group, and when the moiety of the formula (2) is represented by the formula (2-4-t), or formula (2-4-c), $A^6$ is hydrogen atom, or methyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with aminocarbonyl group, and when the moiety of the formula (2) is represented by the formula (2-4-t), or formula (2-4-c), $A^6$ is hydrogen atom, or methyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with aminocarbonyl group, and when the moiety of the formula (2) is represented by the formula (2-4-t), or formula (2-4-c), $A^6$ is hydrogen atom, or methyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with aminocarbonyl group, and when the moiety of the formula (2) is represented by the formula (2-4-t), or formula (2-4-c), $A^6$ is hydrogen atom, or methyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with aminocarbonyl group, and when the moiety of the formula (2) is represented by the formula (2-4-t), or formula (2-4-c), $A^6$ is hydrogen atom, or methyl group;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, and when the moiety of the formula (2) is represented by the formula (2-4-t), or formula (2-4-c), $A^6$ is hydrogen atom;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, and when the moiety of the formula (2) is represented by the formula (2-4-t), or formula (2-4-c), $A^6$ is hydrogen atom;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is hydrogen atom, and when the moiety of the formula (2) is represented by the formula (2-4-t), or formula (2-4-c), $A^6$ is hydrogen atom;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is hydrogen atom, and when the moiety of the formula (2) is represented by the formula (2-4-t), or formula (2-4-c), $A^6$ is hydrogen atom;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group, and when the moiety of the formula (2) is represented by the formula (2-4-t), or formula (2-4-c), $A^6$ is hydrogen atom;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group, and when the moiety of the formula (2) is represented by the formula (2-4-t), or formula (2-4-c), $A^6$ is hydrogen atom;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group, and when the moiety of the formula (2) is represented by the formula (2-4-t), or formula (2-4-c), $A^6$ is hydrogen atom;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group, and when the moiety of the formula (2) is represented by the formula (2-4-t), or formula (2-4-c), $A^6$ is hydrogen atom;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is an aralkyl group, and when the moiety of the formula (2) is represented by the formula (2-4-t), or formula (2-4-c), $A^6$ is hydrogen atom;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is-an aralkyl group, and when the moiety of the formula (2) is represented by the formula (2-4-t), or formula (2-4-c), $A^6$ is hydrogen atom;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is an aralkyl group, and when the moiety of the formula (2) is represented by the formula (2-4-t), or formula (2-4-c), $A^6$ is hydrogen atom;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is an aralkyl group, and when the moiety of the formula (2) is represented by the formula (2-4-t), or formula (2-4-c), $A^6$ is hydrogen atom;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with carboxyl group, and when the moiety of the formula (2) is represented by the formula (2-4-t), or formula (2-4-c), $A^6$ is hydrogen atom;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with carboxyl group, and when the moiety of the formula (2) is represented by the formula (2-4-t), or formula (2-4-c), $A^6$ is hydrogen atom;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with carboxyl group, and when the moiety of the formula (2) is represented by the formula (2-4-t), or formula (2-4-c), $A^6$ is hydrogen atom;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with carboxyl group, and when the moiety of the formula (2) is represented by the formula (2-4-t), or formula (2-4-c), $A^6$ is hydrogen atom;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with cyano group, and when the moiety of the formula (2) is represented by the formula (2-4-t), or formula (2-4-c), $A^6$ is hydrogen atom;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with cyano group, and when the moiety of the formula (2) is represented by the formula (2-4-t), or formula (2-4-c), $A^6$ is hydrogen atom;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with cyano group, and when the moiety of the formula (2) is represented by the formula (2-4-t), or formula (2-4-c), $A^6$ is hydrogen atom;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with cyano group, and when the moiety of the formula (2) is represented by the formula (2-4-t), or formula (2-4-c), $A^6$ is hydrogen atom;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with hydroxyl group, and when the moiety of the formula (2) is represented by the formula (2-4-t), or formula (2-4-c), $A^6$ is hydrogen atom;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with hydroxyl group, and when the moiety of the formula (2) is represented by the formula (2-4-t), or formula (2-4-c), $A^6$ is hydrogen atom;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with hydroxyl group, and when the moiety of the formula (2) is represented by the formula (2-4-t), or formula (2-4-c), $A^6$ is hydrogen atom;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with hydroxyl group, and when the moiety of the formula (2) is represented by the formula (2-4-t), or formula (2-4-c), $A^6$ is hydrogen atom;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkoxyl group, and when the moiety of the formula (2) is represented by the formula (2-4-t), or formula (2-4-c), $A^6$ is hydrogen atom;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkoxyl group, and when the moiety of the formula (2) is represented by the formula (2-4-t), or formula (2-4-c), $A^6$ is hydrogen atom;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkoxyl group, and when the moiety of the formula (2) is represented by the formula (2-4-t), or formula (2-4-c), $A^6$ is hydrogen atom;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkoxyl group, and when the moiety of the formula (2) is represented by the formula (2-4-t), or formula (2-4-c), $A^6$ is hydrogen atom;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with an amino group, and when the moiety of the formula (2) is represented by the formula (2-4-t), or formula (2-4-c), $A^6$ is hydrogen atom;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with an amino group, and when the moiety of the formula (2) is represented by the formula (2-4-t), or formula (2-4-c), $A^6$ is hydrogen atom;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with an amino group, and when the moiety of the formula (2) is represented by the formula (2-4-t), or formula (2-4-c), $A^6$ is hydrogen atom;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with an amino group, and when the moiety of the formula (2) is represented by the formula (2-4-t), or formula (2-4-c), $A^6$ is hydrogen atom;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group of which end is substituted with $N(A^7)$ ($—X^3—A^{71}$), and when the moiety of the formula (2) is represented by the formula (2-4-t), or formula (2-4-c), $A^6$ is hydrogen atom;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group of which end is substituted with $N(A^7)(-X^3-A^{71})$, and when the moiety of the formula (2) is represented by the formula (2-4-t), or formula (2-4-c), $A^6$ is hydrogen atom;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group of which end is substituted with $N(A^7)(-X^3-A^{71})$, and when the moiety of the formula (2) is represented by the formula (2-4-t), or formula (2-4-c), $A^6$ is hydrogen atom;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group of which end is substituted with $N(A^7)(-X^3-A^{71})$, and when the moiety of the formula (2) is represented by the formula (2-4-t), or formula (2-4-c), $A^6$ is hydrogen atom;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkylcarbonylamino group, and when the moiety of the formula (2) is represented by the formula (2-4-t), or formula (2-4-c), $A^6$ is hydrogen atom;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkylcarbonylamino group, and when the moiety of the formula (2) is represented by the formula (2-4-t), or formula (2-4-c), $A^6$ is hydrogen atom;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkylcarbonylamino group, and when the moiety of the formula (2) is represented by the formula (2-4-t), or formula (2-4-c), $A^6$ is hydrogen atom;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with a lower alkylcarbonylamino group, and when the moiety of the formula (2) is represented by the formula (2-4-t), or formula (2-4-c), $A^6$ is hydrogen atom;

compounds wherein $R^1$ is hydrogen atom, chlorine atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with aminocarbonyl group, and when the moiety of the formula (2) is represented by the formula (2-4-t), or formula (2-4-c), $A^6$ is hydrogen atom;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with aminocarbonyl group, and when the moiety of the formula (2) is represented by the formula (2-4-t), or formula (2-4-c), $A^6$ is hydrogen atom;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with aminocarbonyl group, and when the moiety of the formula (2) is represented by the formula (2-4-t), or formula (2-4-c), $A^6$ is hydrogen atom;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is a lower alkyl group substituted with aminocarbonyl group, and when the moiety of the formula (2) is represented by the formula (2-4-t), or formula (2-4-c), $A^6$ is hydrogen atom;

compounds wherein $R^1$ is hydrogen atom, or hydroxyl group, $X^1 \ldots X^2$ is ethylene group, $A^6$ is hydrogen atom, and $A^{61}$ is 2-(2-oxo-1-azetidyl)ethyl group, 2-(2-oxo-1-pyrrolidyl)ethyl group, 2-(2-oxo-1-piperidyl)ethyl group, 3-(2-oxo-1-azetidyl)propyl group, 3-(2-oxo-1-pyrrolidyl)propyl group, or 3-(2-oxo-1-piperidyl)propyl group;

compounds wherein $R^1$ is hydrogen atom, $X^1 \ldots X^2$ is ethylene group, $A^6$ is hydrogen atom, and $A^{61}$ is 2-(2-oxo-1-azetidyl)ethyl group, 2-(2-oxo-1-pyrrolidyl)ethyl group, 2-(2-oxo-1-piperidyl)ethyl group, 3-(2-oxo-1-azetidyl)propyl group, 3-(2-oxo-1-pyrrolidyl)propyl group, or 3-(2-oxo-1-piperidyl)propyl group;

compounds wherein $R^1$ is hydroxyl group, $X^1 \ldots X^2$ is ethylene group, $A^6$ is hydrogen atom, and $A^{61}$ is 2-(2-oxo-1-azetidyl)ethyl group, 2-(2-oxo-1-pyrrolidyl)ethyl group, 2-(2-oxo-1-piperidyl)ethyl group, 3-(2-oxo-1-azetidyl)propyl group, 3-(2-oxo-1-pyrrolidyl)propyl group, or 3-(2-oxo-1-piperidyl)propyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is 2-(2-oxo-1-azetidyl)ethyl group, 2-(2-oxo-1-pyrrolidyl)ethyl group, 2-(2-oxo-1-piperidyl)ethyl group, 3-(2-oxo-1-azetidyl)propyl group, 3-(2-oxo-1-pyrrolidyl)propyl group, or 3-(2-oxo-1-piperidyl)propyl group, and when the moiety of the formula (2) can be represented by the formula (2-4-t), or formula (2-4-c), $A^6$ is hydrogen atom, or a lower alkyl group;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is 2-(2-oxo-1-azetidyl)ethyl group, 2-(2-oxo-1-pyrrolidyl)ethyl group, 2-(2-oxo-1-piperidyl)ethyl group, 3-(2-oxo-1-azetidyl)propyl group, 3-(2-oxo-1-pyrrolidyl)propyl group, or 3-(2-oxo-1-piperidyl)propyl group, and when the moiety of the formula (2) can be represented by the formula (2-4-t), or formula (2-4-c), $A^6$ is hydrogen atom, or a lower alkyl group;

compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is 2-(2-oxo-1-azetidyl)ethyl group, 2-(2-oxo-1-pyrrolidyl)ethyl group, 2-(2-oxo-1-piperidyl)ethyl group, 3-(2-oxo-1-azetidyl)propyl group, 3-(2-oxo-1-pyrrolidyl)propyl group, or 3-(2-oxo-1-piperidyl)propyl group, and when the moiety of the formula (2) can be represented by the formula (2-4-t), or formula (2-4-c), $A^6$ is hydrogen atom, or a lower alkyl group;

compounds wherein $R^1$ is hydrogen atom, or hydroxyl group, $X^1 \ldots X^2$ is ethylene group, the moiety of the formula (2) is represented by the formula (2-1), formula (2-2), formula (2-4-t), or formula (2-4-c), $A^{61}$ is 2-(2-oxo-1-azetidyl)ethyl group, 2-(2-oxo-1-pyrrolidyl)ethyl group, 2-(2-oxo-1-piperidyl)ethyl group, 3-(2-oxo-1-azetidyl)propyl group, 3-(2-oxo-1-pyrrolidyl)propyl group, or 3-(2-oxo-1-piperidyl)propyl group, and when the moiety of the formula (2) can be represented by the formula (2-4-t), or formula (2-4-c), $A^6$ is hydrogen atom;

compounds wherein $R^1$ is hydrogen atom, $X^1 \ldots X^2$ is ethylene group, the moiety of the formula (2) is represented by the formula (2-1), formula (2-2), formula (2-4-t), or formula (2-4-c), $A^{61}$ is 2-(2-oxo-1-azetidyl)ethyl group, 2-(2-oxo-1-pyrrolidyl)ethyl group, 2-(2-oxo-1-piperidyl) ethyl group, 3-(2-oxo-1-azetidyl)propyl group, 3-(2-oxo-1-pyrrolidyl)propyl group, or 3-(2-oxo-1-piperidyl)propyl group, and when the moiety of the formula (2) can be represented by the formula (2-4-t), or formula (2-4-c), $A^6$ is hydrogen atom; and compounds wherein $R^1$ is hydroxyl group, $X^1 \ldots X^2$ is ethylene group, the moiety of the formula (2) is represented by the formula (2-1), formula (2-2), formula (2-4-t), or formula (2-4-c), $A^{61}$ is 2-(2-oxo-1-azetidyl)ethyl group, 2-(2-oxo-1-pyrrolidyl)ethyl group, 2-(2-oxo-1-piperidyl) ethyl group, 3-(2-oxo-1-azetidyl)propyl group, 3-(2-oxo-1-pyrrolidyl)propyl group, or 3-(2-oxo-1-piperidyl)propyl group, and when the moiety of the formula (2) can be represented by the formula (2-4-t), or formula (2-4-c), $A^6$ is hydrogen atom.

Specific examples of the compounds of the present invention represented by the formula (1) further include, for example, the compounds described in Tables 1 to 10 mentioned below. In the tables, Me represents methyl, and Bn represents benzyl. The compounds of Table 1 have a structure represented by the formula (1-A), the compounds of Table 2 have a structure represented by the formula (1-B), the compounds of Table 3 have a structure represented by the formula (1-C), the compounds of Table 4 have a structure represented by the formula (1-D), the compounds of Table 5 have a structure represented by the formula (1-E), the compounds of Table 6 have a structure represented by the formula (1-G), the compounds of Table 7 have a structure represented by the formula (1-F), the compounds of Table 8 have a structure represented by the formula (1-H), the compounds of Table 9 have a structure represented by the formula (1-I), and the compounds of Table 10 have a structure represented by the formula (1-J), respectively. However, the scope of the present invention is not limited to these compounds.

The compounds mentioned in Table 1 are compounds having a structure represented by the following formula (1-A):

TABLE 1

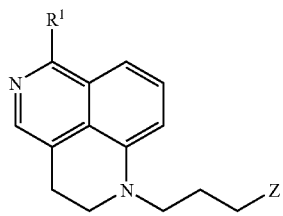

(1-A)

| Exemplary Compound No. | $R^1$ | Z |
|---|---|---|
| 1-1 | H | OH |
| 1-2 | H | $NH_2$ |
| 1-3 | H | NHMe |
| 1-4 | H | NHBn |
| 1-5 | H | $NH(CH_2COOH)$ |
| 1-6 | H | $NH(CH_2CH_2COOH)$ |
| 1-7 | H | $NH(CH_2CH_2CH_2COOH)$ |

TABLE 1-continued (1-A)

| Exemplary Compound No. | $R^1$ | Z |
|---|---|---|
| 1-8 | H | $NH(CH_2CN)$ |
| 1-9 | H | $NH(CH_2CH_2CN)$ |
| 1-10 | H | $NH(CH_2CH_2CH_2CN)$ |
| 1-11 | H | $NH(CH_2CH_2OH)$ |
| 1-12 | H | $NH(CH_2CH_2CH_2OH)$ |
| 1-13 | H | $NH(CH_2CH_2CH_2CH_2OH)$ |
| 1-14 | H | $NH(CH_2CH_2OMe)$ |
| 1-15 | H | $NH(CH_2CH_2CH_2OMe)$ |
| 1-16 | H | $NH(CH_2CH_2CH_2CH_2OMe)$ |
| 1-17 | H | $NH(CH_2CH_2NH_2)$ |
| 1-18 | H | $NH(CH_2CH_2CH_2NH_2)$ |
| 1-19 | H | $NH(CH_2CH_2CH_2CH_2NH_2)$ |
| 1-20 | H | $NH(CH_2CH_2NHMe)$ |
| 1-21 | H | $NH(CH_2CH_2CH_2NHMe)$ |
| 1-22 | H | $NH(CH_2CH_2CH_2CH_2NHMe)$ |
| 1-23 | H | $NH(CH_2CH_2NMe_2)$ |
| 1-24 | H | $NH(CH_2CH_2CH_2NMe_2)$ |
| 1-25 | H | $NH(CH_2CH_2CH_2CH_2NMe_2)$ |
| 1-26 | H | $NH(CH_2CONH_2)$ |
| 1-27 | H | $NH(CH_2CH_2CONH_2)$ |
| 1-28 | H | NMeBn |
| 1-29 | H | $NMC(CH_2COOH)$ |
| 1-30 | H | $NMe(CH_2CH_2COOH)$ |
| 1-31 | H | $NMe(CH_2CH_2CH_2COOH)$ |
| 1-32 | H | $NMe(CH_2CN)$ |
| 1-33 | H | $NMe(CH_2CH_2CN)$ |
| 1-34 | H | $NMe(CH_2CH_2CH_2CN)$ |
| 1-35 | H | $NMe(CH_2CH_2OH)$ |
| 1-36 | H | $NMe(CH_2CH_2CH_2OH)$ |
| 1-37 | H | $NMe(CH_2CH_2CH_2CH_2OH)$ |
| 1-38 | H | $NMe(CH_2CH_2OMe)$ |
| 1-39 | H | $NMe(CH_2CH_2CH_2OMe)$ |
| 1-40 | H | $NMe(CH_2CH_2CH_2CH_2OMe)$ |
| 1-41 | H | $NMe(CH_2CH_2NH_2)$ |
| 1-42 | H | $NMe(CH_2CH_2CH_2NH_2)$ |
| 1-43 | H | $NMe(CH_2CH_2CH_2CH_2NH_2)$ |
| 1-44 | H | $NMe(CH_2CH_2NHMe)$ |
| 1-45 | H | $NMe(CH_2CH_2CH_2NHMe)$ |
| 1-46 | H | $NMe(CH_2CH_2CH_2CH_2NHMe)$ |
| 1-47 | H | $NMe(CH_2CH_2NMe_2)$ |
| 1-48 | H | $NMe(CH_2CH_2CH_2NMe_2)$ |
| 1-49 | H | $NMe(CH_2CH_2CH_2CH_2NMe_2)$ |
| 1-50 | H | $NMe(CH_2CONH_2)$ |
| 1-51 | H | $NMe(CH_2CH_2CONH_2)$ |
| 1-52 | OH | OH |
| 1-53 | OH | $NH_2$ |
| 1-54 | OH | NHMe |
| 1-55 | OH | NHBn |
| 1-56 | OH | $NH(CH_2COOH)$ |
| 1-57 | OH | $NH(CH_2CH_2COOH)$ |
| 1-58 | OH | $NH(CH_2CH_2CH_2COOH)$ |
| 1-59 | OH | $NH(CH_2CN)$ |
| 1-60 | OH | $NH(CH_2CH_2CN)$ |
| 1-61 | OH | $NH(CH_2CH_2CH_2CN)$ |
| 1-62 | OH | $NH(CH_2CH_2OH)$ |
| 1-63 | OH | $NH(CH_2CH_2CH_2OH)$ |
| 1-64 | OH | $NH(CH_2CH_2CH_2CH_2OH)$ |
| 1-65 | OH | $NH(CH_2CH_2OMe)$ |
| 1-66 | OH | $NH(CH_2CH_2CH_2OMe)$ |
| 1-67 | OH | $NH(CH_2CH_2CH_2CH_2OMe)$ |
| 1-68 | OH | $NH(CH_2CH_2NH_2)$ |
| 1-69 | OH | $NH(CH_2CH_2CH_2NH_2)$ |
| 1-70 | OH | $NH(CH_2CH_2CH_2CH_2NH_2)$ |
| 1-71 | OH | $NH(CH_2CH_2NHMe)$ |

TABLE 1-continued (1-A)

[Structure: isoquinoline fused with tetrahydro ring bearing R¹ and N-CH₂CH₂CH₂-Z substituent]

| Exemplary Compound No. | R¹ | Z |
|---|---|---|
| 1-72 | OH | NH(CH₂CH₂CH₂NHMe) |
| 1-73 | OH | NH(CH₂CH₂CH₂CH₂NHMe) |
| 1-74 | OH | NH(CH₂CH₂NMe₂) |
| 1-75 | OH | NH(CH₂CH₂CH₂NMe₂) |
| 1-76 | OH | NH(CH₂CH₂CH₂CH₂NMe₂) |
| 1-77 | OH | NH(CH₂CONH₂) |
| 1-78 | OH | NH(CH₂CH₂CONH₂) |
| 1-79 | OH | NMeBn |
| 1-80 | OH | NMe(CH₂COOH) |
| 1-81 | OH | NMe(CH₂CH₂COOH) |
| 1-82 | OH | NMe(CH₂CH₂CH₂COOH) |
| 1-83 | OH | NMe(CH₂CN) |
| 1-84 | OH | NMe(CH₂CH₂CN) |
| 1-85 | OH | NMe(CH₂CH₂CH₂CN) |
| 1-86 | OH | NMe(CH₂CH₂OH) |
| 1-87 | OH | NMe(CH₂CH₂CH₂OH) |
| 1-88 | OH | NMe(CH₂CH₂CH₂CH₂OH) |
| 1-89 | OH | NMe(CH₂CH₂OMe) |
| 1-90 | OH | NMe(CH₂CH₂CH₂OMe) |
| 1-91 | OH | NMe(CH₂CH₂CH₂CH₂OMe) |
| 1-92 | OH | NMe(CH₂CH₂NH₂) |
| 1-93 | OH | NMe(CH₂CH₂CH₂NH₂) |
| 1-94 | OH | NMe(CH₂CH₂CH₂CH₂NH₂) |
| 1-95 | OH | NMe(CH₂CH₂NHMe) |
| 1-96 | OH | NMe(CH₂CH₂CH₂NHMe) |
| 1-97 | OH | NMe(CH₂CH₂CH₂CH₂NHMe) |
| 1-98 | OH | NMe(CH₂CH₂NMe₂) |
| 1-99 | OH | NMe(CH₂CH₂CH₂NMe₂) |
| 1-100 | OH | NMe(CH₂CH₂CH₂CH₂NMe₂) |
| 1-101 | OH | NMe(CH₂CONH₂) |
| 1-102 | OH | NMe(CH₂CH₂CONH₂) |
| 1-103 | H | NH(CH₂CH₂NHCOMe) |
| 1-104 | H | NH(CH₂CH₂NHCOCH₂Me) |
| 1-105 | H | NH(CH₂CH₂NHCOCH₂CH₂Me) |
| 1-106 | H | NH(CH₂CH₂NHCOCHMe₂) |
| 1-107 | H | NH(CH₂CH₂NHCOCMe₃) |
| 1-108 | H | NH(CH₂CH₂CH₂NHCOMe) |
| 1-109 | H | NH(CH₂CH₂CH₂NHCOCH₂Me) |
| 1-110 | H | NH(CH₂CH₂CH₂NHCOCH₂CH₂Me) |
| 1-111 | H | NH(CH₂CH₂CH₂NHCOCHMe₂) |
| 1-112 | H | NH(CH₂CH₂CH₂NHCOCMe₃) |
| 1-113 | OH | NH(CH₂CH₂NHCOMe) |
| 1-114 | OH | NH(CH₂CH₂NHCOCH₂Me) |
| 1-115 | OH | NH(CH₂CH₂NHCOCH₂CH₂Me) |
| 1-116 | OH | NH(CH₂CH₂NHCOCHMe₂) |
| 1-117 | OH | NH(CH₂CH₂NHCOCMe₃) |
| 1-118 | OH | NH(CH₂CH₂CH₂NHCOMe) |
| 1-119 | OH | NH(CH₂CH₂CH₂NHCOCH₂Me) |
| 1-120 | OH | NH(CH₂CH₂CH₂NHCOCH₂CH₂Me) |
| 1-121 | OH | NH(CH₂CH₂CH₂NHCOCHMe₂) |
| 1-122 | OH | NH(CH₂CH₂CH₂NHCOCMe₃) |

Among the compounds mentioned above, preferred compounds are Exemplary Compound Nos. 1-2, 1-3, 1-5, 1-6, 1-7, 1-11, 1-12, 1-13, 1-17, 1-18, 1-19, 1-20, 1-21, 1-22, 1-23, 1-24, 1-25, 1-35, 1-36, 1-37, 1-53, 1-54, 1-56, 1-57, 1-58, 1-62, 1-63, 1-64, 1-68, 1-69, 1-70, 1-71, 1-72, 1-73, 1-74, 1-75, 1-76, 1-86, 1-87, and 1-88. Exemplary Compound Nos. 1-103, 1-104, 1-105, 1-108, 1-109, 1-110, 1-113, 1-114, 1-115, 1-118, 1-119, and 1-120 are also preferred compounds.

More preferred compounds are Exemplary Compound Nos. 1-2, 1-3, 1-5, 1-6, 1-11, 1-12, 1-17, 1-18, 1-20, 1-21, 1-23, 1-24, 1-35, 1-36, 1-53, 1-54, 1-56, 1-57, 1-62, 1-63, 1-68, 1-69, 1-71, 1-72, 1-74, 1-75, 1-86, and 1-87. Exemplary Compound Nos. 1-103, 1-104, 1-108, 1-109, 1-113, 1-114, 1-118, and 1-119 are also more preferred compounds.

The compounds mentioned in Table 2 are compounds having a structure represented by the following formula (1-B):

TABLE 2

(1-B)

[Structure: isoquinoline fused with tetrahydro ring bearing R¹ and N-cyclohexyl-Z substituent]

| Exemplary Compound No. | R¹ | Z |
|---|---|---|
| 2-1 | H | OH |
| 2-2 | H | NH₂ |
| 2-3 | H | NHMe |
| 2-4 | H | NHBn |
| 2-5 | H | NH(CH₂COOH) |
| 2-6 | H | NH(CH₂CH₂COOH) |
| 2-7 | H | NH(CH₂CH₂CH₂COOH) |
| 2-8 | H | NH(CH₂CN) |
| 2-9 | H | NH(CH₂CH₂CN) |
| 2-10 | H | NH(CH₂CH₂CH₂CN) |
| 2-11 | H | NH(CH₂CH₂OH) |
| 2-12 | H | NH(CH₂CH₂CH₂OH) |
| 2-13 | H | NH(CH₂CH₂CH₂CH₂OH) |
| 2-14 | H | NH(CH₂CH₂OMe) |
| 2-15 | H | NH(CH₂CH₂CH₂OMe) |
| 2-16 | H | NH(CH₂CH₂CH₂CH₂OMe) |
| 2-17 | H | NH(CH₂CH₂NH₂) |
| 2-18 | H | NH(CH₂CH₂CH₂NH₂) |
| 2-19 | H | NH(CH₂CH₂CH₂CH₂NH₂) |
| 2-20 | H | NH(CH₂CH₂NHMe) |
| 2-21 | H | NH(CH₂CH₂CH₂NHMe) |
| 2-22 | H | NH(CH₂CH₂CH₂CH₂NHMe) |
| 2-23 | H | NH(CH₂CH₂NMe₂) |
| 2-24 | H | NH(CH₂CH₂CH₂NMe₂) |
| 2-25 | H | NH(CH₂CH₂CH₂CH₂NMe₂) |
| 2-26 | H | NH(CH₂CONH₂) |
| 2-27 | H | NH(CH₂CH₂CONH₂) |
| 2-28 | H | NMeBn |
| 2-29 | H | NMe(CH₂COOH) |
| 2-30 | H | NMe(CH₂CH₂COOH) |
| 2-31 | H | NMe(CH₂CH₂CH₂COOH) |
| 2-32 | H | NMe(CH₂CN) |
| 2-33 | H | NMe(CH₂CH₂CN) |
| 2-34 | H | NMe(CH₂CH₂CH₂CN) |
| 2-35 | H | NMe(CH₂CH₂OH) |
| 2-36 | H | NMe(CH₂CH₂CH₂OH) |
| 2-37 | H | NMe(CH₂CH₂CH₂CH₂OH) |
| 2-38 | H | NMe(CH₂CH₂OMe) |
| 2-39 | H | NMe(CH₂CH₂CH₂OMe) |
| 2-40 | H | NMe(CH₂CH₂CH₂CH₂OMe) |
| 2-41 | H | NMe(CH₂CH₂NH₂) |
| 2-42 | H | NMe(CH₂CH₂CH₂NH₂) |

TABLE 2-continued (1-B)

[Structure: R¹-substituted diazaphenalene with cyclohexyl-Z substituent]

| Exemplary Compound No. | R¹ | Z |
|---|---|---|
| 2-43 | H | NMe(CH₂CH₂CH₂CH₂NH₂) |
| 2-44 | H | NMe(CH₂CH₂NHMe) |
| 2-45 | H | NMe(CH₂CH₂CH₂NHMe) |
| 2-46 | H | NMe(CH₂CH₂CH₂CH₂NHMe) |
| 2-47 | H | NMe(CH₂CH₂NMe₂) |
| 2-48 | H | NMe(CH₂CH₂CH₂NMe₂) |
| 2-49 | H | NMe(CH₂CH₂CH₂CH₂NMe₂) |
| 2-50 | H | NMe(CH₂CONH₂) |
| 2-51 | H | NMe(CH₂CH₂CONH₂) |
| 2-52 | OH | OH |
| 2-53 | OH | NH₂ |
| 2-54 | OH | NHMe |
| 2-55 | OH | NHBn |
| 2-56 | OH | NH(CH₂COOH) |
| 2-57 | OH | NH(CH₂CH₂COOH) |
| 2-58 | OH | NH(CH₂CH₂CH₂COOH) |
| 2-59 | OH | NH(CH₂CN) |
| 2-60 | OH | NH(CH₂CH₂CN) |
| 2-61 | OH | NH(CH₂CH₂CH₂CN) |
| 2-62 | OH | NH(CH₂CH₂OH) |
| 2-63 | OH | NH(CH₂CH₂CH₂OH) |
| 2-64 | OH | NH(CH₂CH₂CH₂CH₂OH) |
| 2-65 | OH | NH(CH₂CH₂OMe) |
| 2-66 | OH | NH(CH₂CH₂CH₂OMe) |
| 2-67 | OH | NH(CH₂CH₂CH₂CH₂OMe) |
| 2-68 | OH | NH(CH₂CH₂NH₂) |
| 2-69 | OH | NH(CH₂CH₂CH₂NH₂) |
| 2-70 | OH | NH(CH₂CH₂CH₂CH₂NH₂) |
| 2-71 | OH | NH(CH₂CH₂NHMe) |
| 2-72 | OH | NH(CH₂CH₂CH₂NHMe) |
| 2-73 | OH | NH(CH₂CH₂CH₂CH₂NHMe) |
| 2-74 | OH | NH(CH₂CH₂NMe₂) |
| 2-75 | OH | NH(CH₂CH₂CH₂NMe₂) |
| 2-76 | OH | NH(CH₂CH₂CH₂CH₂NMe₂) |
| 2-77 | OH | NH(CH₂CONH₂) |
| 2-78 | OH | NH(CH₂CH₂CONH₂) |
| 2-79 | OH | NMeBn |
| 2-80 | OH | NMe(CH₂COOH) |
| 2-81 | OH | NMe(CH₂CH₂COOH) |
| 2-82 | OH | NMe(CH₂CH₂CH₂COOH) |
| 2-83 | OH | NMe(CH₂CN) |
| 2-84 | OH | NMe(CH₂CH₂CN) |
| 2-85 | OH | NMe(CH₂CH₂CH₂CN) |
| 2-86 | OH | NMe(CH₂CH₂OH) |
| 2-87 | OH | NMe(CH₂CH₂CH₂OH) |
| 2-88 | OH | NMe(CH₂CH₂CH₂CH₂OH) |
| 2-89 | OH | NMe(CH₂CH₂OMe) |
| 2-90 | OH | NMe(CH₂CH₂CH₂OMe) |
| 2-91 | OH | NMe(CH₂CH₂CH₂CH₂OMe) |
| 2-92 | OH | NMe(CH₂CH₂NH₂) |
| 2-93 | OH | NMe(CH₂CH₂CH₂NH₂) |
| 2-94 | OH | NMe(CH₂CH₂CH₂CH₂NH₂) |
| 2-95 | OH | NMe(CH₂CH₂NHMe) |
| 2-96 | OH | NMe(CH₂CH₂CH₂NHMe) |
| 2-97 | OH | NMe(CH₂CH₂CH₂CH₂NHMe) |
| 2-98 | OH | NMe(CH₂CH₂NMe₂) |
| 2-99 | OH | NMe(CH₂CH₂CH₂NMe₂) |
| 2-100 | OH | NMe(CH₂CH₂CH₂CH₂NMe₂) |
| 2-101 | OH | NMe(CH₂CONH₂) |
| 2-102 | OH | NMe(CH₂CH₂CONH₂) |

TABLE 2-continued (1-B)

[Structure: R¹-substituted diazaphenalene with cyclohexyl-Z substituent]

| Exemplary Compound No. | R¹ | Z |
|---|---|---|
| 2-103 | H | NH(CH₂CH₂NHCOMe) |
| 2-104 | H | NH(CH₂CH₂NHCOCH₂Me) |
| 2-105 | H | NH(CH₂CH₂NHCOCH₂CH₂Me) |
| 2-106 | H | NH(CH₂CH₂NHCOCHMe₂) |
| 2-107 | H | NH(CH₂CH₂NHCOCMe₃) |
| 2-108 | H | NH(CH₂CH₂CH₂NHCOMe) |
| 2-109 | H | NH(CH₂CH₂CH₂NHCOCH₂Me) |
| 2-110 | H | NH(CH₂CH₂CH₂NHCOCH₂CH₂Me) |
| 2-111 | H | NH(CH₂CH₂CH₂NHCOCHMe₂) |
| 2-112 | H | NH(CH₂CH₂CH₂NHCOCMe₃) |
| 2-113 | OH | NH(CH₂CH₂NHCOMe) |
| 2-114 | OH | NH(CH₂CH₂NHCOCH₂Me) |
| 2-115 | OH | NH(CH₂CH₂NHCOCH₂CH₂Me) |
| 2-116 | OH | NH(CH₂CH₂NHCOCHMe₂) |
| 2-117 | OH | NH(CH₂CH₂NHCOCMe₃) |
| 2-118 | OH | NH(CH₂CH₂CH₂NHCOMe) |
| 2-119 | OH | NH(CH₂CH₂CH₂NHCOCH₂Me) |
| 2-120 | OH | NH(CH₂CH₂CH₂NHCOCH₂CH₂Me) |
| 2-121 | OH | NH(CH₂CH₂CH₂NHCOCHMe₂) |
| 2-122 | OH | NH(CH₂CH₂CH₂NHCOCMe₃) |

Among the compounds mentioned above, preferred compounds are Exemplary Compound Nos. 2-2, 2-3, 2-5, 2-6, 2-7, 2-11, 2-12, 2-13, 2-17, 2-18, 2-19, 2-20, 2-21, 2-22, 2-23, 2-24, 2-25, 2-35, 2-36, 2-37, 2-53, 2-54, 2-56, 2-57, 2-58, 2-62, 2-63, 2-64, 2-68, 2-69, 2-70, 2-71, 2-72, 2-73, 2-74, 2-75, 2-76, 2-86, 2-87, and 2-88. Exemplary Compound Nos. 2-103, 2-104, 2-105, 2-108, 2-109, 2-110, 2-113, 2-114, 2-115, 2-118, 2-119, and 2-120 are also preferred compounds.

More preferred compounds are Exemplary Compound Nos. 2-2, 2-3, 2-5, 2-6, 2-11, 2-12, 2-17, 2-18, 2-20, 2-21, 2-23, 2-24, 2-35, 2-36, 2-53, 2-54, 2-56, 2-57, 2-62, 2-63, 2-68, 2-69, 2-71, 2-72, 2-74, 2-75, 2-86, and 2-87. Exemplary Compound Nos. 2-103, 2-104, 2-108, 2-109, 2-113, 2-114, 2-118, and 2-119 are also more preferred compounds.

Further, trans-[4-(2,3-dihydro-1,5-diazaphenalen-1-yl) cyclohexyl]dimethylamine (Exemplary Compound No. 2-123), and trans-1-(4-dimethylaminocyclohexyl)-2,3-dihydro-1H-1,5-diazaphenalen-6-ol (Exemplary Compound No. 2-124) are also preferred compounds.

The compounds mentioned in Table 3 are compounds having a structure represented by the following formula (1-C):

TABLE 3

(1-C)

[Structure: Fused tricyclic isoquinoline-containing ring system with R¹ substituent and N-cyclohexyl group bearing Z substituent]

| Exemplary Compound No. | R¹ | Z |
|---|---|---|
| 3-1 | H | OH |
| 3-2 | H | NH₂ |
| 3-3 | H | NHMe |
| 3-4 | H | NHBn |
| 3-5 | H | NH(CH₂COOH) |
| 3-6 | H | NH(CH₂CH₂COOH) |
| 3-7 | H | NH(CH₂CH₂CH₂COOH) |
| 3-8 | H | NH(CH₂CN) |
| 3-9 | H | NH(CH₂CH₂CN) |
| 3-10 | H | NH(CH₂CH₂CH₂CN) |
| 3-11 | H | NH(CH₂CH₂OH) |
| 3-12 | H | NH(CH₂CH₂CH₂OH) |
| 3-13 | H | NH(CH₂CH₂CH₂CH₂OH) |
| 3-14 | H | NH(CH₂CH₂OMe) |
| 3-15 | H | NH(CH₂CH₂CH₂OMe) |
| 3-16 | H | NH(CH₂CH₂CH₂CH₂OMe) |
| 3-17 | H | NH(CH₂CH₂NH₂) |
| 3-18 | H | NH(CH₂CH₂CH₂NH₂) |
| 3-19 | H | NH(CH₂CH₂CH₂CH₂NH₂) |
| 3-20 | H | NH(CH₂CH₂NHMe) |
| 3-21 | H | NH(CH₂CH₂CH₂NHMe) |
| 3-22 | H | NH(CH₂CH₂CH₂CH₂NHMe) |
| 3-23 | H | NH(CH₂CH₂NMe₂) |
| 3-24 | H | NH(CH₂CH₂CH₂NMe₂) |
| 3-25 | H | NH(CH₂CH₂CH₂CH₂NMe₂) |
| 3-26 | H | NH(CH₂CONH₂) |
| 3-27 | H | NH(CH₂CH₂CONH₂) |
| 3-28 | H | NMeBn |
| 3-29 | H | NMe(CH₂COOH) |
| 3-30 | H | NMe(CH₂CH₂COOH) |
| 3-31 | H | NMe(CH₂CH₂CH₂COOH) |
| 3-32 | H | NMe(CH₂CN) |
| 3-33 | H | NMe(CH₂CH₂CN) |
| 3-34 | H | NMe(CH₂CH₂CH₂CN) |
| 3-35 | H | NMe(CH₂CH₂OH) |
| 3-36 | H | NMe(CH₂CH₂CH₂OH) |
| 3-37 | H | NMe(CH₂CH₂CH₂CH₂OH) |
| 3-38 | H | NMe(CH₂CH₂OMe) |
| 3-39 | H | NMe(CH₂CH₂CH₂OMe) |
| 3-40 | H | NMe(CH₂CH₂CH₂CH₂OMe) |
| 3-41 | H | NMe(CH₂CH₂NH₂) |
| 3-42 | H | NMe(CH₂CH₂CH₂NH₂) |
| 3-43 | H | NMe(CH₂CH₂CH₂CH₂NH₂) |
| 3-44 | H | NMe(CH₂CH₂NHMe) |
| 3-45 | H | NMe(CH₂CH₂CH₂NHMe) |
| 3-46 | H | NMe(CH₂CH₂CH₂CH₂NHMe) |
| 3-47 | H | NMe(CH₂CH₂NMe₂) |
| 3-48 | H | NMe(CH₂CH₂CH₂NMe₂) |
| 3-49 | H | NMe(CH₂CH₂CH₂CH₂NMe₂) |
| 3-50 | H | NMe(CH₂CONH₂) |
| 3-51 | H | NMe(CH₂CH₂CONH₂) |
| 3-52 | OH | OH |
| 3-53 | OH | NH₂ |
| 3-54 | OH | NHMe |
| 3-55 | OH | NHBn |
| 3-56 | OH | NH(CH₂COOH) |
| 3-57 | OH | NH(CH₂CH₂COOH) |
| 3-58 | OH | NH(CH₂CH₂CH₂COOH) |
| 3-59 | OH | NH(CH₂CN) |
| 3-60 | OH | NH(CH₂CH₂CN) |
| 3-61 | OH | NH(CH₂CH₂CH₂CN) |
| 3-62 | OH | NH(CH₂CH₂OH) |
| 3-63 | OH | NH(CH₂CH₂CH₂OH) |
| 3-64 | OH | NH(CH₂CH₂CH₂CH₂OH) |
| 3-65 | OH | NH(CH₂CH₂OMe) |
| 3-66 | OH | NH(CH₂CH₂CH₂OMe) |
| 3-67 | OH | NH(CH₂CH₂CH₂CH₂OMe) |
| 3-68 | OH | NH(CH₂CH₂NH₂) |
| 3-69 | OH | NH(CH₂CH₂CH₂NH₂) |
| 3-70 | OH | NH(CH₂CH₂CH₂CH₂NH₂) |
| 3-71 | OH | NH(CH₂CH₂NHMe) |
| 3-72 | OH | NH(CH₂CH₂CH₂NHMe) |
| 3-73 | OH | NH(CH₂CH₂CH₂CH₂NHMe) |
| 3-74 | OH | NH(CH₂CH₂NMe₂) |
| 3-75 | OH | NH(CH₂CH₂CH₂NMe₂) |
| 3-76 | OH | NH(CH₂CH₂CH₂CH₂NMe₂) |
| 3-77 | OH | NH(CH₂CONH₂) |
| 3-78 | OH | NH(CH₂CH₂CONH₂) |
| 3-79 | OH | NMeBn |
| 3-80 | OH | NMe(CH₂COOH) |
| 3-81 | OH | NMe(CH₂CH₂COOH) |
| 3-82 | OH | NMe(CH₂CH₂CH₂COOH) |
| 3-83 | OH | NMe(CH₂CN) |
| 3-84 | OH | NMe(CH₂CH₂CN) |
| 3-85 | OH | NMe(CH₂CH₂CH₂CN) |
| 3-86 | OH | NMe(CH₂CH₂OH) |
| 3-87 | OH | NMe(CH₂CH₂CH₂OH) |
| 3-88 | OH | NMe(CH₂CH₂CH₂CH₂OH) |
| 3-89 | OH | NMe(CH₂CH₂OMe) |
| 3-90 | OH | NMe(CH₂CH₂CH₂OMe) |
| 3-91 | OH | NMe(CH₂CH₂CH₂CH₂OMe) |
| 3-92 | OH | NMe(CH₂CH₂NH₂) |
| 3-93 | OH | NMe(CH₂CH₂CH₂NH₂) |
| 3-94 | OH | NMe(CH₂CH₂CH₂CH₂NH₂) |
| 3-95 | OH | NMe(CH₂CH₂NHMe) |
| 3-96 | OH | NMe(CH₂CH₂CH₂NHMe) |
| 3-97 | OH | NMe(CH₂CH₂CH₂CH₂NHMe) |
| 3-98 | OH | NMe(CH₂CH₂NMe₂) |
| 3-99 | OH | NMe(CH₂CH₂CH₂NMe₂) |
| 3-100 | OH | NMe(CH₂CH₂CH₂CH₂NMe₂) |
| 3-101 | OH | NMe(CH₂CONH₂) |
| 3-102 | OH | NMe(CH₂CH₂CONH₂) |
| 3-103 | H | NH(CH₂CH₂NHCOMe) |
| 3-104 | H | NH(CH₂CH₂NHCOCH₂Me) |
| 3-105 | H | NH(CH₂CH₂NHCOCH₂CH₂Me) |
| 3-106 | H | NH(CH₂CH₂NHCOCHMe₂) |
| 3-107 | H | NH(CH₂CH₂NHCOCMe₃) |
| 3-108 | H | NH(CH₂CH₂CH₂NHCOMe) |
| 3-109 | H | NH(CH₂CH₂CH₂NHCOCH₂Me) |
| 3-110 | H | NH(CH₂CH₂CH₂NHCOCH₂CH₂Me) |
| 3-111 | H | NH(CH₂CH₂CH₂NHCOCHMe₂) |
| 3-112 | H | NH(CH₂CH₂CH₂NHCOCMe₃) |
| 3-113 | OH | NH(CH₂CH₂NHCOMe) |
| 3-114 | OH | NH(CH₂CH₂NHCOCH₂Me) |
| 3-115 | OH | NH(CH₂CH₂NHCOCH₂CH₂Me) |
| 3-116 | OH | NH(CH₂CH₂NHCOCHMe₂) |
| 3-117 | OH | NH(CH₂CH₂NHCOCMe₃) |
| 3-118 | OH | NH(CH₂CH₂CH₂NHCOMe) |
| 3-119 | OH | NH(CH₂CH₂CH₂NHCOCH₂Me) |
| 3-120 | OH | NH(CH₂CH₂CH₂NHCOCH₂CH₂Me) |

TABLE 3-continued (1-C)

[Structure of formula (1-C): R¹-substituted diazaphenalene with N-cyclohexyl-Z group]

| Exemplary Compound No. | R¹ | Z |
|---|---|---|
| 3-121 | OH | NH(CH₂CH₂CH₂NHCOCHMe₂) |
| 3-122 | OH | NH(CH₂CH₂CH₂NHCOCMe₃) |

Among the compounds mentioned above, preferred compounds are Exemplary Compound Nos. 3-2, 3-3, 3-5, 3-6, 3-7, 3-11, 3-12, 3-13, 3-17, 3-18, 3-19, 3-20, 3-21, 3-22, 3-23, 3-24, 3-25, 3-35, 3-36, 3-37, 3-53, 3-54, 3-56, 3-57, 3-58, 3-62, 3-63, 3-64, 3-68, 3-69, 3-70, 3-71, 3-72, 3-73, 3-74, 3-75, 3-76, 3-86, 3-87, and 3-88. Exemplary Compound Nos. 3-103, 3-104, 3-105, 3-108, 3-109, 3-110, 3-113, 3-114, 3-115, 3-118, 3-119, and 3-120 are also preferred compounds.

More preferred compounds are Exemplary Compound Nos. 3-2, 3-3, 3-5, 3-6, 3-11, 3-12, 3-17, 3-18, 3-20, 3-21, 3-23, 3-24, 3-35, 3-36, 3-53, 3-54, 3-56, 3-57, 3-62, 3-63, 3-68, 3-69, 3-71, 3-72, 3-74, 3-75, 3-86, and 3-87. Exemplary Compound Nos. 3-103, 3-104, 3-108, 3-109, 3-113, 3-114, 3-118, and 3-119 are also more preferred compounds.

Further, cis-[4-(2,3-dihydro-1,5-diazaphenalen-1-yl)cyclohexyl]dimethylamine (Exemplary Compound No. 3-123), and cis-1-(4-dimethylaminocyclohexyl)-2,3-dihydro-1H-1,5-diazaphenalen-6-ol (Exemplary Compound No. 3-124) are also preferred compounds.

The compounds mentioned in Table 4 are compounds having a structure represented by the following formula (1-D):

TABLE 4

(1-D)

[Structure of formula (1-D): R¹-substituted diazaphenalene with N-CH₂-cyclohexyl-Z group]

| Exemplary Compound No. | R¹ | Z |
|---|---|---|
| 4-1 | H | OH |
| 4-2 | H | NH₂ |
| 4-3 | H | NHMe |
| 4-4 | H | NHBn |
| 4-5 | H | NH(CH₂COOH) |
| 4-6 | H | NH(CH₂CH₂COOH) |
| 4-7 | H | NH(CH₂CH₂CH₂COOH) |
| 4-8 | H | NH(CH₂CN) |
| 4-9 | H | NH(CH₂CH₂CN) |
| 4-10 | H | NH(CH₂CH₂CH₂CN) |
| 4-11 | H | NH(CH₂CH₂OH) |
| 4-12 | H | NH(CH₂CH₂CH₂OH) |
| 4-13 | H | NH(CH₂CH₂CH₂CH₂OH) |
| 4-14 | H | NH(CH₂CH₂OMe) |
| 4-15 | H | NH(CH₂CH₂CH₂OMe) |
| 4-16 | H | NH(CH₂CH₂CH₂CH₂OMe) |
| 4-17 | H | NH(CH₂CH₂NH₂) |
| 4-18 | H | NH(CH₂CH₂CH₂NH₂) |
| 4-19 | H | NH(CH₂CH₂CH₂CH₂NH₂) |
| 4-20 | H | NH(CH₂CH₂NHMe) |
| 4-21 | H | NH(CH₂CH₂CH₂NHMe) |
| 4-22 | H | NH(CH₂CH₂CH₂CH₂NHMe) |
| 4-23 | H | NH(CH₂CH₂NMe₂) |
| 4-24 | H | NH(CH₂CH₂CH₂NMe₂) |
| 4-25 | H | NH(CH₂CH₂CH₂CH₂NMe₂) |
| 4-26 | H | NH(CH₂CONH₂) |
| 4-27 | H | NH(CH₂CH₂CONH₂) |
| 4-28 | H | NMeBn |
| 4-29 | H | NMe(CH₂COOH) |
| 4-30 | H | NMe(CH₂CH₂COOH) |
| 4-31 | H | NMe(CH₂CH₂CH₂COOH) |
| 4-32 | H | NMe(CH₂CN) |
| 4-33 | H | NMe(CH₂CH₂CN) |
| 4-34 | H | NMe(CH₂CH₂CH₂CN) |
| 4-35 | H | NMe(CH₂CH₂OH) |
| 4-36 | H | NMe(CH₂CH₂CH₂OH) |
| 4-37 | H | NMe(CH₂CH₂CH₂CH₂OH) |
| 4-38 | H | NMe(CH₂CH₂OMe) |
| 4-39 | H | NMe(CH₂CH₂CH₂OMe) |
| 4-40 | H | NMe(CH₂CH₂CH₂CH₂OMe) |
| 4-41 | H | NMe(CH₂CH₂NH₂) |
| 4-42 | H | NMe(CH₂CH₂CH₂NH₂) |
| 4-43 | H | NMe(CH₂CH₂CH₂CH₂NH₂) |
| 4-44 | H | NMe(CH₂CH₂NHMe) |
| 4-45 | H | NMe(CH₂CH₂CH₂NHMe) |
| 4-46 | H | NMe(CH₂CH₂CH₂CH₂NHMe) |
| 4-47 | H | NMe(CH₂CH₂NMe₂) |
| 4-48 | H | NMe(CH₂CH₂CH₂NMe₂) |
| 4-49 | H | NMe(CH₂CH₂CH₂CH₂NMe₂) |
| 4-50 | H | NMe(CH₂CONH₂) |
| 4-51 | H | NMe(CH₂CH₂CONH₂) |
| 4-52 | OH | OH |
| 4-53 | OH | NH₂ |
| 4-54 | OH | NHMe |
| 4-55 | OH | NHBn |
| 4-56 | OH | NH(CH₂COOH) |
| 4-57 | OH | NH(CH₂CH₂COOH) |
| 4-58 | OH | NH(CH₂CH₂CH₂COOH) |
| 4-59 | OH | NH(CH₂CN) |
| 4-60 | OH | NH(CH₂CH₂CN) |
| 4-61 | OH | NH(CH₂CH₂CH₂CN) |
| 4-62 | OH | NH(CH₂CH₂OH) |
| 4-63 | OH | NH(CH₂CH₂CH₂OH) |
| 4-64 | OH | NH(CH₂CH₂CH₂CH₂OH) |
| 4-65 | OH | NH(CH₂CH₂OMe) |
| 4-66 | OH | NH(CH₂CH₂CH₂OMe) |
| 4-67 | OH | NH(CH₂CH₂CH₂CH₂OMe) |
| 4-68 | OH | NH(CH₂CH₂NH₂) |
| 4-69 | OH | NH(CH₂CH₂CH₂NH₂) |
| 4-70 | OH | NH(CH₂CH₂CH₂CH₂NH₂) |
| 4-71 | OH | NH(CH₂CH₂NHMe) |
| 4-72 | OH | NH(CH₂CH₂CH₂NHMe) |

More preferred compounds are Exemplary Compound Nos. 4-2, 4-3, 4-5, 4-6, 4-11, 4-12, 4-17, 4-18, 4-20, 4-21, 4-23, 4-24, 4-35, 4-36, 4-53, 4-54, 4-56, 4-57, 4-62, 4-63, 4-68, 4-69, 4-71, 4-72, 4-74, 4-75, 4-86, and 4-87. Exemplary Compound Nos. 4-103, 4-104, 4-108, 4-109, 4-113, 4-114, 4-118, and 4-119 are also more preferred compounds.

The compounds mentioned in Table 5 are compounds having a structure represented by the following formula (1-E):

TABLE 4-continued (1-D)

| Exemplary Compound No. | $R^1$ | Z |
|---|---|---|
| 4-73 | OH | NH(CH$_2$CH$_2$CH$_2$CH$_2$NHMe) |
| 4-74 | OH | NH(CH$_2$CH$_2$NMe$_2$) |
| 4-75 | OH | NH(CH$_2$CH$_2$CH$_2$NMe$_2$) |
| 4-76 | OH | NH(CH$_2$CH$_2$CH$_2$CH$_2$NMe$_2$) |
| 4-77 | OH | NH(CH$_2$CONH$_2$) |
| 4-78 | OH | NH(CH$_2$CH$_2$CONH$_2$) |
| 4-79 | OH | NMeBn |
| 4-80 | OH | NMe(CH$_2$COOH) |
| 4-81 | OH | NMe(CH$_2$CH$_2$COOH) |
| 4-82 | OH | NMe(CH$_2$CH$_2$CH$_2$COOH) |
| 4-83 | OH | NMe(CH$_2$CN) |
| 4-84 | OH | NMe(CH$_2$CH$_2$CN) |
| 4-85 | OH | NMe(CH$_2$CH$_2$CH$_2$CN) |
| 4-86 | OH | NMe(CH$_2$OH) |
| 4-87 | OH | NMe(CH$_2$CH$_2$OH) |
| 4-88 | OH | NMe(CH$_2$CH$_2$CH$_2$OH) |
| 4-89 | OH | NMe(CH$_2$CH$_2$OMe) |
| 4-90 | OH | NMe(CH$_2$CH$_2$CH$_2$OMe) |
| 4-91 | OH | NMe(CH$_2$CH$_2$CH$_2$CH$_2$OMe) |
| 4-92 | OH | NMe(CH$_2$CH$_2$NH$_2$) |
| 4-93 | OH | NMe(CH$_2$CH$_2$CH$_2$NH$_2$) |
| 4-94 | OH | NMe(CH$_2$CH$_2$CH$_2$CH$_2$NH$_2$) |
| 4-95 | OH | NMe(CH$_2$CH$_2$NHMe) |
| 4-96 | OH | NMe(CH$_2$CH$_2$CH$_2$NHMe) |
| 4-97 | OH | NMe(CH$_2$CH$_2$CH$_2$CH$_2$NHMe) |
| 4-98 | OH | NMe(CH$_2$CH$_2$NMe$_2$) |
| 4-99 | OH | NMe(CH$_2$CH$_2$CH$_2$NMe$_2$) |
| 4-100 | OH | NMe(CH$_2$CH$_2$CH$_2$CH$_2$NMe$_2$) |
| 4-101 | OH | NMe(CH$_2$CONH$_2$) |
| 4-102 | OH | NMe(CH$_2$CH$_2$CONH$_2$) |
| 4-103 | H | NH(CH$_2$CH$_2$NHCOMe) |
| 4-104 | H | NH(CH$_2$CH$_2$NHCOCH$_2$Me) |
| 4-105 | H | NH(CH$_2$CH$_2$NHCOCH$_2$CH$_2$Me) |
| 4-106 | H | NH(CH$_2$CH$_2$NHCOCHMe$_2$) |
| 4-107 | H | NH(CH$_2$CH$_2$NHCOCMe$_3$) |
| 4-108 | H | NH(CH$_2$CH$_2$CH$_2$NHCOMe) |
| 4-109 | H | NH(CH$_2$CH$_2$CH$_2$NHCOCH$_2$Me) |
| 4-110 | H | NH(CH$_2$CH$_2$CH$_2$NHCOCH$_2$CH$_2$Me) |
| 4-111 | H | NH(CH$_2$CH$_2$CH$_2$NHCOCHMe$_2$) |
| 4-112 | H | NH(CH$_2$CH$_2$CH$_2$NHCOCMe$_3$) |
| 4-113 | OH | NH(CH$_2$CH$_2$NHCOMe) |
| 4-114 | OH | NH(CH$_2$CH$_2$NHCOCH$_2$Me) |
| 4-115 | OH | NH(CH$_2$CH$_2$NHCOCH$_2$CH$_2$Me) |
| 4-116 | OH | NH(CH$_2$CH$_2$NHCOCHMe$_2$) |
| 4-117 | OH | NH(CH$_2$CH$_2$NHCOCMe$_3$) |
| 4-118 | OH | NH(CH$_2$CH$_2$CH$_2$NHCOMe) |
| 4-119 | OH | NH(CH$_2$CH$_2$CH$_2$NHCOCH$_2$Me) |
| 4-120 | OH | NH(CH$_2$CH$_2$CH$_2$NHCOCH$_2$CH$_2$Me) |
| 4-121 | OH | NH(CH$_2$CH$_2$CH$_2$NHCOCHMe$_2$) |
| 4-122 | OH | NH(CH$_2$CH$_2$CH$_2$NHCOCMe$_3$) |

Among the compounds mentioned above, preferred compounds are Exemplary Compound Nos. 4-2, 4-3, 4-5, 4-6, 4-7, 4-11, 4-12, 4-13, 4-17, 4-18, 4-19, 4-20, 4-21, 4-22, 4-23, 4-24, 4-25, 4-35, 4-36, 4-37, 4-53, 4-54, 4-56, 4-57, 4-58, 4-62, 4-63, 4-64, 4-68, 4-69, 4-70, 4-71, 4-72, 4-73, 4-74, 4-75, 4-76, 4-86, 4-87, and 4-88. Exemplary Compound Nos. 4-103, 4-104, 4-105, 4-108, 4-109, 4-110, 4-113, 4-114, 4-115, 4-118, 4-119, and 4-120 are also preferred compounds.

TABLE 5 (1-E)

| Exemplary Compound No. | $R^1$ | Z |
|---|---|---|
| 5-1 | H | OH |
| 5-2 | H | NH$_2$ |
| 5-3 | H | NHMe |
| 5-4 | H | NHBn |
| 5-5 | H | NH(CH$_2$COOH) |
| 5-6 | H | NH(CH$_2$CH$_2$COOH) |
| 5-7 | H | NH(CH$_2$CH$_2$CH$_2$COOH) |
| 5-8 | H | NH(CH$_2$CN) |
| 5-9 | H | NH(CH$_2$CH$_2$CN) |
| 5-10 | H | NH(CH$_2$CH$_2$CH$_2$CN) |
| 5-11 | H | NH(CH$_2$CH$_2$OH) |
| 5-12 | H | NH(CH$_2$CH$_2$CH$_2$OH) |
| 5-13 | H | NH(CH$_2$CH$_2$CH$_2$CH$_2$OH) |
| 5-14 | H | NH(CH$_2$CH$_2$OMe) |
| 5-15 | H | NH(CH$_2$CH$_2$CH$_2$OMe) |
| 5-16 | H | NH(CH$_2$CH$_2$CH$_2$CH$_2$OMe) |
| 5-17 | H | NH(CH$_2$CH$_2$NH$_2$) |
| 5-18 | H | NH(CH$_2$CH$_2$CH$_2$NH$_2$) |
| 5-19 | H | NH(CH$_2$CH$_2$CH$_2$CH$_2$NH$_2$) |
| 5-20 | H | NH(CH$_2$CH$_2$NHMe) |
| 5-21 | H | NH(CH$_2$CH$_2$CH$_2$NHMe) |
| 5-22 | H | NH(CH$_2$CH$_2$CH$_2$CH$_2$NHMe) |
| 5-23 | H | NH(CH$_2$CH$_2$NMe$_2$) |
| 5-24 | H | NH(CH$_2$CH$_2$CH$_2$NMe$_2$) |
| 5-25 | H | NH(CH$_2$CH$_2$CH$_2$CH$_2$NMe$_2$) |
| 5-26 | H | NH(CH$_2$CONH$_2$) |
| 5-27 | H | NH(CH$_2$CH$_2$CONH$_2$) |
| 5-28 | H | NMeBn |
| 5-29 | H | NMe(CH$_2$COOH) |
| 5-30 | H | NMe(CH$_2$CH$_2$COOH) |
| 5-31 | H | NMe(CH$_2$CH$_2$CH$_2$COOH) |
| 5-32 | H | NMe(CH$_2$CN) |
| 5-33 | H | NMe(CH$_2$CH$_2$CN) |
| 5-34 | H | NMe(CH$_2$CH$_2$CH$_2$CN) |
| 5-35 | H | NMe(CH$_2$OH) |
| 5-36 | H | NMe(CH$_2$CH$_2$OH) |
| 5-37 | H | NMe(CH$_2$CH$_2$CH$_2$OH) |
| 5-38 | H | NMe(CH$_2$CH$_2$OMe) |
| 5-39 | H | NMe(CH$_2$CH$_2$CH$_2$OMe) |
| 5-40 | H | NMe(CH$_2$CH$_2$CH$_2$CH$_2$OMe) |
| 5-41 | H | NMe(CH$_2$CH$_2$NH$_2$) |
| 5-42 | H | NMe(CH$_2$CH$_2$CH$_2$NH$_2$) |
| 5-43 | H | NMe(CH$_2$CH$_2$CH$_2$CH$_2$NH$_2$) |
| 5-44 | H | NMe(CH$_2$CH$_2$NHMe) |
| 5-45 | H | NMe(CH$_2$CH$_2$CH$_2$NHMe) |
| 5-46 | H | NMe(CH$_2$CH$_2$CH$_2$CH$_2$NHMe) |
| 5-47 | H | NMe(CH$_2$CH$_2$NMe$_2$) |
| 5-48 | H | NMe(CH$_2$CH$_2$CH$_2$NMe$_2$) |
| 5-49 | H | NMe(CH$_2$CH$_2$CH$_2$CH$_2$NMe$_2$) |
| 5-50 | H | NMe(CH$_2$CONH$_2$) |
| 5-51 | H | NMe(CH$_2$CH$_2$CONH$_2$) |
| 5-52 | OH | OH |

TABLE 5-continued (1-E)

| Exemplary Compound No. | R¹ | Z |
|---|---|---|
| 5-53 | OH | NH₂ |
| 5-54 | OH | NHMe |
| 5-55 | OH | NHBn |
| 5-56 | OH | NH(CH₂COOH) |
| 5-57 | OH | NH(CH₂CH₂COOH) |
| 5-58 | OH | NH(CH₂CH₂CH₂COOH) |
| 5-59 | OH | NH(CH₂CN) |
| 5-60 | OH | NH(CH₂CH₂CN) |
| 5-61 | OH | NH(CH₂CH₂CH₂CN) |
| 5-62 | OH | NH(CH₂CH₂OH) |
| 5-63 | OH | NH(CH₂CH₂CH₂OH) |
| 5-64 | OH | NH(CH₂CH₂CH₂CH₂OH) |
| 5-65 | OH | NH(CH₂CH₂OMe) |
| 5-66 | OH | NH(CH₂CH₂CH₂OMe) |
| 5-67 | OH | NH(CH₂CH₂CH₂CH₂OMe) |
| 5-68 | OH | NH(CH₂CH₂NH₂) |
| 5-69 | OH | NH(CH₂CH₂CH₂NH₂) |
| 5-70 | OH | NH(CH₂CH₂CH₂CH₂NH₂) |
| 5-71 | OH | NH(CH₂CH₂NHMe) |
| 5-72 | OH | NH(CH₂CH₂CH₂NHMe) |
| 5-73 | OH | NH(CH₂CH₂CH₂CH₂NHMe) |
| 5-74 | OH | NH(CH₂CH₂NMe₂) |
| 5-75 | OH | NH(CH₂CH₂CH₂NMe₂) |
| 5-76 | OH | NH(CH₂CH₂CH₂CH₂NMe₂) |
| 5-77 | OH | NH(CH₂CONH₂) |
| 5-78 | OH | NH(CH₂CH₂CONH₂) |
| 5-79 | OH | NMeBn |
| 5-80 | OH | NMe(CH₂COOH) |
| 5-81 | OH | NMe(CH₂CH₂COOH) |
| 5-82 | OH | NMe(CH₂CH₂CH₂COOH) |
| 5-83 | OH | NMe(CH₂CN) |
| 5-84 | OH | NMe(CH₂CH₂CN) |
| 5-85 | OH | NMe(CH₂CH₂CH₂CN) |
| 5-86 | OH | NMe(CH₂CH₂OH) |
| 5-87 | OH | NMe(CH₂CH₂CH₂OH) |
| 5-88 | OH | NMe(CH₂CH₂CH₂CH₂OH) |
| 5-89 | OH | NMe(CH₂CH₂OMe) |
| 5-90 | OH | NMe(CH₂CH₂CH₂OMe) |
| 5-91 | OH | NMe(CH₂CH₂CH₂CH₂OMe) |
| 5-92 | OH | NMe(CH₂CH₂NH₂) |
| 5-93 | OH | NMe(CH₂CH₂CH₂NH₂) |
| 5-94 | OH | NMe(CH₂CH₂CH₂CH₂NH₂) |
| 5-95 | OH | NMe(CH₂CH₂NHMe) |
| 5-96 | OH | NMe(CH₂CH₂CH₂NHMe) |
| 5-97 | OH | NMe(CH₂CH₂CH₂CH₂NHMe) |
| 5-98 | OH | NMe(CH₂CH₂NMe₂) |
| 5-99 | OH | NMe(CH₂CH₂CH₂NMe₂) |
| 5-100 | OH | NMe(CH₂CH₂CH₂CH₂NMe₂) |
| 5-101 | OH | NMe(CH₂CONH₂) |
| 5-102 | OH | NMe(CH₂CH₂CONH₂) |
| 5-103 | H | NH(CH₂CH₂NHCOMe) |
| 5-104 | H | NH(CH₂CH₂NHCOCH₂Me) |
| 5-105 | H | NH(CH₂CH₂NHCOCH₂CH₂Me) |
| 5-106 | H | NH(CH₂CH₂NHCOCHMe₂) |
| 5-107 | H | NH(CH₂CH₂NHCOCMe₃) |
| 5-108 | H | NH(CH₂CH₂CH₂NHCOMe) |
| 5-109 | H | NH(CH₂CH₂CH₂NHCOCH₂Me) |
| 5-110 | H | NH(CH₂CH₂CH₂NHCOCH₂CH₂Me) |
| 5-111 | H | NH(CH₂CH₂CH₂NHCOCHMe₂) |
| 5-112 | H | NH(CH₂CH₂CH₂NHCOCMe₃) |
| 5-113 | OH | NH(CH₂CH₂NHCOMe) |
| 5-114 | OH | NH(CH₂CH₂NHCOCH₂Me) |
| 5-115 | OH | NH(CH₂CH₂NHCOCH₂CH₂Me) |

TABLE 5-continued (1-E)

| Exemplary Compound No. | R¹ | Z |
|---|---|---|
| 5-116 | OH | NH(CH₂CH₂NHCOCHMe₂) |
| 5-117 | OH | NH(CH₂CH₂NHCOCMe₃) |
| 5-118 | OH | NH(CH₂CH₂CH₂NHCOMe) |
| 5-119 | OH | NH(CH₂CH₂CH₂NHCOCH₂Me) |
| 5-120 | OH | NH(CH₂CH₂CH₂NHCOCH₂CH₂Me) |
| 5-121 | OH | NH(CH₂CH₂CH₂NHCOCHMe₂) |
| 5-122 | OH | NH(CH₂CH₂CH₂NHCOCMe₃) |

Among the compounds mentioned above, preferred compounds are Exemplary Compound Nos. 5-2, 5-3, 5-5, 5-6, 5-7, 5-11, 5-12, 5-13, 5-17, 5-18, 5-19, 5-20, 5-21, 5-22, 5-23, 5-24, 5-25, 5-35, 5-36, 5-37, 5-53, 5-54, 5-56, 5-57, 5-58, 5-62, 5-63, 5-64, 5-68, 5-69, 5-70, 5-71, 5-72, 5-73, 5-74, 5-75, 5-76, 5-86, 5-87, and 5-88. Exemplary Compound Nos. 5-103, 5-104, 5-105, 5-108, 5-109, 5-110, 5-113, 5-114, 5-115, 5-118, 5-119, and 5-120 are also preferred compounds.

More preferred compounds are Exemplary Compound Nos. 5-2, 5-3, 5-5, 5-6, 5-11, 5-12, 5-17, 5-18, 5-20, 5-21, 5-23, 5-24, 5-35, 5-36, 5-53, 5-54, 5-56, 5-57, 5-62, 5-63, 5-68, 5-69, 5-71, 5-72, 5-74, 5-75, 5-86, and 5-87. Exemplary Compound Nos. 5-103, 5-104, 5-108, 5-109, 5-113, 5-114, 5-118, and 5-119 are also more preferred compounds.

The compounds mentioned in Table 6 are compounds having a structure represented by the following formula (1-F):

TABLE 6

(1-F)

| Exemplary Compound No. | R¹ | Z |
|---|---|---|
| 6-1 | H | OH |
| 6-2 | H | NH₂ |
| 6-3 | H | NHMe |
| 6-4 | H | NHBn |
| 6-5 | H | NH(CH₂COOH) |
| 6-6 | H | NH(CH₂CH₂COOH) |
| 6-7 | H | NH(CH₂CH₂CH₂COOH) |
| 6-8 | H | NH(CH₂CN) |
| 6-9 | H | NH(CH₂CH₂CN) |
| 6-10 | H | NH(CH₂CH₂CH₂CN) |
| 6-11 | H | NH(CH₂CH₂OH) |

TABLE 6-continued (1-F)

| Exemplary Compound No. | R¹ | Z |
|---|---|---|
| 6-12 | H | NH(CH$_2$CH$_2$CH$_2$OH) |
| 6-13 | H | NH(CH$_2$CH$_2$CH$_2$CH$_2$OH) |
| 6-14 | H | NH(CH$_2$CH$_2$OMe) |
| 6-15 | H | NH(CH$_2$CH$_2$CH$_2$OMe) |
| 6-16 | H | NH(CH$_2$CH$_2$CH$_2$CH$_2$OMe) |
| 6-17 | H | NH(CH$_2$CH$_2$NH$_2$) |
| 6-18 | H | NH(CH$_2$CH$_2$CH$_2$NH$_2$) |
| 6-19 | H | NH(CH$_2$CH$_2$CH$_2$CH$_2$NH$_2$) |
| 6-20 | H | NH(CH$_2$CH$_2$NHMe) |
| 6-21 | H | NH(CH$_2$CH$_2$CH$_2$NHMe) |
| 6-22 | H | NH(CH$_2$CH$_2$CH$_2$CH$_2$NHMe) |
| 6-23 | H | NH(CH$_2$CH$_2$NMe$_2$) |
| 6-24 | H | NH(CH$_2$CH$_2$CH$_2$NMe$_2$) |
| 6-25 | H | NH(CH$_2$CH$_2$CH$_2$CH$_2$NMe$_2$) |
| 6-26 | H | NH(CH$_2$CONH$_2$) |
| 6-27 | H | NH(CH$_2$CH$_2$CONH$_2$) |
| 6-28 | H | NMeBn |
| 6-29 | H | NMe(CH$_2$COOH) |
| 6-30 | H | NMe(CH$_2$CH$_2$COOH) |
| 6-31 | H | NMe(CH$_2$CH$_2$CH$_2$COOH) |
| 6-32 | H | NMe(CH$_2$CN) |
| 6-33 | H | NMe(CH$_2$CH$_2$CN) |
| 6-34 | H | NMe(CH$_2$CH$_2$CH$_2$CN) |
| 6-35 | H | NMe(CH$_2$CH$_2$OH) |
| 6-36 | H | NMe(CH$_2$CH$_2$CH$_2$OH) |
| 6-37 | H | NMe(CH$_2$CH$_2$CH$_2$CH$_2$OH) |
| 6-38 | H | NMe(CH$_2$CH$_2$OMe) |
| 6-39 | H | NMe(CH$_2$CH$_2$CH$_2$OMe) |
| 6-40 | H | NMe(CH$_2$CH$_2$CH$_2$CH$_2$OMe) |
| 6-41 | H | NMe(CH$_2$CH$_2$NH$_2$) |
| 6-42 | H | NMe(CH$_2$CH$_2$CH$_2$NH$_2$) |
| 6-43 | H | NMe(CH$_2$CH$_2$CH$_2$CH$_2$NH$_2$) |
| 6-44 | H | NMe(CH$_2$CH$_2$NHMe) |
| 6-45 | H | NMe(CH$_2$CH$_2$CH$_2$NHMe) |
| 6-46 | H | NMe(CH$_2$CH$_2$CH$_2$CH$_2$NHMe) |
| 6-47 | H | NMe(CH$_2$CH$_2$NMe$_2$) |
| 6-48 | H | NMe(CH$_2$CH$_2$CH$_2$NMe$_2$) |
| 6-49 | H | NMe(CH$_2$CH$_2$CH$_2$CH$_2$NMe$_2$) |
| 6-50 | H | NMe(CH$_2$CONH$_2$) |
| 6-51 | H | NMe(CH$_2$CH$_2$CONH$_2$) |
| 6-52 | OH | OH |
| 6-53 | OH | NH$_2$ |
| 6-54 | OH | NHMe |
| 6-55 | OH | NHBn |
| 6-56 | OH | NH(CH$_2$COOH) |
| 6-57 | OH | NH(CH$_2$CH$_2$COOH) |
| 6-58 | OH | NH(CH$_2$CH$_2$CH$_2$COOH) |
| 6-59 | OH | NH(CH$_2$CN) |
| 6-60 | OH | NH(CH$_2$CH$_2$CN) |
| 6-61 | OH | NH(CH$_2$CH$_2$CH$_2$CN) |
| 6-62 | OH | NH(CH$_2$CH$_2$OH) |
| 6-63 | OH | NH(CH$_2$CH$_2$CH$_2$OH) |
| 6-64 | OH | NH(CH$_2$CH$_2$CH$_2$CH$_2$OH) |
| 6-65 | OH | NH(CH$_2$CH$_2$OMe) |
| 6-66 | OH | NH(CH$_2$CH$_2$CH$_2$OMe) |
| 6-67 | OH | NH(CH$_2$CH$_2$CH$_2$CH$_2$OMe) |
| 6-68 | OH | NH(CH$_2$CH$_2$NH$_2$) |
| 6-69 | OH | NH(CH$_2$CH$_2$CH$_2$NH$_2$) |
| 6-70 | OH | NH(CH$_2$CH$_2$CH$_2$CH$_2$NH$_2$) |
| 6-71 | OH | NH(CH$_2$CH$_2$NHMe) |
| 6-72 | OH | NH(CH$_2$CH$_2$CH$_2$NHMe) |
| 6-73 | OH | NH(CH$_2$CH$_2$CH$_2$CH$_2$NHMe) |
| 6-74 | OH | NH(CH$_2$CH$_2$NMe$_2$) |
| 6-75 | OH | NH(CH$_2$CH$_2$CH$_2$NMe$_2$) |
| 6-76 | OH | NH(CH$_2$CH$_2$CH$_2$CH$_2$NMe$_2$) |
| 6-77 | OH | NH(CH$_2$CONH$_2$) |
| 6-78 | OH | NH(CH$_2$CH$_2$CONH$_2$) |
| 6-79 | OH | NMeBn |
| 6-80 | OH | NMe(CH$_2$COOH) |
| 6-81 | OH | NMe(CH$_2$CH$_2$COOH) |
| 6-82 | OH | NMe(CH$_2$CH$_2$CH$_2$COOH) |
| 6-83 | OH | NMe(CH$_2$CN) |
| 6-84 | OH | NMe(CH$_2$CH$_2$CN) |
| 6-85 | OH | NMe(CH$_2$CH$_2$CH$_2$CN) |
| 6-86 | OH | NMe(CH$_2$CH$_2$OH) |
| 6-87 | OH | NMe(CH$_2$CH$_2$CH$_2$OH) |
| 6-88 | OH | NMe(CH$_2$CH$_2$CH$_2$CH$_2$OH) |
| 6-89 | OH | NMe(CH$_2$CH$_2$OMe) |
| 6-90 | OH | NMe(CH$_2$CH$_2$CH$_2$OMe) |
| 6-91 | OH | NMe(CH$_2$CH$_2$CH$_2$CH$_2$OMe) |
| 6-92 | OH | NMe(CH$_2$CH$_2$NH$_2$) |
| 6-93 | OH | NMe(CH$_2$CH$_2$CH$_2$NH$_2$) |
| 6-94 | OH | NMe(CH$_2$CH$_2$CH$_2$CH$_2$NH$_2$) |
| 6-95 | OH | NMe(CH$_2$CH$_2$NHMe) |
| 6-96 | OH | NMe(CH$_2$CH$_2$CH$_2$NHMe) |
| 6-97 | OH | NMe(CH$_2$CH$_2$CH$_2$CH$_2$NHMe) |
| 6-98 | OH | NMe(CH$_2$CH$_2$NMe$_2$) |
| 6-99 | OH | NMe(CH$_2$CH$_2$CH$_2$NMe$_2$) |
| 6-100 | OH | NMe(CH$_2$CH$_2$CH$_2$CH$_2$NMe$_2$) |
| 6-101 | OH | NMe(CH$_2$CONH$_2$) |
| 6-102 | OH | NMe(CH$_2$CH$_2$CONH$_2$) |
| 6-103 | H | NH(CH$_2$CH$_2$NHCOMe) |
| 6-104 | H | NH(CH$_2$CH$_2$NHCOCH$_2$Me) |
| 6-105 | H | NH(CH$_2$CH$_2$NHCOCH$_2$CH$_2$Me) |
| 6-106 | H | NH(CH$_2$CH$_2$NHCOCHMe$_2$) |
| 6-107 | H | NH(CH$_2$CH$_2$NHCOCMe$_3$) |
| 6-108 | H | NH(CH$_2$CH$_2$CH$_2$NHCOMe) |
| 6-109 | H | NH(CH$_2$CH$_2$CH$_2$NHCOCH$_2$Me) |
| 6-110 | H | NH(CH$_2$CH$_2$CH$_2$NHCOCH$_2$CH$_2$Me) |
| 6-111 | H | NH(CH$_2$CH$_2$CH$_2$NHCOCHMe$_2$) |
| 6-112 | H | NH(CH$_2$CH$_2$CH$_2$NHCOCMe$_3$) |
| 6-113 | OH | NH(CH$_2$CH$_2$NHCOMe) |
| 6-114 | OH | NH(CH$_2$CH$_2$NHCOCH$_2$Me) |
| 6-115 | OH | NH(CH$_2$CH$_2$NHCOCH$_2$CH$_2$Me) |
| 6-116 | OH | NH(CH$_2$CH$_2$NHCOCHMe$_2$) |
| 6-117 | OH | NH(CH$_2$CH$_2$NHCOCMe$_3$) |
| 6-118 | OH | NH(CH$_2$CH$_2$CH$_2$NHCOMe) |
| 6-119 | OH | NH(CH$_2$CH$_2$CH$_2$NHCOCH$_2$Me) |
| 6-120 | OH | NH(CH$_2$CH$_2$CH$_2$NHCOCH$_2$CH$_2$Me) |
| 6-121 | OH | NH(CH$_2$CH$_2$CH$_2$NHCOCHMe$_2$) |
| 6-122 | OH | NH(CH$_2$CH$_2$CH$_2$NHCOCMe$_3$) |

Among the compounds mentioned above, preferred compounds are Exemplary Compound Nos. 6-2, 6-3, 6-5, 6-6, 6-7, 6-11, 6-12, 6-13, 6-17, 6-18, 6-19, 6-20, 6-21, 6-22, 6-23, 6-24, 6-25, 6-35, 6-36, 6-37, 6-53, 6-54, 6-56, 6-57, 6-58, 6-62, 6-63, 6-64, 6-68, 6-69, 6-70, 6-71, 6-72, 6-73, 6-74, 6-75, 6-76, 6-86, 6-87, and 6-88. Exemplary Compound Nos. 6-103, 6-104, 6-105, 6-108, 6-109, 6-110, 6-113, 6-114, 6-115, 6-118, 6-119, and 6-120 are also preferred compounds.

More preferred compounds are Exemplary Compound Nos. 6-2, 6-3, 6-5, 6-6, 6-11, 6-12, 6-17, 6-18, 6-20, 6-21, 6-23, 6-24, 6-35, 6-36, 6-53, 6-54, 6-56, 6-57, 6-62, 6-63, 6-68, 6-69, 6-71, 6-72, 6-74, 6-75, 6-86, and 6-87. Exemplary Compound Nos. 6-103, 6-104, 6-108, 6-109, 6-113, 6-114, 6-118, and 6-119 are also more preferred compounds.

The compounds mentioned in Table 7 are compounds having a structure represented by the following formula (1-G):

TABLE 7

(1-G)

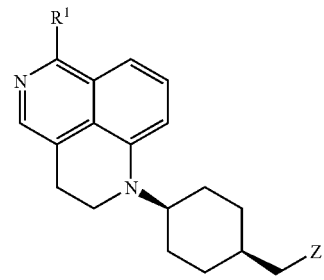

| Exemplary Compound No. | $R^1$ | Z |
|---|---|---|
| 7-1 | H | OH |
| 7-2 | H | $NH_2$ |
| 7-3 | H | NHMe |
| 7-4 | H | NHBn |
| 7-5 | H | $NH(CH_2COOH)$ |
| 7-6 | H | $NH(CH_2CH_2COOH)$ |
| 7-7 | H | $NH(CH_2CH_2CH_2COOH)$ |
| 7-8 | H | $NH(CH_2CN)$ |
| 7-9 | H | $NH(CH_2CH_2CN)$ |
| 7-10 | H | $NH(CH_2CH_2CH_2CN)$ |
| 7-11 | H | $NH(CH_2CH_2OH)$ |
| 7-12 | H | $NH(CH_2CH_2CH_2OH)$ |
| 7-13 | H | $NH(CH_2CH_2CH_2CH_2OH)$ |
| 7-14 | H | $NH(CH_2CH_2OMe)$ |
| 7-15 | H | $NH(CH_2CH_2CH_2OMe)$ |
| 7-16 | H | $NH(CH_2CH_2CH_2CH_2OMe)$ |
| 7-17 | H | $NH(CH_2CH_2NH_2)$ |
| 7-18 | H | $NH(CH_2CH_2CH_2NH_2)$ |
| 7-19 | H | $NH(CH_2CH_2CH_2CH_2NH_2)$ |
| 7-20 | H | $NH(CH_2CH_2NHMe)$ |
| 7-21 | H | $NH(CH_2CH_2CH_2NHMe)$ |
| 7-22 | H | $NH(CH_2CH_2CH_2CH_2NHMe)$ |
| 7-23 | H | $NH(CH_2CH_2NMe_2)$ |
| 7-24 | H | $NH(CH_2CH_2CH_2NMe_2)$ |
| 7-25 | H | $NH(CH_2CH_2CH_2CH_2NMe_2)$ |
| 7-26 | H | $NH(CH_2CONH_2)$ |
| 7-27 | H | $NH(CH_2CH_2CONH_2)$ |
| 7-28 | H | NMeBn |
| 7-29 | H | $NMe(CH_2COOH)$ |
| 7-30 | H | $NMe(CH_2CH_2COOH)$ |
| 7-31 | H | $NMe(CH_2CH_2CH_2COOH)$ |
| 7-32 | H | $NMe(CH_2CN)$ |
| 7-33 | H | $NMe(CH_2CH_2CN)$ |
| 7-34 | H | $NMe(CH_2CH_2CH_2CN)$ |
| 7-35 | H | $NMe(CH_2CH_2OH)$ |
| 7-36 | H | $NMe(CH_2CH_2CH_2OH)$ |
| 7-37 | H | $NMe(CH_2CH_2CH_2CH_2OH)$ |
| 7-38 | H | $NMe(CH_2CH_2OMe)$ |
| 7-39 | H | $NMe(CH_2CH_2CH_2OMe)$ |
| 7-40 | H | $NMe(CH_2CH_2CH_2CH_2OMe)$ |
| 7-41 | H | $NMe(CH_2CH_2NH_2)$ |
| 7-42 | H | $NMe(CH_2CH_2CH_2NH_2)$ |
| 7-43 | H | $NMe(CH_2CH_2CH_2CH_2NH_2)$ |
| 7-44 | H | $NMe(CH_2CH_2NHMe)$ |
| 7-45 | H | $NMe(CH_2CH_2CH_2NHMe)$ |
| 7-46 | H | $NMe(CH_2CH_2CH_2CH_2NHMe)$ |
| 7-47 | H | $NMe(CH_2CH_2NMe_2)$ |
| 7-48 | H | $NMe(CH_2CH_2CH_2NMe_2)$ |
| 7-49 | H | $NMe(CH_2CH_2CH_2CH_2NMe_2)$ |
| 7-50 | H | $NMe(CH_2CONH_2)$ |
| 7-51 | H | $NMe(CH_2CH_2CONH_2)$ |
| 7-52 | OH | OH |
| 7-53 | OH | $NH_2$ |
| 7-54 | OH | NHMe |
| 7-55 | OH | NHBn |
| 7-56 | OH | $NH(CH_2COOH)$ |
| 7-57 | OH | $NH(CH_2CH_2COOH)$ |
| 7-58 | OH | $NH(CH_2CH_2CH_2COOH)$ |
| 7-59 | OH | $NH(CH_2CN)$ |
| 7-60 | OH | $NH(CH_2CH_2CN)$ |
| 7-61 | OH | $NH(CH_2CH_2CH_2CN)$ |
| 7-62 | OH | $NH(CH_2CH_2OH)$ |
| 7-63 | OH | $NH(CH_2CH_2CH_2OH)$ |
| 7-64 | OH | $NH(CH_2CH_2CH_2CH_2OH)$ |
| 7-65 | OH | $NH(CH_2CH_2OMe)$ |
| 7-66 | OH | $NH(CH_2CH_2CH_2OMe)$ |
| 7-67 | OH | $NH(CH_2CH_2CH_2CH_2OMe)$ |
| 7-68 | OH | $NH(CH_2CH_2NH_2)$ |
| 7-69 | OH | $NH(CH_2CH_2CH_2NH_2)$ |
| 7-70 | OH | $NH(CH_2CH_2CH_2CH_2NH_2)$ |
| 7-71 | OH | $NH(CH_2CH_2NHMe)$ |
| 7-72 | OH | $NH(CH_2CH_2CH_2NHMe)$ |
| 7-73 | OH | $NH(CH_2CH_2CH_2CH_2NHMe)$ |
| 7-74 | OH | $NH(CH_2CH_2NMe_2)$ |
| 7-75 | OH | $NH(CH_2CH_2CH_2NMe_2)$ |
| 7-76 | OH | $NH(CH_2CH_2CH_2CH_2NMe_2)$ |
| 7-77 | OH | $NH(CH_2CONH_2)$ |
| 7-78 | OH | $NH(CH_2CH_2CONH_2)$ |
| 7-79 | OH | NMeBn |
| 7-80 | OH | $NMe(CH_2COOH)$ |
| 7-81 | OH | $NMe(CH_2CH_2COOH)$ |
| 7-82 | OH | $NMe(CH_2CH_2CH_2COOH)$ |
| 7-83 | OH | $NMe(CH_2CN)$ |
| 7-84 | OH | $NMe(CH_2CH_2CN)$ |
| 7-85 | OH | $NMe(CH_2CH_2CH_2CN)$ |
| 7-86 | OH | $NMe(CH_2CH_2OH)$ |
| 7-87 | OH | $NMe(CH_2CH_2CH_2OH)$ |
| 7-88 | OH | $NMe(CH_2CH_2CH_2CH_2OH)$ |
| 7-89 | OH | $NMe(CH_2CH_2OMe)$ |
| 7-90 | OH | $NMe(CH_2CH_2CH_2OMe)$ |
| 7-91 | OH | $NMe(CH_2CH_2CH_2CH_2OMe)$ |
| 7-92 | OH | $NMe(CH_2CH_2NH_2)$ |
| 7-93 | OH | $NMe(CH_2CH_2CH_2NH_2)$ |
| 7-94 | OH | $NMe(CH_2CH_2CH_2CH_2NH_2)$ |
| 7-95 | OH | $NMe(CH_2CH_2NHMe)$ |
| 7-96 | OH | $NMe(CH_2CH_2CH_2NHMe)$ |

TABLE 7-continued (1-G)

| Exemplary Compound No. | R¹ | Z |
|---|---|---|
| 7-97 | OH | NMe(CH$_2$CH$_2$CH$_2$CH$_2$NHMe) |
| 7-98 | OH | NMe(CH$_2$CH$_2$NMe$_2$) |
| 7-99 | OH | NMe(CH$_2$CH$_2$CH$_2$NMe$_2$) |
| 7-100 | OH | NMe(CH$_2$CH$_2$CH$_2$CH$_2$NMe$_2$) |
| 7-101 | OH | NMe(CH$_2$CONH$_2$) |
| 7-102 | OH | NMe(CH$_2$CH$_2$CONH$_2$) |
| 7-103 | H | NH(CH$_2$CH$_2$NHCOMe) |
| 7-104 | H | NH(CH$_2$CH$_2$NHCOCH$_2$Me) |
| 7-105 | H | NH(CH$_2$CH$_2$NHCOCH$_2$CH$_2$Me) |
| 7-106 | H | NH(CH$_2$CH$_2$NHCOCHMe$_2$) |
| 7-107 | H | NH(CH$_2$CH$_2$NHCOCMe$_3$) |
| 7-108 | H | NH(CH$_2$CH$_2$CH$_2$NHCOMe) |
| 7-109 | H | NH(CH$_2$CH$_2$CH$_2$NHCOCH$_2$Me) |
| 7-110 | H | NH(CH$_2$CH$_2$CH$_2$NHCOCH$_2$CH$_2$Me) |
| 7-111 | H | NH(CH$_2$CH$_2$CH$_2$NHCOCHMe$_2$) |
| 7-112 | H | NH(CH$_2$CH$_2$CH$_2$NHCOCMe$_3$) |
| 7-113 | OH | NH(CH$_2$CH$_2$NHCOMe) |
| 7-114 | OH | NH(CH$_2$CH$_2$NHCOCH$_2$Me) |
| 7-115 | OH | NH(CH$_2$CH$_2$NHCOCH$_2$CH$_2$Me) |
| 7-116 | OH | NH(CH$_2$CH$_2$NHCOCHMe$_2$) |
| 7-117 | OH | NH(CH$_2$CH$_2$NHCOCMe$_3$) |
| 7-118 | OH | NH(CH$_2$CH$_2$CH$_2$NHCOMe) |
| 7-119 | OH | NH(CH$_2$CH$_2$CH$_2$NHCOCH$_2$Me) |
| 7-120 | OH | NH(CH$_2$CH$_2$CH$_2$NHCOCH$_2$CH$_2$Me) |
| 7-121 | OH | NH(CH$_2$CH$_2$CH$_2$NHCOCHMe$_2$) |
| 7-122 | OH | NH(CH$_2$CH$_2$CH$_2$NHCOCMe$_3$) |

Among the compounds mentioned above, preferred compounds are Exemplary Compound Nos. 7-2, 7-3, 7-5, 7-6, 7-7, 7-11, 7-12, 7-13, 7-17, 7-18, 7-19, 7-20, 7-21, 7-22, 7-23, 7-24, 7-25, 7-35, 7-36, 7-37, 7-53, 7-54, 7-56, 7-57, 7-58, 7-62, 7-63, 7-64, 7-68, 7-69, 7-70, 7-71, 7-72, 7-73, 7-74, 7-75, 7-76, 7-86, 7-87, and 7-88. Exemplary Compound Nos. 7-103, 7-104, 7-105, 7-108, 7-109, 7-110, 7-113, 7-114, 7-115, 7-118, 7-119, and 7-120 are also preferred compounds.

More preferred compounds are Exemplary Compound Nos. 7-2, 7-3, 7-5, 7-6, 7-11, 7-12, 7-17, 7-18, 7-20, 7-21, 7-23, 7-24, 7-35, 7-36, 7-53, 7-54, 7-56, 7-57, 7-62, 7-63, 7-68, 7-69, 7-71, 7-72, 7-74, 7-75, 7-86, and 7-87. Exemplary Compound Nos. 7-103, 7-104, 7-108, 7-109, 7-113, 7-114, 7-118, and 7-119 are also more preferred compounds.

The compounds mentioned in Table 8 are compounds having a structure represented by the following formula (1-H):

TABLE 8

(1-H)

| Exemplary Compound No. | R¹ | A⁶¹ |
|---|---|---|
| 8-1 | H | H |
| 8-2 | H | Me |
| 8-3 | H | CH$_2$COOH |
| 8-4 | H | CH$_2$CH$_2$COOH |
| 8-5 | H | CH$_2$CH$_2$CH$_2$COOH |
| 8-6 | H | CH$_2$CN |
| 8-7 | H | CH$_2$CH$_2$CN |
| 8-8 | H | CH$_2$CH$_2$CH$_2$CN |
| 8-9 | H | CH$_2$CH$_2$OH |
| 8-10 | H | CH$_2$CH$_2$CH$_2$OH |
| 8-11 | H | CH$_2$CH$_2$CH$_2$CH$_2$OH |
| 8-12 | H | CH$_2$CH$_2$OMe |
| 8-13 | H | CH$_2$CH$_2$CH$_2$OMe |
| 8-14 | H | CH$_2$CH$_2$CH$_2$CH$_2$OMe |
| 8-15 | H | CH$_2$CH$_2$NH$_2$ |
| 8-16 | H | CH$_2$CH$_2$CH$_2$NH$_2$ |
| 8-17 | H | CH$_2$CH$_2$CH$_2$CH$_2$NH$_2$ |
| 8-18 | H | CH$_2$CH$_2$NHMe |
| 8-19 | H | CH$_2$CH$_2$CH$_2$NHMe |
| 8-20 | H | CH$_2$CH$_2$CH$_2$CH$_2$NHMe |
| 8-21 | H | CH$_2$CH$_2$NMe$_2$ |
| 8-22 | H | CH$_2$CH$_2$CH$_2$NMe$_2$ |
| 8-23 | H | CH$_2$CH$_2$CH$_2$CH$_2$NMe$_2$ |
| 8-24 | H | CH$_2$CONH$_2$ |
| 8-25 | H | CH$_2$CH$_2$CONH$_2$ |
| 8-26 | OH | H |
| 8-27 | OH | Me |
| 8-28 | OH | CH$_2$COOH |
| 8-29 | OH | CH$_2$CH$_2$COOH |
| 8-30 | OH | CH$_2$CH$_2$CH$_2$COOH |
| 8-31 | OH | CH$_2$CN |
| 8-32 | OH | CH$_2$CH$_2$CN |
| 8-33 | OH | CH$_2$CH$_2$CH$_2$CN |
| 8-34 | OH | CH$_2$CH$_2$OH |
| 8-35 | OH | CH$_2$CH$_2$CH$_2$OH |
| 8-36 | OH | CH$_2$CH$_2$CH$_2$CH$_2$OH |
| 8-37 | OH | CH$_2$CH$_2$OMe |
| 8-38 | OH | CH$_2$CH$_2$CH$_2$OMe |
| 8-39 | OH | CH$_2$CH$_2$CH$_2$CH$_2$OMe |
| 8-40 | OH | CH$_2$CH$_2$NH$_2$ |
| 8-41 | OH | CH$_2$CH$_2$CH$_2$NH$_2$ |
| 8-42 | OH | CH$_2$CH$_2$CH$_2$CH$_2$NH$_2$ |
| 8-43 | OH | CH$_2$CH$_2$NHMe |
| 8-44 | OH | CH$_2$CH$_2$CH$_2$NHMe |
| 8-45 | OH | CH$_2$CH$_2$CH$_2$CH$_2$NHMe |
| 8-46 | OH | CH$_2$CH$_2$NMe$_2$ |
| 8-47 | OH | CH$_2$CH$_2$CH$_2$NMe$_2$ |
| 8-48 | OH | CH$_2$CH$_2$CH$_2$CH$_2$NMe$_2$ |
| 8-49 | OH | CH$_2$CONH$_2$ |
| 8-50 | OH | CH$_2$CH$_2$CONH$_2$ |
| 8-51 | H | CH$_2$CH$_2$NHCOMe |
| 8-52 | H | CH$_2$CH$_2$NHCOCH$_2$Me |
| 8-53 | H | CH$_2$CH$_2$NHCOCH$_2$CH$_2$Me |
| 8-54 | H | CH$_2$CH$_2$NHCOCHMe$_2$ |
| 8-55 | H | CH$_2$CH$_2$NHCOCMe$_3$ |
| 8-56 | H | CH$_2$CH$_2$CH$_2$NHCOMe |
| 8-57 | H | CH$_2$CH$_2$CH$_2$NHCOCH$_2$Me |
| 8-58 | H | CH$_2$CH$_2$CH$_2$NHCOCH$_2$CH$_2$Me |
| 8-59 | H | CH$_2$CH$_2$CH$_2$NHCOCHMe$_2$ |
| 8-60 | H | CH$_2$CH$_2$CH$_2$NHCOCMe$_3$ |
| 8-61 | OH | CH$_2$CH$_2$NHCOMe |

TABLE 8-continued (1-H)

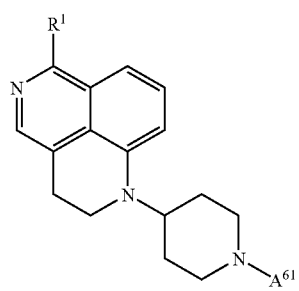

| Exemplary Compound No. | R¹ | A⁶¹ |
|---|---|---|
| 8-62 | OH | CH₂CH₂NHCOCH₂Me |
| 8-63 | OH | CH₂CH₂NHCOCH₂CH₂Me |
| 8-64 | OH | CH₂CH₂NHCOCHMe₂ |
| 8-65 | OH | CH₂CH₂NHCOCMe₃ |
| 8-66 | OH | CH₂CH₂CH₂NHCOMe |
| 8-67 | OH | CH₂CH₂CH₂NHCOCH₂Me |
| 8-68 | OH | CH₂CH₂CH₂NHCOCH₂CH₂Me |
| 8-69 | OH | CH₂CH₂CH₂NHCOCHMe₂ |
| 8-70 | OH | CH₂CH₂CH₂NHCOCMe₃ |

Among the compounds mentioned above, preferred compounds are Exemplary Compound Nos. 8-1, 8-2, 8-3, 8-4, 8-5, 8-9, 8-10, 8-11, 8-15, 8-16, 8-17, 8-18, 8-19, 8-20, 8-21, 8-22, 8-23, 8-26, 8-27, 8-28, 8-29, 8-30, 8-34, 8-35, 8-36, 8-40, 8-41, 8-42, 8-43, 8-44, 8-45, 8-46, 8-47, and 8-48. Exemplary Compound Nos. 8-51, 8-52, 8-53, 8-56, 8-57, 8-58, 8-61, 8-62, 8-63, 8-66, 8-67, and 8-68 are also preferred compounds.

More preferred compounds are Exemplary Compound Nos. 8-1, 8-3, 8-4, 8-9, 8-10, 8-15, 8-16, 8-18, 8-19, 8-21, 8-22, 8-26, 8-28, 8-29, 8-34, 8-35, 8-40, 8-41, 8-43, 8-44, 8-46, and 8-47. Exemplary Compound Nos. 8-51, 8-52, 8-56, 8-57, 8-61, 8-62, 8-66, and 8-67 are also more preferred compounds.

Further, N-{2-[3-(2,3-dihydro-1,5-diazaphenalen-1-yl) pyrrolidin-1-yl]ethyl}-N-methylacetamide (Exemplary Compound No. 8-71), N-{2-[3-(6-hydroxy-2,3-dihydro-1,5-diazaphenalen-1-yl)pyrrolidin-1-yl]ethyl}-N-methylacetamide (Exemplary Compound No. 8-72), 1-{2-[3-(2,3-dihydro-1,5-diazaphenalen-1-yl)pyrrolidin-1-yl]ethyl}azetidin-2-one (Exemplary Compound No. 8-73), 1-{2-[3-(6-hydroxy-2,3-dihydro-1,5-diazaphenalen-1-yl)pyrrolidin-1-yl]ethyl}azetidin-2-one (Exemplary Compound No. 8-74), 1-{2-[3-(2,3-dihydro-1,5-diazaphenalen-1-yl)pyrrolidin-1-yl]ethyl}pyrrolidin-2-one (Exemplary Compound No. 8-75), 1-{2-[3-(6-hydroxy-2,3-dihydro-1,5-diazaphenalen-1-yl)pyrrolidin-1-yl]ethyl}pyrrolidin-2-one (Exemplary Compound No. 8-76), 1-{2-[3-(2,3-dihydro-1,5-diazaphenalen-1-yl)pyrrolidin-1-yl]ethyl}piperidin-2-one (Exemplary Compound No. 8-77), and 1-{2-[3-(6-hydroxy-2,3-dihydro-1,5-diazaphenalen-1-yl)pyrrolidin-1-yl]ethyl}piperidin-2-one (Exemplary Compound No. 8-78) are also preferred compounds. Further, Exemplary Compound Nos. 8-71, 8-72, 8-73, and 8-74 are also more preferred compounds.

The compounds mentioned in Table 9 are compounds having a structure represented by the following formula (1-I):

TABLE 9

(1-I)

| Exemplary Compound No. | R¹ | A⁶¹ |
|---|---|---|
| 9-1 | H | H |
| 9-2 | H | Me |
| 9-3 | H | CH₂COOH |
| 9-4 | H | CH₂CH₂COOH |
| 9-5 | H | CH₂CH₂CH₂COOH |
| 9-6 | H | CH₂CN |
| 9-7 | H | CH₂CH₂CN |
| 9-8 | H | CH₂CH₂CH₂CN |
| 9-9 | H | CH₂CH₂OH |
| 9-10 | H | CH₂CH₂CH₂OH |
| 9-11 | H | CH₂CH₂CH₂CH₂OH |
| 9-12 | H | CH₂CH₂OMe |
| 9-13 | H | CH₂CH₂CH₂OMe |
| 9-14 | H | CH₂CH₂CH₂CH₂OMe |
| 9-15 | H | CH₂CH₂NH₂ |
| 9-16 | H | CH₂CH₂CH₂NH₂ |
| 9-17 | H | CH₂CH₂CH₂CH₂NH₂ |
| 9-18 | H | CH₂CH₂NHMe |
| 9-19 | H | CH₂CH₂CH₂NHMe |
| 9-20 | H | CH₂CH₂CH₂CH₂NHMe |
| 9-21 | H | CH₂CH₂NMe₂ |
| 9-22 | H | CH₂CH₂CH₂NMe₂ |
| 9-23 | H | CH₂CH₂CH₂CH₂NMe₂ |
| 9-24 | H | CH₂CONH₂ |
| 9-25 | H | CH₂CH₂CONH₂ |
| 9-26 | OH | H |
| 9-27 | OH | Me |
| 9-28 | OH | CH₂COOH |
| 9-29 | OH | CH₂CH₂COOH |
| 9-30 | OH | CH₂CH₂CH₂COOH |
| 9-31 | OH | CH₂CN |
| 9-32 | OH | CH₂CH₂CN |
| 9-33 | OH | CH₂CH₂CH₂CN |
| 9-34 | OH | CH₂CH₂OH |
| 9-35 | OH | CH₂CH₂CH₂OH |
| 9-36 | OH | CH₂CH₂CH₂CH₂OH |
| 9-37 | OH | CH₂CH₂OMe |
| 9-38 | OH | CH₂CH₂CH₂OMe |
| 9-39 | OH | CH₂CH₂CH₂CH₂OMe |
| 9-40 | OH | CH₂CH₂NH₂ |
| 9-41 | OH | CH₂CH₂CH₂NH₂ |
| 9-42 | OH | CH₂CH₂CH₂CH₂NH₂ |
| 9-43 | OH | CH₂CH₂NHMe |
| 9-44 | OH | CH₂CH₂CH₂NHMe |
| 9-45 | OH | CH₂CH₂CH₂CH₂NHMe |
| 9-46 | OH | CH₂CH₂NMe₂ |
| 9-47 | OH | CH₂CH₂CH₂NMe₂ |
| 9-48 | OH | CH₂CH₂CH₂CH₂NMe₂ |
| 9-49 | OH | CH₂CONH₂ |
| 9-50 | OH | CH₂CH₂CONH₂ |
| 9-51 | H | CH₂CH₂NHCOMe |
| 9-52 | H | CH₂CH₂NHCOCH₂Me |
| 9-53 | H | CH₂CH₂NHCOCH₂CH₂Me |
| 9-54 | H | CH₂CH₂NHCOCHMe₂ |
| 9-55 | H | CH₂CH₂NHCOCMe₃ |
| 9-56 | H | CH₂CH₂CH₂NHCOMe |
| 9-57 | H | CH₂CH₂CH₂NHCOCH₂Me |
| 9-58 | H | CH₂CH₂CH₂NHCOCH₂CH₂Me |
| 9-59 | H | CH₂CH₂CH₂NHCOCHMe₂ |
| 9-60 | H | CH₂CH₂CH₂NHCOCMe₃ |

TABLE 9-continued (1-I)

[Structure: fused tricyclic system with R¹ on position, N in ring, CH₂ group, piperidine ring with N-A⁶¹]

| Exemplary Compound No. | R¹ | A⁶¹ |
|---|---|---|
| 9-61 | OH | CH₂CH₂NHCOMe |
| 9-62 | OH | CH₂CH₂NHCOCH₂Me |
| 9-63 | OH | CH₂CH₂NHCOCH₂CH₂Me |
| 9-64 | OH | CH₂CH₂NHCOCHMe₂ |
| 9-65 | OH | CH₂CH₂NHCOCMe₃ |
| 9-66 | OH | CH₂CH₂CH₂NHCOMe |
| 9-67 | OH | CH₂CH₂CH₂NHCOCH₂Me |
| 9-68 | OH | CH₂CH₂CH₂NHCOCH₂CH₂Me |
| 9-69 | OH | CH₂CH₂CH₂NHCOCHMe₂ |
| 9-70 | OH | CH₂CH₂CH₂NHCOCMe₃ |

Among the compounds mentioned above, preferred compounds are Exemplary Compound Nos. 9-1, 9-2, 9-3, 9-4, 9-5, 9-9, 9-10, 9-11, 9-15, 9-16, 9-17, 9-18, 9-19, 9-20, 9-21, 9-22, 9-23, 9-26, 9-27, 9-28, 9-29, 9-30, 9-34, 9-35, 9-36, 9-40, 9-41, 9-42, 9-43, 9-44, 9-45, 9-46, 9-47, and 9-48. Exemplary Compound Nos. 9-51, 9-52, 9-53, 9-56, 9-57, 9-58, 9-61, 9-62, 9-63, 9-66, 9-67, and 9-68 are also preferred compounds.

More preferred compounds are Exemplary Compound Nos. 9-1, 9-3, 9-4, 9-9, 9-10, 9-15, 9-16, 9-18, 9-19, 9-21, 9-22, 9-26, 9-28, 9-29, 9-34, 9-35, 9-40, 9-41, 9-43, 9-44, 9-46, and 9-47. Exemplary Compound Nos. 9-51, 9-52, 9-56, 9-57, 9-61, 9-62, 9-66, and 9-67 are also more preferred compounds.

Further, N-{2-[4-(2,3-dihydro-1,5-diazaphenalen-1-yl)piperidin-1-yl]ethyl}-N-methylacetamide (Exemplary Compound No. 9-71), N-{2-[4-(6-hydroxy-2,3-dihydro-1,5-diazaphenalen-1-yl)piperidin-1-yl]ethyl}-N-methylacetamide (Exemplary Compound No. 9-72), 1-{2-[4-(2,3-dihydro-1,5-diazaphenalen-1-yl)piperidin-1-yl]ethyl}azetidin-2-one (Exemplary Compound No. 9-73), 1-{2-[4-(6-hydroxy-2,3-dihydro-1,5-diazaphenalen-1-yl)piperidin-1-yl]ethyl}azetidin-2-one (Exemplary Compound No. 9-74), 1-{2-[4-(2,3-dihydro-1,5-diazaphenalen-1-yl)piperidin-1-yl]ethyl}pyrrolidin-2-one (Exemplary Compound No. 9-75), 1-{2-[4-(6-hydroxy-2,3-dihydro-1,5-diazaphenalen-1-yl)piperidin-1-yl]ethyl}pyrrolidin-2-one (Exemplary Compound No. 9-76), 1-{2-[4-(2,3-dihydro-1,5-diazaphenalen-1-yl)piperidin-1-yl]ethyl}piperidin-2-one (Exemplary Compound No. 9-77), 1-{2-[4-(6-hydroxy-2,3-dihydro-1,5-diazaphenalen-1-yl)piperidin-1-yl]ethyl}piperidin-2-one (Exemplary Compound No. 9-78), 1-(3-fluoropiperidin-4-yl)-2,3-dihydro-1H-1,5-diazaphenalene (Exemplary Compound No. 9-79), and 1-(3-fluoropiperidin-4-yl)-2,3-dihydro-1H-1,5-diazaphenalen-6-ol (Exemplary Compound No. 9-80) are also preferred compounds. Further, Exemplary Compound Nos. 9-71, 9-72, 9-73, 9-74, 9-79, and 9-80 are also more preferred compounds.

The compounds mentioned in Table 10 are compounds having a structure represented by the following formula (1-J):

TABLE 10

(1-J)

| Exemplary Compound No. | R¹ | A61 |
|---|---|---|
| 10-1 | H | H |
| 10-2 | H | Me |
| 10-3 | H | CH₂COOH |
| 10-4 | H | CH₂CH₂COOH |
| 10-5 | H | CH₂CH₂CH₂COOH |
| 10-6 | H | CH₂CN |
| 10-7 | H | CH₂CH₂CN |
| 10-8 | H | CH₂CH₂CH₂CN |
| 10-9 | H | CH₂CH₂OH |
| 10-10 | H | CH₂CH₂CH₂OH |
| 10-11 | H | CH₂CH₂CH₂CH₂OH |
| 10-12 | H | CH₂CH₂OMe |
| 10-13 | H | CH₂CH₂CH₂OMe |
| 10-14 | H | CH₂CH₂CH₂CH₂OMe |
| 10-15 | H | CH₂CH₂NH₂ |
| 10-16 | H | CH₂CH₂CH₂NH₂ |
| 10-17 | H | CH₂CH₂CH₂CH₂NH₂ |
| 10-18 | H | CH₂CH₂NHMe |
| 10-19 | H | CH₂CH₂CH₂NHMe |
| 10-20 | H | CH₂CH₂CH₂CH₂NHMe |
| 10-21 | H | CH₂CH₂NMe₂ |
| 10-22 | H | CH₂CH₂CH₂NMe₂ |
| 10-23 | H | CH₂CH₂CH₂CH₂NMe₂ |
| 10-24 | H | CH₂CONH₂ |
| 10-25 | H | CH₂CH₂CONH₂ |
| 10-26 | OH | H |
| 10-27 | OH | Me |
| 10-28 | OH | CH₂COOH |
| 10-29 | OH | CH₂CH₂COOH |
| 10-30 | OH | CH₂CH₂CH₂COOH |
| 10-31 | OH | CH₂CN |
| 10-32 | OH | CH₂CH₂CN |
| 10-33 | OH | CH₂CH₂CH₂CN |
| 10-34 | OH | CH₂CH₂OH |
| 10-35 | OH | CH₂CH₂CH₂OH |
| 10-36 | OH | CH₂CH₂CH₂CH₂OH |
| 10-37 | OH | CH₂CH₂OMe |
| 10-38 | OH | CH₂CH₂CH₂OMe |
| 10-39 | OH | CH₂CH₂CH₂CH₂OMe |
| 10-40 | OH | CH₂CH₂NH₂ |
| 10-41 | OH | CH₂CH₂CH₂NH₂ |
| 10-42 | OH | CH₂CH₂CH₂CH₂NH₂ |
| 10-43 | OH | CH₂CH₂NHMe |
| 10-44 | OH | CH₂CH₂CH₂NHMe |
| 10-45 | OH | CH₂CH₂CH₂CH₂NHMe |
| 10-46 | OH | CH₂CH₂NMe₂ |
| 10-47 | OH | CH₂CH₂CH₂NMe₂ |
| 10-48 | OH | CH₂CH₂CH₂CH₂NMe₂ |
| 10-49 | OH | CH₂CONH₂ |
| 10-50 | OH | CH₂CH₂CONH₂ |
| 10-51 | H | CH₂CH₂NHCOMe |
| 10-52 | H | CH₂CH₂NHCOCH₂Me |
| 10-53 | H | CH₂CH₂NHCOCH₂CH₂Me |
| 10-54 | H | CH₂CH₂NHCOCHMe₂ |
| 10-55 | H | CH₂CH₂NHCOCMe₃ |
| 10-56 | H | CH₂CH₂CH₂NHCOMe |
| 10-57 | H | CH₂CH₂CH₂NHCOCH₂Me |
| 10-58 | H | CH₂CH₂CH₂NHCOCH₂CH₂Me |
| 10-59 | H | CH₂CH₂CH₂NHCOCHMe₂ |
| 10-60 | H | CH₂CH₂CH₂NHCOCMe₃ |

TABLE 10-continued (1-J)

R$^1$ structure with N, N-A$^{61}$ piperidine

| Exemplary Compound No. | R$^1$ | A61 |
|---|---|---|
| 10-61 | OH | CH$_2$CH$_2$NHCOMe |
| 10-62 | OH | CH$_2$CH$_2$NHCOCH$_2$Me |
| 10-63 | OH | CH$_2$CH$_2$NHCOCH$_2$CH$_2$Me |
| 10-64 | OH | CH$_2$CH$_2$NHCOCHMe$_2$ |
| 10-65 | OH | CH$_2$CH$_2$NHCOCMe$_3$ |
| 10-66 | OH | CH$_2$CH$_2$CH$_2$NHCOMe$_3$ |
| 10-67 | OH | CH$_2$CH$_2$CH$_2$NHCOCH$_2$Me |
| 10-68 | OH | CH$_2$CH$_2$CH$_2$NHCOCH$_2$CH$_2$Me |
| 10-69 | OH | CH$_2$CH$_2$CH$_2$NHCOCHMe$_2$ |
| 10-70 | OH | CH$_2$CH$_2$CH$_2$NHCOCMe$_3$ |

Among the compounds mentioned above, preferred compounds are Exemplary Compound Nos. 10-1, 10-2, 10-3, 10-4, 10-5, 10-9, 10-10, 10-11, 10-15, 10-16, 10-17, 10-18, 10-19, 10-20, 10-21, 10-22, 10-23, 10-26, 10-27, 10-28, 10-29, 10-30, 10-34, 10-35, 10-36, 10-40, 10-41, 10-42, 10-43, 10-44, 10-45, 10-46, 10-47, and 10-48. Exemplary Compound Nos. 10-51, 10-52, 10-53, 10-56, 10-57, 10-58, 10-61, 10-62, 10-63, 10-66, 10-67, and 10-68 are also preferred compounds.

More preferred compounds are Exemplary Compound Nos. 10-1, 10-3, 10-4, 10-9, 10-10, 10-15, 10-16, 10-18, 10-19, 10-21, 10-22, 10-26, 10-28, 10-29, 10-34, 10-35, 10-40, 10-41, 10-43, 10-44, 10-46, and 10-47. Exemplary Compound Nos. 10-51, 10-52, 10-56, 10-57, 10-61, 10-62, 10-66, and 10-67 are also more preferred compounds.

Further, N-{2-[4-(2,3-dihydro-1,5-diazaphenalen-1-ylmethyl)piperidin-1-yl]ethyl}-N-methylacetamide (Exemplary Compound No. 10-71), N-{2-[4-(6-hydroxy-2,3-dihydro-1,5-diazaphenalen-1-ylmethyl)piperidin-1-yl]ethyl}-N-methylacetamide (Exemplary Compound No. 10-72), 1-{2-[4-(2,3-dihydro-1,5-diazaphenalen-1-yl)piperidin-1-ylmethyl]ethyl}azetidin-2-one (Exemplary Compound No. 10-73), 1-{2-[4-(6-hydroxy-2,3-dihydro-1,5-diazaphenalen-1-ylmethyl)piperidin-1-yl]ethyl}azetidin-2-one (Exemplary Compound No. 10-74), 1-{2-[4-(2,3-dihydro-1,5-diazaphenalen-1-ylmethyl)piperidin-1-yl]ethyl}pyrrolidin-2-one (Exemplary Compound No. 10-75), 1-{2-[4-(6-hydroxy-2,3-dihydro-1,5-diazaphenalen-1-ylmethyl)piperidin-1-yl]ethyl}pyrrolidin-2-one (Exemplary Compound No. 10-76), 1-{2-[4-(2,3-dihydro-1,5-diazaphenalen-1-ylmethyl)piperidin-1-yl]ethyl}piperidin-2-one (Exemplary Compound No. 10-77), and 1-{2-[4-(6-hydroxy-2,3-dihydro-1,5-diazaphenalen-1-ylmethyl)piperidin-1-yl]ethyl}piperidin-2-one (Exemplary Compound No. 10-78) are also preferred compounds. Further, Exemplary Compound Nos. 10-71, 10-72, 10-73, and 10-74 are also more preferred compounds.

The compounds of the present invention represented by the formula (1) may have one or more asymmetric carbons, and stereoisomers based on such asymmetric carbons such as optical antipodes and diastereoisomer may exist. The stereoisomers in pure forms, any mixtures, racemates and the like of the stereoisomers all fall within the scope of the present invention. Further, when the compounds of the present invention have an olefinic double bond or a cyclic structure, two or more kinds of stereoisomers may exist, and such stereoisomers in pure forms, any mixtures, and the like of such stereoisomers all fall within the scope of the present invention. Furthermore, the compounds of the present invention represented by the formula (1) may exist as tautomers. Existence of such tautomers is apparent to those skilled in the art, and such tautomers all fall within the scope of the present invention.

The compounds of the present invention may also exist as salts. Forms of the salts are not particularly limited. Acid addition salts are generally formed, or base addition salts may be formed depending on the types of substituents. The types of physiologically acceptable salts are well known to those skilled in the art, and examples include, for example, those described by Berge et al. in J. Pharm. Sci., 66, 1–19 (1977). Examples of the acid addition salts include, for example, mineral acid salts such as hydrochlorides, hydrobromides, hydroiodides, nitrates, sulfates, and hydrogensulfates, phosphates, hydrogenphosphates, organic acid salts such as acetates, trifluoroacetates, gluconates, lactates, salicylates, citrates, tartrates, ascorbates, succinates, maleates, fumarates, formates, benzoates, methanesulfonates, ethanesulfonates, benzenesulfonates and p-toluenesulfonates. Where one or more substituents contain an acidic moiety, examples of suitable pharmacologically acceptable base addition salts include, for example, metal salts such as sodium salts, potassium salts, magnesium salts, lithium salts, calcium salts, aluminum salts and zinc salts, and salts of organic amines such as ethanolamine.

Methods for preparation of the compounds represented by the formula (1) are not particularly limited. For example, they can be prepared according to the methods described below.

(Preparation Method 1)

The compounds represented by the formula (1) can be prepared from a compound represented by the following formula (A):

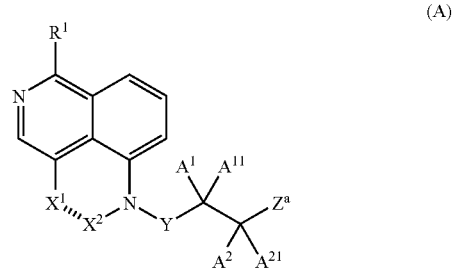

(A)

wherein R$^1$ represents hydrogen atom, chlorine atom, or hydroxyl group;

X$^1$ ... X$^2$ represents —CH(R$^2$)—CH(R$^3$)—, —CH(R$^2$)—CH(R$^3$)—CH(R$^4$)—, —C(R$^2$)=C(R$^3$)—, or —C(R$^2$)=C(R$^3$)—CH(R$^4$)—;

R$^2$, R$^3$, and R$^4$ independently represent hydrogen atom, or an alkyl group;

A$^1$, A$^{11}$, A$^2$, and A$^{21}$ independently represent hydrogen atom, or an alkyl group;

Y represents —CH(A$^3$)—, —CH(A$^3$)—C(A$^4$)(A$^{41}$)—, —CH(A$^3$)—C(A$^4$)(A$^{41}$)—C(A$^5$)(A$^{51}$)—, or a single bond;

A$^3$, A$^4$, A$^{41}$, A$^5$, and A$^{51}$ independently represent hydrogen atom, or an alkyl group;

$Z^a$ represents —O(PG$^1$), —OH, —N(A$^6$)(PG$^2$), —NH(A$^6$), —N(A$^6$)(A$^{62}$), or —N(A$^6$)(A$^{63}$);

PG$^1$ represents a protective group of hydroxyl group, PG$^2$ represents an amino protective group;

A$^{62}$ represents an alkyl group, an aralkyl group, an alkyl group substituted with carboxyl group, an alkyl group substituted with carboxyl group protected with a protective group for carboxyl group PG$^3$, an alkyl group substituted with cyano group, an alkyl group substituted with hydroxyl group, an alkyl group substituted with hydroxyl group protected with PG$^1$, an alkyl group substituted with an alkoxyl group, an alkyl group substituted with amino group, an alkyl group substituted with amino group protected with PG$^2$, an alkyl group of which end is substituted with N(A$^7$)(—X$^3$—A$^{71}$), or an alkyl group substituted with aminocarbonyl group;

A$^{63}$ represents an alkyl group of which end is substituted with NH(A$^7$), where A$^7$ in this case represents hydrogen atom, or an alkyl group; and groups in one or more combinations selected from the group consisting of combinations of A$^6$ and A$^3$, A$^6$ and A$^4$, A$^6$ and A$^1$, A$^6$ and A$^2$, A$^2$ and A$^3$, A$^2$ and A$^4$, A$^6$ and A$^5$, A$^3$ and A$^1$, and A$^5$ and A$^1$ may bind to each other to form a 5- or 6-membered ring, by removing a protective group of the compound (Step 1-1) if the protective group exists in the compound.

The PG$^1$ group used herein is not particularly limited so long as it protects hydroxyl group, does not react in reactions in this preparation process other than the deprotection step, and further can be easily removed. Preferred examples of the protective group of hydroxyl group include a trialkylsilyl group such as tert-butyldimethylsilyl group (TBDMS group), an acyl group such as acetyl group, benzyl group (Bn group), and tetrahydropyranyl (THP) group, and particularly preferred examples include Bn group and THP group.

The PG$^2$ group is not particularly limited so long as it protects amino group, does not react in reactions in this preparation process other than the deprotection step, and further can be easily removed. Preferred examples include t-butoxycarbonyl group (Boc group), benzyloxycarbonyl group (Cbz group), benzyl group (Bn group), phthaloyl group, and triphenylmethyl group, and particularly preferred examples include Boc group, Cbz group, and Bn group.

The PG$^3$ group is not particularly limited so long as it protects carboxyl group, does not react in reactions in this preparation process other than the deprotection step, and further can be easily removed. Examples include alkyl groups, and specifically, tert-butyl group is preferred, for example.

In the aforementioned deprotection steps, when PG$^1$, PG$^2$, or PG$^3$ exists in a compound of the formula (A), it can be removed by a known reaction depending on a kind of the protective group. These methods are apparent to those skilled in the art by referring to prior art described in, for example, Greene, T. W. and Wuts, P. G. M. "Protective Groups in Organic Synthesis", John Wiley and Sons Inc. (3rd edition); and Kocienski, P. J., "Protecting Groups", Georg Thieme Verlag (1994).

More specific explanation will be set forth below. For example, a method of preparing the compounds of the formula (1) by removing Bn group from a compound of the formula (A) wherein PG$^1$ represents Bn group can be performed by using known reduction conditions of hydrogenation. Examples of the method include a method performed in an alcohol, ethyl acetate, an ether solvent such as 1,4-dioxane, or a mixed solvent thereof, and examples of catalyst include, for example, palladium/carbon. Examples of the reaction include a method of performing the reaction at 0 to 80° C., preferably 10 to 40° C.

For example, examples of a method of preparing the compounds of the formula (1), by removing THP group from a compound of the formula (A) wherein PG$^1$ represents THP group, include a method utilizing acidolysis. Examples of the acid include mineral acids, and specific examples are hydrochloric acid, sulfuric acid, nitric acid, phosphoric acid, and the like, and hydrochloric acid is preferred. The acid is preferably used in an amount of 1 to 100 fold moles. Examples of the solvent include water, alcohols, ether type solvents such as 1,4-dioxane, and mixed solvents thereof. The reaction is preferably performed in the temperature range of from room temperature to reflux temperature of the solvent.

For example, a method of preparing the compounds of the formula (1) by removing Boc group from a compound of the formula (A) wherein PG$^2$ represents Boc group can be performed by using known acidic conditions. As for the solvent used for the reaction, the reaction can be performed, for example, without solvent, or in water, an alcohol, acetonitrile, an ether solvent such as 1,4-dioxane, or a mixed solvent thereof. As the acid, a mineral acid and organic acid can be used. Specific examples include hydrochloric acid, sulfuric acid, nitric acid, acetic acid, methanesulfonic acid, phosphoric acid, and the like, and hydrochloric acid is preferred. The acid is preferably used in an amount of 1 to 100 fold moles based on the compound of the formula (A). The reaction is preferably performed in the temperature range of from room temperature to the reflux temperature of the solvent. Alternatively, the removal of Boc group can be performed by using trifluoroacetic acid. Examples of this method include a method of using trifluoroacetic acid alone, and a method of using trifluoroacetic acid as a mixed solvent system with water or dichloromethane. The reaction is performed, for example, in the temperature range of from 0 to 100° C., preferably from room temperature to 50° C. As for the amount of trifluoroacetic acid, 1 to 100 fold moles are preferably used based on the compound of the formula (A).

Further, the method of preparing the compounds of the formula (1) by removing Cbz group (or Bn group) from a compound of the formula (A) wherein PG$^2$ represents Cbz group or Bn group can be performed by using known reduction conditions of hydrogenation. Examples of the method include a method performed in an alcohol, ethyl acetate, an ether type solvent such as 1,4-dioxane, or a mixed solvent thereof, and examples of catalyst include, for example, palladium/carbon. The reaction is performed, for example, at 0 to 100° C., preferably 10 to 80° C.

Further, the method of preparing the compounds of the formula (1) by removing tert-butyl group from a compound of the formula (A) wherein PG$^3$ represents tert-butyl group can be performed by known acidolysis. Examples of the acid include mineral acids. Specific examples include hydrochloric acid, sulfuric acid, nitric acid, phosphoric acid, and the like, and hydrochloric acid is preferred. As for the amount of the acid used, it is preferable to use 1 to 100 fold moles. Examples of the solvent used for the reaction include, for example, water, alcohols, ether solvents such as 1,4-dioxane and mixed solvents thereof, and 1,4-dioxane is preferred. The reaction is preferably performed in the temperature range of from room temperature to the reflux temperature of the solvent.

When $Z^a$ represents the same group as that represented by Z in the general formula (1), such compounds of the formula (A) constitute a part of the compounds of the formula (1), and thus Step 1-1 mentioned above is unnecessary.

Furthermore, the compounds represented by the aforementioned formula (A) can be prepared by the following methods. i) When a compound represented by the formula (A-a):

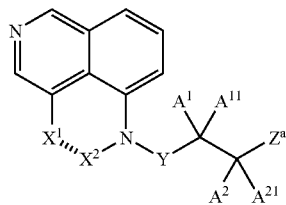

(A-a)

wherein Y, $A^1$, $A^{11}$, $A^2$, $A^{21}$, $Z^a$, and $X^1 \ldots X^2$ have the same meanings as those defined above, which corresponds to a compound of the formula (A) wherein $R^1$ is hydrogen atom, said compound can be used as it is, ii) when a compound represented by the formula (A-b):

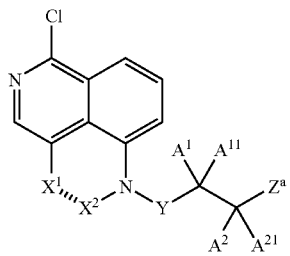

(A-b)

wherein Y, $A^1$, $A^{11}$, $A^2$, $A^{21}$, $Z^a$, and $X^1 \ldots X^2$ have the same meanings as those defined above, which corresponds to a compound of the formula (A) wherein $R^1$ is chlorine atom, is prepared, the compound of the aforementioned formula (A-a) can be oxidized to prepare a compound represented by the formula (B):

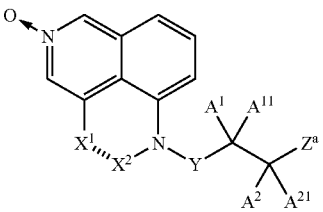

(B)

wherein Y, $A^1$, $A^{11}$, $A^2$, $A^{21}$, $Z^a$, and $X^1 \ldots X^2$ have the same meanings as those defined above, and this compound can be chlorinated to obtain a compound of the formula (A-b), and thereby obtain a compound of the formula (A), or iii) when a compound represented by the formula (A-c):

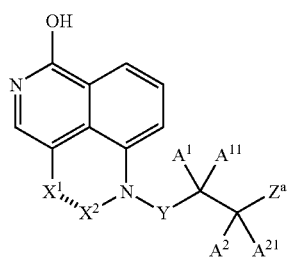

(A-c)

wherein Y, $A^1$, $A^{11}$, $A^2$, $A^{21}$, $Z^a$, and $X^1 \ldots X^2$ have the same meanings as those defined above, which corresponds to a compound of the formula (A) wherein $R^1$ is hydroxyl group, is prepared, a compound of the aforementioned formula (A-b) can be hydroxylated to obtain a compound of the formula (A-c), and thereby obtain a compound of the formula (A).

The compounds of the aforementioned formula (B) can be prepared by oxidizing a compound of the aforementioned formula (A-a) (Step 1-2). Examples of oxidizing agent include aqueous hydrogen peroxide, sodium periodate, sodium perborate, 3-chloroperbenzoic acid, ruthenium trichloride, and dimethyldioxirane. The oxidizing agent is preferably used in an amount of 0.1 fold mole or more, most preferably 1 to 20 fold moles, based on the compound of the formula (A-a). Examples of the solvent include acetic acid, trifluoroacetic acid, dichloromethane, 1,2-dichloroethane, chloroform, acetonitrile, acetone, trichlorofluoromethane, benzene, 1,4-dioxane, tert-butanol, water, and mixed solvents of these, and preferred examples include acetic acid. The reaction is preferably performed at room temperature or a higher temperature. This step is preferably preformed with a compound wherein $Z^a$ is —O(PG$^1$), —N(A$^6$)(PG$^2$), or —N(A$^6$)(A$^{62}$).

Further, the compounds of the aforementioned formula (A-b) can be prepared by allowing a chlorination reagent to react on a compound of the aforementioned formula (B) to chlorinating the compound (Step 1-3). Examples of the chlorination reagent include phosphorus trichloride, phosphorus pentachloride, and phosphorous oxychloride, and phosphorous oxychloride is preferred. The chlorination reagent is preferably used in an amount of 0.1 fold mole or more, most preferably 1 to 10 fold moles, based on the compound of the formula (B). As for the solvent, examples of methods include those performed without solvent or in an inert solvent, and the method is preferably performed, for example, without solvent or by using dichloromethane, 1,2-dichloroethane, chloroform, or toluene as a solvent. The reaction is preferably performed at room temperature or a higher temperature. This step is preferably preformed with a compound wherein $Z^a$ is —O(PG$^1$), —N(A$^6$)(PG$^2$), or —N(A$^6$)(A$^{62}$).

The compounds represented by the aforementioned formula (A-c) can be prepared by hydroxylating a compound of the aforementioned formula (A-b) (Step 1-4). A hydrolysis reaction performed under an acidic condition is preferred, and the reaction is more preferably carried out in a mineral acid. Examples of the mineral acid to be used include hydrochloric acid, sulfuric acid, nitric acid and the like, and a particularly preferred example is hydrochloric acid. The acid is preferably used in an amount of 0.1 fold mole or more, most preferably 1 to 100 fold moles, based on the compound of the formula (A-b). As for the reaction solvent, the reaction is performed, for example, without solvent or in an inert solvent, and the reaction is preferably performed, for example, without solvent, or in an ether type solvent such as tetrahydrofuran, and 1,4-dioxane. The reaction is carried out, for example, at room temperature or a higher temperature. This step is preferably preformed with a compound wherein $Z^a$ is —O(PG$^1$), —N(A$^6$)(PG$^2$), or —N(A$^6$)(A$^{62}$).

Further, as for the compounds of the formula (A-a), the compounds of the formula (A-a) wherein $Z^a$ is —N(A$^6$)(A$^{62}$) can be prepared by deprotecting a compound of the formula (A-a) wherein $Z^a$ is —N(A$^6$)(PG$^2$) to prepare a compound of the formula (A-a) wherein $Z^a$ is —NH(A$^6$) (Step 1-5), and reacting this compound with a compound represented as A$^{62}$—W wherein A$^{62}$ has the same meaning as defined above, and W represents a leaving group (Step 1-6).

For the deprotection step performed for the preparation of a compound of the formula (A-a) wherein $Z^a$ is —NH(A$^6$) from a compound of the formula (A-a) wherein $Z^a$ is —N(A$^6$)(PG$^2$), an ordinary deprotection reaction can be utilized as explained above.

W in A$^{62}$—W used for the preparation of a compound of the formula (A-a) wherein $Z^a$ is —N(A$^6$)(A$^{62}$) from a compound of the formula (A-a) wherein $Z^a$ is —NH(A$^6$) is not particularly limited so long as W is a leaving group. Examples include, for example, a halogen atom, an alkylsulfonyloxy group, and an arylsulfonyloxy group, preferred examples include chlorine atom, bromine atom, iodine atom, methanesulfonyloxy group, and p-toluenesulfonyloxy group, particularly preferred examples are chlorine atom, bromine atom, and iodine atom, and a still more particularly preferred examples are chlorine atom, and bromine atom.

Conditions of the reaction for preparing the compounds of the formula (A-a) wherein $Z^a$ is —N(A$^6$)(A$^{62}$) from a compound of the formula (A-a) wherein $Z^a$ is —NH(A$^6$) are as follows. That is, the reaction is usually performed in the presence of a base, and a mineral base is preferred. Examples include potassium carbonate, sodium carbonate, cesium carbonate, sodium hydrogencarbonate, potassium hydroxide, and sodium hydroxide, and potassium carbonate is particularly preferred.

The compound represented as A$^{62}$—W is preferably used in an amount of 1 fold mole or more, most preferably 2 to 10 fold moles, based on the compound of the aforementioned formula (A-a) wherein $Z^a$ is —NH(A$^6$).

Examples of the reaction solvent include inert solvents, for example, alcoholic solvents such as methanol and ethanol, dimethylformamide, dimethylacetamide, tetrahydrofuran, 1,4-dioxane, acetone, 2-butanone, dimethyl sulfoxide, acetonitrile, and the like, which can be used alone or as a mixed solvent thereof, and water, dimethylformamide and acetone are preferred.

The reaction temperature is, for example, −10° C. or higher, preferably 10 to 40° C. The reaction time is, for example, usually 0.5 hour or more, preferably 2 to 10 hours.

Further, as for the compounds of the formula (A-a), in the same manners as Steps 1-5 and 1-6 mentioned above, a compound of the formula (A-a) wherein $Z^a$ is —N(A$^6$)(PG$^2$) can be deprotected to prepare a compound of the formula (A-a) wherein $Z^a$ is —NH(A$^6$), and this compound can be further reacted with a compound represented as A$^{63}$—W wherein A$^{63}$ and W have the same meanings as defined above to prepare a compound of the formula (A-a) wherein $Z^a$ is —N(A$^6$)(A$^{63}$).

As for the compounds represented by the formula (B), in the same manners as Steps 1-5 and 1-6 mentioned above, a compound of the formula (B) wherein $Z^a$ is —N(A$^6$)(PG$^2$) can be deprotected to prepare a compound of the formula (B) wherein $Z^a$ is —NH(A$^6$), and this compound can be further reacted with a compound represented as A$^{62}$—W wherein A$^{62}$ has the same meaning as defined above, and W represents a leaving group, or A$^{63}$—W wherein A$^{63}$ and W have the same meanings as defined above to prepare a compound of the formula (B) wherein $Z^a$ is —N(A$^6$)(A$^{62}$), or —N(A$^6$)(A$^{63}$).

Also as for the compounds represented by the formula (A-b), in the same manners as Steps 1-5 and 1-6 mentioned above, a compound of the formula (A-b) wherein $Z^a$ is —N(A$^6$)(PG$^2$) can be deprotected to prepare a compound of the formula (A-b) wherein $Z^a$ is —NH(A$^6$), and this compound can be further reacted with a compound represented as A$^{62}$—W wherein A$^{62}$ has the same meaning as defined above, and W represents a leaving group, or A$^{63}$—W wherein A$^{63}$ and W have the same meanings as defined above to prepare a compound of the formula (A-b) wherein $Z^a$ is —N(A$^6$)(A$^{62}$), or —N(A$^6$)(A$^{63}$).

Furthermore, as for the compounds represented by the formula (A-c), in the same manners as Steps 1-5 and 1-6 mentioned above, a compound of the formula (A-c) wherein $Z^a$ is —N(A$^6$)(PG$^2$) can be deprotected to prepare a compound of the formula (A-c) wherein $Z^a$ is —NH(A$^6$), and this compound can be reacted with a compound represented as A$^{62}$—W wherein A$^{62}$ has the same meaning as defined above, and W represents a leaving group, or A$^{63}$—W wherein A$^{63}$ and W have the same meanings as defined above to prepare a compound of the formula (A-c) wherein $Z^a$ is —N(A$^6$)(A$^{62}$), or —N(A$^6$)(A$^{63}$).

Further, the compounds of the formula (A-a) wherein $Z^a$ is —N(A$^6$)(A$^{62}$), and A$^{62}$ is an alkyl group of which end is substituted with N(A$^7$)(—X$^3$—A$^{71}$), where —X$^3$— has the same meaning as defined above, A$^7$ represents hydrogen atom, or an alkyl group, and A$^{71}$ represents an alkyl group, an aralkyl group, or an aryl group, can be prepared by reacting the compound of the formula (A-a) wherein $Z^a$ is —N(A$^6$)(A$^{63}$) obtained above with an acylation reagent suitably corresponding to an objective compound to be prepared (Step 1-6-1). Examples of the acylation reagent include carboxylic acid chlorides, carboxylic acid anhydrides, carboxylic acid active esters, carboxylic acids, and the like. Examples of acetylation reagent include, for example, acetyl chloride, acetic anhydride, acetic acid active esters, acetic acid, and the like. Examples of the carboxylic acid active esters include carboxylic acid succinimides, imidazole carboxylates, carboxylic acid 4-nitrophenyl esters, carboxylic acid pentafluorophenyl esters, and the like. The acylation reagent is usually used preferably in an amount of 1 or more fold moles, most preferably 1.1 to 10 fold moles, based on the compound of the aforementioned formula (A-a) wherein $Z^a$ is —N(A$^6$)(A$^{63}$). When a carboxylic acid is directly used as the acylation reagent, it is usually preferable to perform the reaction in the presence of a dehydration condensing agent. Examples of the dehydration condensing agent used herein include N,N-dicyclohexylcarbodiimide, N,N-diisopropylcarbodiimide, 1-ethyl-3-(3-dimethylaminopropyl)carbodiimide (EDC), 2-chloro-1-methylpyridinium iodide, 2-(1H-benzotriazol-1-yl)-1,1,3,3-tetramethyluronium tetrafluoroborate (TBTU), benzotriazol-1-yloxytris(dimethylamino)phosphonium hexafluorophosphate (BOP), 2-(1H-benzotriazol-1-yl)-1,1, 3,3-tetramethyluronium hexafluorophosphate (HBTU), O—(N-succinimidyl)-1,1,3,3-tetramethyluronium tetrafluoroborate (TSTU), benzotriazol-1-yloxytrispyrrolidinophosphonium hexafluorophosphate (PyBOP), bromotrispyrrolidinophosphonium hexafluorophosphate (PyBrOP), tetramethylfluoroformamidinium hexafluorophosphate (TFFH), 2-chloro-1-methylpyridinium iodide, 2,2-dipyridyl disulfide/triphenylphosphine, diethyl azodicarboxylate/triphenylphosphine, and the like. These dehydration condensing agent is usually preferably used in an amount of 1 or more fold moles, most preferably 1.1 to 10 fold moles, based on the compound of the aforementioned formula (A-a) wherein $Z^a$ is —N($A^6$)($A^{63}$).

The acylation reaction is also preferably performed, for example, in the presence of an additive such as 1-hydroxybenzotriazole (HOBt), 1-hydroxy-7-azabenzotriazole (HOAt), N-hydroxysuccinimide (HOSu), 4-nitrophenol (HONp) and pentafluorophenol (HOPfp). As for the amount of the additive, preferably 0.01 to 10 fold moles or more, most preferably 0.1 to 5 fold moles, are usually used based on the compound of the aforementioned formula (A-a) wherein $Z^a$ is —N($A^6$)($A^{63}$).

The acylation reaction is also preferably performed, for example, in the presence of an organic tertiary amine such as triethylamine, N,N-diisopropylethylamine, pyridine, 4-dimethylaminopyridine, and 1,8-diazabicyclo[5.4.0]undec-7-ene, or an inorganic base such as potassium carbonate, sodium carbonate, cesium carbonate, sodium hydrogencarbonate, potassium hydroxide, and sodium hydroxide. As for the amount of the base, preferably 0.01 to 10 fold moles or more, most preferably 0.1 to 5 fold moles, are usually used based on the compound of the aforementioned formula (A-a) wherein $Z^a$ is —N($A^6$)($A^{63}$).

As the reaction solvent, an inert solvent, for example, water, an alcoholic solvent such as tert-butanol, N,N-dimethylformamide, N,N-dimethylacetamide, 1-methylpyrolidone, tetrahydrofuran, 1,4-dioxane, 1,2-dimethoxyethane, dichloromethane, chloroform, benzene, toluene, dimethyl sulfoxide, sulfolane, acetonitrile, or the like can be used as each kind, or a mixed solvent thereof.

The reaction temperature is, for example, −10° C. or higher, preferably 10 to 40° C. The reaction time is, for example, usually 0.5 hour or more, preferably 2 to 10 hours.

Further, the compounds of the formula (A-a) wherein $A^{62}$ is an alkyl group of which end is substituted with N($A^7$)(—$X^3$—$A^{71}$), and $A^7$ and $A^{71}$ together become an alkylene group, or an alkylene group substituted with an alkyl group to form a ring can be prepared in the same manner as Step 1-6 by reacting the "compound of the formula (A-a) wherein $A^7$ is hydrogen atom" obtained above as a starting material with a compound represented as (PG$^3$)O—$X^3$—$A^{72}$ where PG$^3$ and —$X^3$— have the same meanings as defined above, and $A^{72}$ represents an alkyl group of which end is substituted with a leaving group (the alkyl group may be substituted with another alkyl group), then removing PG$^3$ in a known manner, and cyclizing the resultant using a dehydration condensing agent similar to those used in the aforementioned acylation reaction (Step 1-6-2). The leaving group is the same as that described above.

The compounds of the aforementioned formula (A-a) can be classified into compounds represented by the formula (A-a-1):

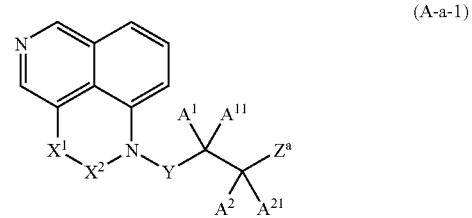

(A-a-1)

wherein Y, $A^1$, $A^{11}$, $A^2$, $A^{21}$, and $Z^a$ have the same meanings as those defined above, and $X^1$—$X^2$ represents —CH($R^2$)—CH($R^3$)—, or —CH($R^2$)—CH($R^3$)—CH($R^4$)—, and compounds represented by the formula (A-a-2):

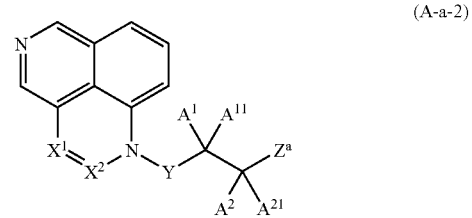

(A-a-2)

wherein Y, $A^1$, $A^{11}$, $A^2$, $A^{21}$, and $Z^a$ have the same meanings as those defined above, and $X^1$—$X^2$ represents —C($R^2$)=C($R^3$)—, or —C($R^2$)=C($R^3$)—CH($R^4$)—. As explained below, the compounds of the formula (A-a-2) are prepared from a compound of the formula (A-a-1), and the compounds of the formula (A-a-1) can be prepared from a compound of the following formula (C).

The compounds of the formula (A-a-1) can be prepared by cyclizing a compound represented by the following formula (C):

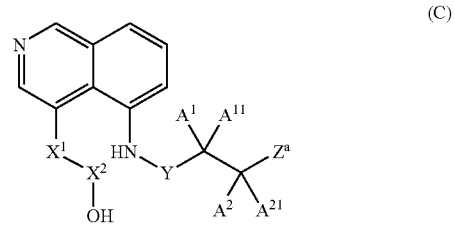

(C)

wherein Y, $A^1$, $A^{11}$, $A^2$, $A^{21}$, $Z^a$, and $X^1$—$X^2$ have the same meanings as those defined above (Step 1-7).

Examples of the cyclization method include a method of performing the cyclization in the presence of a phosphorus reagent and an azo compound, and a method of reacting the compound with an alkylsulfonyl chloride, an arylsulfonyl chloride, an alkylsulfonic acid anhydride or an arylsulfonic acid anhydride in the presence of a base, and a preferred method is a method of performing the cyclization in the presence of a phosphorus reagent and an azo compound in an inert solvent (see, for example, Tsunoda et al., Chemistry Letters, 539 (1994); or Mitsunobu, O., Synthesis, 1 (1981)). Examples of the inert solvent include, for example, tetrahydrofuran, toluene, and dichloromethane, and a preferred example is tetrahydrofuran. Examples of the phosphorus reagent include, for example, triphenylphosphine, and tri(n- butyl)phosphine. Example of the azo compound include, for example, diethyl azodicarboxylate, di(iso-propyl) azodicarboxylate, and 1,1'-azobis(N,N-dimethylformamide). Each of the phosphorus reagent and the azo compound may be the same or different, and is used in an amount of 1 fold mole or more, preferably 2 to 4 fold moles, based on the compound of the formula (C). The reaction temperature is, for example, −10° C. or higher, preferably about 0 to 60° C. This step is preferably preformed with a compound wherein $Z^a$ is —$O(PG^1)$, —$N(A^6)(PG^2)$, or —$N(A^6)(A^{62})$.

The compounds of the formula (A-a-2) can be prepared by dehydrogenation of a compound of the formula (A-a-1) in an inert solvent (Step 1-8). As the catalyst, for example, palladium catalysts such as 5% palladium/carbon, 10% palladium/carbon, or palladium black, and sulfur are preferred. Examples of the inert solvent include xylene, mesitylene, toluene, and the like, and xylene is preferred. The reaction temperature is 60° C. or higher, preferably 120 to 150° C.

The compounds of the aforementioned formula (C) can be prepared by hydration of a compound represented by the following formula (D):

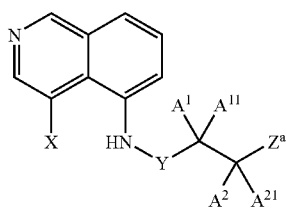

(D)

wherein Y, $A^1$, $A^{11}$, $A^2$, $A^{21}$, and $Z^a$ have the same meanings as those defined above, and X represents —$C(R^2)$=$CH(R^3)$, or —$CH(R^2)$—$C(R^3)$=$CH(R^4)$ (Step 1-9).

For example, a compound of the formula (D) can be hydroborated with a boron reagent, then oxidized and hydrolyzed to obtain the compound. As for the hydroboration, examples of the boron reagent include dicyclohexylborane, disyamyl borane, thexyl borane, catechol borane, 9-borabicyclo[3.3.1]nonane (9-BBN) dimmer, 9-BBN monomer, and the like, and 9-BBN dimmer, and 9-BBN monomer are preferred. The boron reagent is preferably used in an amount of usually 1 fold mole or more, preferably 2 to 5 fold moles. Examples of the solvent include ether type solvents such as tetrahydrofuran and 1,4-dioxane, and the like, and tetrahydrofuran is preferred. The reaction temperature is 0° C. to the boiling temperature of the solvent used, preferably 10 to 60° C. The reaction time is 2 hours or more, preferably 10 to 20 hours. As for the subsequent oxidization and hydrolysis, examples of the oxidizing agent include 30% aqueous hydrogen peroxide, sodium peroxoborate, N-methylmorpholine N-oxide, triethylamine N-oxide, and the like, and 30% aqueous hydrogen peroxide, and sodium peroxoborate are preferred. The oxidizing agent is used in an amount of, for example, 1 fold mole or more, preferably 2 to 20 fold moles. The reaction time is, for example, 0.25 to 10 hours, preferably 0.5 to 4 hours. Then, the hydrolysis is performed in the presence of an alkali, and examples of the alkali include aqueous sodium hydroxide, aqueous potassium hydroxide, and the like. The alkali is used in an amount of, for example, usually 2 to 100 fold moles, preferably 3 to 20 fold moles, and the reaction time is, for example, 2 hours or more, preferably 2 to 4 hours. This step is preferably preformed with a compound wherein $Z^a$ is —$O(PG^1)$, —$N(A^6)(PG^2)$, or —$N(A^6)(A^{62})$.

The compounds represented by the formula (D) can be prepared by reacting a compound represented by the following formula (E):

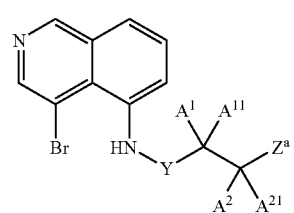

(E)

wherein Y, $A^1$, $A^{11}$, $A^2$, $A^{21}$, and $Z^a$ have the same meanings as those defined above, with a tin compound represented by the following formula (F):

$$X—SnBu_3 \quad (F)$$

wherein X has the same meaning as defined above, and Bu represents n-butyl (Step 1-10). Examples of the tin compound represented by the formula (F) include those commercially available and those known from literatures (see, for example, Seyferth et al., Chem. Ind., 402 (1959); J. Amer. Chem. Soc., 361 (1962); and J. Amer. Chem. Soc., 515 (1957)). The amount of this tin compound is, for example, 1 fold mole or more, preferably 1 to 3 fold moles, based on the compound of the formula (E). This step is preferably preformed with a compound wherein $Z^a$ is —$O(PG^1)$, —$N(A^6)(PG^2)$, or —$N(A^6)(A^{62})$.

As for the preparation of the compounds of the formula (D) by the coupling reaction of a compound of the formula (E), and a compound of the formula (F), preferable examples include, for example, the following two kinds of reaction conditions.

The first reaction condition corresponds to a method of performing the reaction in toluene or an ether type solvent in the presence of tetrakis(triphenylphosphine)palladium(0) as a catalyst, and 2,6-di(tert-butyl)-4-cresol (BHT) as a polymerization inhibitor. Based on the compound of the formula (E), tetrakis(triphenylphosphine)palladium(0) is used in an amount of, for example, 0.001 fold mole or more, preferably 0.01 to 0.2 fold mole, and BHT is used in an amount of, for example, 0.001 fold mole or more, preferably 0.005 to 0.01 fold mole. As the solvent, toluene or 1,4-dioxane is preferred, and the reaction temperature is, for example, 10° C. or higher, preferably 80 to 120° C. This step is preferably preformed with a compound wherein $Z^a$ is —$O(PG^1)$, —$N(A^6)(PG^2)$, or —$N(A^6)(A^{62})$.

The second reaction condition corresponds to a method of performing the reaction in an ether type solvent in the presence of a palladium compound such as tetrakis(triphenylphosphine)palladium(0), palladium(II) acetate, or tris(dibenzylideneacetone)dipalladium(0), or a phosphorus compound such as triphenylphosphine or tri(tert-butyl)phosphine, and cesium fluoride as an additive. As the palladium compound, tris(dibenzylideneacetone)dipalladium(0) is preferred, and tri(tert-butyl)phosphine is preferred as the phosphorus compound. The solvent is preferably 1,4-dioxane.

Based on the compound of the formula (E), the palladium compound is used in an amount of, for example, 0.001 fold mole or more, preferably 0.01 to 0.2 fold mole, and the phosphorus compound is preferably used in an amount of about 4 fold moles. Cesium fluoride is preferably used in an amount of about 1 to 3 fold moles based on the tin compound of the formula (F). The reaction temperature is, for example, 10° C. or higher, preferably 60 to 100° C. This step is preferably preformed with a compound wherein $Z^a$ is —O(PG$^1$), —N(A$^6$)(PG$^2$), or —N(A$^6$)(A$^{62}$). As for these reactions, Gregory, C, Fu et al., Angew. Chem. Int. Ed., 2411 (1999) can be referred to.

The compounds of the formula (E) can be prepared from 5-amino-4-bromoisoquinoline (Reference Example 1), and a carbonyl compound represented by the following formula (G):

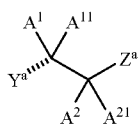
(G)

wherein the bond represented by the broken line represents a single bond, or a double bond;

when the bond represented by the broken line is a single bond, $Y^a$ represents —C(A$^3$)=O, —C(A$^4$)(A$^{41}$)—C(A$^3$)=O, or —C(A$^5$)(A$^{51}$)—C(A$^4$)(A$^{41}$)—C(A$^3$)=O, A$^{11}$, A$^{21}$, A$^{41}$, and A$^{51}$ have the same meanings as those defined above;

A$^1$, A$^2$, Z$^a$, A$^3$, A$^4$, and A$^5$ have the same meanings as those defined above, provided that when any of combinations of A$^6$ and A$^3$, A$^6$ and A$^4$, A$^6$ and A$^1$, A$^6$ and A$^2$, A$^2$ and A$^3$, A$^2$ and A$^4$, A$^6$ and A$^5$, A$^3$ and A$^1$, and A$^5$ and A$^1$ is not present, said combination is excluded;

when the bond represented by the broken line is a double bond, $Y^a$ is oxygen atom, A$^{11}$ is hydrogen atom, A$^{21}$, A$^{41}$, and A$^{51}$ have the same meanings as those defined above; and A$^1$, A$^2$, Z$^a$, A$^3$, A$^4$, and A$^5$ have the same meanings as those defined above, provided that when any of combinations of A$^6$ and A$^3$, A$^6$ and A$^4$, A$^6$ and A$^1$, A$^6$ and A$^2$, A$^2$ and A$^3$, A$^2$ and A$^4$, A$^6$ and A$^5$, A$^3$ and A$^1$, and A$^5$ and A$^1$ is not present, said combination is excluded, which carbonyl compound is commercially available, or can be prepared (Step 1-11).

This step includes a step of forming a Schiff base from known 5-amino-4-bromoisoquinoline and a compound of the formula (G), and a reduction step. This step is preferably preformed with a compound wherein $Z^a$ is —O(PG$^1$), —N(A$^6$)(PG$^2$), or —N(A$^6$)(A$^{62}$).

As for the Schiff base formation step, two kinds of reaction conditions can be mentioned as preferred examples.

The first condition corresponds to a method of forming a Schiff base in a solvent such as benzene, toluene, dichloromethane, 1,4-dioxane, tetrahydrofuran, and an alcohol in the presence of an acid. Examples of the acid include hydrochloric acid, methanesulfonic acid, p-toluenesulfonic acid, and camphorsulfonic acid, and p-toluenesulfonic acid (monohydrate) is preferred. Based on 5-amino-4-bromoisoquinoline, the compound of the formula (G) is used in an amount of, for example, 1 fold mole or more, preferably 1 to 2 fold moles, and p-toluenesulfonic acid is used in an amount of, for example, 0.0001 fold mole or more, preferably 0.01 to 0.2 fold mole. The reaction temperature is, for example, 0° C. or higher, preferably 20 to 120° C. The reaction time is, for example, 0.1 hour or more, preferably 0.3 to 12 hours.

The second condition corresponds to a method of forming a Schiff base without solvent, or in an inert solvent such as tetrahydrofuran, 1,4-dioxane, toluene, and dichloromethane in the presence of titanium(IV) isopropoxide or titanium tetrachloride. It is preferable to carry out the reaction without solvent, or in tetrahydrofuran, or dichloromethane in the presence of titanium(IV) isopropoxide. Based on 5-amino-4-bromoisoquinoline, the compound of the formula (G) is used in an amount of, for example, 1 fold mole or more, preferably 1 to 2 fold moles, and titanium(IV) isopropoxide is used in an amount of, for example, 1 fold mole or more, preferably 2 to 3 fold moles. The reaction temperature is, for example, −20° C. to the reflux temperature of the solvent, preferably 10 to 60° C. The reaction time is, for example, 10 to 72 hours, preferably 20 to 60 hours.

The reduction step can be performed by allowing a reducing agent to act on the aforementioned Schiff base in a solvent without isolating the Schiff base. Examples of the solvent include, in addition to the solvents used for the Schiff base formation reaction, alcohols such as methanol, ethanol, and isopropanol, and preferred examples are methanol, and ethanol. Examples of the reducing agent include metal hydride reducing agents such as sodium borohydride, potassium borohydride, lithium borohydride, zinc borohydride, sodium cyanoborohydride, and sodium triacetoxyborohydride, borane/tetrahydrofuran complex, borane/pyridine complex, borane/triethylamine complex, borane/dimethyl sulfide complex, and lithium triethylborohydride, and a preferred example is sodium borohydride. Based on 5-amino-4-bromoisoquinoline, sodium borohydride is used in an amount of, for example, 0.5 fold mole or more, preferably 1 to 20 fold moles. The reaction temperature is, for example, 0° C. or higher, preferably 10 to 80° C. The reaction time is, for example, 0.1 hour or more, preferably 0.5 to 12 hours.

As an alternative method, the compounds of the formula (D) can be prepared by using a compound represented by the following formula (H):

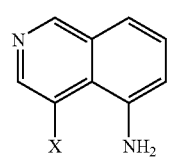
(H)

wherein X has the same meaning as defined above, as a starting material instead of 5-amino-4-bromoisoquinoline, and subjecting it to the same conditions as those used in Step 1-11 (Step 1-12). The compounds of the formula (H) can be prepared by using 5-amino-4-bromoisoquinoline as a starting material instead of the compound of the formula (E), and subjecting it to the same conditions as those used in Step 1-10 (Step 1-13).

(Preparation Method 2)

The compounds represented by the following formula (1-a):

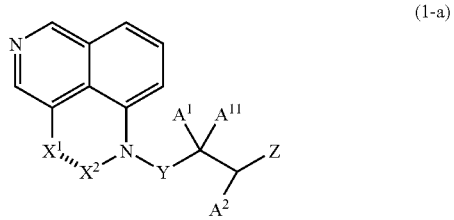

wherein $A^{11}$, and $X^1 \ldots X^2$ have the same meanings as those defined above; and Y, $A^1$, $A^2$, and Z have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded, which correspond to the compounds of the formula (1) wherein both of $A^{21}$ and $R^1$ are hydrogen atoms, can be prepared from a compound represented by the following formula (J):

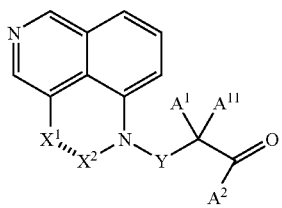

wherein $A^{11}$, and $X^1 \ldots X^2$ have the same meanings as those defined above; and Y, $A^1$, and $A^2$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded (Step 2-1).

Examples of the method for producing the compounds of the formula (1-a) wherein Z is hydroxyl group include a method of allowing a reducing agent to react on the starting compound in a solvent. Examples of the reducing agent include metal hydride reducing agents such as sodium borohydride, zinc borohydride, borane/tetrahydrofuran complex, borane/pyridine complex, borane/triethylamine complex, borane/dimethyl sulfide complex, and lithium triethylboride, and sodium borohydride is preferred. Based on the compound of the formula (J), sodium borohydride is used in an amount of, for example, 0.5 fold mole or more, preferably 1 to 20 fold moles. Examples of the solvent include alcohols such as methanol, ethanol, and isopropanol, ethers such as tetrahydrofuran, 1,2-dimethoxyethane, and 1,4-dioxane, dichloromethane, and N,N-dimethylformamide, and methanol and ethanol are preferred. The reaction temperature is, for example, 0° C. or higher, preferably 10° C. to the reflux temperature of the solvent. The reaction time is, for example, 0.1 hour or more, preferably 0.5 to 12 hours.

Further, the compounds of the formula (1-a) wherein Z is $-N(A^6)(A^{61})$ can be prepared by subjecting the starting compound to the same conditions as those of Step 2-1 in the presence of a compound represented by the formula $NH(A^6)(A^{61})$ wherein $A^6$ and $A^{61}$ have the same meanings as those defined above (Step 2-2). The aforementioned compound of the formula $NH(A^6)(A^{61})$ is used in an amount of, for example, 1 fold mole or more, preferably 1 to 10 fold moles, based on the compound of the formula (J).

The compounds of the formula (J) can be prepared form a compound represented by the following formula (K):

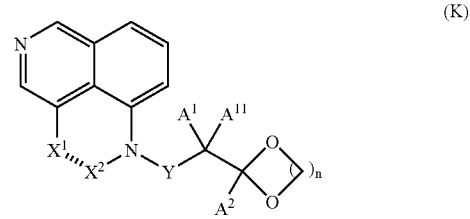

wherein n represents 2 or 3, $A^{11}$, and $X^1 \ldots X^2$ have the same meanings as those defined above; and Y, $A^1$, and $A^2$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded (Step 2-3). This step is performed by a method of carrying out the reaction in a solvent in the presence of an acid catalyst. Examples of the solvent include alcohols such as methanol, ethanol, tert-butanol, and ethylene glycol, ethers such as tetrahydrofuran, 1,2-dimethoxyethane, and 1,4-dioxane, nitromethane, dimethyl sulfoxide, N,N-dimethylformamide, N,N-dimethylacetamide, 1-methylpyrolidone, sulfolane, acetic acid, and water, and methanol, ethanol, tert-butanol, tetrahydrofuran, and 1,4-dioxane are preferred. Examples of the acid include mineral acids such as hydrochloric acid, sulfuric acid, and nitric acid, methanesulfonic acid, p-toluenesulfonic acid, trifluoromethanesulfonic acid, trifluoroacetic acid, perchloric acid, and the like, and hydrochloric acid, and perchloric acid are preferred. The reaction temperature is, for example, 0° C. or higher, preferably 10 to 120° C. The reaction time is, for example, 0.1 hour or more, preferably 0.5 to 12 hours.

The compounds of the formula (K) can be classified into the following two types of compounds, namely, compounds represented by the following formula (K-a):

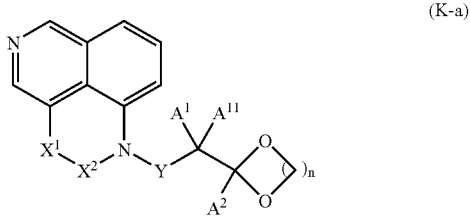

wherein n, $A^{11}$, and $X^1-X^2$ have the same meanings as those defined above; and Y, $A^1$, and $A^2$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded, and compounds represented by the following formula (K-b):

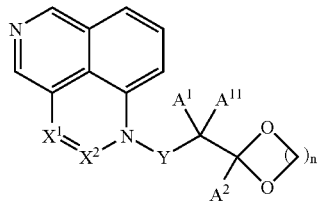

wherein n, $A^{11}$, and $X^1=X^2$ have the same meanings as those defined above; and Y, $A^1$, and $A^2$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded. As explained below, the compounds of the formula (K-b) can be prepared from a compound of the formula (K-a), and the compounds of the formula (K-a) can be prepared from a compound of the following formula (L).

The compounds of the formula (K-a) can be prepared by using a compound represented by the following formula (L):

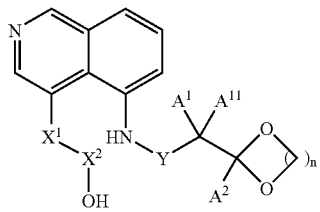

wherein n, $A^{11}$, and $X^1—X^2$ have the same meanings as those defined above; and Y, $A^1$, and $A^2$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded, instead of the compound of the formula (C), and cyclizing it in the same manner as that of Step 1-7 (Step 2-4).

The compounds of the formula (K-b) can be prepared by using a compound of the formula (K-a) instead of the compound of the formula (A-a-1), and subjecting it to dehydrogenation in the same manner as that of Step 1-8 (Step 2-5).

The compounds of the aforementioned formula (L) can be prepared by using a compound represented by the following formula (M):

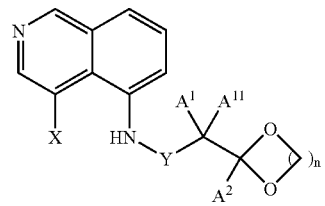

wherein n, $A^{11}$, and X have the same meanings as those defined above; and

Y, $A^1$, and $A^2$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded, instead of the compound of the formula (D), and subjecting it to hydration in the same manner as that of Step 1-9 (Step 2-6).

The compounds of the formula (M) can be prepared by using a compound represented by the following formula (N):

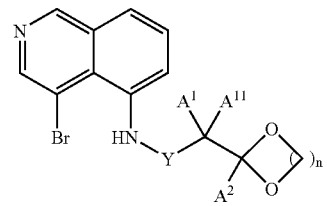

wherein n, and All have the same meanings as those defined above; and

Y, $A^1$, and $A^2$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded, and a compound of the aforementioned formula (F) instead of the compound of the formula (E), and subjecting them to a substitution reaction in the same manner as that of Step 1-10 (Step 2-7).

The compounds of the formula (N) can be prepared by using 5-amino-4-bromoisoquinoline mentioned above and a compound represented by the following formula (P):

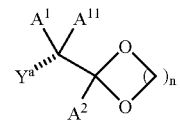

wherein n, and $A^{11}$ have the same meanings as those defined above; and $Y^a$, $A^1$, and $A^2$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded, instead of the compound of the formula (G), and subjecting them to reductive amination in the same manner as that of Step 1-11 (Step 2-8). The compounds of the aforementioned formula (M) can also be prepared by subjecting a compound of the aforementioned formula (H), and a compound of the formula (P) to reductive amination in the same manner as that of Step 1-11.

(Preparation Method 3)

The compounds represented by the following formula (1-b):

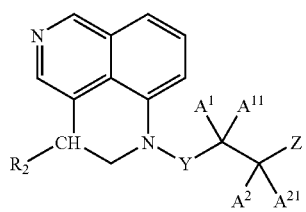

(1-b)

wherein $R^2$, $A^{11}$, and $A^{21}$ have the same meanings as those defined above; and $Y$, $A^1$, $A^2$, and $Z$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded, which correspond to the compounds of the formula (1) wherein $R^1$ is hydrogen atom, and $X^1 \ldots X^2$ is —CH($R^2$)—CH$_2$—, can be prepared by subjecting a compound represented by the following formula (A-d):

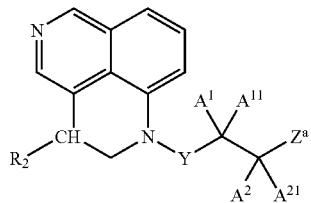

(A-d)

wherein $R^2$, $A^{11}$, and $A^{21}$ have the same meanings as those defined above; and $Y$, $A^1$, $A^2$, and $Z^a$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded, to the deprotection reaction of Step 1-1 (Step 3-1).

When Z and $Z^a$ in the formula (1-b) represent the same group, the compounds of the formula (A-d) constitute a part of the compounds of the formula (1-b), and Step 3-1 mentioned above is unnecessary.

Further, in the case of the compounds of the aforementioned formula (A-d) wherein $Z^a$ in the formula (A-d) is —N($A^6$)($A^{62}$), it is also possible to prepare a compound of the formula (1-b) by using any of Step 1-5, Step 1-6, Step 1-6-1, and Step 1-6-2 in combination.

The compounds of the formula (A-d) can be prepared by cyclizing a compound represented by the following formula (D-a):

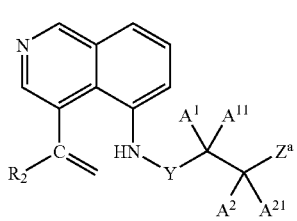

(D-a)

wherein $R^2$, $A^{11}$, and $A^{21}$ have the same meanings as those defined above; and $Y$, $A^1$, $A^2$, and $Z^a$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded (Step 3-2). Examples of the method for the cyclization include a method of allowing a base to react on the compound in an inert solvent. Examples of the inert solvent include ether type solvents such as tetrahydrofuran, 1,2-dimethoxyethane, and 1,4-dioxane, benzene, toluene, dimethyl sulfoxide, N,N-dimethylformamide, 1-methylpyrolidone, and sulfolane, and tetrahydrofuran, and 1,4-dioxane are preferred. Examples of the base include alkali metals such as sodium and potassium, alkali metal hydrides such as sodium hydride, and potassium hydride, alkali metal alkoxides such as sodium methoxide, potassium methoxide, sodium ethoxide, sodium isopropoxide, sodium tert-butoxide, and potassium tert-butoxide, organic metal bases such as methyl lithium, n-butyl lithium, phenyl lithium, tert-butyl lithium, lithium diisopropylamide, sodium bis(trimethylsilyl)amide, potassium bis(trimethylsilyl)amide, and lithium 2,2,6,6-tetramethylpiperizide, and the like, potassium, potassium hydride, potassium tert-butoxide, and potassium bis(trimethylsilyl)amide are preferred, and potassium tert-butoxide is particularly preferred.

The amount of the base used is, for example, 0.01 fold mole or more, preferably 0.1 to 5 fold moles, based on the compound of the formula (D-a). The reaction temperature is, for example, 0° C. or higher, preferably 10 to 120° C. The reaction time is, for example, 0.001 hour or more, preferably 0.01 to 5 hours.

The compounds of the formula (D-a) can be prepared by, for example, subjecting a compound of the aforementioned formula (E), and a tin compound represented by the following formula (F-a):

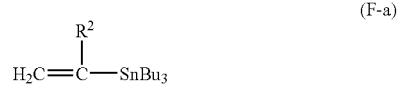

(F-a)

wherein $R^2$ and Bu have the same meanings as those defined above, to the same conditions as those of Step 1-10 mentioned above (Step 3-3).

Alternatively, the compounds of the formula (D-a) can be prepared by, for example, subjecting a compound represented by the following formula (H-a):

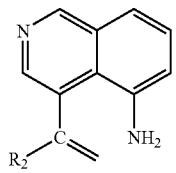

(H-a)

wherein R² has the same meaning as defined above, and a compound of the aforementioned formula (G) to the same conditions as those of Step 1-11 mentioned above (Step 3-4).

The compounds of the formula (H-a) can be prepared by, for example, subjecting 5-amino-4-bromoisoquinoline mentioned above and a compound of the aforementioned formula (F-a) to the same conditions as those of Step 1-10 (Step 3-5).

The compounds of the aforementioned formula (A-d) can be prepared also by the following method. The compounds of the formula (A-d) can be prepared by reacting a compound represented by the following formula (Q):

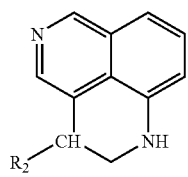

(Q)

wherein R² has the same meaning as defined above, and a compound represented by the following formula (S):

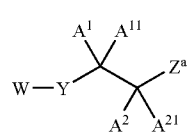

(S)

wherein $A^{11}$, $A^{21}$ and W have the same meanings as those defined above; and Y, $A^1$, $A^2$, and $Z^a$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded (Step 3-6). This step is preferably preformed with a compound wherein $Z^a$ is —O(PG¹), —N(A⁶)(PG²), or —N(A⁶)(A⁶²). For example, it is preferred that the reaction is performed in an inert solvent in the presence of a base. Examples of the inert solvent include water, alcohol type solvents such as methanol, and ethanol, ether type solvents such as tetrahydrofuran, 1,2-dimethoxyethane, and 1,4-dioxane, benzene, toluene, dimethyl sulfoxide, N,N-dimethylformamide, 1-methylpyrolidone, sulfolane, and the like, and tetrahydrofuran, N,N-dimethylformamide, and 1,4-dioxane, for example, are preferred. Examples of the base include alkali metals such as sodium and potassium, alkali metal hydrides such as sodium hydride, and potassium hydride, alkali metal hydroxides such as potassium hydroxide, and sodium hydroxide, and the like, and sodium hydride, and potassium hydride are preferred. The amount of the base used is, for example, 1 fold mole or more, preferably 1.5 to 10 fold moles, based on the compound of the formula (Q). The reaction temperature is, for example, 0° C. or higher, preferably 10 to 80° C. The reaction time is, for example, 1 hour or more, preferably 10 to 40 hours.

Further, the compounds of the formula (Q) can also be prepared by using a compound of the formula (H-a) instead of the compound of the formula (D-a) and subjecting it to the same conditions as those of Step 3-2 mentioned above (Step 3-7).

(Preparation Method 4)

The compounds represented by the following formula (1-c):

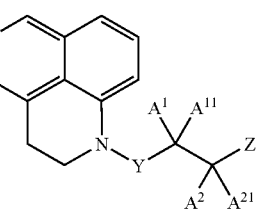

(1-c)

wherein $A^{11}$, and $A^{21}$ have the same meanings as those defined above; and Y, $A^1$, $A^2$, and Z have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded, which correspond to the compounds of the formula (1) wherein R¹ is hydrogen atom, and $X^1 \ldots X^2$ is —CH₂—CH₂—, can be prepared by subjecting a compound represented by the following formula (A-e):

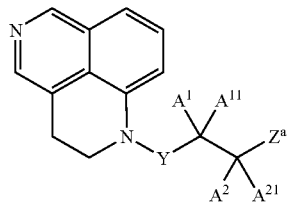

(A-e)

wherein $A^{11}$, and $A^{21}$ have the same meanings as those defined above; and Y, $A^1$, $A^2$, and $Z^a$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded, to the deprotection reaction of Step 1-1 (Step 4-1).

When Z and $Z^a$ in the formula (1-c) represent the same group, the compounds of the formula (A-e) constitute a part of the compounds of the formula (1-c), and Step 4-1 mentioned above is unnecessary.

Further, in the case of the compounds of the aforementioned formula (A-e) wherein $Z^a$ in the formula (A-e) is —N(A⁶)(A⁶²), it is also possible to prepare a compound of the formula (1-c) by using any of Step 1-5, Step 1-6, Step 1-6-1, and Step 1-6-2 in combination.

The compounds of the formula (A-e) can be prepared by using a compound represented by the following formula (T):

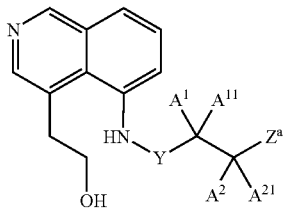

(T)

wherein $A^{11}$, and $A^{21}$ have the same meanings as those defined above; and Y, $A^1$, $A^2$, and $Z^a$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded instead of the compound of the formula (C), and cyclizing it according to Step 1-7 (Step 4-2). This step is preferably preformed with a compound wherein $Z^a$ is —O(PG$^1$), —N($A^6$)(PG$^2$), or —N($A^6$)($A^{62}$).

The compounds of the formula (T) can be prepared by subjecting a compound represented by following formula (U):

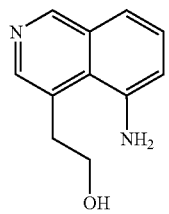

(U)

to reductive amination together with a carbonyl compound of the aforementioned formula (G) under the same conditions as those of Step 1-11 (Step 4-3).

The compounds of the formula (U) can be prepared by reducing a compound represented by following formula (V):

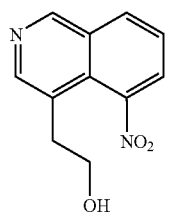

(V)

(for the nitro group moiety) (Step 4-4). Examples of the method for the reduction include a method of performing hydrogenation in an alcohol solvent in the presence of a metal catalyst. As the solvent, methanol, and ethanol are preferred. Examples of the metal catalyst include palladium black, 5% palladium/carbon, 10% palladium/carbon, palladium hydroxide, Raney nickel, and platinum oxide, and platinum oxide is a preferred example. The hydrogen pressure is preferably ordinary pressure to 4 atm. The reaction temperature is, for example, −20° C. or higher, preferably 10 to 50° C. The reaction time is, for example, 2 hours or more, preferably 4 to 15 hours.

The compounds of the formula (V) can be prepared by subjecting a compound represented by following formula (W):

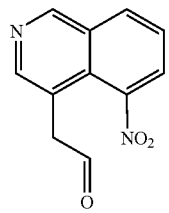

(W)

to reduction (for the aldehyde moiety) (Step 4-5). Examples of the method for the reduction include a method of allowing a reducing agent to react on the compound in a solvent. Examples of the solvent include, alcohols such as methanol, ethanol, and isopropanol, ethers such as tetrahydrofuran, 1,2-dimethoxyethane, and 1,4-dioxane, dichloromethane, and N,N-dimethylformamide, and methanol, and ethanol are preferred. Examples of the reducing agent include metal hydride reducing agents such as sodium borohydride, zinc borohydride, borane/tetrahydrofuran complex, borane/pyridine complex, borane/triethylamine complex, borane/dimethyl sulfide complex, and lithium triethylboride, and a preferred example is sodium borohydride. Based on the compound of the formula (W), sodium borohydride is used in an amount of, for example, 0.5 fold mole or more, preferably 1 to 20 fold moles. The reaction temperature is, for example, 0° C. or higher, preferably 10° C. to the reflux temperature of the solvent. The reaction time is, for example, 0.1 hour or more, preferably 0.5 to 12 hours.

The compounds of the formula (W) can be prepared by cleaving a diol represented by following formula (X):

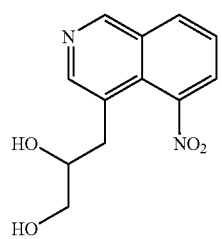

(X)

through oxidization (Step 4-6). Oxidization with sodium periodate is preferably used. Examples of the solvent include mixtures of a solvent such as tetrahydrofuran, dimethyl sulfoxide, tert-butanol, acetone, or 1,4-dioxane, and water, and a mixed solvent of tetrahydrofuran and water is preferred. Based on the compound of the formula (X), sodium periodate is used in an amount of, for example, 1 fold mole or more, preferably 1.3 to 5 fold moles. The reaction temperature is, for example, −20° C. or higher, preferably −10 to 20° C. The reaction time is, for example, 0.01 hour or more, preferably 0.5 to 1 hour.

The compounds of the formula (X) can be prepared by converting an allyl compound represented by following formula (Y):

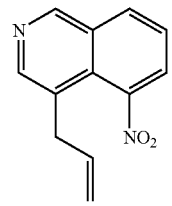

(Y)

into a diol (Step 4-7). This is performed by a method of performing a reaction with osmium tetroxide or microencapsulated osmium tetroxide (Wako Pure Chemical Industries) in a solvent in the presence of N-methylmorpholine N-oxide (NMO) (for example, Kobayashi. S. et al., J. Org. Chem., 6094 (1998)). Examples of the solvent include mixed solvents of a solvent such as acetone or 2-butanone, and water, and a mixed solvent of acetone and water is preferred. Based on the compound of the formula (Y), NMO is used in an amount of, for example, 1 fold mole or more, preferably 1.3 to 3 fold moles. Osmium tetroxide or microencapsulated osmium tetroxide is used in an amount of, for example, 0.01 to 0.2 fold mole, preferably 0.03 to 0.1 fold mole. The reaction temperature is, for example, 0° C. or higher, preferably 20 to 80° C. The reaction time is, for example, 1 hour or more, preferably 5 to 20 hours.

The compounds of the formula (Y) can be prepared by allylating known 4-bromo-5-nitroisoquinoline (Reference Example 1) using allyltributyltin as a compound of the formula (F) under the same conditions as those of Step 1-10 (Step 4-8).

(Preparation Method 5)

The compounds represented by the following formula (1-b-1):

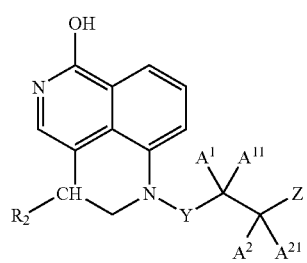

(1-b-1)

wherein $R^2$, $A^{11}$, and $A^{21}$ have the same meanings as those defined above; and Y, $A^1$, $A^2$, and Z have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded, which correspond to the compounds of the formula (1) wherein $R^1$ is hydroxyl group, and $X^1$ . . . $X^2$ is —CH($R^2$)—CH$_2$—, can be prepared by subjecting a compound represented by the following formula (A-c-1):

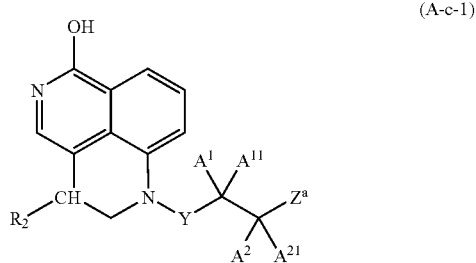

(A-c-1)

wherein $R^2$, $A^{11}$, and $A^{21}$ have the same meanings as those defined above; and Y, $A^1$, $A^2$, and $Z^a$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded, to a deprotection reaction (Step 5-1). This step can be performed by referring to Step 1-1 mentioned above. When Z and $Z^a$ in the formula (1-b-1) represent the same group, the compounds of the formula (A-c-1) constitute a part of the compounds of the formula (1-b-1), and Step 5-1 mentioned above is unnecessary.

Further, in the case of the compounds of the aforementioned formula (A-c-1) wherein $Z^a$ in the formula (A-c-1) is —N($A^6$)($A^{62}$), it is also possible to prepare a compound of the formula (1-b-1) by using any of Step 1-5, Step 1-6, Step 1-6-1, and Step 1-6-2 in combination.

The compounds of the formula (A-c-1) mentioned above can be prepared by hydroxylating a compound represented by the following formula (A-b-1):

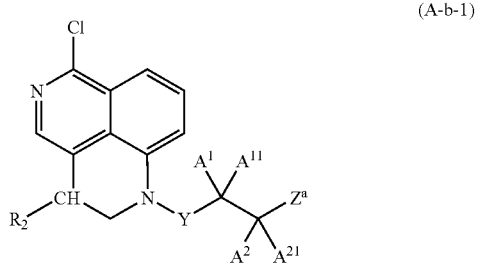

(A-b-1)

wherein $R^2$, $A^{11}$, and $A^{21}$ have the same meanings as those defined above; and Y, $A^1$, $A^2$, and $Z^a$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded (Step 5-2). This step can be performed by referring to Step 1-4 mentioned above.

The compounds represented by the following formula (1-b-2):

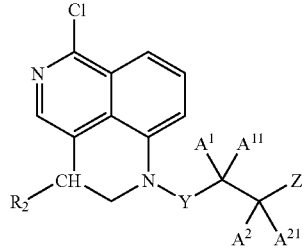

(1-b-2)

wherein $R^2$, $A^{11}$, and $A^{21}$ have the same meanings as those defined above; and Y, $A^1$, $A^2$, and Z have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded, which correspond to the compounds of the formula (1) wherein $R^1$ is chlorine atom, and $X^1 \ldots X^2$ is —CH($R^2$)—CH$_2$—, can be prepared by subjecting a compound represented by the aforementioned formula (A-b-1) to a deprotection reaction (Step 5-3). This step can be performed by referring to Step 1-1 mentioned above. When Z and $Z^a$ in the formula (1-b-2) represent the same group, the compounds of the formula (A-b-1) constitute a part of the compounds of the formula (1-b-2), and Step 5-3 mentioned above is unnecessary. Further, in the case of the compounds of the aforementioned formula (A-b-1) wherein $Z^a$ in the formula (A-b-1) is —N($A^6$)($A^{62}$), it is also possible to prepare a compound of the formula (1-b-2) by using any of Step 1-5, Step 1-6, Step 1-6-1, and Step 1-6-2 in combination.

The compounds of the formula (A-b-1) can be prepared by cyclizing a compound represented by the following formula (D-a-1):

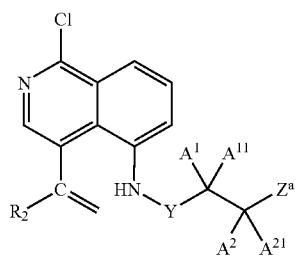

(D-a-1)

wherein $R^2$, $A^{11}$, and $A^{21}$ have the same meanings as those defined above; and Y, $A^1$, $A^2$, and $Z^a$ have the same meanings as those defined above, provided that when any of combinations of $A^6$ and $A^3$, $A^6$ and $A^4$, $A^6$ and $A^1$, $A^6$ and $A^2$, $A^2$ and $A^3$, $A^2$ and $A^4$, $A^6$ and $A^5$, $A^3$ and $A^1$, and $A^5$ and $A^1$ is not present, said combination is excluded (Step 5-4). This step can be performed by referring to Step 3-2 mentioned above.

The compounds of the formula (D-a-1) can be prepared from, for example, a compound represented by the following formula (H-a-1):

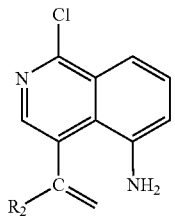

(H-a-1)

wherein $R^2$ has the same meaning as defined above, and a compound of the aforementioned formula (G) (Step 5-5). This step can be performed by referring to Step 1-11 (or Step 3-4) mentioned above.

The compounds of the formula (H-a-1) can be prepared by reducing (for the nitro group moiety) a compound represented by following formula (H-a-2):

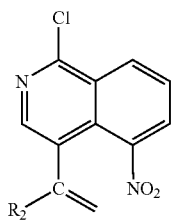

(H-a-2)

wherein $R^2$ has the same meaning as defined above (Step 5-6). This reduction is preferably performed in an inert solvent. Examples of the inert solvent include alcohols, ethers, and esters, and preferred examples are esters. A particularly preferred example is ethyl acetate. Examples of the reduction reagent include tin (divalent) reagents. Preferred examples of the tin (divalent) reagents include stannous chloride, and hydrate thereof. The reaction temperature is, for example, −20° C. or higher, preferably 10 to 50° C. The reaction time is, for example, 2 hours or more, preferably 4 to 15 hours.

The compounds of the formula (H-a-2) can be prepared by chlorinating a compound represented by the following formula (H-a-3):

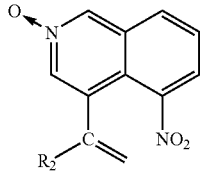

(H-a-3)

wherein $R^2$ has the same meaning as defined above (Step 5-7). This step can be performed by referring to Step 1-3 mentioned above.

The compounds of the formula (H-a-3) can be prepared by oxidizing a compound represented by the following formula (H-a-4):

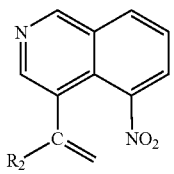

(H-a-4)

wherein R² has the same meaning as defined above (Step 5-8). This step can be performed by referring to Step 1-2 mentioned above.

The compounds of the formula (H-a-4) can be prepared by, for example, subjecting known 4-bromo-5-nitroisoquinoline (Reference Example 1) to the same conditions as those of Step 1-10 (Step 5-9).

The compounds of the present invention represented by the aforementioned formula (1) and salts thereof have cell movement inhibitory actions on the basis of inhibition against phosphorylation of the myosin regulatory light chain in the cells, and are useful as active ingredients of medicaments. Among the cell movement inhibitory actions of the compounds of the present invention, the cell contraction inhibitory action can be confirmed by measuring vasoconstriction inhibitory activity, intraocular pressure reducing activity, or the like. The action to regulate change of cell morphology can be confirmed by, for example, measuring neurite outgrowth of nerve cells, or the like. The inhibitory action on cell migration (the action will be abbreviated as "cell migration inhibitory action") can be confirmed by measuring neutrophil migration inhibitory activity, respiratory tract inflammation suppressing activity, or the like. The cell release inhibitory action can be confirmed by measuring the chemical mediator releasing amount from neutrophils. The cell aggregation inhibitory action can be confirmed by measuring platelet aggregation inhibitory activity, or the like. Further, the apoptosis inhibitory action can be confirmed by, for example, giving stimulation to induce apoptosis to cells and then measuring cell viability or occurring frequencies of morphological changes of cells characteristic to apoptosis such as nuclear condensation, nuclear fragmentation, and blebbing of cells.

However, since the cell movement inhibitory actions on the basis of the inhibition of phosphorylation of the myosin regulatory light chain in the cells are known to be associated with various biological actions as described in the section of related art in the specification, the cell movement inhibitory actions must be construed in their broadest sense including the aforementioned cell contraction inhibitory action, action to regulate change of cell morphology, cell migration inhibitory action, cell release inhibitory action, cell aggregation inhibitory action, and apoptosis inhibitory action.

For example, the compounds of the present invention represented by the aforementioned formula (1) and salts thereof have an inhibitory activity against phosphorylation of the myosin regulatory light chain (see, Test Example 1 of the specification), vasoconstriction inhibitory activity (see, Test Example 2 in the specification), respiratory tract constriction suppressing activity (see, Test Example 3 in the specification), intraocular pressure reducing activity (see, Test Example 4 in the specification), neurite outgrowth activity(see, Test Example 5 in the specification), neutrophil migration inhibitory activity (see, Test Example 6 in the specification), respiratory tract inflammation suppressing activity (see, Test Example 7 in the specification), and pulmonary inflammation suppressing activity (see, Test Example 8 in the specification). Further, as demonstrated by the test examples, the compounds represented by the aforementioned formula (1) and salts thereof have notably higher vasoconstriction inhibitory activity, respiratory tract constriction inhibitory activity, intraocular pressure reducing activity, neurite outgrowth activity, neutrophil migration inhibitory activity, and respiratory tract inflammation suppression activity as compared with the conventional isoquinoline compounds. Therefore, the compounds represented by the aforementioned formula (1) and salts thereof are useful as active ingredients of medicaments for prophylactic and/or therapeutic treatment of diseases relating to contraction of various cells, diseases relating to morphological change of various cells, diseases relating to migration of various cells, diseases relating to release of various cells, diseases relating to aggregation of various cells, and/or diseases relating to apoptosis of various cells, and the like.

Although it is not intended to be bound by any specific theory, action mechanism of the compounds of the present invention represented by the aforementioned general formula (1) and salts thereof can be presumed as follows. It is known that increase of the amount of phosphorylated myosin regulatory light chain activates the actomyosin system, which is a movement apparatus of cytoskeleton, and activates cell movements. Therefore, it is considered that the phosphorylation reaction of myosin regulatory light chain is important for cell movements (Kamm, K., et al., Annu. Rev. Physiol., 51, pp. 299–313, 1989; Niggli, V., FEBS Lett., 445, pp. 69–72, 1999; Itoh, K., et al., Biochim. Biophys. Acta., 1136, pp. 52–56, 1992; Kitani, S., et al., Biochem. Biophys. Res. Commun., 183, pp. 48–54, 1992). Measurement of the amount of phosphorylated myosin regulatory light chain in the cells revealed that the compounds represented by the aforementioned formula (1) and salts thereof decrease the amount of phosphorylated myosin regulatory light chain in the cells (refer to Test Example 1 in the specification).

It is known that the amount of phosphorylated myosin regulatory light chain in the cells is determined by activated states of two reaction routes including Reaction route 1 and Reaction route 2 described below (Fukata, Y., et al., Trends Pharmacol. Sci., 22, pp. 32–39, 2001).

<Reaction Route 1>

Increase of intracellular calcium concentration→Activation of myosin light chain kinase→Increase of amount of phosphorylated myosin regulatory light chain <Reaction Route 2>

Activation of low molecular weight G protein Rho→Activation of Rho kinase→Phosphorylation (inactivation) of myosin phosphatase→Increase of amount of phosphorylated myosin regulatory light chain It is considered that a compound that inhibits Reaction route 1 and/or Reaction route 2 mentioned above has an activity for decreasing the amount of phosphorylated myosin regulatory light chain. In order to estimate whether either or both of Reaction route 1 and Reaction route 2 mentioned above are the target site for the compounds of the present invention represented by the aforementioned formula (1) and salts thereof, effects of the compounds of the present invention represented by the aforementioned formula (1) and salts thereof on increase of intracellular calcium concentration and activity of myosin light chain kinase were examined. As a result, it was found that the compounds of the present invention and salts thereof gave no influence on the increase of intracellular calcium concentration (see, Test Example 9), and did not inhibit the myosin light chain kinase activity (see, Test Example 10). Therefore, it is presumed that the compounds of the formula (1) according to the present invention do not inhibit Reaction route 1 mentioned above, but inhibit Reaction route 2 mentioned above to decrease the amount of phosphorylated myosin regulatory light chain. Thus, the compounds of the present invention can be used as inhibitors of the Rho/Rho kinase pathway. The inhibition of Reaction route 2 mentioned above by the compounds of the present invention represented by the aforementioned formula (1) and salts thereof may be confirmed by measuring the inhibitory activity for the Rho kinase activity, or alternatively, by measuring the inhibitory activity for the phosphorylation reaction of myosin phosphatase.

The activity of Rho kinase can be measured by the method disclosed in WO01/56988. More specifically, ATP ($\gamma^{32}$P-ATP) is added to a substrate (Ribosomal S6 kinase substrate) together with a commercially available Rho kinase (Upstate) to start the enzymatic reaction and phosphorylate the substrate. The substrate is adsorbed on filter paper, and ATP is washed off with the phosphate buffer. Then, the amount of the phosphorylated substrate is measured by using a liquid scintillation counter. The inhibitory activity of the compounds of the present invention represented by the aforementioned formula (1) for the Rho kinase activity can be determined by adding the compounds before starting the enzymatic reaction, and measuring suppression of the phosphorylation amount of the substrate. The phosphorylation reaction of myosin phosphatase can be measured by, for example, using an antibody specifically recognizing the phosphorylated myosin phosphatase (Feng, J. et al., J. Biol. Chem., 274, pp. 37385–37390, 1999). More specifically, proteins including myosin phosphatase are extracted from a tissue, subjected to electrophoresis on acrylamide gel, and transferred to a nitrocellulose membrane. The proteins are reacted with antibodies specifically recognizing phosphorylated myosin phosphatase to detect the amount of phosphorylated myosin phosphatase. The inhibitory activity on the phosphorylation reaction of myosin phosphatase can be determined by adding the compounds before starting the extraction from the tissue, and measuring suppression of the phosphorylation amount of the myosin phosphatase.

It is considered that the compounds of the present invention represented by the aforementioned formula (1) and salts thereof inhibit the Rho/Rho kinase pathway, which is Reaction route 2 mentioned above, and exhibit more potent cell contraction inhibitory activity and cell migration inhibitory activity compared with the conventional isoquinoline compounds. It is known that the Rho/Rho kinase route plays an important role for cell contraction and cell migration. Other than the above, it has been reported that the Rho/Rho kinase pathway controls a variety of cellular functions such as aggregation, release, production, division, apoptosis, and gene expression in various cell lines (Fukata, Y., et al., Trends in Pharmacological Sciences, 22, pp. 32–39, 2001; Murata T., et al., J. Hepatotol., 35, pp. 474–481, 2001; Ohnaka, K., et al., Biochem. Biophys. Res. Commun., 287, pp. 337–342, 2001; Yuhong, S., et al., Exp. Cell Res., 278, pp. 45–52, 2002; Arakawa, Y. et al., BIO Clinica, 17(13), pp. 26–28, 2002). Therefore, the compounds of the present invention which inhibit the Rho/Rho kinase pathway exhibit, based on that effect, more potent cell contraction inhibitory activity (Test Examples 2, 3, and 4), cell morphology change regulating activity (Test Example 5), cell migration inhibitory activity (Test Examples 6, 7, and 8), cell release inhibitory activity, cell aggregation inhibitory activity, apoptosis inhibitory activity, and activity of regulating gene expression compared with the conventional isoquinoline compounds, and are useful as active ingredients of medicaments for prophylactic and/or therapeutic treatment of diseases relating to contraction of various cells, diseases relating to morphological change of various cells, diseases relating to migration of various cells, diseases relating to release from various cells, diseases relating to aggregation of various cells, diseases relating to apoptosis of various cells, and/or diseases relating to abnormal gene expression in various cells (Jikken Igaku (Experimental Medicine) Vol. 17, 7, 1999).

Examples of the diseases relating to contraction of various cells include, for example, as those relating to vascular smooth muscles, hypertension, arteriosclerosis, cerebral circulatory disturbance, brain function disorder with the aforementioned disease (mental disorder, memory disorder, dementia, delirium, poriomania, dyskinesia and the like), dizziness, cardiac diseases, pokkuri-byou (sudden death), disturbances of peripheral circulation, disturbances of retinal circulation, renal failure and the like, as those relating to airway smooth muscles, asthma, acute respiratory distress syndrome (ARDS), pulmonary emphysema, peripheral respiratory tract disease, chronic bronchitis, chronic obstructive pulmonary disease (COPD), and the like (Ueki, J. et al., Gendai Iryo (Contemporary Medical Care), Vol.34, No.9, pp. 87–92, 2002), as those relating to digestive tract smooth muscles, vomiting, chronic gastritis, reflux esophagitis, irritable bowel syndrome and the like, as those relating to smooth muscle cells existing in eyes, glaucoma, and the like, as those relating to vitreum of eyes, vitreoretinal diseases, and the like (Hirayama, K., et al., Preliminary Published Abstracts of the 42nd Congress of the Vitreoretina Society of Japan), as those relating to smooth muscles of bladder and urethra, dysuria, pollakiuria, incontinence and the like, as those relating to smooth muscles of uterus, gestational toxicosis, threatened premature delivery, abortion and the like, and as those relating to smooth muscles of penis, erectile dysfunction is known. However, the diseases are not limited to the aforementioned examples.

More precisely, examples of hypertension include essential hypertension, renal hypertension, renovascular hypertension, hypertension during pregnancy, endocrine hypertension, cardiovascular hypertension, neurogenic hypertension, iatrogenic hypertension, pulmonary hypertension and the like, and examples of arteriosclerosis include those in which pathological change is observed in major arteries in whole body such as coronary artery, aorta abdominalis, renal artery, carotid artery, ophthalmic artery, and cerebral artery. Examples of cerebral circulatory disturbance include cerebral thrombosis, cerebral infarction, cerebral hemorrhage, transient brain ischemic attack, hypertensive encephalopathy, cerebral arteriosclerosis, subdural hemorrhage, epidural hemorrhage, subarachnoid hemorrhage, brain hypoxia, cerebral edema, encephalitis, brain tumor, head injury, mental disorder, metabolic intoxication, drug intoxication, transient aphyxia, deep anesthesia in operation and the like. The cardiac diseases include congestive heart failure, acute myocardial infarction, previous myocardial infarction, subendocardial infarction, right ventricular infarction, atypical myocardial infarction, ischemic cardiomyopathy, variant angina pectoris, stable angina, effort angina, coronary vasospasm, postinfarction angina, unstable angina pectoris, arrhythmia, and acute cardiac death.

The peripheral circulatory disturbances include aortic diseases such as Buerger's disease, arteriosclerotic obliteration, and Raynaud's syndrome, venous diseases such as venous thrombosis and thrombophlebitis, hyperviscosity syndrome, frostbite and chilblain, psychoesthesia and hypnagogic disturbance due to feeling of cold, bedsore, cleft, and alopecia. Examples of the retinal circulatory disturbances include retinal vascular obstruction, arteriosclerotic retinopathy, vasospastic retinopathy, hypertonic fundus, hypertensive retinopathy, renal retinopathy, hypertensive neuroretinopathy, diabetic retinopathy and the like. Glaucoma includes primary glaucoma, secondary glaucoma, developmental glaucoma, childhood secondary glaucoma and the like, as well as more narrowly classified types of the foregoings, including primary open-angle glaucoma, primary angle-closure glaucoma, mixed-type glaucoma, ocular hypertension, and the like (Japanese Journal of Ophthalmology, vol. 107, No. 3, 2003). Further, examples of the vitreoretinal diseases include retinal detachment, retinoschisis, vitreoretinal interface syndrome, retinal pigment epitheliosis, macular hole, phacomatosis, vitreous hemorrhage, retinal circulatory disturbances, and the like (the vitreoretinal diseases mentioned herein include more narrowly classified diseases belonging to each of the categories according to the pathological typology described in Shin Zusetsu Rinsho Ganka Koza (Illustrative Lecture of Clinical Ophthalmology, New Edition), Ed. By Tano, Y., Araie, M., et al, Vol. 5, Vitreoretinal Diseases, MEDICAL VIEW, 2003). The urinary disturbances include dysuria, bladder neck contracture, bladder neck occlusion, urethral syndrome, detrusor sphincter dyssynergia, unstable bladder, chronic prostatitis, chronic cystitis, prostate pain, Hinman's syndrome, Fowler's syndrome, psychogenic dysuria, drug-induced dysuria, dysuria with aging and the like. The erectile dysfunction include organic erectile dysfunction accompanying diseases of diabetes mellitus, arteriosclerosis, hypertension, multiple-sclerotic cardiac diseases, hyperlipidemia, depression and the like, functional erectile dysfunction, erectile dysfunction with aging, and erectile dysfunction after spinal cord injury or radical prostatectomy.

Examples of the diseases relating to morphological change of various cells include, for example, various nerve dysfunctions as those relating to nerve cells. As the nerve dysfunctions, for example, neural damages caused by trauma (spinal cord injury and the like), neurodegenerative diseases such as Alzheimer's disease, Parkinson's disease, diabetic retinopathy, and glaucoma, and the like can be exemplified. Glaucoma refers to the same as that mentioned above.

Examples of the diseases relating to migration of various cells include, for example, as those relating to cancer cells, infiltration and metastasis of cancer. Examples of those relating to vascular endothelial cells include angiogenesis, neovascular maculopathy, macular edema, and the like (the macular diseases mentioned herein include more narrowly classified diseases belonging to each of the categories according to the pathological typology described in Shin Zusetsu Rinsho Ganka Koza (Illustrative Lecture of Clinical Ophthalmology, New Edition), Ed. By Tano, Y., Araie, M., et al, Vol. 5, Vitreoretinal Diseases, MEDICAL VIEW, 2003). Examples of those relating to leukocytes include bacterial infection, allergic hypersensitive diseases (e.g., bronchial asthma, atopic dermatitis, pollinosis, anaphylactic shock and the like), collagen diseases (e.g., rheumatoid arthritis, systemic lupus erythematodes, multiple sclerosis, Sjogren's disease and the like), angiitis, inflammatory bowel diseases (e.g., ulcerative colitis, Crohn's disease and the like), ischemic reperfusion injury of visceral organs, traumatic spinal cord injury, pneumonia, hepatitis, nephritis, pancreatitis, otitis media, sinusitis, arthritis (for example, osteoarthritis, gout and the like can be exemplified), fibrosis, AIDS, adult T-cell leukemia, rejection after organ transplantation (graft versus host reaction), vascular restenosis, and endotoxin shock. Example of the cancer include myelocytic leukemia, lymphatic leukemia, gastric cancer, carcinoma of the colon and rectum, lung cancer, pancreatic carcinoma, hepatocellular carcinoma, carcinoma of the esophagus, ovarian cancer, breast cancer, skin cancer, head and neck cancer, cancer of the testicles, neuroblastoma, urinary tract epithelial cancer, multiple myeloma, carcinoma uteri, melanoma, brain tumor and the like. Examples of hepatitis include hepatitis by virus infection (e.g., hepatitis B, hepatitis C and the like), and alcoholic hepatitis. Examples of the pneumonia include chronic obstructive pulmonary disease (COPD) and interstitial pneumonia, which may shift to fibrosis. Examples of nephritis include chronic nephritic syndrome, asymptomatic proteinuria, acute nephritic syndrome, nephrotic syndrome, IgA nephropathy, pyelonephritis, glomerulonephritis and the like. Fibrosis include chronic pathological changes characterized by excess deposition of connective tissue proteins in lung, skin, heart, liver, pancreas, kidney and the like. The major pathological conditions are pulmonary fibrosis, hepatic fibrosis, and skin fibrosis. However, fibrosis is not limited to these examples. In hepatic fibrosis, viral hepatitis progresses by infection of, in particular, hepatitis B virus or hepatitis C virus, thus hepatic cells cause necrosis, and thereby fibrosis progresses, which means macronodular hepatic cirrhosis. Further, hepatic fibrosis also includes micronodular hepatic cirrhosis caused by progress of alcoholic hepatitis.

Examples of diseases relating to release of various cells include, as those relating to leukocytes, for example, allergic diseases.

Examples of the allergic diseases include asthma, atopic dermatitis, allergic conjunctivitis, allergic arthritis, allergic rhinitis, allergic pharyngitis and the like.

Examples of the diseases relating to aggregation of various cells include, as those relating to platelets, for example, thrombosis.

Thrombosis include the aforementioned circulatory disturbances of major arteries, major veins and peripheral arteries and veins in whole body, as well as shock caused by hemorrhage, drug intoxication, or endotoxin, disseminated intravascular coagulation (DIC) following it, and multiple organ failure (MOF).

Examples of the diseases relating to apoptosis of various cells include, as those relating to nerves, for example, neurodegenerative diseases such as Alzheimer's disease, Parkinson's disease, diabetic peripheral neuropathy, retinopathy, amyotrophic lateral sclerosis due to cerebral ischemia, pigmented retinitis, and cerebellar degeneration, and glaucoma. Examples of glaucoma are mentioned above. AIDS, and fulminant hepatites are examples of disease relating to viruses, chronic heart failure due to myocardial ischemia is an example of diseases relating to smooth muscles, myelodysplasia, aplastic anemia, sideroblastic anemia, and graft-versus-host disease (GVHD) after organ transplantation are examples of diseases relating to blood, arthrosteitis, and osteoporosis is an example of diseases relating to bones.

Examples of the diseases relating to abnormal gene expression of various cells include, for example, bone diseases as those relating to bone cells, AIDS as one relating to virus, and cancers as those relating to cancer cells.

Examples of the bone diseases include osteoporosis, hypercalcemia, bone Paget's disease, renal osteodystrophy, rheumatoid arthritis, osteoarthritis, osteogenesis imperfecta tarda, bone damage, periodontal bone disorder, and the like. Examples of AIDS include acquired immunodeficiency syndrome caused by human immunodeficiency virus (HIV) infection. Examples of the cancers include gastric cancer, carcinoma of the colon and rectum, hepatocellular carcinoma, pancreatic carcinoma, lung cancer, leukemia, malignant lymphoma, carcinoma uteri, ovarian cancer, breast cancer, skin cancer and the like.

Usefulness of the compounds of the present invention represented by the aforementioned formula (1) and salts thereof as active ingredients of medicaments for prophylactic and/or therapeutic treatment of hypertension can be confirmed by, for example, administering the compound to various hypertension model animals or the like. Examples of hypertension animal models include spontaneous hypertensive rat (SHR), renal hypertensive rat, DOCA-salt hypertensive rat and the like (Uehata, M. et al., Nature, 389, 990–994, 1997). A compound is orally, intravenously or intraperitoneally administered to a hypertension model animal at a dose of 0.1 to 1,000 mg/kg, preferably 0.1 to 100 mg/kg, and the diastolic blood pressure is measured. The usefulness as a medicament for hypertension can be confirmed based on an action of reducing the diastolic blood pressure.

Usefulness of the compounds of the present invention represented by the aforementioned formula (1) and salts thereof as active ingredients of medicaments for prophylactic and/or therapeutic treatment of pulmonary hypertension can be confirmed by using, for example, a rat model of pulmonary hypertension created by administering monocrotaline to a rat for 2 to 3 weeks (Ito, K. M. et al., Am. J. Physiol., 279, H1786–H1795, 2000). A compound is orally, intravenously or intraperitoneally administered to a model animal of pulmonary hypertension at a dose of 0.1 to 1,000 mg/kg, preferably 0.1 to 100 mg/kg, and the intrapulmonary pressure is measured. The usefulness as a medicament for pulmonary hypertension can be confirmed based on an action of decreasing the intrapulmonary pressure.

Usefulness of the compounds of the present invention represented by the aforementioned formula (1) and salts thereof as active ingredients of medicaments for prophylactic and/or therapeutic treatment of arteriosclerosis can be confirmed by using, for example, a rat model of L-NAME-induced arteriosclerosis (Cir. Res. 89(5):415–21, 2001), a rat model of balloon-induced neointimal formation (Sawada N. et al., Circulation 101 (17):2030–3, 2000) or the like. A compound is orally, intravenously or intraperitoneally administered to a model animal of arteriosclerosis at a dose of 0.1 to 1,000 mg/kg, preferably 0.1 to 100 mg/kg, and thickening of arteries is observed. The usefulness as a medicament for arteriosclerosis can be confirmed based on an action of suppressing neointimal formation in arteries.

Usefulness of the compounds of the present invention represented by the aforementioned formula (1) and salts thereof as active ingredients of medicaments for prophylactic and/or therapeutic treatment of cerebral circulatory dysfunction can be confirmed by using, for example, a gerbil model of hippocampal neuronal death (Kirino et al., Brain Res., 239, 57–69, 1982) or the like. A compound is orally, intravenously or intraperitoneally administered to the model animal at a dose of 0.1 to 1,000 mg/kg, preferably 0.1 to 100 mg/kg, and the amount of energy-related substances and survival period of gerbil, or inhibition of late-onset of neuronal death is measured. The usefulness as a medicament for cerebral circulatory dysfunction can be confirmed based on actions for maintaining, improving and activating cerebral metabolic ability, brain and nerve protective action, and action for suppressing formation of cerebral infarction.

Usefulness of the compounds of the present invention represented by the aforementioned formula (1) and salts thereof as active ingredients of medicaments for prophylactic and/or therapeutic treatment of cardiac diseases can be confirmed by using, for example, a rat model of myocardial infarction based on the ligation of artery (Xia Q. G. et al., Cardiovasc. Res., 49(1):110–7, 2001) or the like. Effectiveness as a medicament for cardiac diseases can be confirmed by orally, intravenously or intraperitoneally administering a compound to the model animal at a dose of 0.1 to 1,000 mg/kg, preferably 0.1 to 100 mg/kg, and observing a cardiac tissue fixed by formalin perfusion after ischemic reperfusion.

Usefulness of the compounds of the present invention represented by the aforementioned formula (1) and salts thereof as active ingredients of medicaments for prophylactic and/or therapeutic treatment of disturbances of peripheral circulation can be confirmed by using, for example, a rat model of bedsore (Pierce S. M. et al., Am. J. Physiol. Heart Circ. Physiol., 281(1):H67–74, 2001) or the like. Effectiveness as a medicament for bedsore (peripheral circulatory disturbance) can be confirmed by orally, intravenously or intraperitoneally administering a compound to the model animal at a dose of 0.1 to 1,000 mg/kg, preferably 0.1 to 100 mg/kg, compressing the hind leg skin at a pressure of 50 mmHg, and then observing a tissue of necrotic area of the lesion or measuring epithelial blood flow of the same.

Usefulness of the compounds of the present invention represented by the aforementioned formula (1) and salts thereof as active ingredients of medicaments for prophylactic and/or therapeutic treatment of disturbances of retinal circulation can be confirmed by using, for example, rabbit model of rose bengal-mediated argon laser retinal vein photothrombosis (Jpn. J. Ophthalmol., 45(4):359–62, 2001), or the like. Effectiveness as a medicament for retinal circulatory disturbance can be confirmed by orally, intravenously or intraperitoneally administering a compound to the model animal at a dose of 0.1 to 1,000 mg/kg, preferably 0.1 to 100 mg/kg, comparing the degree of retinal circulatory disturbance with that of a control based on count of laser spots.

Usefulness of the compounds of the present invention represented by the aforementioned formula (1) and salts thereof as active ingredients of medicaments for prophylactic and/or therapeutic treatment of renal failure can be confirmed by using, for example, a rat model of one-kidney, one-clip renal hypertension (Kiso to Rinsho, 30, 511–524, 1996). Effectiveness as a medicament for renal failure can be confirmed by orally, intravenously or intraperitoneally administering a compound to the model animal at a dose of 0.1 to 1,000 mg/kg, preferably 0.1 to 100 mg/kg, and measuring the diuretic effect.

Usefulness of the compounds of the present invention represented by the aforementioned formula (1) and salts thereof as active ingredients of medicaments for prophylactic and/or therapeutic treatment of asthma, for example, bronchial asthma, can be confirmed by using, for example, suppression of constriction of an isolated trachea, a model animal of bronchial asthma, inhibition of chemotaxis of human peripheral leucocytes (Kunihiko Iizuka, Allergy, 47:943, 1998; Kunihiko Iizuka, and Akihiro Yoshii, Jpn.J-.Respirol Soc, 37:196, 1999.), or the like. The usefulness as a medicament for bronchial asthma can be confirmed by orally, intravenously or intraperitoneally administering a compound to the model animal at a dose of 0.1 to 1,000 mg/kg, preferably 0.1 to 100 mg/kg, and measuring elevation of airway resistance caused by acetylcholine inhalation, or performing histological analysis.

Usefulness of the compounds of the present invention represented by the aforementioned formula (1) and salts thereof as active ingredients of medicaments for prophylactic and/or therapeutic treatment of irritable bowel syndrome can be confirmed by administering the compounds to a stress burden model animal, or the like. Examples of the stress burden model animal include, for example, a rat model of arresting stress (Miyata, K. et al., J. Pharmacol. Exp. Ther., 259, pp. 815–819, 1991), a CRH-administered rat model (Miyata, K. et al., Am. J. Physiol., 274, G827–831, 1998), and the like. A compound is orally, intravenously or intraperitoneally administered to a stress burden model animal at a dose of 0.1 to 1,000 mg/kg, preferably 0.1 to 100 mg/kg, and counting the number of fecal pellets. The usefulness as a medicament for curative medicine of irritable bowel syndrome can be confirmed based on effect for reducing the number of fecal pellets.

Usefulness of the compounds of the present invention represented by the aforementioned formula (1) and salts thereof as active ingredients of medicaments for prophylactic and/or therapeutic treatment of glaucoma can be confirmed by, for example, measuring intraocular pressure of a rabbit, cat or monkey after administration of the medicaments by instillation (Surv. Ophthalmol. 41:S9–S18, 1996). The usefulness as a medicament for glaucoma can be confirmed by instilling or orally, intravenously or intraperitoneally administering a compound to a locally anesthetized rat or monkey model animal at a dose of 0.1 to 1,000 mg/kg, preferably 0.1 to 100 mg/kg, and measuring the intraocular pressure over time using an tonometer.

Usefulness of the compounds of the present invention represented by the aforementioned formula (1) and salts thereof as active ingredients of medicaments for prophylactic and/or therapeutic treatment of vitreoretinal diseases can be confirmed by a known method, for example, the methods described in Oshima, Y. et al., Gene Ther., 9(18), pp. 1214–20, 2002; and Ito, S., et al., Graefes Arch. Clin. Exp. Ophthalmol., 237(8), pp. 691–6., 1999. The usefulness as a medicament for vitreoretinal diseases can be confirmed by orally, intravenously, intraperitoneally, or intraocularly administering (direct administration to vitreum or retina) a compound to a rabbit in which retinal detachment is induced by cell transfer to the vitreoretinal interface, vitrectomy, or the like at a dose of 0.1 to 1,000 mg/kg, preferably 0.1 to 100 mg/kg, and evaluating amelioration of the pathological conditions on the basis of histological analysis.

Usefulness of the compounds of the present invention represented by the aforementioned formula (1) and salts thereof as active ingredients of medicaments for prophylactic and/or therapeutic treatment of dysuria can be confirmed by using, for example, a model of rhythmic bladder contraction (Kaneko S. et al., Folia Pharmacol. Japon, Vol. 93(2), 55–60, 1989; Nomura N. et al., Folia Pharmacol. Japon, Vol. 94(3), 173-, 1989.) or the like. The usefulness as a medicament for urinary disturbance can be confirmed by orally, intravenously or intraperitoneally administering a compound to an anesthetized rat or dog at a dose of 0.1 to 1,000 mg/kg, preferably 0.1 to 100 mg/kg, and measuring the number of rhythmic contraction of filled bladder (micturition).

Usefulness of the compounds of the present invention represented by the aforementioned formula (1) and salts thereof as active ingredients of medicaments for prophylactic and/or therapeutic treatment of erectile dysfunction can be confirmed by a known method, for example, the method described in J. Uro., 151, 797–800, 1994. A compound is dissolved in a hydrophilic ointment, 30 mg of the ointment was applied to a rat penis, and the rat is held in an acrylic cylinder for 10 minutes so that the rat was not able to lick the penis. The rat is moved to an acrylic cage of 30 cm×30 cm, and videotaped for 60 minutes from the side and the bottom of the cage. Then, the number of erection of the penis per 30 minutes can be counted to confirm the usefulness as a medicament for erectile dysfunction.

Usefulness of the compounds of the present invention represented by the aforementioned formula (1) and salts thereof as active ingredients of medicaments for suppressing cancer metastasis and invasion can be confirmed by, for example, the method described in Cancer Res., 55:3551–3557 (1995). The usefulness as a medicament for cancer metastasis and invasion can be confirmed by orally, intravenously or intraperitoneally administering a compound at a dose of 0.1 to 1,000 mg/kg, preferably 0.1 to 100 mg/kg, to a nude mouse transplanted with human cancer cell suspension transplantable to immunodeficient mice at the same site (spontaneous metastasis model), and measuring the metastasized lesion.

Usefulness of the compounds of the present invention represented by the aforementioned formula (1) and salts thereof as active ingredients of medicaments for prophylactic and/or therapeutic treatment of collagen disease can be confirmed by using, for example, collagen-induced arthritis model of a rat or mouse (Griffith, M. M. et al., Arthritis Rheumatism, 24:781, 1981; Wooley, P. H. et al., J. Exp. Med., 154:688, 1981). The usefulness as a medicament for collagen disease can be confirmed by orally, intravenously or intraperitoneally administering a compound to the model mouse or rat at a dose of 0.1 to 1,000 mg/kg, preferably 0.1 to 100 mg/kg, and measuring footpad volume or progression of bone destruction.

Usefulness of the compounds of the present invention represented by the aforementioned formula (1) and salts thereof as active ingredients of medicaments for prophylactic and/or therapeutic treatment of inflammatory bowel disease can be confirmed by using a rat model of idiopathic ulcerative colitis induced by subserosal injection of acetic acid, a model of sodium dextransulfate-induced colitis, a model of trinitrobenzenesulfonic acid-induced colitis (Kojima et al., Folia. Pharmacol. Jpn., 118, 123–130, 2001), or the like. The usefulness as a medicament for inflammatory bowel disease can be confirmed by, for example, orally, intravenously or intraperitoneally administering a compound at a dose of 0.1 to 1,000 mg/kg, preferably 0.1 to 100 mg/kg, to a rat in which colitis is induced by intraintestinal injection of acetic acid, dissecting the rat after several days to two weeks, then observing and measuring the ulcer area of the intestinal epithelium, and amount of leucotriene B4 in a colon homogenate.

Usefulness of the compounds of the present invention represented by the aforementioned formula (1) and salts thereof as active ingredients of medicaments for prophylactic and/or therapeutic treatment of spinal cord injury can be confirmed by using, for example, a rat model of spinal cord ablation (Sayer F. T. et al., Exp. Neurol., 175(1):282–96, 2002) or the like. Effectiveness as a medicament for spinal cord injury can be confirmed by orally, intravenously or intraperitoneally administering a compound to the model animal at a dose of 0.1 to 1,000 mg/kg, preferably 0.1 to 100 mg/kg, and, after several weeks, examining a tissue of the spinal cord with a microscope to measure a degree of nerve regeneration.

Usefulness of the compounds of the present invention represented by the aforementioned formula (1) and salts thereof as active ingredients of medicaments for prophylactic and/or therapeutic treatment of pneumonia can be confirmed by using, for example, a mouse model of OVA-induced chronic pneumonia (Henderson W. R. et al., Am. J. Respir. Crit. Care Med., 165(1):108–16, 2002), a mouse model of LPS-induced acute pneumonia (Gonzales de Moraes, V L., et al., Br. J. Pharmacol., 123, pp. 631–6, 1998), or the like. Effectiveness as a medicament for pneumonia can be confirmed by orally, intravenously or intraperitoneally administering a compound to the model animal at a dose of 0.1 to 1,000 mg/kg, preferably 0.1 to 100 mg/kg, and counting number of eosinophils or monocytes in the pulmonary cavity.

Usefulness of the compounds of the present invention represented by the aforementioned formula (1) and salts thereof as active ingredients of medicaments for prophylactic and/or therapeutic treatment of hepatitis can be confirmed by using a mouse model of endotoxin-induced liver injury according to, for example, the method described in J. Immunol., 159, 3961–3967, 1997. The usefulness as a medicament for hepatitis can be confirmed by orally, intravenously or intraperitoneally administering a compound to the mouse model of endotoxin-induced liver injury at a dose of 0.1 to 1,000 mg/kg, preferably 0.1 to 100 mg/kg, and measuring the plasmic transaminase level or amount of hydroxyproline in a hepatic tissue, which are indicators of liver function, or performing histological analysis.

Usefulness of the compounds of the present invention represented by the aforementioned formula (1) and salts thereof as active ingredients of medicaments for prophylactic and/or therapeutic treatment of pancreatitis can be confirmed by using, for example, a mouse model of cerulein-inducted acute pancreatitis (Niedirau, C. et al., Gastroenterology 88 (5 Pt 1):1192–204, 1985) or the like. Effectiveness as a medicament for pancreatitis can be confirmed by orally, intravenously or intraperitoneally administering a compound to the model animal at a dose of 0.1 to 1,000 mg/kg, preferably 0.1 to 100 mg/kg, and measuring the serum amylase activity, or weight of pancreas.

Usefulness of the compounds of the present invention represented by the aforementioned formula (1) and salts thereof as active ingredients of medicaments for prophylactic and/or therapeutic treatment of nephritis can be confirmed by using, for example, a nephritis rat model prepared by administering anti-GBM antibodies obtained by immunizing a rabbit with a GBM fraction derived from a rat to a rat (WO01/56988), or the like. A compound is orally, intravenously or intraperitoneally administered to the nephritis rat model at a dose of 0.1 to 1,000 mg/kg, preferably 0.1 to 100 mg/kg, and the urinary proteins are measured. The usefulness as a medicament for nephritis can be confirmed based on an action of reducing the urinary protein level.

Usefulness of the compounds of the present invention represented by the aforementioned formula (1) and salts thereof as active ingredients for suppressing allograft rejection at the time of organ transplantation can be confirmed by using, for example, a rat model of skin transplantation, rat model of heart transplantation (Ochiai T. et al., Transplant. Proc., 19, 1284–1286, 1987), or the like. Effectiveness as a medicament for suppressing rejection at the time of organ transplantation can be confirmed by orally, intravenously or intraperitoneally administering a compound to a model animal at a dose of 0.1 to 1,000 mg/kg, preferably 0.1 to 100 mg/kg, and estimating the graft survival ratio.

Usefulness of the compounds of the present invention represented by the aforementioned formula (1) and salts thereof as active ingredients of medicaments for prophylactic and/or therapeutic treatment of rheumatoid arthritis can be confirmed by using collagen-induced arthritis model of a rat or mouse (Griffith, M. M. et al., Arthritis Rheumatism, 24:781, 1981; Wooley, P. H. et al., J. Exp. Med., 154:688, 1981). The usefulness as a medicament for rheumatoid arthritis can be confirmed by orally, intravenously or intraperitoneally administering a compound to a model mouse or model rat at a dose of 0.1 to 1,000 mg/kg, preferably 0.1 to 100 mg/kg, and measuring footpad volume or progression of bone destruction.

Usefulness of the compounds of the present invention represented by the aforementioned formula (1) and salts thereof as active ingredients of medicaments for prophylactic and/or therapeutic treatment of chronic obstructive pulmonary disease (COPD) can be confirmed by using, for example, suppression of constriction of an isolated trachea, a model animal of bronchial asthma, a guinea pig model of tobacco smoke exposition (Fuchigami J. et al., 73rd Meeting of Japanese Pharmacological Society, Collection of Abstracts, 2000), inhibition of chemotaxis of human peripheral leucocytes or the like. The usefulness as a medicament for COPD can be confirmed by orally, intravenously or intraperitoneally administering a compound to a guinea pig exposed to tobacco smoke at a dose of 0.1 to 1,000 mg/kg, preferably 0.1 to 100 mg/kg, and counting the number of migrating leucocytes in a bronchoalveolar lavage fluid, or performing histological analysis.

Usefulness of the compounds of the present invention represented by the aforementioned formula (1) and salts thereof as active ingredients of medicaments for prophylactic and/or therapeutic treatment of hepatic fibrosis can be confirmed by using a carbon tetrachloride-induced hepatic fibrosis model according to, for example, the method described in J. Hepatol., 35(4), 474–81, 2001. The usefulness as a medicament for hepatic fibrosis can be confirmed by orally, intravenously or intraperitoneally administering a compound to the hepatic fibrosis model at a dose of 0.1 to 1,000 mg/kg, preferably 0.1 to 100 mg/kg, and measuring the plasmic transaminase level, or amount of hydroxyproline in a hepatic tissue, which are indicators of liver function, or performing histological analysis.

Usefulness of the compounds of the present invention represented by the aforementioned formula (1) and salts thereof as active ingredients of medicaments for prophylactic and/or therapeutic treatment of pulmonary fibrosis can be confirmed by using an animal model of Bleomycin-induced pulmonary fibrosis according to the method described in, for example, Am. J. Respir. Crit. Care Med., 163(1), pp. 210–217, 2001. The usefulness as a medicament for pulmonary fibrosis can be confirmed by orally, intravenously or intraperitoneally administering a compound to the pulmonary fibrosis mouse model at a dose of 0.1 to 1,000 mg/kg, preferably 0.1 to 100 mg/kg, and measuring respiratory function, or amount of hydroxyproline in a pulmonary tissue.

Usefulness of the compounds of the present invention represented by the aforementioned formula (1) and salts thereof as active ingredients of medicaments for prophylactic and/or therapeutic treatment of allergy can be confirmed by using an atopic dermatitis mouse model or the like according to the method described in, for example, Allergy, 50 (12) 1152–1162, 2001. The usefulness as a medicament for allergy can be confirmed by orally, intravenously or intraperitoneally administering a compound to an NC/Nga mouse pretreated with a surfactant or an organic solvent at a dose of 0.1 to 1,000 mg/kg, preferably 0.1 to 100 mg/kg, when eruption is induced in the mouse by using housedust mite antigens, and measuring the plasmic IgE level, number of eosinophils and the like.

Usefulness of the compounds of the present invention represented by the aforementioned formula (1) and salts thereof as active ingredients of medicaments for prophylactic and/or therapeutic treatment of thrombosis can be confirmed by using, for example, a rabbit model of experimentally-induced venous thrombus (Maekawa, T. et al., Trombos. Diathes. Haemorrh., 60, pp. 363–370, 1974), or the like. Effectiveness as a medicament for thrombosis can be confirmed by orally, intravenously or intraperitoneally administering a compound to the model animal at a dose of 0.1 to 1,000 mg/kg, preferably 0.1 to 100 mg/kg, and estimating the incidence of thrombus.

Usefulness of the compounds of the present invention represented by the aforementioned formula (1) as active ingredients of medicaments for prophylactic and/or therapeutic treatment of Alzheimer's disease can be confirmed by using, for example, an in vitro culture system of nerve cells derived from rat embryos (Yankner, B. A. et al., Science, 250, pp. 279–282, 1990), or the like. Effectiveness as a medicament for Alzheimer's disease can be confirmed by adding 0.1 to 1 mM, preferably 0.1 to 100 µM, of a compound, and measuring suppression ratio for cell death induced by beta-amyloid proteins.

Usefulness of the compounds of the present invention represented by the aforementioned formula (1) and salts thereof as active ingredients of medicaments for prophylactic and/or therapeutic treatment of bone disease can be confirmed by using, for example, a mouse model of osteoporosis prepared by ovariectomy (OVX mouse, Golub, L. M. et al., Ann. N.Y. Acad. Sci., 878, pp. 290–310, 1999). A compound is orally, intravenously or intraperitoneally administered to the OVX mouse at a dose of 0.1 to 1,000 mg/kg, preferably 0.1 to 100 mg/kg, and deciduous dental roots are measured, or weight of skeletal bones is measured. The usefulness as a medicament for periodontal bone disorder or osteoporosis can be confirmed based on an action for suppressing periodontal breakdowns, or an action for suppressing skeletal bone weight loss.

Usefulness of the compounds of the present invention represented by the aforementioned formula (1) and salts thereof as active ingredients of medicaments for prophylactic and/or therapeutic treatment of AIDS can be confirmed by using, for example, a rhesus monkey model of SIV-infection (Crub S. et al., Acta Neuropathol., 101(2), pp. 85–91, 2001) or the like. Effectiveness as a medicament for AIDS can be confirmed by orally, intravenously or intraperitoneally administering a compound to the model animal at a dose of 0.1 to 1,000 mg/kg, preferably 0.1 to 100 mg/kg, and quantifying the SIV mRNA level in blood.

Usefulness of the compounds of the present invention represented by the aforementioned formula (1) and salts thereof as active ingredients of medicaments for prophylactic and/or therapeutic treatment of cancer can be confirmed by using, for example, a mouse model of ultraviolet ray irradiation-induced skin cancer, a nude mouse model of tumor xenograft (Orengo I. F. et al., Arch Dermatol., 138(6), pp. 823–4, 2002; Ki D. W. et al., Anticancer Res., 22(2A), pp. 777–88, 2002) or the like. Effectiveness as a medicament for cancer can be confirmed by orally, intravenously or intraperitoneally administering a compound to a model animal at a dose of 0.1 to 1,000 mg/kg, preferably 0.1 to 100 mg/kg, and observing progression or reduction of the grafted cancer tissues on the body surface.

Further, when test compounds of the compounds of the present invention or salts thereof were introduced into wells of a 96-well plate at a concentration three times higher than the $IC_{50}$ values obtained in Test Example 1, and the cell suspension prepared in Test Example 1 was added at a density of $10^6$/well, incubated for 30 minutes at room temperature and stained with trypan blue to determine the survival rates of the cells, a viability as high as 90% or more was observed in all the wells. Furthermore, when the compounds of the present invention or salts thereof were orally administered to mice every day at a dose of 30 mg/kg for 5 days, death was not observed. Therefore, the compounds of the present invention had no particular problem also in safety.

As the active ingredients of the medicaments of the present invention, the compounds represented by the aforementioned formula (1), or physiologically acceptable salts thereof may be used. The aforementioned substance, per se, may be administered as the medicament of the present invention. However, a pharmaceutical composition containing one or more kinds of the aforementioned substances as the active ingredients and one or more kinds of pharmaceutical additives can be generally prepared and administrated orally or parenterally (e.g., intravenous administration, intramuscular administration, subcutaneous administration, transrectal administration, transdermal administration, inhalation, instillation, intraurethral administration, intrarectal administration, and the like) to human or an animal other than human. The aforementioned pharmaceutical composition can be prepared in a dosage form suitable for an intended administration route. More specifically, examples of the pharmaceutical composition suitable for oral administration include oral drug products (tablets, capsules, powders, granules, syrups, pills, troches, and the like), and examples of the pharmaceutical composition suitable for parenteral administration include injections (liquid dosage forms, suspensions, and the like), drip infusions, inhalants, suppositories, transdermally absorbed agents (e.g., tapes), ointments, ophthalmic solutions, ophthalmic ointments, ophthalmic membrane adherent agents, and the like.

These pharmaceutical compositions can be prepared in a conventional manner by using pharmaceutical additives ordinarily used in this field (e.g., excipients, disintegrants, binders, lubricants, colorants, buffering agents, coating agents, flavors, fragrances, emulsifying agents, isotonic agents, solubilizing agents, preservatives, viscosity improvers, pH adjusters and the like). Examples include tablets prepared by adding crystalline cellulose, magnesium stearate, or the like to the compounds of the present of invention or salts thereof.

A content of the active ingredient in the aforementioned pharmaceutical composition can be suitably chosen depending on a dosage form. The content may be, for example, about 0.1 to 100% by weight, preferably about 1 to 50% by weight, based on the total weight of the composition. A dose of the medicament of the present invention can be suitably determined for each administration in consideration of the age, weight, sexuality of a patient, the type of a disease, the severity of pathological condition and the like. Examples of the doses include, for example, about 1 to 500 mg, preferably about 1 to 100 mg, and most preferably about 1 to 30 mg. These doses can be administered once in a day or several times a day as divided portions.

EXAMPLES

The present invention will be further specifically explained with reference to the following examples. However, the present invention is not limited to these examples.

For thin layer chromatography (TLC), Precoated Silica Gel 60 F254 (produced by Merck) was used. After development with chloroform:methanol (100:1 to 4:1), or ethyl acetate:n-hexane (100:1 to 1:10), spots were observed by UV irradiation (254 nm) or coloration with ninhydrine or phosphomolybdic acid. For drying organic solvent, anhydrous magnesium sulfate or anhydrous sodium sulfate was used. For flash column chromatography, Silica gel 60N (spherical shape, neutral, 40 to 100 μm, produced by Kanto Chemicals) was used. For preparative thin layer chromatography (PTLC), Precoated Silica Gel 60 F254 (20×20 cm, thickness: 2 mm, produced by Merck) was used. For the measurement of nuclear magnetic resonance (NMR) spectra, the measurement was performed by using Gemini-300 (FT-NMR, produced by Varian), or AL-300 (FT-NMR, produced by JOEL). As a solvent, deuterated chloroform was used, unless otherwise indicated. Chemical shifts were measured by using tetramethylsilane (TMS) as an internal standard, and indicated with δ (ppm), and binding constant was indicated with J (Hz). Mass spectrum (MS) was measured by liquid chromatography-mass spectrometry (LC-MS). Platform-LC type mass spectrometry apparatus (produced by Micromass) was used as the mass spectrometer, and the measurement was performed by the electrospray ionization (ESI) method. As the liquid chromatography apparatus, an apparatus produced by GILSON was used. As the separation column, Mightysil RP-18 GP 50–4.6 (produced by Kanto Chemicals) was used. Elution was generally performed at a flow rate of 2 ml/minute using a linear gradient of 5 to 100% (v/v) Solution B [acetonitrile containing 0.1% (v/v) acetic acid] in Solution A [water containing 0.1% (v/v) acetic acid] from 0 minute to 5 minutes as the solvent.

Reference Example 1

4-Bromo-5-aminoisoquinoline (Step A) Synthesis of 4-bromo-5-nitroisoquinoline

With vigorous stirring, concentrated sulfuric acid (36 ml) was added with 4-bromoisoquinoline (10.0 g, Tokyo Kasei Kogyo) to such an extent that the temperature should not exceed 10° C. and stirred for a while to attain complete dissolution. Potassium nitrate (4.9 g, Kanto Chemicals) was dissolved in concentrated sulfuric acid (20 ml), added dropwise to the aforementioned solution at a temperature below −5° C. and further stirred for 2 hours while maintaining that temperature. Disappearance of 4-bromoisoquinoline was confirmed by thin layer chromatography (n-hexane:ethyl acetate=1:1), and then the reaction mixture was slowly poured into cold aqueous ammonia (200 ml, Wako Pure Chemical Industries) with vigorous stirring. The reaction mixture was stirred for 15 minutes and then extracted three times with ethyl acetate (150 ml for each time), and the combined organic layer was washed successively with water (250 ml) and saturated brine (250 ml) and dried over anhydrous sodium sulfate. The solvent was evaporated under reduced pressure, and the residue was recrystallized with ethyl acetate to obtain the title compound (5.9 g) as thick yellow needle-like crystals.

(Step B) Synthesis of 5-amino-4-bromoisoquinoline

The synthesized 4-bromo-5-nitroisoquinoline (1.0 g) and stannous chloride dihydrate (4.5 g, Wako Pure Chemical Industries) were suspended in ethanol (30 ml), added with concentrated hydrochloric acid (2.3 ml) and stirred at 80° C. for 30 minutes and at room temperature for further 12 hours. The reaction mixture was adjusted to pH 12 with addition of 2 N aqueous sodium hydroxide. The target compound was extracted three times with ethyl acetate (100 ml for each time), and the combined organic layer was washed with water (200 ml) and saturated brine (200 ml) and dried over anhydrous sodium sulfate. The solvent was evaporated under reduced pressure, and then the residue was purified by silica gel column chromatography (n-hexane:ethyl acetate=3:1) to obtain the title compound (493 mg) as yellow powdery crystals.

$^1$H-NMR(CDCl$_3$) δ (ppm): 5.23 (2H, br.s), 6.92 (1H, dd, J=1.6, 7.3 Hz), 7.38 (2H, m), 8.50 (1H, s), 8.98 (1H, s)

Example 1

Exemplary Compound No. 8-1

(Step A) 5-Amino-4-vinylisoquinoline (Intermediate 1)

A suspension of 5-amino-4-bromoisoquinoline obtained in Reference Example 1 (10 g), tri(n-butyl)vinyltin (21.0 ml, Tokyo Kasei Kogyo), tetrakis(triphenylphosphine)palladium(0) (1.04 g, Aldrich), and 2,6-di-tert-butyl-p-cresol (11.3 mg, Tokyo Kasei Kogyo) in toluene (90 ml) was stirred at 110° C. for 15 hours. The reaction mixture was cooled to room temperature, then added with 10% aqueous potassium fluoride (90 ml), and stirred for 4 hours. The reaction mixture was added with ethyl acetate (100 ml), and the precipitates were removed by filtration. Then, the organic layer was separated, and dried over anhydrous magnesium sulfate. The solvent was evaporated under reduced pressure, and then the residue was purified by silica gel column chromatography (n-hexane:ethyl acetate=3:1) to obtain the title compound (7.00 g).

(Step B) 3-(4-Vinyl-5-isoquinolyl)amino-1-(tert-butoxycarbonyl)pyrrolidine (Intermediate 2)

A solution of Intermediate 1 (251 mg), and tert-butyl 3-oxo-1-pyrrolidinecarboxylate (563 mg, AstaTech) in dichloromethane (85 ml) was added with titanium tetraisopropoxide (905 μl, Aldrich) at room temperature, and stirred at room temperature for 19 hours. The reaction mixture was added with methanol (6 ml), and sodium borohydride (249 mg, Kanto Chemicals), and stirred at room temperature for 3.5 hours. The reaction mixture was added with saturated aqueous sodium hydrogencarbonate (20 ml), and ethyl acetate (20 ml), and then the precipitates were removed by filtration. Then, the organic layer was separated, and the solvent was evaporated under reduced pressure. The residue was purified by silica gel column chromatography (n-hexane:ethyl acetate=4:1) to obtain the title compound (321 mg).

(Step C) (Intermediate 3)

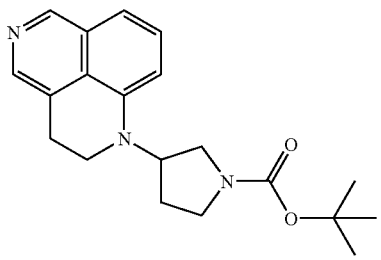

A suspension of Intermediate 2 (321 mg), and potassium tert-butoxide (212 mg, Tokyo Kasei Kogyo) in THF (6 ml) was stirred at 50° C. for 4 hours. The suspension was cooled to room temperature, then insoluble solids were removed by filtration, and the solvent was evaporated under reduced pressure. The residue was purified by silica gel column chromatography (n-hexane:ethyl acetate=2:1) to obtain the title compound (117 mg).

(Step D)

Intermediate 3 (117 mg) was added with a 10% hydrochloric acid/methanol solution (1 ml, Tokyo Kasei Kogyo), and stirred at room temperature for 2 hours. The solvent was evaporated under reduced pressure from the reaction mixture to obtain the compound of Exemplary Compound No. 8-1 as a hydrochloride (41.8 mg).

$^1$H-NMR (DMSO-$d_6$) δ (ppm): 2.06–2.14 (2H, m), 2.23–2.33 (2H, m), 3.20–3.30 (2H, m), 3.30–3.60 (4H, m), 4.90–4.98 (1H, m), 7.34–7.41 (1H, m), 7.66–7.82 (2H, m), 8.36–8.39 (2H, m), 9.53 (1H, s) MS (m/z): 240 (MH+)

Example 2

Exemplary Compound No. 8-9

(Step A) (Intermediate 4)

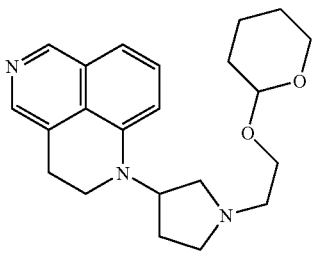

A suspension of the hydrochloride of Exemplary Compound 8-1 (95.8 mg), and potassium carbonate (228 mg, Wako Pure Chemical Industries) in N,N-dimethylformamide (2.7 ml) was added with 2-(2-bromoethoxy)tetrahydro-2H-pyran (181.2 µl, Aldrich), and stirred at room temperature for 18 hours. The reaction mixture was added with acetone (10 ml), insoluble solids were removed by filtration, and then the solvent was evaporated under reduced pressure. The residue was purified by silica gel column chromatography (chloroform/methanol mixed solvent system) to obtain the title compound (91.3 mg).

(Step B)

According to the method of the Example 1, Step D, deprotection was performed by using Intermediate 4 (86.2 mg), and a 10% hydrochloric acid/methanol solution (5 ml) (room temperature, 2 hours). The solvent was evaporated under reduced pressure to obtain the compound of Exemplary Compound No. 8-9 (53.1 mg) as a hydrochloride (53.1 mg).

MS (m/z): 284 (MH+)

Example 3

Exemplary Compound No. 8-4

(Step A) (Intermediate 5)

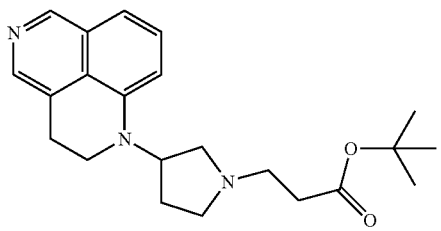

A suspension of the hydrochloride of Exemplary Compound 8-1 (95.8 mg), and potassium carbonate (228 mg) in N,N-dimethylformamide (2.7 ml) was added with tert-butyl acrylate (174 µl, Aldrich), and stirred at room temperature for 40 hours. The reaction mixture was added with acetone (10 ml), insoluble solids were removed by filtration, and then the solvent was evaporated under reduced pressure. The residue was purified by silica gel column chromatography (chloroform/methanol mixed solvent system) to obtain the title compound (52.6 mg).

(Step B)

Intermediate 5 (47.3 mg) was added with a 4 N hydrochloric acid/dioxane solution (3 ml, Kokusan Kagaku) at room temperature, and stirred for 4 hours. After the reaction, the solvent was evaporated under reduced pressure to obtain the compound of Exemplary Compound No. 8-4 as a hydrochloride (18.5 mg).

MS (m/z): 312 (MH+)

Example 4

Exemplary Compound No. 8-6

A suspension of the hydrochloride of Exemplary Compound 8-1 (95.8 mg), and potassium carbonate (228 mg) in N,N-dimethylformamide (2.7 ml) was added with bromoacetonitrile (41.8 µl, Aldrich), and stirred at room temperature for 18 hours. The reaction mixture was added with acetone (10 ml), insoluble solids were removed by filtration, and then the solvent was evaporated under reduced pressure. The residue was purified by silica gel column chromatography (chloroform/methanol mixed solvent system), then added with a 10% hydrochloric acid/methanol solution (5 ml), and stirred at room temperature for 2 hours. The solvent was evaporated under reduced pressure to obtain the compound of Exemplary Compound No. 8-6 as a hydrochloride (43.4 mg).

MS (m/z): 279 (MH+)

Example 5

Exemplary Compound No. 8-10

According to the method of Example 2, alkylation with 2-(3-bromopropoxy)tetrahydro-2H-pyran (Aldrich), and deprotection were performed by using the hydrochloride of Exemplary Compound 8-1 to obtain the compound of Exemplary Compound No. 8-10 as a hydrochloride.

MS (m/z): 298 (MH+)

Example 6

Exemplary Compound No. 8-15

According to the method of Example 2, alkylation with tert-butyl N-(2-bromoethyl)carbamate (Fluka), and deprotection were performed by using the hydrochloride of Exemplary Compound 8-1 to obtain the compound of Exemplary Compound No. 8-15 as a hydrochloride.

MS (m/z): 283 (MH+)

Example 7

Exemplary Compound No. 8-16

According to the method of Example 2, alkylation with tert-butyl N-(3-bromopropyl)carbamate (Tokyo Kasei Kogyo), and deprotection were performed by using the hydrochloride of Exemplary Compound 8-1 to obtain the compound of Exemplary Compound No. 8-16 as a hydrochloride.

MS (m/z): 297 (MH+)

Example 8

Exemplary Compound No. 8-3

According to the method of Example 3, alkylation with tert-butyl bromoacetate (Aldrich), and deprotection were performed by using the hydrochloride of Exemplary Compound 8-1 to obtain the compound of Exemplary Compound No. 8-3 as a hydrochloride.

MS (m/z): 298 (MH+)

Example 9

Exemplary Compound No. 8-12

According to the method of Example 4, alkylation with 2-bromoethyl methyl ether (Tokyo Kasei Kogyo) was performed by using the hydrochloride of Exemplary Compound 8-1 to obtain the compound of Exemplary Compound No. 8-12 as a hydrochloride.

MS (m/z): 298 (MH+)

Example 10

Exemplary Compound No. 8-24

According to the method of Example 4, alkylation with 2-bromoacetamide (Aldrich) was performed by using the hydrochloride of Exemplary Compound 8-1 to obtain the compound of Exemplary Compound No. 8-24 as a hydrochloride.

MS (m/z): 297 (MH+)

Example 11

Exemplary Compound No. 9-1

(Step A) 4-(4-Bromo-5-isoquinolyl)amino-1-(tert-butoxycarbonyl)piperidine (Intermediate 6)

A mixture of 5-amino-4-bromoisoquinoline (3.00 g) obtained in Reference Example 1, and tert-butyl 4-oxo-1-piperidinecarboxylate (5.50 g, Aldrich) was added with titanium tetraisopropoxide (8.20 ml) at room temperature, and stirred at room temperature for 15 hours. Subsequently, the reaction mixture was added with methanol (60 ml) and sodium borohydride (2.21 g), and stirred at room temperature for further 19 hours. The reaction mixture was added with saturated aqueous sodium hydrogencarbonate (100 ml) and ethyl acetate (100 ml), and the precipitates were removed by filtration. Then, the organic layer was separated, and the solvent was evaporated under reduced pressure. The residue was purified by silica gel column chromatography (n-hexane:acetone:isopropylamine=150:10:2) to obtain the title compound (2.92 g).

(Step B) 4-(4-Vinyl-5-isoquinolyl)amino-1-(tert-butoxycarbonyl)piperidine (Intermediate 7)

A suspension of Intermediate 6 (8.00 g), tri(n-butyl)vinyltin (8.63 ml), tetrakis(triphenylphosphine)palladium(0) (455 mg), and 2,6-di-tert-butyl-p-cresol (8.7 mg) in toluene (120 ml) was stirred at 110° C. for 2 hours. The reaction mixture was cooled to room temperature, then added with 10% aqueous potassium fluoride (120 ml), and stirred for 15 hours. After the precipitates were removed by filtration, the organic layer was separated, and dried over anhydrous magnesium sulfate. The solvent was evaporated under reduced pressure, and then the residue was purified by silica gel column chromatography (n-hexane:ethyl acetate=2:1) to obtain the title compound (6.72 g).

(Step C) (Intermediate 8)

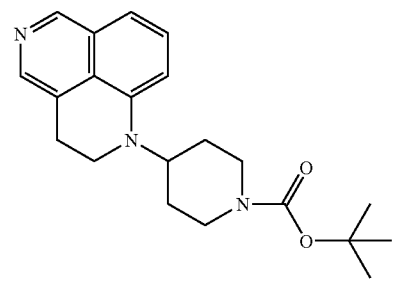

A suspension of Intermediate 7 (6.50 g), and potassium tert-butoxide (4.10 g) in tetrahydrofuran (92 ml) was stirred at 50° C. for 1 hour. The reaction mixture was added with water (100 ml), saturated aqueous ammonium chloride (50 ml), and ethyl acetate (100 ml), and the precipitates were removed by filtration. Then, the organic layer was separated, and dried over anhydrous sodium sulfate. The solvent was evaporated under reduced pressure, and then the residue was purified by silica gel column chromatography (n-hexane:ethyl acetate=1:2) to obtain the title compound (4.45 g).

(Step D)

According to the method of the Example 1, step D, deprotection was performed by using Intermediate 8 (4.23 g), and a 10% hydrochloric acid/methanol solution (60 ml) (50° C., 2 hours). The solvent was evaporated under reduced pressure to obtain the compound of Exemplary Compound No. 9-1 as a hydrochloride (3.71 g).

$^1$H-NMR (DMSO-d$_6$) δ (ppm): 1.85–1.91 (2H, m), 2.03–2.12 (2H, m), 3.05–3.20 (2H, m), 3.21–3.27 (2H, m), 3.37–3.42 (4H, m), 4.24–4.34 (1H, m), 7.45 (1H, d, J=8.1 Hz), 7.66 (1H, d, J=8.1 Hz), 7.78 (1H, t, J=8.1 Hz), 8.35 (1H, s), 9.05 (1H, brs), 9.51 (1H, s) MS (m/z): 254 (MH+)

Example 12

Exemplary Compound No. 9-9

According to the method of Example 2, alkylation with 2-(2-bromoethoxy)tetrahydro-2H-pyran, and deprotection were performed by using the hydrochloride of Exemplary Compound 9-1 to obtain the compound of Exemplary Compound No. 9-9 as a hydrochloride.

$^1$H-NMR (DMSO-d$_6$) δ (ppm): 1.88–1.95 (2H, m), 2.28–2.38 (2H, m), 3.05–3.20 (6H, m), 3.35–3.45 (2H, m), 3.62–3.68 (2H, m), 3.79–3.85 (2H, m), 4.25–4.35 (1H, m), 7.43 (1H, d, J=8.1 Hz), 7.67 (1H, d, J=8.1 Hz), 7.78 (1H, t, J=8.1 Hz), 8.36 (1H, s), 9.53 (1H, s) MS (m/z): 298 (MH+)

Example 13

Exemplary Compound No. 9-10

According to the method of Example 2, alkylation with 2-(3-bromopropoxy)tetrahydro-2H-pyran, and deprotection were performed by using the hydrochloride of Exemplary Compound 9-1 to obtain the compound of Exemplary Compound No. 9-10 as a hydrochloride.

$^1$H-NMR (DMSO-d$_6$) δ (ppm): 1.88–1.95 (2H, m), 2.32–2.38 (2H, m), 3.05–3.11 (2H, m), 3.15–3.21 (2H, m), 3.23–3.27 (2H, m), 3.36–3.44 (2H, m), 3.48–3.54 (2H, m), 3.57–3.61 (2H, m), 4.26–4.36 (1H, m), 7.43 (1H, d, J=8.1 Hz), 7.67 (1H, d, J=8.1 Hz), 7.79 (1H, t, J=8.1 Hz), 8.37 (1H, s), 9.53 (1H, s) MS (m/z): 312 (MH+)

Example 14

Exemplary Compound No. 9-15

According to the method of Example 2, alkylation with tert-butyl N-(2-bromoethyl)carbamate, and deprotection were performed by using the hydrochloride of Exemplary Compound 9-1 to obtain the compound of Exemplary Compound No. 9-15 as a hydrochloride.

$^1$H-NMR (DMSO-d$_6$) δ (ppm): 1.92–1.98 (2H, m), 2.33–2.39 (2H, m), 3.20–3.80 (12H, m), 4.33–4.43 (1H, m), 7.45 (1H, d, J=8.1 Hz), 7.69 (1H, d, J=8.1 Hz), 7.80 (1H, t, J=8.1 Hz), 8.37 (1H, s), 8.59 (2H, brs), 9.56 (1H, s) MS (m/z): 297 (MH+)

Example 15

Exemplary Compound No. 9-16

According to the method of Example 2, alkylation with tert-butyl N-(3-bromopropyl)carbamate, and deprotection were performed by using the hydrochloride of Exemplary Compound 9-1 to obtain the compound of Exemplary Compound No. 9-16 as a hydrochloride.

$^1$H-NMR (DMSO-d$_6$) δ (ppm): 1.88–1.95 (2H, m), 2.08–2.14 (2H, m), 2.38–2.44 (2H, m), 2.92–2.98 (2H, m), 3.19–3.60 (10H, m), 4.31–4.41 (1H, m), 7.46 (1H, d, J=8.1 Hz), 7.67 (1H, d, J=8.1 Hz), 7.79 (1H, t, J=8.1 Hz), 8.22 (2H, brs), 8.37 (1H, s), 9.54 (1H, s) MS (m/z): 311 (MH+)

Example 16

Exemplary Compound No. 9-4

According to the method of Example 3, alkylation with tert-butyl acrylate, and deprotection were performed by using the hydrochloride of Exemplary Compound 9-1 to obtain the compound of Exemplary Compound No. 9-4 as a hydrochloride.

$^1$H-NMR (DMSO-d$_6$) δ (ppm): 1.88–1.95 (2H, m), 2.30–2.36 (2H, m), 2.87–2.93 (2H, m), 3.20–3.30 (6H, m), 3.37–3.41 (2H, m), 3.57–3.61 (2H, m), 4.27–4.37 (1H, m), 7.47 (1H, d, J=8.1 Hz), 7.71 (1H, d, J=8.1 Hz), 7.81 (1H, t, J=8.1 Hz), 8.38 (1H, s), 9.58 (1H, s) MS (m/z): 326 (MH+)

Example 17

Exemplary Compound No. 9-3

According to the method of Example 3, alkylation with tert-butyl bromoacetate, and deprotection were performed by using the hydrochloride of Exemplary Compound 9-1 to obtain the compound of Exemplary Compound No. 9-3 as a hydrochloride.

$^1$H-NMR (DMSO-d$_6$) δ (ppm): 1.88–1.95 (2H, m), 2.27–2.32 (2H, m), 3.22–3.30 (2H, m), 3.32–3.40 (4H, m), 3.61–3.67 (2H, m), 4.17 (2H, s), 4.24–4.34 (1H, m), 7.47 (1H, d, J=8.1 Hz), 7.69 (1H, d, J=8.1 Hz), 7.80 (1H, t, J=8.1 Hz), 8.37 (1H, s), 9.55 (1H, s) MS (m/z): 312 (MH+)

Example 18

Exemplary Compound No. 9-6

According to the method of Example 4, alkylation with bromoacetonitrile, and formation of hydrochloride were performed by using the hydrochloride of Exemplary Compound 9-1 to obtain the compound of Exemplary Compound No. 9-6 as a hydrochloride.

$^1$H-NMR (DMSO-d$_6$) δ (ppm): 1.88–1.94 (2H, m), 2.18–2.24 (2H, m), 3.07–3.13 (2H, m), 3.23–3.29 (2H, m), 3.35–3.43 (4H, m), 4.19–4.29 (1H, m), 4.36 (2H, s), 7.51 (1H, d, J=8.1 Hz), 7.69 (1H, d, J=8.1 Hz), 7.80 (1H, t, J=8.1 Hz), 8.37 (1H, s), 9.57 (1H, s) MS (m/z): 293 (MH+)

Example 19

Exemplary Compound No. 9-12

According to the method of Example 4, alkylation with 2-bromoethyl methyl ether, and formation of hydrochloride were performed by using the hydrochloride of Exemplary Compound 9-1 to obtain the compound of Exemplary Compound No. 9-12 as a hydrochloride.

$^1$H-NMR (DMSO-d$_6$) δ (ppm): 1.88–1.95 (2H, m), 2.32–2.38 (2H, m), 3.20–3.45 (9H, m), 3.55–3.65 (2H, m), 3.72–3.82 (2H, m), 4.25–4.35 (1H, m), 7.45 (1H, d, J=8.1 Hz), 7.68 (1H, d, J=8.1 Hz), 7.79 (1H, t, J=8.1 Hz), 8.37 (1H, s), 9.55 (1H, s) MS (m/z): 312 (MH+)

Example 20

Exemplary Compound No. 9-24

According to the method of Example 4, alkylation with 2-bromoacetamide, and formation of hydrochloride were performed by using the hydrochloride of Exemplary Compound 9-1 to obtain the compound of Exemplary Compound No. 9-24 as a hydrochloride.

$^1$H-NMR (DMSO-$d_6$) δ (ppm): 1.88–1.95 (2H, m), 2.26–2.34 (2H, m), 3.23–3.29 (2H, m), 3.35–3.43 (4H, m), 3.58–3.64 (2H, m), 4.24–4.34 (3H, m), 7.47 (1H, d, J=8.1 Hz), 7.68 (1H, d, J=8.1 Hz), 7.79 (1H, t, J=8.1 Hz), 8.18 (2H, brs), 8.37 (1H, s), 9.55 (1H, s) MS (m/z): 311 (MH+)

Example 21

Exemplary Compound No. 2-2

(Step A) tert-Butyl N-benzyl-(4-oxo-cyclohexyl)carbamate (Intermediate 9)

A solution of 1,4-cyclohexanedione monoethylene ketal (10 g, Tokyo Kasei Kogyo) in 1,2-dichloroethane (65 ml) was added with benzylamine (7.69 ml, Tokyo Kasei Kogyo), acetic acid (3.67 ml, Wako Pure Chemical Industries), and sodium triacetoxyborohydride (19.09 g, Aldrich) under ice cooling, and stirred at room temperature for 0.5 hour. The reaction mixture was added with 1 N aqueous sodium hydroxide (80 ml), and extracted 5 times with chloroform (50 ml). The extract was dried over anhydrous magnesium sulfate, and the solvent was evaporated under reduced pressure. The obtained residue was added with tetrahydrofuran (90 ml) and 5 N aqueous hydrochloric acid (50 ml), and stirred at 100° C. for 15 hours. The reaction mixture was added with 2 N aqueous sodium hydroxide (60 ml), and extracted with dichloromethane (150 ml). The extract was dried over anhydrous magnesium sulfate, and the solvent was evaporated under reduced pressure. The obtained residue was added with methanol (100 ml), triethylamine (9.82 ml, Wako Pure Chemical Industries), and di-t-butyl dicarbonate (26.5 ml, Wako Pure Chemical Industries), and stirred at 60° C. for 2 hours. The solvent was evaporated under reduced pressure, and then the residue was added with 1 N aqueous hydrochloric acid (15 ml), and extracted twice with dichloromethane (50 ml). The extract was dried over anhydrous magnesium sulfate, and then the solvent was evaporated under reduced pressure. The residue was added with isopropyl alcohol, and the precipitates were taken by filtration to obtain the title compound (13.5 g).

(Step B) tert-Butyl N-benzyl-[4-(4-vinyl-isoquinolin-5-ylamino)cyclohexyl]carbamate (Intermediate 10)

A solution of Intermediate 9 (5.73 g), Intermediate 1 (2.92 g), and para-toluenesulfonic acid monohydrate (163 mg, Wako Pure Chemical Industries) in toluene (50 ml) was refluxed by heating for 1 hour. The reaction mixture was cooled to room temperature, then added with methanol (75 ml) and sodium borohydride (6.48 g), and stirred at room temperature for 1 hour. The reaction mixture was added with water (5 ml), and then the solvent was evaporated under reduced pressure. The residue was added with ethyl acetate (100 ml), and the organic layer was washed twice with water (50 ml), and dried over anhydrous magnesium sulfate. Then, the solvent was evaporated under reduced pressure. The residue was purified by silica gel column chromatography (n-hexane:ethyl acetate=2:1) to obtain the title compound (2.2 g of trans-isomer, 1.8 g of cis-isomer).

(Step C) (Intermediate 11)

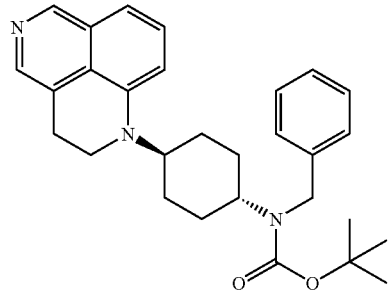

A suspension of the trans-isomer of Intermediate 10 (2.18 g), and potassium tert-butoxide (1.07 g) in 1,4-dioxane (50 ml) was stirred at 100° C. for 2 hours. After insoluble solids were removed by filtration, the solvent was evaporated under reduced pressure. The residue was purified by silica gel column chromatography (n-hexane:ethyl acetate=1:2) to obtain the title compound (1.82 g).

(Step D) (Intermediate 12)

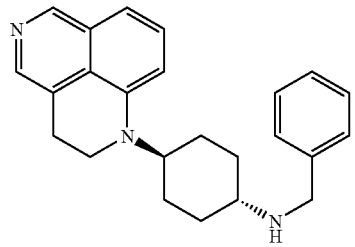

According to the method of the Example 1, Step D, deprotection was performed by using Intermediate 11 (789 mg), and a 10% hydrochloric acid/methanol solution (10 ml) (50° C., 2 hours). The reaction mixture was cooled to room temperature to obtain the title compound, trans-benzyl-[4-(2,3-dihydro-1,5-diazaphenalen-1-yl)cyclohexyl]amine (687 mg), as a hydrochloride.

(Step E)

The hydrochloride of Intermediate 12 (500 mg) was added with 1 N aqueous sodium hydroxide (20 ml), and stirred for 0.5 hour. The reaction mixture was added with chloroform (30 ml), and the organic layer was separated. The aqueous layer was further extracted twice with chloroform (30 ml for each time), and the combined organic layer was dried over anhydrous sodium sulfate. The solvent was evaporated under reduced pressure, and then the residue was added with ethanol (30 ml) and 10% palladium/carbon (50 mg, Wako Pure Chemical Industries), and stirred at 70° C. for 14 hours under hydrogen atmosphere. The reaction mixture was filtered through Cerite, and then the solvent was evaporated under reduced pressure. The residue was added with a 10% hydrochloric acid/methanol solution (5 ml), and stirred at room temperature for 0.5 hour. The solvent was evaporated under reduced pressure to obtain the compound of Exemplary Compound No. 2-2 as a hydrochloride (240 mg).

$^1$H-NMR (DMSO-$d_6$) δ (ppm): 1.55–1.81 (6H, m), 2.06–2.10 (2H, m), 3.00–3.16 (1H, m), 3.20 (2H, t, J=5.9

Hz), 3.40 (2H, t, J=5.9 Hz), 3.85–3.89 (1H, m), 7.34 (1H, d, J=8.1 Hz), 7.61 (1H, d, J=8.1 Hz), 7.76 (1H, t, J=8.1 Hz), 8.17 (2H, brs), 8.32 (1H, s), 9.49 (1H, s) MS (m/z): 268 (MH+)

Example 22

Exemplary Compound No. 2-11

According to the method of Example 2, alkylation with 2-(2-bromoethoxy)tetrahydro-2H-pyran, and deprotection were performed by using the hydrochloride of Exemplary Compound 2-2 to obtain the compound of Exemplary Compound No. 2-11 as a hydrochloride.
$^1$H-NMR (DMSO-d$_6$) δ (ppm): 1.68–1.74 (4H, m), 1.82–1.88 (2H, m), 2.20–2.26 (2H, m), 3.02–3.12 (3H, m), 3.19–3.23 (2H, m), 3.39–3.43 (2H, m), 3.70–3.74 (2H, m), 3.82–3.92 (1H, m), 7.34 (1H, d, J=8.1 Hz), 7.63 (1H, d, J=8.1 Hz), 7.77 (1H, t, J=8.1 Hz), 8.17 (2H, brs), 8.33 (1H, s), 9.02 (2H, brs), 9.51 (1H, s) MS (m/z): 312 (MH+)

Example 23

Exemplary Compound No. 2-12

According to the method of Example 2, alkylation with 2-(3-bromopropoxy)tetrahydro-2H-pyran, and deprotection were performed by using the hydrochloride of Exemplary Compound 2-2 to obtain Exemplary Compound No. 2-12 as a hydrochloride.
MS (m/z): 326 (MH+)

Example 24

Exemplary Compound No. 2-17

According to the method of Example 2, alkylation with tert-butyl N-(2-bromoethyl)carbamate, and deprotection were performed by using the hydrochloride of Exemplary Compound 2-2 to obtain the compound of Exemplary Compound No. 2-17 as a hydrochloride.
$^1$H-NMR (DMSO-d$_6$) δ (ppm): 1.68–1.74 (4H, m), 1.82–1.88 (2H, m), 2.20–2.26 (2H, m), 3.02–3.60 (9H, m), 3.91–3.99 (1H, m), 7.36 (1H, d, J=8.1 Hz), 7.62 (1H, d, J=8.1 Hz), 7.77 (1H, t, J=8.1 Hz), 8.33 (1H, s), 8.45 (2H, brs), 9.02 (2H, brs), 9.50 (1H, s), 9.73 (1H, brs) MS (m/z): 311 (MH+)

Example 25

Exemplary Compound No. 2-18

According to the method of Example 2, alkylation with tert-butyl N-(3-bromopropyl)carbamate, and deprotection were performed by using the hydrochloride of Exemplary Compound 2-2 to obtain the compound of Exemplary Compound No. 2-18 as a hydrochloride.
MS (m/z): 325 (MH+)

Example 26

Exemplary Compound No. 2-6

According to the method of Example 3, alkylation with tert-butyl acrylate, and deprotection were performed by using the hydrochloride of Exemplary Compound 2-2 to obtain the compound of Exemplary Compound No. 2-6 as a hydrochloride.
MS (m/z): 340 (MH+)

Example 27

Exemplary Compound No. 2-5

According to the method of Example 3, alkylation with tert-butyl bromoacetate, and deprotection were performed by using the hydrochloride of Exemplary Compound 2-2 to obtain the compound of Exemplary Compound No. 2-5 as a hydrochloride.
MS (m/z): 326 (MH+)

Example 28

Exemplary Compound No. 2-8

According to the method of Example 4, alkylation with bromoacetonitrile, and formation of hydrochloride were performed by using the hydrochloride of Exemplary Compound 2-2 to obtain the compound of Exemplary Compound No. 2-8 as a hydrochloride.
MS (m/z): 307 (MH+)

Example 29

Exemplary Compound No. 2-14

According to the method of Example 4, alkylation with 2-bromoethyl methyl ether, and formation of hydrochloride were performed by using the hydrochloride of Exemplary Compound 2-2 to obtain the compound of Exemplary Compound No. 2-14 as a hydrochloride.
MS (m/z): 326 (MH+)

Example 30

Exemplary Compound No. 2-26

According to the method of Example 4, alkylation with 2-bromoacetamide, and formation of hydrochloride were performed by using the hydrochloride of Exemplary Compound 2-2 to obtain Exemplary Compound No. 2-26 as a hydrochloride.
MS (m/z): 325 (MH+)

Example 31

Exemplary Compound No. 3-2

(Step A) (Intermediate 13)

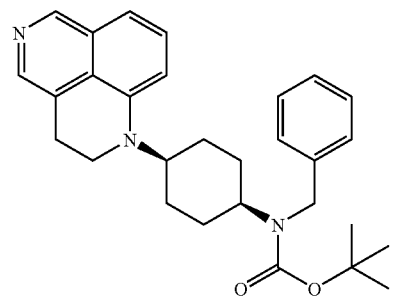

A solution of the cis-isomer of Intermediate 10 (2.18 g) obtained in Example 21, Step B, and potassium tert-butoxide (1.07 g) in 1,4-dioxane (50 ml) was stirred at 100° C. for 2 hours. After insoluble solids were removed by filtration, the solvent was evaporated under reduced pressure. The residue was purified by silica gel column chromatography (n-hexane:ethyl acetate=1:2) to obtain the title compound (155 mg).

(Step B) (Intermediate 14)

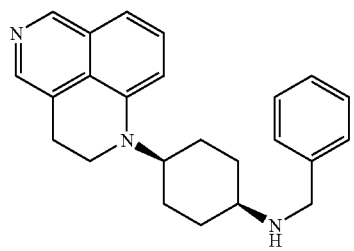

According to the method of the Example 1, Step D, deprotection was performed by using Intermediate 13 (155 mg), and a 10% hydrochloric acid/methanol solution (1 ml) (50° C., 2 hours). The reaction mixture was cooled to room temperature to obtain the title compound (102 mg).

(Step C)

The hydrochloride of Intermediate 14 (200 mg) was added with 1 N aqueous sodium hydroxide (10 ml), and stirred for 0.5 hour. The reaction mixture was added with chloroform (15 ml), and the organic layer was separated. The aqueous layer was further extracted twice with chloroform (15 ml for each time), and the combined organic layer was dried over anhydrous sodium sulfate. The solvent was evaporated under reduced pressure, and then the residue was added with ethanol (12 ml) and 10% palladium/carbon (20 mg), and stirred at 70° C. for 14 hours under hydrogen atmosphere. The reaction mixture was filtered through Cerite, and then the solvent was evaporated under reduced pressure. The residue was added with a 10% hydrochloric acid/methanol solution (2 ml), and stirred at room temperature for 0.5 hour. The solvent was evaporated under reduced pressure to obtain the compound of Exemplary Compound No. 3-2 as a hydrochloride (84 mg).

$^1$H-NMR (DMSO-$d_6$) δ (ppm): 1.60–1.64 (2H, m), 1.83–2.08 (6H, m), 3.20–3.24 (1H, m), 3.37–3.39 (2H, m), 3.51 (2H, m), 3.92–3.98 (1H, m), 7.33–7.36 (1H, m), 7.58–7.61 (1H, m), 7.72–7.77 (1H, m), 8.23 (2H, brs), 8.31 (1H, s), 9.49 (1H, s) MS (m/z): 268 (MH+)

Example 32

Exemplary Compound No. 3-11

According to the method of Example 2, alkylation with 2-(3-bromoethoxy)tetrahydro-2H-pyran, and deprotection were performed by using the hydrochloride of Exemplary Compound 3-2 to obtain the compound of Exemplary Compound No. 3-11 as a hydrochloride.

MS (m/z): 312 (MH+)

Example 33

Exemplary Compound No. 3-12

According to the method of Example 2, alkylation with 2-(3-bromopropoxy)tetrahydro-2H-pyran, and deprotection were performed by using the hydrochloride of Exemplary Compound 3-2 to obtain the compound of Exemplary Compound No. 3-12 as a hydrochloride.

MS (m/z): 326 (MH+)

Example 34

Exemplary Compound No. 3-17

According to the method of Example 2, alkylation with tert-butyl N-(2-bromoethyl)carbamate, and deprotection were performed by using the hydrochloride of Exemplary Compound 3-2 to obtain the compound of Exemplary Compound No. 3-17 as a hydrochloride.

MS (m/z): 311 (MH+)

Example 35

Exemplary Compound No. 3-18

According to the method of Example 2, alkylation with tert-butyl N-(3-bromopropyl)carbamate, and deprotection were performed by using the hydrochloride of Exemplary Compound 3-2 to obtain the compound of Exemplary Compound No. 3-18 as a hydrochloride.

MS (m/z): 325 (MH+)

Example 36

Exemplary Compound No. 3-6

According to the method of Example 3, alkylation with tert-butyl acrylate, and deprotection were performed by using the hydrochloride of Exemplary Compound 3-2 to obtain the compound of Exemplary Compound No. 3-6 as a hydrochloride.

MS (m/z): 340 (MH+)

Example 37

Exemplary Compound No. 3-5

According to the method of Example 3, alkylation with tert-butyl bromoacetate, and deprotection were performed by using the hydrochloride of Exemplary Compound 3-2 to obtain the compound of Exemplary Compound No. 3-5 as a hydrochloride.

MS (m/z): 326 (MH+)

Example 38

Exemplary Compound No. 3-8

According to the method of Example 4, alkylation with bromoacetonitrile, and formation of hydrochloride were performed by using the hydrochloride of Exemplary Compound 3-2 to obtain the compound of Exemplary Compound No. 3-8 as a hydrochloride.

MS (m/z): 307 (MH+)

Example 39

Exemplary Compound No. 3-14

According to the method of Example 4, alkylation with 2-bromoethyl methyl ether, and formation of hydrochloride were performed by using the hydrochloride of Exemplary Compound 3-2 to obtain the compound of Exemplary Compound No. 3-14 as a hydrochloride.

MS (m/z): 326 (MH+)

Example 40

Exemplary Compound No. 3-26

According to the method of Example 4, alkylation with 2-bromoacetamide, and formation of hydrochloride were performed by using the hydrochloride of Exemplary Compound 3-2 to obtain the compound of Exemplary Compound No. 3-26 as a hydrochloride.

MS (m/z): 325 (MH+)

Example 41

Exemplary Compound No. 2-3

(Step A) Intermediate 15

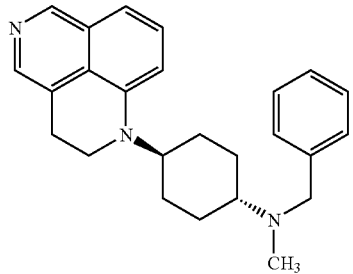

The hydrochloride of Intermediate 12 (100 mg) was added with 1 N aqueous sodium hydroxide (4 ml), and stirred for 0.5 hour. The reaction mixture was added with chloroform (6 ml), and the organic layer was separated. The aqueous layer was further extracted twice with chloroform (6 ml for each time), and the combined organic layer was dried over anhydrous sodium sulfate. The solvent was evaporated under reduced pressure, and then the residue was added with ethanol (2 ml), formalin (2 ml, Wako Pure Chemical Industries), and 10% palladium/carbon (10 mg), and stirred at room temperature for 14 hours under hydrogen atmosphere. The reaction mixture was filtered through Cerite, and then the solvent was evaporated under reduced pressure to obtain the title compound (40.5 mg).

(Step B)

Intermediate 15 (40.5 mg) was added with ethanol (2 ml) and 10% palladium/carbon (4 mg), and stirred at 70° C. for 14 hours under hydrogen atmosphere. The reaction mixture was filtered through Cerite, and then the solvent was evaporated under reduced pressure. Then, the residue was added with a 10% hydrochloric acid/methanol solution (1 ml), and stirred at room temperature for 0.5 hour. The solvent was evaporated under reduced pressure to obtain the compound of Exemplary Compound No. 2-3 as a hydrochloride (22.3 mg).

$^1$H-NMR (DMSO-$d_6$) δ (ppm): 1.63–1.77 (4H, m), 1.83–1.90 (2H, m), 2.17–2.22 (2H, m), 2.52 (3H, s), 2.93–3.06 (1H, m), 3.16–3.23 (2H, m), 3.36–3.47 (2H, m), 3.83–3.93 (1H, m), 7.36 (1H, d, J=8.1 Hz), 7.64 (1H, d, J=8.1 Hz), 7.78 (1H, t, J=8.1 Hz), 8.34 (1H, s), 9.24 (1H, brs), 9.53 (1H, s) MS (m/z): 282 (MH+)

Example 42

Exemplary Compound No. 9-51

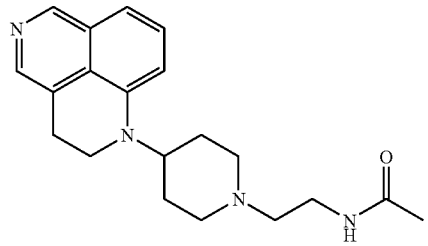

The hydrochloride of Exemplary Compound No. 9-15 (50 mg) was added with dichloromethane (1 ml), N,N-diisopropylethylamine (110 μl, Tokyo Kasei Kogyo), 1-ethyl-3-(3-dimethylaminopropyl)carbodiimide hydrochloride (70.9 mg, Kokusan Kagaku), and acetic acid (7.8 μl, Wako Pure Chemical Industries), and stirred at room temperature for two hours. The reaction mixture was added with saturated aqueous sodium hydrogencarbonate (1 ml), and stirred at room temperature for 10 minutes. Then, the organic layer was separated, and the solvent was evaporated under reduced pressure. The residue was purified by silica gel column chromatography (chloroform:methanol=9:1), and the solvent was evaporated under reduced pressure to obtain the compound of Exemplary Compound No. 9-51 (28.6 mg).

$^1$H-NMR (CDCl$_3$) δ (ppm): 1.86–1.90 (4H, m), 2.02 (3H, s), 2.15–2.24 (2H, m), 2.52–2.56 (2H, m), 3.05–3.16 (4H, m), 3.35–3.43 (4H, m), 3.72–3.82 (1H, m), 6.02 (1H, brs), 6.78 (1H, d, J=8.1 Hz), 7.23 (1H, d, J=8.1 Hz), 7.42 (1H, t, J=8.1 Hz), 8.16 (1H, s), 8.99 (1H, s) MS (m/z): 339 (MH+)

Example 43

Exemplary Compound No. 9-52

According to the method of Example 42, condensation with propionic acid was performed by using the hydrochloride of Exemplary Compound No. 9-15 to obtain the compound of Exemplary Compound No. 9-52.

MS (m/z): 353 (MH+)

Example 44

Exemplary Compound No. 9-53

According to the method of Example 42, condensation with butyric acid was performed by using the hydrochloride of Exemplary Compound No. 9-15 to obtain the compound of Exemplary Compound No. 9-53.

MS (m/z): 367 (MH+)

Example 45

Exemplary Compound No. 9-54

According to the method of Example 42, condensation with isobutyric acid was performed by using the hydrochloride of Exemplary Compound No. 9-15 to obtain the compound of Exemplary Compound No. 9-54.

MS (m/z): 367 (MH+)

Example 46

Exemplary Compound No. 9-55

According to the method of Example 42, condensation with pivalic acid was performed by using the hydrochloride of Exemplary Compound No. 9-15 to obtain the compound of Exemplary Compound No. 9-55.

MS (m/z): 381 (MH+)

Example 47

Exemplary Compound No. 9-56

According to the method of Example 42, condensation with acetic acid was performed by using the hydrochloride of Exemplary Compound No. 9-41 to obtain the compound of Exemplary Compound No. 9-56.

MS (m/z): 353 (MH+)

Example 48

Exemplary Compound No. 9-57

According to the method of Example 42, condensation with propionic acid was performed by using the hydrochloride of Exemplary Compound No. 9-41 to obtain the compound of Exemplary Compound No. 9-57.

MS (m/z): 367 (MH+)

Example 49

Exemplary Compound No. 9-58

According to the method of Example 42, condensation with butyric acid was performed by using the hydrochloride of Exemplary Compound No. 9-41 to obtain the compound of Exemplary Compound No. 9-58.

MS (m/z): 381 (MH+)

Example 50

Exemplary Compound No. 9-59

According to the method of Example 42, condensation with isobutyric acid was performed by using the hydrochloride of Exemplary Compound No. 9-41 to obtain the compound of Exemplary Compound No. 9-59.

MS (m/z): 381 (MH+)

Example 51

Exemplary Compound No. 9-60

According to the method of Example 42, condensation with pivalic acid was performed by using the hydrochloride of Exemplary Compound No. 9-41 to obtain the compound of Exemplary Compound No. 9-60.

MS (m/z): 395 (MH+)

Example 52

Exemplary Compound No. 9-2

A solution of the compound of Exemplary Compound No. 9-1 (53 mg) in ethanol (1.5 ml) and 37% formalin (1.5 ml, Wako Pure Chemical Industries) was added with 10% palladium/carbon (5 mg), and stirred at 70° C. for 8 hours under hydrogen atmosphere. The reaction mixture was filtered through Cerite, and then the solvent was evaporated under reduced pressure. The residue was purified by silica gel column chromatography (chloroform:methanol=9:1), and the solvent was evaporated under reduced pressure to obtain the title compound (35 mg).

MS (m/z): 268 (MH+)

Example 53

Exemplary Compound No. 2-123

A solution of the compound of Exemplary Compound No. 2-2 (100 mg) in ethanol (2.5 ml) and 37% formalin (2.5 ml) was added with 10% palladium/carbon (10 mg), and stirred at 70° C. for 12 hours under hydrogen atmosphere. The reaction mixture was filtered through Cerite, and then the solvent was evaporated under reduced pressure. The residue was purified by silica gel column chromatography (chloroform:methanol=9:1), and the solvent was evaporated under reduced pressure to obtain the title compound (70 mg).

MS (m/z): 296 (MH+)

Example 54

Exemplary Compound No. 9-79

According to the method of Example 1, the title compound was obtained from Intermediate 1 and tert-butyl 3-fluoro-4-oxo-1-piperidinecarboxylate prepared according to the method of Collins et al. (J. Med. Chem., 42, 12, 1999, 2087).

$^1$H-NMR (DMSO-$d_6$) δ (ppm): 1.90 (1H, d, J=13 Hz), 2.45 (1H, m), 3.0–3.7 (8H, m), 4.54 (1H, m), 5.27 (1H, d, J=48 Hz), 7.45 (1H, d, J=7.8 Hz), 7.71 (1H, d, J=7.8 Hz), 7.78 (1H, t, J=7.8 Hz), 8.37 (1H, s), 9.53 (1H, s) MS (m/z): 272 (MH+)

Example 55

Exemplary Compound No. 2-12

According to the method of Example 2, alkylation with 2-(3-bromopropoxy)tetrahydro-2H-pyran, and deprotection were performed by using the hydrochloride of Exemplary Compound No. 2-2 to obtain the title compound as a hydrochloride.

MS (m/z): 326 (MH+)

Example 56

Exemplary Compound No. 2-35

According to the method of Example 53, the title compound was obtained from the compound of Exemplary Compound No. 2-2.

MS (m/z): 326 (MH+)

Example 57

Exemplary Compound No. 9-18

A solution of the hydrochloride of Exemplary Compound No. 9-1 (3 g) in N,N-dimethylformamide (100 ml) was added with bromoacetaldehyde dimethylacetal (4.35 ml, Tokyo Kasei Kogyo) and potassium carbonate (7.62 g), and stirred at 30° C. for 48 hours. The reaction mixture was cooled to 0° C., added with water (100 ml), and extracted twice with ethyl acetate (200 ml for each time). The combined organic layer was washed three times with saturated brine (200 ml for each time), and dried over anhydrous sodium sulfate. The solvent was evaporated under reduced pressure, and the residue was purified by silica gel column chromatography (chloroform:methanol=19:1). Subsequently, the resultant was added with 5 N hydrochloric acid (50 ml), and stirred at room temperature for 72 hours. The reaction mixture was cooled to 0° C., neutralized with 2 N aqueous sodium hydroxide (pH 7.5), and extracted three times with ethyl acetate (100 ml for each time). The combined organic layer was dried over anhydrous sodium sulfate, and the solvent was evaporated under reduced pressure. The residue was dissolved in methanol (15 ml) and methylene chloride (30 ml), added with 40% methylamine/methanol solution (30 ml, Tokyo Kasei Kogyo), and stirred at room temperature for one hour. Then, the reaction mixture was added with sodium borohydride (121 mg), and stirred at room temperature for 16 hours. The reaction mixture was cooled to 0° C., added with water (100 ml), and extracted twice with methylene chloride (200 ml for each time). The combined organic layer was dried over anhydrous sodium sulfate, and the solvent was evaporated under reduced pressure. The residue was purified by silica gel column chromatography (chloroform:methanol:isopropylamine=92.0:7.9:0.1) to obtain the title compound (962 mg).

MS (m/z): 311 (MH+)

Example 58

Exemplary Compound No. 9-21

According to the method of Example 53, the title compound was obtained from the compound of Exemplary Compound No. 9-18.

MS (m/z): 325 (MH+)

Example 59

Exemplary Compound No. 9-71

According to the method of Example 42, condensation with acetic acid was performed by using the compound of Exemplary Compound No. 9-18 to obtain the title compound.

MS (m/z): 353 (MH+)

Example 60

Exemplary Compound number No. 9-73

A solution of the compound of Exemplary Compound No. 9-15 (364 mg) and tert-butyl acrylate (450 μl, Tokyo Kasei Kogyo) in N,N-dimethylformamide (12 ml) was added with potassium carbonate (849 mg), and stirred at room temperature for 72 hours. The reaction mixture was cooled to 0° C., added with water (30 ml), and extracted three times with ethyl acetate (50 ml for each time). The combined organic layer was washed three times with saturated brine (50 ml for each time), and dried over anhydrous sodium sulfate. The solvent was evaporated under reduced pressure, and the residue was purified by silica gel column chromatography (ethyl acetate:methanol:isopropylamine=95:4.9:0.1). Subsequently, the resultant was added with 4 N hydrogen chloride/1,4-dioxane solution (4 ml, Kokusan Kagaku), and stirred at room temperature for 1.5 hours. The solvent was evaporated under reduced pressure, and a suspension of the residue in methylene chloride (12 ml) was added with 2-chloro-1-methylpyridinium iodide (64 mg, Aldrich) and triethylamine (138 μl) and stirred at room temperature for 48 hours. The solvent was evaporated under reduced pressure, and the residue was purified by silica gel column chromatography (ethyl acetate:methanol:isopropylamine=95:4.9:0.1). Subsequently, the resultant was added with 4 N hydrogen chloride/1,4-dioxane solution (0.2 ml), and stirred at room temperature for 0.5 hour. The solvent was evaporated under reduced pressure to obtain the title compound as a hydrochloride (15 mg).

$^1$H-NMR (DMSO-$d_6$) δ (ppm): 1.93 (2H, m), 2.24 (2H, m), 2.89 (2H, m), 3.1–3.7 (14H, m), 4.19 (1H, m), 7.06 (1H, d, J=7.8 Hz), 7.36 (1H, d, J=7.8 Hz), 7.51 (1H, t, J=7.8 Hz), 8.19 (1H, s), 9.06 (1H, s) MS (m/z): 351 (MH+)

Example 61

6-Chloro-1-(piperidin-4-yl)-2,3-dihydro-1H-1,5-diazaphenalene (Step A) 5-Nitro-4-vinylisoquinoline A suspension of 4-bromo-5-nitroisoquinoline (52 g) obtained in Reference Example 1, Step A, tri(n-butyl)vinyltin (105 g), tetrakis(triphenylphosphine)palladium(0) (4.8 g), and 2,6-di-tert-butyl-p-creosol (11.3 mg) in toluene (300 ml) was stirred at 110° C. for three hours. The reaction mixture was cooled to room temperature, then added with 10% aqueous potassium fluoride (400 ml), and stirred for 0.5 hour. The reaction mixture was added with ethyl acetate (250 ml), and the precipitates were removed by filtration. Then, the organic layer was separated, and dried over anhydrous magnesium sulfate. The solvent was evaporated under reduced pressure, and then the residue was purified by silica gel column chromatography (n-hexane/ethyl acetate) to obtain the title compound (24 g).

$^1$H-NMR (CDCl$_3$) δ (ppm): 5.48 (1H, d, J=11 Hz), 5.63 (1H, d, J=17 Hz), 6.87 (1H, dd, J=11 Hz, 17 Hz), 7.68 (1H, t, J=8.1 Hz), 7.94 (1H, d, J=8.1 Hz), 8.20 (1H, d, J=8.1 Hz), 8.64 (1H, s), 9.28 (1H, s)

(Step B) 5-Nitro-4-vinylisoquinoline N-oxide

The 5-nitro-4-vinylisoquinoline (23 g) obtained in Step A mentioned above was dissolved in dichloromethane (400 ml), then slowly added with m-chloroperbenzoic acid (43 g, Tokyo Kasei Kogyo), and stirred for 3.5 hours. The reaction mixture was cooled on ice, and then neutralized by addition of saturated aqueous sodium hydrogencarbonate. Then, the organic layer was separated, and dried over anhydrous magnesium sulfate. The solvent was evaporated under reduced pressure to obtain the title compound (27 g).

(Step C) 1-Chloro-5-nitro-4-vinylisoquinoline

The 5-nitro-4-vinylisoquinoline N-oxide (27 g) obtained in Step B mentioned above was suspended in chloroform (300 ml), and added dropwise with phosphorus oxychloride (22.3 ml, Wako Pure Chemical Industries) under ice cooling. After the addition, the reaction mixture was warmed to 60° C., and stirred at the same temperature for one hour. The reaction mixture was poured into in ice water, and neutralized with 2 N sodium hydroxide with stirring. The organic layer was separated, and dried over anhydrous magnesium sulfate. The solvent was evaporated under reduced pressure to obtain the title compound (15 g).

¹H-NMR (CDCl₃) δ (ppm): 5.49 (1H, d, J=11 Hz), 5.63 (1H, d, J=17 Hz), 6.81 (1H, dd, J=11 Hz, 17 Hz), 7.77 (1H, t, J=8.1 Hz), 7.97 (1H, d, J=8.1 Hz), 8.36 (1H, s), 8.64 (1H, d, J=8.1 Hz)

(Step D) 5-Amino-1-chloro-4-vinylisoquinoline

The 1-chloro-5-nitro-4-vinylisoquinoline (15 g) obtained in Step C mentioned above was dissolved in ethyl acetate (700 ml), added with stannous chloride dihydrate (72 g), and stirred for two hours. The reaction mixture was poured on ice, and then added with 5 N aqueous sodium hydroxide. The organic layer was separated, and dried over anhydrous sodium sulfate. The solvent was evaporated under reduced pressure, and then the residue was purified by silica gel column chromatography (n-hexane:ethyl acetate=3:1) to obtain the title compound (10 g).

¹H-NMR (CDCl₃) δ (ppm): 5.54 (1H, dd, J=1.5, 10.8 Hz), 5.65 (1H, dd, J=1.5, 17.1 Hz), 6.92 (1H, d, J=7.8 Hz), 7.41–7.64 (2H, m), 7.77 (1H, d, J=8.7 Hz), 7.94 (1H, s) MS (m/z): 205 (MH+)

(Step E) 4-(1-Chloro-4-vinylisoquinolin-5-yl)aminopiperidine-1-carbonxylic acid tert-butyl ester According to the method of Example 1, Step B, the 5-amino-1-chloro-4-vinylisoquinoline mentioned above was reacted and condensed with tert-butyl 4-oxo-1-piperidinecarboxylate instead of tert-butyl 3-oxo-1-pyrrolidinecarboxylate to obtain the title compound.

MS (m/z): 388 (MH+)

(Step F) 4-(6-Chloro-2,3-dihydro-1,5-diazaphenalen-1-yl)piperidine-1-carbonxylic acid tert-butyl ester According to the method of Example 11, Step C, the 4-(1-chloro-4-vinylisoquinolin-5-yl)aminopiperidine-1-carbonxylic acid tert-butyl ester mentioned above was cyclized to obtain the title compound.

MS (m/z): 388 (MH+)

(Step G) 6-Chloro-1-(piperidin-4-yl)-2,3-dihydro-1H-1,5-diazaphenalene

The 4-(6-chloro-2,3-dihydro-1,5-diazaphenalen-1-yl)piperidine-1-carbonxylic acid tert-butyl ester (12.1 g) mentioned above was added with 4 N hydrogen chloride/1,4-dioxane solution (155 ml), and stirred for 1.5 hours. The precipitated solid was taken by filtration to obtain the title compound as a hydrochloride.

¹H-NMR (DMSO-d₆) δ (ppm): 1.87 (2H, m), 2.08 (2H, m), 3.07–3.18 (4H, m), 3.30–3.41 (4H, m), 4.23 (1H, m), 7.19 (1H, d, J=8.3 Hz), 7.45 (1H, d, J=8.3 Hz), 7.59 (1H, t, J=8.3 Hz), 7.96 (1H, s) MS (m/z): 288 (MH+)

Example 62

Exemplary Compound No. 9-26

The 4-(6-chloro-2,3-dihydro-1,5-diazaphenalen-1-yl)piperidine-1-carbonxylic acid tert-butyl ester obtained Example 61, Step F was added with concentrated hydrochloric acid, and stirred at 90° C. for 17 hours. After the reaction, the solvent was concentrated under reduced pressure to obtain the title compound as a hydrochloride.

¹H-NMR (DMSO-d₆) δ (ppm): 1.81 (2H, m), 2.03 (2H, m), 2.77 (2H, m), 3.00–3.25 (4H, m), 3.36 (2H, d, J=12 Hz), 4.15 (1H, m), 6.82 (1H, s), 7.13 (1H, d, J=7.8 Hz), 7.29 (1H, t, J=7.8 Hz), 7.47 (1H, d, J=7.8 Hz) MS (m/z): 270 (MH+)

Example 63

Exemplary Compound No. 9-34

According to the method of Example 2, Step A, alkylation was performed by using the hydrochloride obtained in Example 61, and then the reaction mixture was added with concentrated hydrochloric acid, and stirred at 90° C. for 17 hours. After the reaction, the solvent was concentrated under reduced pressure to obtain the title compound as a hydrochloride.

MS (m/z): 314 (MH+)

Example 64

Exemplary Compound No. 9-35

According to the method of Example 2, Step A, alkylation with 2-(3-bromopropoxy)tetrahydro-2H-pyran was performed by using the hydrochloride obtained in Example 61, and then the reaction mixture was added with concentrated hydrochloric acid, and stirred at 90° C. for 17 hours. After the reaction, the solvent was concentrated under reduced pressure to obtain the title compound as a hydrochloride.

MS (m/z): 328 (MH+)

Example 65

Exemplary Compound No. 9-40

According to the method of Example 2, Step A, alkylation with tert-butyl N-(2-bromoethyl)carbamate was performed by using the hydrochloride obtained in Example 61, and then the reaction mixture was added with concentrated hydrochloric acid, and stirred at 90° C. for 17 hours. After the reaction, the solvent was concentrated under reduced pressure to obtain the title compound as a hydrochloride.

MS (m/z): 313 (MH+)

Example 66

Exemplary Compound No. 9-41

According to the method of Example 2, Step A, alkylation with tert-butyl N-(3-bromopropyl)carbamate was performed by using the hydrochloride obtained in Example 61, and then the reaction mixture was added with concentrated hydrochloric acid, and stirred at 90° C. for 17 hours. After the reaction, the solvent was concentrated under reduced pressure to obtain the title compound as a hydrochloride.

MS (m/z): 327 (MH+)

Example 67

Exemplary Compound No. 9-61

According to the method of Example 42, condensation with acetic acid was performed by using the hydrochloride obtained in Example 65 to obtain the title compound.

MS (m/z): 355 (MH+)

Example 68

Exemplary Compound No. 9-62

According to the method of Example 42, condensation with propionic acid was performed by using the hydrochloride obtained in Example 65 to obtain the title compound.
MS (m/z): 369 (MH+)

Example 69

Exemplary Compound No. 9-63

According to the method of Example 42, condensation with butyric acid was performed by using the hydrochloride obtained in Example 65 to obtain the title compound.
MS (m/z): 383 (MH+)

Example 70

Exemplary Compound No. 9-64

According to the method of Example 42, condensation with isobutyric acid was performed by using the hydrochloride obtained in Example 65 to obtain the title compound.
MS (m/z): 383 (MH+)

Example 71

Exemplary Compound No. 9-65

According to the method of Example 42, condensation with pivalic acid was performed by using the hydrochloride obtained in Example 65 to obtain the title compound.
MS (m/z): 397 (MH+)

Example 72

Exemplary Compound No. 9-66

According to the method of Example 42, condensation with acetic acid was performed by using the hydrochloride obtained in Example 66 to obtain the title compound.
MS (m/z): 369 (MH+)

Example 73

Exemplary Compound No. 9-67

According to the method of Example 42, condensation with propionic acid was performed by using the hydrochloride obtained in Example 66 to obtain the title compound.
MS (m/z): 383 (MH+)

Example 74

Exemplary Compound No. 9-68

According to the method of Example 42, condensation with butyric acid was performed by using the hydrochloride obtained in Example 66 to obtain the title compound.
MS (m/z): 397 (MH+)

Example 75

Exemplary Compound No. 9-69

According to the method of Example 42, condensation with isobutyric acid was performed by using the hydrochloride obtained in Example 66 to obtain the title compound.
MS (m/z): 397 (MH+)

Example 76

Exemplary Compound No. 9-70

According to the method of Example 42, condensation with pivalic acid was performed by using the hydrochloride obtained in Example 66 to obtain the title compound.
MS (m/z): 411 (MH+)

Example 77

Exemplary Compound No. 2-53

(Step A) tert-Butyl trans-N-benzyl-[4-(1-chloro-4-vinylisoquinolin-5-yl)aminocyclohexyl]carbamate A solution of 5-amino-1-chloro-4-vinylisoquinoline (0.6 g) and Intermediate 9 (1.8 g) in dichloromethane (13 ml) was added with titanium tetraisopropoxide (1.7 ml) at room temperature, and stirred at room temperature for 22 hours. The reaction mixture was added with methanol (13 ml), and sodium borohydride (444 mg), and stirred at room temperature for two hours. The reaction mixture was added with saturated aqueous sodium hydrogencarbonate (60 ml), and ethyl acetate (60 ml), and the precipitates were removed by filtration. Then, the organic layer was separated, and the solvent was evaporated under reduced pressure. The residue was purified by silica gel column chromatography (n-hexane:acetone=5:4) to obtain the title compound (890 mg).
MS (m/z): 492 (MH+)

(Step B) tert-Butyl trans-N-benzyl-[4-(6-chloro-2,3-dihydro-1,5-diazaphenalen-1-yl)cyclohexyl]carbamate According to the method of Example 21, Step C, the tert-butyl trans-N-benzyl-[4-(1-chloro-4-vinylisoquinolin-5-yl)aminocyclohexyl]carbamate obtained in Step A mentioned above was used for the cyclization instead of the trans-isomer of Intermediate 10 to obtain the title compound.
MS (m/z): 492 (MH+)

(Step C) Trans-1-(4-benzylaminocyclohexyl)-2,3-dihydro-1H-1,5-diazaphenalen-6-ol Concentrated hydrochloric acid was added with tert-butyl trans-N-benzyl-[4-(6-chloro-2,3-dihydro-1,5-diazaphenalen-1-yl)cyclohexyl]carbamate, and stirred at 90° C. for 17 hours. After the reaction, the solvent was concentrated under reduced pressure to obtain the title compound as a hydrochloride.
MS (m/z): 374 (MH+)

(Step D) (Exemplary Compound No. 2-53)
According to the method of Example 21, Step E, the trans-1-(4-benzylaminocyclohexyl)-2,3-dihydro-1H-1,5-diazaphenalen-6-ol obtained in Step C mentioned above was subjected to the debenzylation reaction instead of Intermediate 12 to obtain the title compound.

$^1$H-NMR (DMSO-$d_6$) δ (ppm): 1.60–1.80 (6H, m), 1.81 (2H, m), 2.74 (2H, m), 3.02 (1H, m), 3.18 (2H, m), 3.71 (1H, m), 6.79 (1H, s), 6.98 (1H, d, J=8.1 Hz), 7.28 (1H, t, J=8.1 Hz), 7.43 (1H, d, J=8.1 Hz) MS (m/z): 284 (MH+)

Example 78

Exemplary Compound No. 2-62

According to the method of Example 63, alkylation and deprotection were performed by using the compound obtained in Example 77 to obtain the title compound as a hydrochloride.

MS (m/z): 328 (MH+)

Example 79

Exemplary Compound No. 2-63

According to the method of Example 64, alkylation and deprotection were performed by using the compound obtained in Example 77 to obtain the title compound as a hydrochloride.

MS (m/z): 342 (MH+)

Example 80

Exemplary Compound No. 2-68

According to the method of Example 65, alkylation and deprotection were performed by using the compound obtained in Example 77 to obtain the title compound as a hydrochloride.

MS (m/z): 327 (MH+)

Example 81

Exemplary Compound No. 2-69

According to the method of Example 66, alkylation and deprotection were performed by using the compound obtained in Example 77 to obtain the title compound as a hydrochloride.

MS (m/z): 341 (MH+)

Example 82

Exemplary Compound No. 2-113

According to the method of Example 42, condensation with acetic acid was performed by using the hydrochloride obtained in Example 80 to obtain the title compound as a hydrochloride.

MS (m/z): 369 (MH+)

Example 83

Exemplary Compound No. 2-114

According to the method of Example 42, condensation with propionic acid was performed by using the compound obtained in Example 80 to obtain the title compound as a hydrochloride.

MS (m/z): 383 (MH+)

Example 84

Exemplary Compound No. 2-115

According to the method of Example 42, condensation with butyric acid was performed by using the compound obtained in Example 80 to obtain the title compound as a hydrochloride.

MS (m/z): 397 (MH+)

Example 85

Exemplary Compound No. 2-116

According to the method of Example 42, condensation with isobutyric acid was performed by using the compound obtained in Example 80 to obtain the title compound as a hydrochloride.

MS (m/z): 397 (MH+)

Example 86

Exemplary Compound No. 2-117

According to the method of Example 42, condensation with pivalic acid was performed by using the compound obtained in Example 80 to obtain the title compound as a hydrochloride.

MS (m/z): 411 (MH+)

Example 87

Exemplary Compound No. 2-118

According to the method of Example 42, condensation with acetic acid was performed by using the hydrochloride obtained in Example 81 to obtain the title compound as a hydrochloride.

MS (m/z): 383 (MH+)

Example 88

Exemplary Compound No. 2-119

According to the method of Example 42, condensation with propionic acid was performed by using the compound obtained in Example 81 to obtain the title compound as a hydrochloride.

MS (m/z): 397 (MH+)

Example 89

Exemplary Compound No. 2-120

According to the method of Example 42, condensation with butyric acid was performed by using the compound obtained in Example 81 to obtain the title compound as a hydrochloride.

MS (m/z): 411 (MH+)

Example 90

Exemplary Compound No. 2-121

According to the method of Example 42, condensation with isobutyric acid was performed by using the compound obtained in Example 81 to obtain the title compound as a hydrochloride.

MS (m/z): 411 (MH+)

Example 91

Exemplary Compound No. 2-122

According to the method of Example 42, condensation with pivalic acid was performed by using the compound obtained in Example 81 to obtain the title compound as a hydrochloride.

MS (m/z): 425 (MH+)

Test Example 1

Action on Amount of Phosphorylated Myosin Regulatory Light Chain in the Cells

A volume of 50 to 100 ml of peripheral blood collected from healthy volunteers was centrifuged by using Mono-Poly separator solution (Dainippon Pharmaceutical) to prepare a neutrophil containing fraction. The neutrophils were washed with PBS(−) and resuspended in Hanks' Balanced Salt Solution (HBSS+, Gibco) to prepare a cell suspension ($8 \times 10^6$/ml). The cell suspension was diluted to $5 \times 10^6$/ml, introduced into Eppendorf tubes in a volume of 0.4 ml each, then 0.1 ml each of solutions of a test compound at various concentrations were added to the suspension and allowed to react at 25° C. for 5 minutes. After the reaction, 0.1 ml of trichloroacetic acid solution was added to each reaction, the reaction mixture was gently shaken and centrifuged at 12,000 rpm (4° C., 5 minutes), and the supernatant was removed. Subsequently, 3 µl of 1 M Tris solution was added to the residue, the mixture was further mixed with 50 µl of extraction buffer (8 M urea, 0.02% 2-mercaptoethanol, 0.002% bromophenol blue) and left stand at room temperature for 1 hour. Then, the reaction mixture was loaded on a spin column (0.45 µm, Millipore) to remove the insoluble solids and a sample buffer for SDS polyacrylamide gel electrophoresis (25 mM, Tris-HCl pH 6.8, 2.5% 2-mercaptoethanol, 2% sodium dodecylsulfate, 5% sucrose, 0.002% bromophenol blue as final concentrations) was added, and 10 µl of each sample was subjected to electrophoresis.

The gel after the electrophoresis was blotted on a nitrocellulose membrane (BioRad), blocked with 5% skim milk, and reacted successively with antibodies pLC1 (Sakurada K. et al, Am. J. Physiol., 274, C1563–C1572 (1998)), which specifically recognize the phosphorylated myosin regulatory light chain, and donkey anti-mouse IgG (Chemicon) conjugated with horseradish peroxidase. The band of the phosphorylated myosin regulatory light chain was detected on a film by using ECL Plus Kit (Amersham Pharmacia Biotech). This band was subjected to quantification using a densitometer. By using this value, the inhibitory ratio (%) for phosphorylation of the myosin regulatory light chain was calculated by using the following equation.

Phosphorylation inhibition ratio (%)=1−(Band intensity of phosphorylated myosin regulatory light chain with addition of the test compound/Band intensity of phosphorylated myosin regulatory light chain without addition of the test compound)×100

Further, the phosphorylation inhibition ratio was calculated with changing the concentrations of the test compound, and a compound concentration providing an inhibition ratio of 50% was obtained as $IC_{50}$.

The compounds of the present invention obtained in Examples 1, 11, 12, 13, 14, 15, 16, 17, 18, 19, 20, 21, 22, 24, 31, 41 42, 47, 52, 53, 54, 55, 56, 57, 58, 59, 60, 61, 62, 63, 64, 65, 66, 67, 68, 69, 70, 72, 73, 74, 75, 76, 77, 78, 79, 80, 81, 82, 83, 84, 85, 86, 87, 88, 89, 90, and 91 inhibited the phosphorylation of myosin regulatory light chain at a concentration of 40 µM or less, and further, the compounds of Examples 11, 12, 13, 14, 15, 21, 22, 24, 31, and 41 inhibited the phosphorylation of myosin regulatory light chain at a concentration of 10 µM or less. Further, trans-benzyl-[4-(2,3-dihydro-1,5-diazaphenalen-1-yl)cyclohexyl]amine inhibited the phosphorylation of myosin regulatory light chain at a concentration of 40 µM or less.

Test Example 2

Vasoconstriction Inhibitory Action

Rats (Wistar, 11-week old) were bleeded to death and laparotomized to take out the thoracic aorta. That aorta was cut into a ring of a length of about 3 mm in a conventional manner (Asano, T., et al., J. Pharmacol. Exp. Ther., 241, pp. 1033–1040 (1987)) and hung in 10-ml organ bath filled with Krebs-Hensright nutrient solution bubbled with a mixed gas of 95% $O_2$ and 5% $CO_2$. One end of the blood vessel was connected to an isometric transducer (FD Pickup TB-912T, Nihon Kohden) and applied with 2.5 g of resting tension, and constriction and relaxation reactions of the aorta were recorded.

The aorta was constricted with phenylephrine (1 µM, Sigma) and then added with a test compound (1 µM), and the vasoconstriction inhibitory action thereof was observed. The vasoconstriction inhibitory actions of the test compounds were calculated as relaxation ratios, which were based on the vasoconstriction with phenylephrine observed immediately before the addition of the test compounds taken as 100%.

The compounds of the present invention obtained in Examples 16, 17, 19, 20, 24, and 41 exhibited significant vasoconstriction inhibitory action.

Thus, it was confirmed that the compounds of the present invention were useful as medicaments for prophylactic and/or therapeutic treatment of diseases relating to cell contraction.

Test Example 3

Respiratory Tract Constriction Suppressing Action

Four-week old Hartley guinea pigs (male) were immunized by intraperitoneal administration of ovalbumin (Sigma, Grade V) in amounts of 1 mg for each animal on the day on which the experiment was started, 3 mg for each animal after 2 days, and 10 mg for each animal after 4 days.

Twelve to fourteen days after the final immunization, the ovalbumin-immunized guinea pigs were anesthetized by intraperitoneal administration of about 40 mg/kg of pentobarbital (Somnopentyl), and the tracheas were taken out.

Subsequently, a cannula (SP-110, Natsume) was inserted into each trachea, and one end of the cannula was connected to an artificial respirator (Model-b83, Harvard). The aeration conditions were set at 6 ml per kilogram and 60 times per 1 minute. Further, a cannula for medicament administration (JMS wing needle 23G 3/4) was inserted into a hind leg vein. Myoblock (Organon Technica) was administered in an amount of 0.5 mg/kg from the cannula inserted into the hind leg vein to stop the spontaneous breathing, and after 2 or 3 minutes, 0.3 mg/kg of ovalbumin was administered to induce constriction of respiratory tract. The increase of airway resistance value 2 minutes after the induction (measurement apparatuses: pressure transducer TR-603T, respiratory amplifier AR-601G, and recorder RTA-3100, Nihon Kohden Corp.) was confirmed to be above 80 cm $H_2O$ or higher, and then, a solution of a test medicament was administered from the cannula inserted into the hind leg vein, and the airway resistance value was continuously measured for 15 minutes after the administration to determine the effect. As a result, the compounds of the present invention obtained in Examples 11, 14, 15, 17, 20, and 24 significantly improved the constriction of respiratory tract.

Further, the respiratory tract constriction suppression action of the test compounds was also evaluated by inhalation. Twelve to fourteen days after the final sensitization, 10 mg/kg of pyrilamine (Sigma), 5 mg/kg of indomethacin (Wako), or 0.1 mg/kg of propranolol (Sigma) was intraperitoneally administered. Then, 30 minutes after the administration, a 0.1% ovalbumin aqueous solution was inhaled by using a pressurization type nebulizer (PARI-IS2) to induce constriction of the respiratory tract. Ten minutes after the induction, 2 ml of a solution of a test compound prepared at various concentrations was filled in the aforementioned nebulizer, and administered by inhalation over 5 minutes. After the administration of pyrilamine and other drugs, airway resistance value was continuously measured to determine effectiveness. As a result, the compounds of the present invention obtained in Examples 11, 14, 15, 17, 20, and 24 significantly improved the constriction of respiratory tract.

Therefore, it was confirmed that the compounds of the present invention were useful as medicaments for prophylactic and/or therapeutic treatment of bronchial asthma and/or chronic obstructive pulmonary disease (COPD).

Test Example 4

Intraocular Pressure Reducing Action

A Japanese white rabbit having a body weight of about 2 kg was placed in a positioner and naturalized for one week before the experiment. An ophthalmologic local anesthesant (Benoxil) was administered to the left eye, and then intraocular pressure was measured by using a tonometer (Classic 30, Solan). The initial value of the intraocular pressure was measured, then 50 μl of an aqueous solution of a test compound was dropped to the left eye at various concentrations, and the intraocular pressure was measured with passage of time. As a result, the compounds of the present invention obtained in Examples 1, 11, 12, 13, 14, 15, 16, 18, 19, 20, 21, 22, 31, 41, 42, 47, 52, 53, 54, 55, 56, 57, 58, 59, 60, 62, 63, 64, 67, 68, 69, 72, 73, 76, 77, 78, 79, 82, 83, 84, 87, 88, and 91 exhibited significant intraocular pressure reducing action.

Thus, it was confirmed that the compounds of the present invention were useful as medicaments for prophylactic and/or therapeutic treatment of glaucoma.

Test Example 5

Neurite Outgrowth Action

From 18 day-old Sprague-Dawley rats, cerebral hippocampal neurons were prepared according to the method of Neuman et al. (Neuman, H. R. et al., J. Neurosci., 22, pp. 854–862, 2002). The prepared neurons were cultured for 24 hours according to the method of Tanaka et al. (Tanaka, H. et al., J. Cell Biol., 158 (2), pp. 321–329, 2002), then the medium was exchanged with fresh medium, and test medicaments of various concentrations or equivalent amounts of vehicle were added. Twenty-four hours after the addition of the medicaments, neurite length of each neuron was measured for the medicament-added group and the no-addition group, and compared. The neurite length was evaluated according to the method of Neuman et al. (Neuman, H. R. et al., J. Neurosci., 22, pp. 854–862, 2002).

As a result, the compounds of the present invention obtained in Examples 16, 17, 19, 20, 24, and 41 induced significant neurite outgrowth axis extension.

Thus, it was confirmed that the compounds of the present invention were useful as medicaments for prophylactic and/or therapeutic treatment of spinal cord injury.

Test Example 6

Neutrophil Migration Inhibitory Action

Neutrophils were isolated from 50 to 100 ml of peripheral blood collected from healthy human donors by the method described in Test Example 1 to obtain a cell suspension ($8 \times 10^6$/ml). Subsequently, solutions of a test compound of various concentrations were introduced into wells of a 96-well plate in a volume of 125 μl per well, the cell suspension of an equivalent volume was added to it and the plate was preincubated at room temperature for 5 minutes. During the preincubation, FMLP (1 μM, Sigma) solution was added to the lower chamber to set Boyden Chamber, the preincubated cell suspension was added to the upper chamber in a volume of 200 μl per well, and the cells were allowed to migrate at 37° C. under 5% carbon dioxide for 30 minutes. The filter after the migration was collected, and the non-migrated cells adhered to the surface that faced the upper chamber were carefully wiped off. Then, the migrated cells on the back surface were stained with DifQuick dye solution (International Reagents), washed with water and dried, and then absorbance was measured at 595 nm. The inhibition ratio against migration (%) of a test compound was calculated by using the following equation:

Migration inhibition ratio (%)=(1−Absorbance of the group with addition of test compound/Absorbance of the group without addition of test compound)×100

Further, the migration inhibitory ratio was calculated with changing the test compound concentration, and a compound concentration providing an inhibition ratio of 50% was obtained as $IC_{50}$. The compounds of the present invention obtained in Examples 1, 11, 12, 13, 14, 15, 16, 18, 19, 20, 21, 22, 24, 31, 41, 42, 47, 52, 53, 54, 55, 56, 57, 58, 59, 60, 62, 63, 64, 65, 66, 67, 68, 72, 73, 74, 75, 76, 77, 78, 79, 80, 81, 82, 83, 84, 87, 88, 89, 90, and 91 inhibited the migration of neutrophils at a concentration of 40 μM or less, and further, the compounds of Examples 1, 11, 12, 13, 14, 15, 19, 21, 22, 24, 31, and 41 inhibited the migration of neutrophils at a concentration of 10 μM or less. Further, trans-benzyl-

[4-(2,3-dihydro-1,5-diazaphenalen-1-yl)cyclohexyl]amine inhibited the migration of neutrophils at a concentration of 40 µM or less.

Thus, it was confirmed that the compounds of the present invention were useful for prophylactic and/or therapeutic treatment of diseases relating to cell migration.

Test Example 7

Respiratory Tract Inflammation Suppressing Action

According to Henderson, W. R., et al., Am. J. Respir. Cric. Care Med., 165(1), 108–116 (2002), suppressing action on bronchial inflammation was confirmed. BALB/c female mice (7-week old) were used for the test, each group consisting of 7 mice, and the control group consisting of 11 or 12 mice. The mice were intraperitoneally administered with ovalbumin (OVA, 100 ng, Sigma) and 1 mg of aluminum hydroxide for initial immunization, and after 2 weeks, they are subcutaneously administered with 10 ng of OVA as additional immunization. After further 1 week, a test compound was dissolved in water containing 0.5% carboxymethylcellulose and orally administered (30 mg/kg) to the test animals once a day for 5 days. The control group was similarly given only with water containing 0.5% carboxymethylcellulose. After 1 hour, the mice were orally inhaled with 2% OVA for 10 minutes to induce a respiratory tract inflammation. Further, the control group, in which the mice were not given with the test compound, was divided into a positive control group (n=7), in which the mice were inhaled with 2% OVA to induce the reaction, and a negative control group (n=4 or 5), in which the mice were similarly inhaled with physiological saline. After 24 hours, alveoli in the lungs of the test animals were washed with physiological saline, and the total infiltrated white blood cells (WBC) were counted.

As a result, the compounds of the present invention significantly improved the pathological conditions.

Thus, it was confirmed that the compounds of the present invention were useful as medicaments for prophylactic and/or therapeutic treatment of bronchial asthma.

Further, no abnormality was observed in the test animals (mice) in a 5 consecutive day administration test of these compounds, and thus they were safe compounds.

Test Example 8

Pulmonary Inflammation Suppressing Action

According to Gonzales de Moraes, V L., et al., Br. J. Pharmacol., 123, pp. 631–6, 1998, suppressing action on pulmonary inflammation was studied. BALB/c female mice (7-week old) were used for the test, as the compound administration group and positive control group, each consisting of 7 mice, as well as the negative control group consisting of 5 mice. For induction of inflammation, a 0.03% physiological saline solution of a lipopolysaccharide (LPS, a mixture derived from *Escherichia coli* O55 and B5 strains, Sigma) was used. A test compound was dissolved in physiological saline to prepare solutions of various concentrations. The test animals were first inhaled with the aforementioned lipopolysaccharide solution for 10 minutes by using a pressurization type nebulizer (PARI-IS2) to induce inflammation. Then, 1 minute after the completion of the inhalation of the lipopolysaccharide solution, the animals were administered with a solution of test compound at various concentrations over 10 minutes by inhalation using the aforementioned nebulizer. The mice of the positive control group were administered with the same volume of physiological saline instead of the test compound solution over 10 minutes by inhalation. Three hours after the administration of the test compound, pulmonary cavities of the test animals were washed with physiological saline, and the total infiltrated leucocyte (WBC) number was counted. As a result, the compounds of the present invention obtained in Examples 17, 19, 20, 24, and 41 significantly improved the pathological condition.

Thus, it was confirmed that the compounds of the present invention were useful as medicaments for prophylactic and/or therapeutic treatment of pneumonia.

Test Example 9

Action on Increase of Intracellular Calcium Concentration

According to the method described in Test Example 1, a neutrophil containing fraction was prepared. Fura2-AM (Sigma) at a final concentration of 3 µM was added to the human neutrophil fraction and the mixture was incubated at 37° C. for 1 hour. After centrifugation (250 g for 5 minutes), the supernatant was discarded, and the neutrophils were resuspended in Hanks' Balanced Salt Solution (HBSS, Gibco) to prepare a cell suspension ($8 \times 10^6$/ml) for measurement of intracellular calcium concentration. The cell suspension for measurement of intracellular calcium concentration was left stand at room temperature for 30 minutes. Then, 490 µl of the cell suspension for measurement of intracellular calcium concentration was placed in a cuvette, 10 µl of calcium chloride solution at a final concentration of 1 µM was added to it and the cuvette was set in an intracellular calcium concentration analyzer (CAF110, Nippon Bunko). FMLP (Sigma) solution at a final concentration of 1 µM was added to the cell suspension, and F340 and F380, which are fluorescence intensity at 340 nm and 380 nm, respectively, were measured to obtain an R value (F340/F380) as an index of the intracellular calcium concentration. A test compound (1 µM) was added 3 minutes before the addition of fMLP, and the action on the intracellular calcium concentration was observed. The ratios of the maximum R value obtained with addition of each test compound relative to the maximum R value obtained without addition of test compound and taken as 100% were obtained.

It was revealed that the compounds of the present invention had almost no effect on the increase of the intracellular calcium concentration caused by the fMLP stimulation.

Test Example 10

Action on Myosin Light Chain Kinase (MLCK) Activity

A myosin light chain kinase (MLCK) was purified from chicken gizzard smooth muscle by a conventional method (Yoshida, M., et al., J. Biochem., 99, 1027–1036 (1986)). The myosin regulatory light chain as a substrate was purified from the chicken gizzard smooth muscle by a conventional method (Grand, R. J., et al., Biochem. J., 211, 267–272 (1983)). The MLCK activity was measured by ELISA (Sakurada, K., et al., J. Biochem., 115, 18–21 (1994)) using anti-phosphorylated myosin regulatory light chain-recognizing antibodies (Sakurada, K., et al., Am. J. Physiol., 274, C1563–C1572, 1998). The myosin regulatory light chain was diluted in phosphate-buffered saline (PBS, Sigma) to a concentration of 5.0 g/ml, added to 96-well Immunoplate (Nunc) in a volume of 100 µl per well and left stand overnight at 4° C. Each well was washed with PBS, and 25 mM Tris/HCl buffer containing 100 µM ATP, 3 mM MgCl$_2$, 1 mM CaCl$_2$, 100 ng/ml of calmodulin (Sigma) and 100 ng/ml of MLCK (pH 7.4, Buffer A) was added to each well and incubated at 30° C. for 10 minutes. In a volume of 100 µl each of 20% aqueous phosphoric acid solution was added to each well to terminate the enzymatic reaction. Each well was washed with 25 mM Tris/HCl buffer (TTBS) containing 0.1% Tween 20, and then 100 µl of antibodies specifically recognizing phosphorylated myosin regulatory light chain (Sakurada, K., et al., Am. J. Physiol., 274, C1563–C1572, 1998) was added to each well and incubated at room temperature for 90 minutes.

Each well was washed with TTBS, and then 100 µl of the HRP-labeled anti-mouse IgG antibodies (Bio-Rad) were added to each well and incubated at room temperature for 90 minutes. Each well was washed with TTBS, and then 25 mM citrate buffer (pH 5.0) containing orthophenylenediamine (Sigma) as a substrate of HRP and aqueous hydrogen peroxide (0.03%) was added in a volume of 100 µl per well and incubated at room temperature for 5 minutes. 50 µl of 4 N sulfuric acid was added to each well to terminate the reaction, and then absorbance was measured by using an immunoplate reader (Bio-Rad). The MLCK activity inhibition ratio was calculated by adding the test compound to Buffer A at various concentrations to obtain a compound concentration providing an inhibition ratio of 50% as IC$_{50}$.

It was revealed that the compounds of the present invention had almost no inhibitory effect on MLCK.

INDUSTRIAL APPLICABILITY

The compounds of the present invention represented by the formula (1) have an inhibitory action on phosphorylation of myosin regulatory light chain, and are useful as active ingredients of medicaments for prophylactic and/or therapeutic treatment of, for example, diseases relating to contraction of various cells, diseases relating to morphological change of various cells, diseases relating to migration of various cells, diseases relating to release of various cells, diseases relating to aggregation of various cells, diseases relating to apoptosis of various cells, and diseases relating to abnormality of gene expression in various cells.

The invention claimed is:

1. A compound represented by the following formula (1) or a salt thereof:

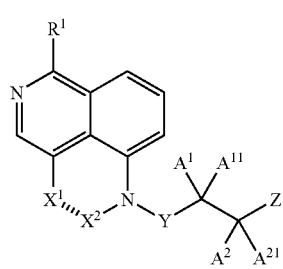

(1)

wherein
R$^1$ represents hydrogen atom, chlorine atom, or hydroxyl group;
X$^1$ . . . X$^2$ represents —CH(R$^2$)—CH(R$^3$)—;
R$^2$, R$^3$, and R$^4$ independently represent hydrogen atom, or an alkyl group;
A$^1$, A$^{11}$, A$^2$, and A$^{21}$ independently represent hydrogen atom, or an alkyl group;
Y represents —CH(A$^3$)—, —CH(A$^3$)—C(A$^4$)(A$^{41}$)—, —CH(A$^3$)—C(A$^4$)(A$^{41}$)—C—(A$^5$)(A$^{51}$)—, or a single bond;
A$^3$, A$^4$, A$^{41}$, A$^5$, and A$^{51}$ independently represent hydrogen atom, or an alkyl group;
Z represents hydroxyl group, or —N(A$^6$)(A$^{61}$);
A$^6$ represents hydrogen atom, or an alkyl group,
A$^{61}$ represents hydrogen atom, an alkyl group, an aralkyl group, an alkyl group substituted with carboxyl group, an alkyl group substituted with cyano group, an alkyl group substituted with hydroxyl group, an alkyl group substituted with an alkoxyl group, an alkyl group substituted with an amino group, an alkyl group substituted with aminocarbonyl group, or an alkyl group of which end is substituted with N(A$^7$)(—X$^3$—A$^{71}$), where —X$^3$— represents carbonyl group,
A$^7$ represents hydrogen atom, or an alkyl group, and
A$^{71}$ represents an alkyl group, an aralkyl group, or an aryl group, or
A$^7$ and A$^{71}$ may together become an alkylene group, or an alkylene group substituted with an alkyl group to form a ring; and
groups in each of one or more combinations selected from the group consisting of combinations of A$^6$ and A$^3$, A$^6$ and A$^4$, A$^6$ and A$^1$, A$^6$ and A$^2$, A$^2$ and A$^3$, A$^2$ and A$^4$, A$^6$ and A$^5$, A$^3$ and A$^1$, and A$^5$ and A$^1$ may bind to each other to form a 5- or 6-membered ring.

2. The compound represented by the formula (1) or salt thereof according to claim 1, wherein A$^{61}$ is hydrogen atom, an alkyl group, an aralkyl group, an alkyl group substituted with carboxyl group, an alkyl group substituted with cyano group, an alkyl group substituted with hydroxyl group, an alkyl group substituted with an alkoxyl group, an alkyl group substituted with an amino group, or an alkyl group substituted with aminocarbonyl group.

3. The compound represented by the formula (1) or salt thereof according to claim 1, wherein X$^1$ . . . X$^2$ is —CH(R$^2$)—CH(R$^3$)—.

4. The compound represented by the formula (1) or salt thereof according to claim 1, wherein R$^1$ is hydrogen atom.

5. The compound represented by the formula (1) or salt thereof according to claim 1, wherein R$^1$ is hydroxyl group.

6. The compound represented by the formula (1) or salt thereof according to claim 1, wherein Y is a single bond, Z is —N(A$^6$)(A$^{61}$), and the groups of A$^6$ and A$^1$ bind to each other to form a 5- or 6-membered ring.

7. The compound represented by the formula (1) or salt thereof according to claim 1, wherein Y is —CH(A$^3$)—, Z is —N(A$^6$)(A$^{61}$), and the groups of A$^6$ and A$^3$ bind to each other to form a 6-membered ring.

8. The compound represented by the formula (1) or salt thereof according to claim 1, wherein Y is —CH(A$^3$)—C(A$^4$)(A$^{41}$)—, Z is —N(A$^6$)(A$^{61}$), and the groups of A$^2$ and A$^3$ bind to each other to form a 6-membered ring.

9. The compound according to claim 1, which is selected from the group consisting of the followings:
(1) 4-(2,3-dihydro-1,5-diazaphenalen-1-yl)cyclohexylamine;

(2) N-[4-(2,3-dihydro-1,5-diazaphenalen-1-yl)cyclohexyl]-N-methylamine;
(3) [4-(2,3-dihydro-1,5-diazaphenalen-1-yl)cyclohexylamino]acetic acid;
(4) 3-[4-(2,3-dihydro-1,5-diazaphenalen-1-yl)cyclohexylamino]propionic acid;
(5) 2-[4-(2,3-dihydro-1,5-diazaphenalen-1-yl)cyclohexylamino]ethanol;
(6) 3-[4-(2,3-dihydro-1,5-diazaphenalen-1-yl)cyclohexylamino]propanol;
(7) N-[4-(2,3-dihydro-1,5-diazaphenalen-1-yl)cyclohexyl]ethylenediamine;
(8) N-[4-(2,3-dihydro-1,5-diazaphenalen-1-yl)cyclohexyl]propane-1,3-diamine;
(9) N-[4-(2,3-dihydro-1,5-diazaphenalen-1-yl)cyclohexyl]-N'-methylpropane-1,3-diamine;
(10) N-[4-(2,3-dihydro-1,5-diazaphenalen-1-yl)cyclohexyl]-N-methylethylenediamine;
(11) N'-[4-(2,3-dihydro-1,5-diazaphenalen-1-yl)cyclohexyl]-N,N-dimethylethylenediamine;
(12) 2-{[4-(2,3-dihydro-1,5-diazaphenalen-1-yl)cyclohexyl]methylamino}ethanol;
(13) 1-(4-aminocyclohexyl)-2,3-dihydro-1H-1,5-diazaphenalen-6-ol;
(14) 1-(4-methylaminocyclohexyl)-2,3-dihydro-1H-1,5-diazaphenalen-6-ol;
(15) [4-(6-hydroxy-2,3-dihydro-1,5-diazaphenalen-1-yl)cyclohexylamino]acetic acid;
(16) 3-[4-(6-hydroxy-2,3-dihydro-1,5-diazaphenalen-1-yl)cyclohexylamino]propionic acid;
(17) 1-[4-(2-hydroxyethylamino)cyclohexyl]-2,3-dihydro-1H-1,5-diazaphenalen-6-ol;
(18) 1-[4-(3-hydroxypropylamino)cyclohexyl]-2,3-dihydro-1H-1,5-diazaphenalen-6-ol;
(19) 1-[4-(2-aminoethylamino)cyclohexyl]-2,3-dihydro-1H-1,5-diazaphenalen-6-ol;
(20) 1-[4-(3-aminopropylamino)cyclohexyl]-2,3-dihydro-1H-1,5-diazaphenalen-6-ol;
(21) 1-[4-(2-(methylamino)ethylamino)cyclohexyl]-2,3-dihydro-1H-1,5-diazaphenalen-6-ol;
(22) 1-[4-(3-(methylamino)propylamino)cyclohexyl]-2,3-dihydro-1H-1,5-diazaphenalen-6-ol
(23) 1-{4-[(2-hydroxyethyl)methylamino]cyclohexyl}-2,3-dihydro-1H-1,5-diazaphenalen-6-ol;
(24) 1-{4-[(3-hydroxypropyl)methylamino]cyclohexyl}-2,3-dihydro-1H-1,5-diazaphenalen-6-ol;
(25) 1-(3-pyrrolidinyl)-2,3-dihydro-1H-1,5-diazaphenalene;
(26) [3-(2,3-dihydro-1,5-diazaphenalen-1-yl)pyrrolidin-1-yl]acetic acid;
(27) 3-[3-(2,3-dihydro-1,5-diazaphenalen-1-yl)pyrrolidin-1-yl]propionic acid;
(28) 2-[3-(2,3-dihydro-1,5-diazaphenalen-1-yl)pyrrolidin-1-yl]ethanol;
(29) 3-[3-(2,3-dihydro-1,5-diazaphenalen-1-yl)pyrrolidin-1-yl]propanol;
(30) 2-[3-(2,3-dihydro-1,5-diazaphenalen-1-yl)pyrrolidin-1-yl]ethylamine;
(31) 3-[3-(2,3-dihydro-1,5-diazaphenalen-1-yl)pyrrolidin-1-yl]propane-1,3-diamine;
(32) N-{2-[3-(2,3-dihydro-1,5-diazaphenalen-1-yl)pyrrolidin-1-yl]ethyl}-N-methylamine;
(33) N-{3-[3-(2,3-dihydro-1,5-diazaphenalen-1-yl)pyrrolidin-1-yl]propyl}-N methylamine;
(34) 1-(3-pyrrolidinyl)-2,3-dihydro-1H-1,5-diazaphenalen-6-ol;
(35) [3-(6-hydroxy-2,3-dihydro-1,5-diazaphenalen-1-yl)pyrrolidin-1-yl]acetic acid;
(36) 3-[3-(6-hydroxy-2,3-dihydro-1,5-diazaphenalen-1-yl)pyrrolidin-1-yl]propionic acid;
(37) 1-[1-(2-hydroxyethyl)pyrrolidin-3-yl]-2,3-dihydro-1H-1,5-diazaphenalen-6-ol;
(38) 1-[1-(3-hydroxypropyl)pyrrolidin-3-yl]-2,3-dihydro-1H-1,5-diazaphenalen-6-ol;
(39) 1-[1-(2-aminoethyl)pyrrolidin-3-yl]-2,3-dihydro-1H-1,5-diazaphenalen-6-ol;
(40) 1-[1-(3-aminopropyl)pyrrolidin-3-yl]-2,3-dihydro-1H-1,5-diazaphenalen-6-ol;
(41) 1-[1-(2-methylaminoethyl)pyrrolidin-3-yl]-2,3-dihydro-1H-1,5-diazaphenalen-6-ol;
(42) 1-[1-(3-methylaminopropyl)pyrrolidin-3-yl]-2,3-dihydro-1H-1,5-diazaphenalen-6-ol;
(43) 1-[1-(2-dimethylaminoethyl)pyrrolidin-3-yl]-2,3-dihydro-1H-1,5-diazaphenalen-6-ol;
(44) 1-[1-(3-dimethylaminopropyl)pyrrolidin-3-yl]-2,3-dihydro-1H-1,5-diazaphenalen-6-ol;
(45) N-{2-[3-(2,3-dihydro-1,5-diazaphenalen-1-yl)pyrrolidin-1-yl]ethyl}acetamide;
(46) N-{2-[3-(2,3-dihydro-1,5-diazaphenalen-1-yl)pyrrolidin-1-yl]ethyl}propionamide;
(47) N-{3-[3-(2,3-dihydro-1,5-diazaphenalen-1-yl)pyrrolidin-1-yl]propyl}acetamide;
(48) N-{3-[3-(2,3-dihydro-1,5-diazaphenalen-1-yl)pyrrolidin-1-yl]propyl}propionamide;
(49) N-{2-[3-(6-hydroxy-2,3-dihydro-1,5-diazaphenalen-1-yl)pyrrolidin-1-yl]ethyl}acetamide;
(50) N-{2-[3-(6-hydroxy-2,3-dihydro-1,5-diazaphenalen-1-yl)pyrrolidin-1-yl]ethyl}propionamide;
(51) N-{3-[3-(6-hydroxy-2,3-dihydro-1,5-diazaphenalen-1-yl)pyrrolidin-1-yl]propyl}acetamide;
(52) N-{3-[3-(6-hydroxy-2,3-dihydro-1,5-diazaphenalen-1-yl)pyrrolidin-1-yl]propyl}propionamide;
(53) 1-(4-piperidinyl)-2,3-dihydro-1H-1,5-diazaphenalene;
(54) [4-(2,3-dihydro-1,5-diazaphenalen-1-yl)piperidin-1-yl]acetic acid;
(55) 3-[4-(2,3-dihydro-1,5-diazaphenalen-1-yl)piperidin-1-yl]propionic acid;
(56) 2-[4-(2,3-dihydro-1,5-diazaphenalen-1-yl)piperidin-1-yl]ethanol;
(57) 3-[4-(2,3-dihydro-1,5-diazaphenalen-1-yl)piperidin-1-yl]propanol;
(58) 2-[4-(2,3-dihydro-1,5-diazaphenalen-1-yl)piperidin-1-yl]ethylamine;
(59) 3-[4-(2,3-dihydro-1,5-diazaphenalen-1-yl)piperidin-1-yl]propylamine;
(60) N-{2-[4-(2,3-dihydro-1,5-diazaphenalen-1-yl)piperidin-1-yl]ethyl}-N-methylamine;
(61) N-{3-[4-(2,3-dihydro-1,5-diazaphenalen-1-yl)piperidin-1-yl]propyl}-N-methylamine;
(62) 1-piperidin-4-yl-2,3-dihydro-1H-1,5-diazaphenalen-6-ol;
(63) [4-(6-hydroxy-2,3-dihydro-1,5-diazaphenalen-1-yl)piperidin-1-yl]acetic acid;
(64) 3-[4-(6-hydroxy-2,3-dihydro-1,5-diazaphenalen-1-yl)piperidin-1-yl]propionic acid;
(65) 1-[1-(2-hydroxyethyl)piperidin-4-yl]-2,3-dihydro-1H-1,5-diazaphenalen-6-ol;
(66) 1-[1-(3-hydroxypropyl)piperidin-4-yl]-2,3-dihydro-1H-1,5-diazaphenalen-6-ol;
(67) 1-[1-(2-aminoethyl)piperidin-4-yl]-2,3-dihydro-1H-1,5-diazaphenalen-6-ol;

(68) 1-[1-(3-aminopropyl)piperidin-4-yl]-2,3-dihydro-1H-1,5-diazaphenalen-6-ol;
(69) 1-[1-(2-methylaminoethyl)piperidin-4-yl]-2,3-dihydro-1H-1,5-diazaphenalen-6-ol;
(70) 1-[1-(3-methylaminopropyl)piperidin-4-yl]-2,3-dihydro-1H-1,5-diazaphenalen-6-ol;
(71) 1-[1-(2-dimethylaminoethyl)piperidin-4-yl]-2,3-dihydro-1H-1,5-diazaphenalen-6-ol;
(72) 1-[1-(3-dimethylaminopropyl)piperidin-4-yl]-2,3-dihydro-1H-1,5-diazaphenalen-6-ol;
(73) N-{2-[4-(2,3-dihydro-1,5-diazaphenalen-1-yl)piperidin-1-yl]ethyl}acetamide;
(74) N-{2-[4-(2,3-dihydro-1,5-diazaphenalen-1-yl)piperidin-1-yl]ethyl}propionamide;
(75) N-{3-[4-(2,3-dihydro-1,5-diazaphenalen-1-yl)piperidin-1-yl]propyl}acetamide;
(76) N-{3-[4-(2,3-dihydro-1,5-diazaphenalen-1-yl)piperidin-1-yl]propyl}propionamide;
(77) N-{2-[4-(6-hydroxy-2,3-dihydro-1,5-diazaphenalen-1-yl)piperidin-1-yl]ethyl}acetamide;
(78) N-{2-[4-(6-hydroxy-2,3-dihydro-1,5-diazaphenalen-1-yl)piperidin-1-yl]ethyl}propionamide;
(79) N-{3-[4-(6-hydroxy-2,3-dihydro-1,5-diazaphenalen-1-yl)piperidin-1-yl]propyl}acetamide;
(80) N-{3-[4-(6-hydroxy-2,3-dihydro-1,5-diazaphenalen-1-yl)piperidin-1-yl]propyl}propionamide;
(81) trans-[4-(2,3-dihydro-1,5-diazaphenalen-1-yl)cyclohexyl]dimethylamine;
(82) trans-1-(4-dimethylaminocyclohexyl)-2,3-dihydro-1H-1,5-diazaphenalen-6-ol;
(83) N-{2-[3-(2,3-dihydro-1,5-diazaphenalen-1-yl)pyrrolidin-1-yl]ethyl}-N-methylacetamide;
(84) N-{2-[3-(6-hydroxy-2,3-dihydro-1,5-diazaphenalen-1-yl)pyrrolidin-1-yl]ethyl}-N-methylacetamide;
(85) 1-{2-[3-(2,3-dihydro-1,5-diazaphenalen-1-yl)pyrrolidin-1-yl]ethyl}azetidin-2-one;
(86) 1-{2-[3-(6-hydroxy-2,3-dihydro-1,5-diazaphenalen-1-yl)pyrrolidin-1-yl]ethyl}azetidin-2-one;
(87) N-{2-[4-(2,3-dihydro-1,5-diazaphenalen-1-yl)piperidin-1-yl]ethyl}-N-methylacetamide;
(88) N-{2-[4-(6-hydroxy-2,3-dihydro-1,5-diazaphenalen-1-yl)piperidin-1-yl]ethyl}-N-methylacetamide;
(89) 1-{2-[4-(2,3-dihydro-1,5-diazaphenalen-1-yl)piperidin-1-yl]ethyl}azetidin-2-one;
(90) 1-{2-[4-(6-hydroxy-2,3-dihydro-1,5-diazaphenalen-1-yl)piperidin-1-yl]ethyl}azetidin-2-one;
(91) 1-(3-fluoropiperidin-4-yl)-2,3-dihydro-1H-1,5-diazaphenalene; and
(92) 1-(3-fluoropiperidin-4-yl)-2,3-dihydro-1H-1,5-diazaphenalen-6-ol.

10. A pharmaceutical composition comprising a therapeutically effective amount of a compound represented by the formula (1) or a physiologically acceptable salt thereof according to claim 1 as an active ingredient, and further comprising a pharmaceutical additive as required.

11. The pharmaceutical composition according to claim 10, which is for inhibiting phosphorylation of myosin regulatory light chain.

12. The pharmaceutical composition according to claim 10, which is for inhibiting Rho/Rho kinase pathway.

13. The pharmaceutical composition according to claim 10, which is used for prophylactic and/or therapeutic treatment of glaucoma.

14. The pharmaceutical composition according to claim 10, which is used for prophylactic and/or therapeutic treatment of bronchial asthma and/or chronic obstructive pulmonary disease.

15. The pharmaceutical composition according to claim 10, which is used for prophylactic and/or therapeutic treatment of a nerve dysfunction.

16. A method of inhibiting the phosphorylation of myosin regulatory light chain, which comprises utilizing a compound represented by the formula (1) or a physiologically acceptable salt thereof according to claim 1.

* * * * *